United States Patent
Behenna et al.

(10) Patent No.: US 9,290,496 B2
(45) Date of Patent: Mar. 22, 2016

(54) PURINE DERIVATIVES

(71) Applicant: PFIZER INC., New York, NY (US)

(72) Inventors: Douglas Carl Behenna, San Juan Capistrano, CA (US); Hengmiao Cheng, San Diego, CA (US); Sujin Cho-Schultz, San Diego, CA (US); Theodore Otto Johnson, Jr., San Diego, CA (US); John Charles Kath, La Mesa, CA (US); Asako Nagata, San Diego, CA (US); Sajiv Krishnan Nair, Vista, CA (US); Simon Paul Planken, San Diego, CA (US)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 14/548,749

(22) Filed: Nov. 20, 2014

(65) Prior Publication Data

US 2015/0141402 A1     May 21, 2015

Related U.S. Application Data

(60) Provisional application No. 61/907,322, filed on Nov. 21, 2013.

(51) Int. Cl.
| | |
|---|---|
| *A61K 31/519* | (2006.01) |
| *C07D 473/18* | (2006.01) |
| *A61P 35/00* | (2006.01) |
| *A61K 31/5377* | (2006.01) |
| *C07D 498/10* | (2006.01) |
| *A61K 31/5386* | (2006.01) |
| *C07D 487/04* | (2006.01) |
| *A61K 31/52* | (2006.01) |
| *C07D 473/16* | (2006.01) |
| *C07D 519/00* | (2006.01) |

(52) U.S. Cl.
CPC ............ *C07D 473/16* (2013.01); *A61K 31/519* (2013.01); *A61K 31/52* (2013.01); *A61K 31/5377* (2013.01); *A61K 31/5386* (2013.01); *C07D 473/18* (2013.01); *C07D 519/00* (2013.01)

(58) Field of Classification Search
USPC .................... 514/210.18, 265.1, 263.2, 234.2; 544/280, 276, 117, 71, 277
See application file for complete search history.

(56) References Cited

U.S. PATENT DOCUMENTS

| | | | |
|---|---|---|---|
| 5,866,702 A | 2/1999 | Mackman et al. | |
| 6,232,320 B1 | 5/2001 | Stewart et al. | |
| 6,579,882 B2 | 6/2003 | Stewart et al. | |
| 6,790,958 B2 | 9/2004 | Lum et al. | |
| 6,794,390 B2 | 9/2004 | Lum et al. | |
| 6,803,371 B2 | 10/2004 | Gray et al. | |
| 6,949,644 B2 | 9/2005 | Ding et al. | |
| 6,951,848 B2 | 10/2005 | Harriman et al. | |
| 7,109,330 B2 | 9/2006 | Lum et al. | |
| 7,176,312 B2 | 2/2007 | Ding et al. | |
| 7,199,119 B2 | 4/2007 | Burkitt et al. | |
| 7,635,695 B2 | 12/2009 | Burkitt et al. | |

(Continued)

FOREIGN PATENT DOCUMENTS

| | | |
|---|---|---|
| CN | 103159742 A | 6/2013 |
| WO | 0222601 A1 | 3/2002 |
| WO | 0222602 A2 | 3/2002 |
| WO | 0222603 A1 | 3/2002 |
| WO | 0222604 A1 | 3/2002 |
| WO | 0222605 A1 | 3/2002 |
| WO | 0222606 A1 | 3/2002 |
| WO | 0222607 A1 | 3/2002 |
| WO | 0222608 A1 | 3/2002 |
| WO | 03/031406 A2 | 4/2003 |

(Continued)

OTHER PUBLICATIONS

Cancer [online], [retrieved on Jun. 6, 2007] Retrieved from the Internet, URL: http://www.nlm.nih.gov/medlineplus/cancer.html.*

(Continued)

*Primary Examiner* — Kristin Vajda
(74) *Attorney, Agent, or Firm* — Suzanne M. Bates; Stephen D. Prodnuk

(57) ABSTRACT

The present invention relates to compounds of formula (I)

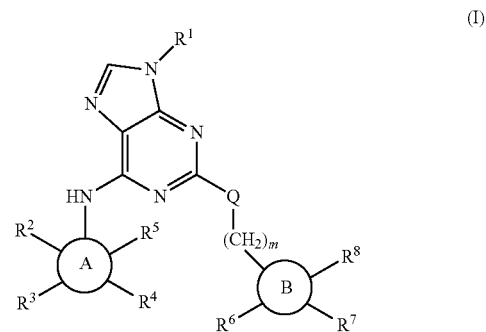

or pharmaceutically acceptable salts thereof, wherein Q, G, ring A, ring B, $R^1$, $R^2$, $R^3$, $R^4$, $R^5$, $R^{5a}$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, and m are defined herein. The novel purine derivatives are useful in the treatment of abnormal cell growth, such as cancer, in mammals. Additional embodiments relate to pharmaceutical compositions containing the compounds and to methods of using the compounds and compositions in the treatment of abnormal cell growth in mammals.

11 Claims, No Drawings

(56) References Cited

U.S. PATENT DOCUMENTS

| | | | |
|---|---|---|---|
| 8,088,752 | B2 | 1/2012 | Miljkovic et al. |
| 8,492,420 | B2 | 7/2013 | Becq et al. |
| 8,642,651 | B2 | 2/2014 | Miljkovic et al. |
| 8,927,281 | B2 | 1/2015 | Boitano et al. |
| 9,040,547 | B2 * | 5/2015 | Cheng et al. ............... 514/265.1 |
| 2003/0220365 | A1 | 11/2003 | Stewart et al. |
| 2004/0235867 | A1 | 11/2004 | Bilodeau et al. |
| 2005/0075348 | A1 | 4/2005 | Harriman et al. |
| 2005/0124637 | A1 | 6/2005 | Cheng et al. |
| 2006/0009642 | A1 | 1/2006 | Ding et al. |
| 2006/0029642 | A1 | 2/2006 | Miljkovic et al. |
| 2007/0161582 | A1 | 7/2007 | Mijikovic et al. |
| 2007/0184067 | A1 | 8/2007 | Miljkovic et al. |
| 2007/0191380 | A1 | 8/2007 | Ding et al. |
| 2007/0253896 | A1 | 11/2007 | Le Brazidec et al. |
| 2007/0275984 | A1 | 11/2007 | Imogai et al. |
| 2009/0176778 | A1 | 7/2009 | Schmitz et al. |
| 2009/0208620 | A1 | 8/2009 | Miljkovic et al. |
| 2009/0209535 | A1 | 8/2009 | Jensen et al. |
| 2009/0253717 | A1 | 10/2009 | Brown et al. |
| 2010/0056494 | A1 | 3/2010 | Winzeler et al. |
| 2011/0046164 | A1 | 2/2011 | Bukanov et al. |
| 2011/0092491 | A1 | 4/2011 | Cheng et al. |
| 2011/0251172 | A1 | 10/2011 | Rivkin et al. |
| 2012/0121540 | A1 | 5/2012 | Schmitz et al. |
| 2012/0149662 | A1 | 6/2012 | Babu et al. |
| 2013/0079324 | A1 | 3/2013 | Cheng et al. |
| 2013/0137694 | A1 | 5/2013 | Batist et al. |
| 2013/0172340 | A1 | 7/2013 | Turkson et al. |
| 2014/0031539 | A1 | 1/2014 | Jensen et al. |
| 2014/0114070 | A1 | 4/2014 | Boitano et al. |
| 2014/0249165 | A1 | 9/2014 | Bukanov et al. |
| 2015/0203502 | A1 | 7/2015 | Cheng et al. |

FOREIGN PATENT DOCUMENTS

| | | |
|---|---|---|
| WO | 2007/071393 A2 | 6/2007 |
| WO | 2007105023 A1 | 9/2007 |
| WO | 2008057402 A2 | 5/2008 |
| WO | 2008107444 A1 | 9/2008 |
| WO | 2009/050199 A1 | 4/2009 |
| WO | 2010118367 A2 | 10/2010 |
| WO | 2013042006 A1 | 3/2013 |
| WO | 2013/106792 A1 | 7/2013 |
| WO | 2014140989 A2 | 9/2014 |

OTHER PUBLICATIONS

Lala et al., Role of nitric oxide in tumor progression: Lessons from experimental tumors, Cancer and Metastasis Reviews (1998), 17, 91-106.*

Golub et al., Molecular Classification of Cancer: Class Discovery and Class Prediction by Gene Expression Monitoring, Science (1999), vol. 286, 531-537.*

International Search Report for International Appln. No. PCT/IB2014/065935 issued Jan. 21, 2015.

* cited by examiner

PURINE DERIVATIVES

CROSS-REFERENCE TO RELATED APPLICATIONS

This patent application claims the benefit of priority to U.S. Provisional Patent Application Ser. No. 61/907,322, filed Nov. 21, 2013, the contents of which are hereby incorporated by reference in their entireties.

FIELD OF THE INVENTION

The present invention relates to novel purine derivatives that are useful in the treatment of abnormal cell growth, such as cancer, in mammals. The present invention also relates to pharmaceutical compositions containing the compounds and to methods of using the compounds and compositions in the treatment of abnormal cell growth in mammals.

BACKGROUND

Lung cancer is the leading cause of cancer death worldwide, with an estimated 1.2 million new cases diagnosed each year. In lung adenocarcinoma, which is the most common form of lung cancer, patients harboring mutations in the epidermal growth factor receptor (EGFR) constitute between 10-30% of the overall population. It is this segment of patients for whom EGFR inhibitors such as erlotinib or gefitinib can be most effective (Paez et al., Science 2004; Lynch et al., NEJM 2004; Pao et al., PNAS 2004). The most common mutations associated with good response to these inhibitors are deletions within exon 19 (e.g. E740-A750) and point mutations in the activation loop (exon 21, in particular, L858R). Additional somatic mutations identified to date but to a lesser extent include point mutations: G719S, G719C, G719A, L861 and small insertions in Exon 20 (Shigematsu et al., JNCI 2005; Fukuoka et al., JCO 2003; Kris et al., JAMA 2003 and Shepherd et al., NEJM 2004).

While these agents can be effective treatments for the EGFR mutant sub-population, the majority of patients who initially respond develop resistance. The primary mechanism of resistance, observed in approximately 50% of patients, is due to a second mutation (T790M) which occurs at the gatekeeper threonine residue (Kosaka et al., CCR 2006; Balak et al., CCR 2006 and Engelman et al., Science 2007).

Thus, there is a need for compounds that inhibit EGFR T790M.

SUMMARY OF THE INVENTION

Each of the embodiments described below can be combined with any other embodiment described herein not inconsistent with the embodiment with which it is combined. Furthermore, each of the embodiments described herein envisions within its scope pharmaceutically acceptable salts of the compounds described herein. Accordingly, the phrase "or a pharmaceutically acceptable salt thereof" is implicit in the description of all compounds described herein.

Embodiments described herein relate to a compound of formula (I):

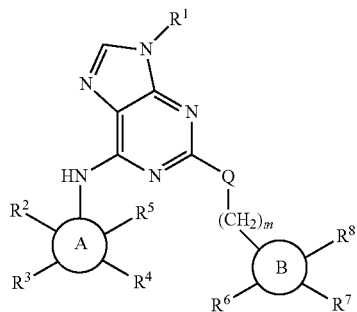

(I)

wherein $R^1$ is hydrogen, $C_1$-$C_6$ alkyl, $C_2$-$C_6$ alkenyl, $C_2$-$C_6$ alkynyl, $C_3$-$C_6$ cycloalkyl, 4-6 membered heterocycloalkyl, or 4-6 membered heteroaryl, wherein the $C_1$-$C_6$ alkyl is optionally substituted by one, two or three substituents selected from the group consisting of halogen, hydroxy, and $C_1$-$C_3$ alkoxy, further wherein the $C_3$-$C_6$ cycloalkyl, the 4-6 membered heterocycloalkyl, and the 4-6 membered heteroaryl are each independently optionally substituted by one, two or three substituents selected from the group consisting of $C_1$-$C_3$ alkyl, hydroxy, and $C_1$-$C_3$ alkoxy;

ring A is $C_6$-$C_{10}$ aryl or 5-12 membered heteroaryl;

$R^2$ and $R^5$ are each independently absent, hydrogen, halogen, cyano, difluoromethyl, trifluoromethyl, $C_1$-$C_6$ alkyl, $C_2$-$C_6$ alkenyl, $C_2$-$C_6$ alkynyl, $C_1$-$C_6$ alkoxy, —N($R^{10}$)($R^{11}$), $C_3$-$C_5$ cycloalkyl, or 4-6 membered heterocycloalkyl, wherein the $C_1$-$C_6$ alkyl is optionally substituted by one, two or three substituents selected from the group consisting of halogen, hydroxy, $C_1$-$C_6$ alkoxy, and —N($R^{12}$)($R^{13}$);

$R^3$ is absent, hydrogen, halogen, $C_1$-$C_6$ alkyl, $C_2$-$C_6$ alkynyl, $C_1$-$C_6$ alkoxy, $C_3$-$C_7$ cycloalkyl, or 3-7 membered heterocycloalkyl, wherein the $C_1$-$C_6$ alkyl and the $C_1$-$C_6$ alkoxy are each optionally substituted by one, two or three $R^{14}$ groups, and further wherein the $C_3$-$C_7$ cycloalkyl and the 3-7 membered heterocycloalkyl are each optionally substituted by one, two or three $R^{15}$ groups;

$R^4$ is absent, hydrogen, halogen, $C_1$-$C_6$ alkyl, or $C_3$-$C_6$ cycloalkyl, wherein $R^2$ and $R^3$ or $R^3$ and $R^4$ may combine to form a $C_5$-$C_7$ cycloalkyl ring or a 5-7 membered heterocycloalkyl ring, further wherein the $C_5$-$C_7$ cycloalkyl ring and the 5-7 membered heterocycloalkyl ring are each independently optionally substituted by one, two or three $R^{14}$ groups;

Q is absent, O, S, or $NR^9$;

ring B is absent, $C_3$-$C_{10}$ cycloalkyl, 3-10 membered heterocycloalkyl, $C_6$-$C_{10}$ aryl, or 5-12 membered heteroaryl;

$R^6$ and $R^8$ are each independently absent, hydrogen, halogen, cyano, hydroxy, difluoromethyl, trifluoromethyl, $C_1$-$C_3$ alkyl, $C_1$-$C_3$ alkoxy, or $C_3$-$C_5$ cycloalkyl, wherein the $C_1$-$C_3$ alkyl is optionally substituted by hydroxy, difluoromethyl, trifluoromethyl, $C_1$-$C_3$ alkoxy, or $C_3$-$C_5$ cycloalkyl;

$R^7$ is

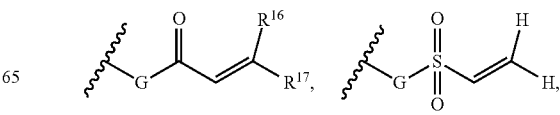

-continued

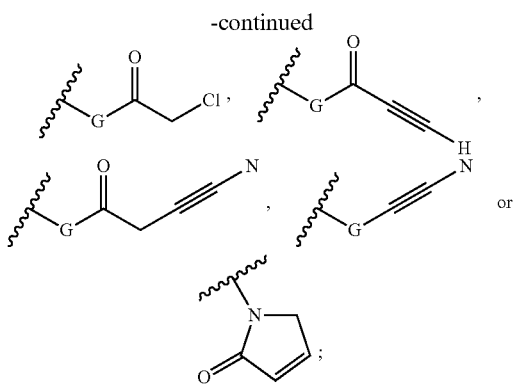

G is absent when the attachment point of $R^7$ on ring B is a nitrogen atom, and G is —$NR^{18}$-when ring B is absent or when the attachment point of $R^7$ on ring B is a carbon atom;

$R^9$, $R^{12}$ and $R^{13}$ are each independently hydrogen or $C_1$-$C_3$ alkyl;

$R^{10}$ and $R^{11}$ are each independently hydrogen or $C_1$-$C_6$ alkyl; or $R^{10}$ and $R^{11}$ together with the nitrogen to which they are attached, may combine to form a 4-7 membered heterocycloalkyl ring, when $R^{10}$ and $R^{11}$ are each $C_1$-$C_3$ alkyl, wherein the 4-7 membered heterocycloalkyl ring formed is optionally substituted by one, two, three or four $R^{15}$ groups;

each $R^{14}$ is independently halogen, cyano, $C_1$-$C_3$ alkyl, hydroxy, $C_1$-$C_6$ alkoxy, —$N(R^{19})(R^{20})$, —$CON(R^{21})(R^{22})$, or 3-7 membered heterocycloalkyl, wherein the 3-7 membered heterocycloalkyl is optionally substituted by one, two, three or four $R^{15}$ groups;

each $R^{15}$ is independently halogen, $C_1$-$C_3$ alkyl, hydroxy, $C_1$-$C_6$ alkoxy, —$NH_2$, —$NHCH_3$, or —$N(CH_3)_2$;

$R^{16}$ and $R^{17}$ are each independently hydrogen or $C_1$-$C_6$ alkyl, wherein the $C_1$-$C_6$ alkyl is optionally substituted by —$N(R^{23})(R^{24})$, provided that $R^{16}$ and $R^{17}$ may form a $C_3$-$C_5$ cycloalkyl ring;

$R^{18}$ is hydrogen or $C_1$-$C_3$ alkyl;

each $R^{19}$, $R^{20}$, $R^{21}$, $R^{22}$, $R^{23}$, and $R^{24}$ is independently hydrogen or $C_1$-$C_3$ alkyl; and m is 0, 1 or 2, provided that when ring B is absent, m is 2; or a pharmaceutically acceptable salt thereof.

Some embodiments relate to a compound of formula (I), or a pharmaceutically acceptable salt thereof, wherein $R^1$ is $C_1$-$C_6$ alkyl or $C_3$-$C_6$ cycloalkyl, wherein the $C_1$-$C_6$ alkyl is optionally substituted by hydroxy, further wherein the $C_3$-$C_6$ cycloalkyl is optionally substituted by $C_1$-$C_3$ alkyl.

Further embodiments relate to a compound of formula (I), or a pharmaceutically acceptable salt thereof, wherein $R^1$ is methyl, ethyl, isopropyl, or tert-butyl.

Additional embodiments relate to a compound of formula (I), or a pharmaceutically acceptable salt thereof, wherein $R^1$ is cyclobutyl optionally substituted by $C_1$-$C_3$ alkyl.

Some embodiments relate to a compound of formula (I), or a pharmaceutically acceptable salt thereof, wherein $R^2$ is hydrogen, methyl, difluoromethyl, or methoxy.

Further embodiments relate to a compound of formula (I), or a pharmaceutically acceptable salt thereof, wherein $R^2$ is hydrogen or methyl.

Some embodiments relate to a compound of formula (I), or a pharmaceutically acceptable salt thereof, wherein $R^5$ is hydrogen, $C_1$-$C_6$ alkyl, or $C_1$-$C_6$ alkoxy.

Further embodiments relate to a compound of formula (I), or a pharmaceutically acceptable salt thereof, wherein $R^5$ is hydrogen, methyl, or methoxy.

Additional embodiments relate to a compound of formula (I), or a pharmaceutically acceptable salt thereof, wherein $R^2$ are $R^5$ are hydrogen.

Some embodiments relate to a compound of formula (I), or a pharmaceutically acceptable salt thereof, wherein $R^3$ is $C_1$-$C_6$ alkyl or 3-7 membered heterocycloalkyl, wherein the $C_1$-$C_6$ alkyl is optionally substituted by one or two $R^{14}$ groups, further wherein the 3-7 membered heterocycloalkyl is optionally substituted by $C_1$-$C_3$ alkyl.

Additional embodiments relate to a compound of formula (I), or a pharmaceutically acceptable salt thereof, wherein $R^3$ is azetidine, pyrrolidine, or piperidine, wherein the azetidine, the pyrrolidine, and the piperidine are each optionally substituted by $C_1$-$C_3$ alkyl.

Additional embodiments relate to a compound of formula (I), or a pharmaceutically acceptable salt thereof, wherein $R^3$ is methyl.

Some embodiments relate to a compound of formula (I), or a pharmaceutically acceptable salt thereof, wherein $R^3$ is 3-7 membered heterocycloalkyl, wherein the 3-7 membered heterocycloalkyl is optionally substituted by one, two or three $R^{15}$ groups.

More embodiments relate to a compound of formula (I), or a pharmaceutically acceptable salt thereof, wherein $R^3$ is piperidine optionally substituted by $C_1$-$C_3$ alkyl.

More embodiments relate to a compound of formula (I), or a pharmaceutically acceptable salt thereof, wherein $R^3$ is piperazine optionally substituted by $C_1$-$C_3$ alkyl.

Further embodiments relate to a compound of formula (I), or a pharmaceutically acceptable salt thereof, wherein $R^3$ is piperazine optionally substituted by methyl.

Additional embodiments relate to a compound of formula (I), or a pharmaceutically acceptable salt thereof, wherein $R^3$ is 4-methylpiperazine.

Additional embodiments relate to a compound of formula (I), or a pharmaceutically acceptable salt thereof, wherein $R^2$ is hydrogen, halogen, trifluoromethyl, $C_1$-$C_6$ alkyl, or $C_1$-$C_6$ alkoxy.

Some embodiments relate to a compound of formula (I), or a pharmaceutically acceptable salt thereof, wherein $R^2$ is hydrogen, fluorine, trifluoromethyl, methyl, or methoxy.

Some embodiments relate to a compound of formula (I), or a pharmaceutically acceptable salt thereof, wherein $R^2$ is hydrogen.

More embodiments relate to a compound of formula (I), or a pharmaceutically acceptable salt thereof, wherein $R^4$ is hydrogen.

Further embodiments relate to a compound of formula (I), or a pharmaceutically acceptable salt thereof, wherein $R^4$ is hydrogen, halogen, or $C_1$-$C_3$ alkyl.

Additional embodiments relate to a compound of formula (I), or a pharmaceutically acceptable salt thereof, wherein Q is absent.

Further embodiments relate to a compound of formula (I), or a pharmaceutically acceptable salt thereof, wherein Q is O.

More embodiments relate to a compound of formula (I), or a pharmaceutically acceptable salt thereof, wherein Q is $NR^9$.

Some embodiments relate to a compound of formula (I), or a pharmaceutically acceptable salt thereof, wherein m is 0.

Additional embodiments relate to a compound of formula (I), or a pharmaceutically acceptable salt thereof, wherein m is 1.

Further embodiments relate to a compound of formula (I), or a pharmaceutically acceptable salt thereof, wherein ring B is 3-10 membered heterocycloalkyl.

Some embodiments relate to a compound of formula (I), or a pharmaceutically acceptable salt thereof, wherein ring B is

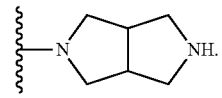

Some embodiments relate to a compound or a pharmaceutically acceptable salt of any of the embodiments of the compounds of formula (I), having formula (Ia):

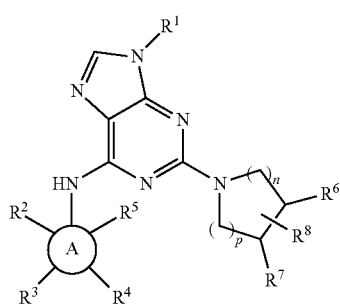

(Ia)

wherein n is 0, 1, or 2; and p is 0, 1, or 2.

Some embodiments relate to a compound of formula (Ia), or a pharmaceutically acceptable salt thereof, wherein n is 0.

Further embodiments relate to a compound of formula (Ia), or a pharmaceutically acceptable salt thereof, wherein n is 1.

Additional embodiments relate to a compound of formula (Ia), or a pharmaceutically acceptable salt thereof, wherein p is 1.

Additional embodiments relate to a compound of formula (Ia), or a pharmaceutically acceptable salt thereof, wherein n is 1 and p is 1.

More embodiments relate to a compound of formula (Ia), or a pharmaceutically acceptable salt thereof, wherein $R^6$ and $R^8$ are each independently hydrogen, halogen, $C_1$-$C_3$ alkyl, or $C_1$-$C_3$ alkoxy.

Some embodiments relate to a compound of formula (Ia), or a pharmaceutically acceptable salt thereof, wherein $R^6$ is hydrogen, fluorine, methyl, or methoxy.

Some embodiments relate to a compound of formula (Ia), or a pharmaceutically acceptable salt thereof, wherein $R^6$ is fluorine.

More embodiments relate to a compound of formula (Ia), or a pharmaceutically acceptable salt thereof, wherein $R^8$ is hydrogen, fluorine, or methyl.

Additional embodiments relate to a compound of formula (Ia), or a pharmaceutically acceptable salt thereof, wherein $R^8$ is methyl.

Some embodiments relate to a compound of formula (Ia), or a pharmaceutically acceptable salt thereof, wherein $R^7$ is

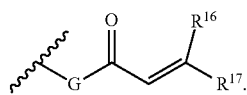

Some embodiments relate to a compound or a pharmaceutically acceptable salt of any of the embodiments of the compounds of formula (I), having formula (Ib):

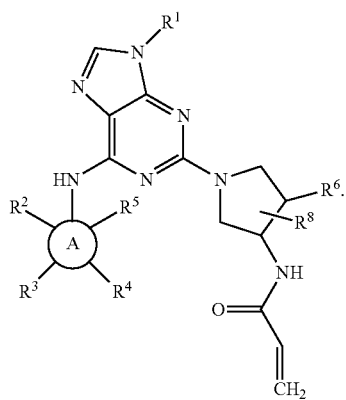

(Ib)

Additional embodiments relate to a compound of formula (Ib), or a pharmaceutically acceptable salt thereof, wherein $R^6$ and $R^8$ are each independently hydrogen, halogen, $C_1$-$C_3$ alkyl, or $C_1$-$C_3$ alkoxy.

More embodiments relate to a compound of formula (Ib), or a pharmaceutically acceptable salt thereof, wherein $R^6$ is hydrogen, fluorine, methyl, or methoxy.

Some embodiments relate to a compound of formula (Ib), or a pharmaceutically acceptable salt thereof, wherein $R^6$ is fluorine.

Further embodiments relate to a compound of formula (Ib), or a pharmaceutically acceptable salt thereof, wherein $R^8$ is hydrogen, fluorine, or methyl.

Additional embodiments relate to a compound of formula (Ib), or a pharmaceutically acceptable salt thereof, wherein $R^8$ is methyl.

Some embodiments relate to a compound or a pharmaceutically acceptable salt of any of the embodiments of the compounds of formula (I), having formula (Ic):

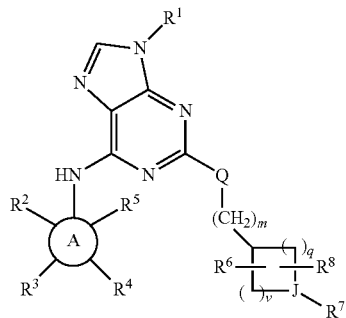

(Ic)

wherein

J is C or N;

q is 0, 1, 2, or 3; and v is 0, 1, 2, or 3, provided that q and v cannot both be 0.

Further embodiments relate to a compound of formula (Ic), or a pharmaceutically acceptable salt thereof, wherein J is C.

Additional embodiments relate to a compound of formula (Ic), or a pharmaceutically acceptable salt thereof, wherein J is N.

Some embodiments relate to a compound of formula (Ic), or a pharmaceutically acceptable salt thereof, wherein q is 1.

Some embodiments relate to a compound of formula (Ic), or a pharmaceutically acceptable salt thereof, wherein q is 2.

More embodiments relate to a compound of formula (Ic), or a pharmaceutically acceptable salt thereof, wherein q is 3.

More embodiments relate to a compound of formula (Ic), or a pharmaceutically acceptable salt thereof, wherein v is 1.

Further embodiments relate to a compound of formula (Ic), or a pharmaceutically acceptable salt thereof, wherein q is 1 and v is 1.

Additional embodiments relate to a compound of formula (Ic), or a pharmaceutically acceptable salt thereof, wherein q is 2 and v is 1.

Additional embodiments relate to a compound of formula (Ic), or a pharmaceutically acceptable salt thereof, wherein q is 3 and v is 1.

More embodiments relate to a compound of formula (Ic), or a pharmaceutically acceptable salt thereof, wherein $R^6$ is hydrogen, halogen, or $C_1$-$C_3$ alkoxy.

Some embodiments relate to a compound of formula (Ic), or a pharmaceutically acceptable salt thereof, wherein $R^6$ is hydrogen, fluorine, or methoxy.

More embodiments relate to a compound of formula (Ic), or a pharmaceutically acceptable salt thereof, wherein $R^8$ is hydrogen or $C_1$-$C_3$ alkyl.

Additional embodiments relate to a compound of formula (Ic), or a pharmaceutically acceptable salt thereof, wherein $R^8$ is hydrogen or methyl.

Some embodiments relate to a compound of formula (Ic), or a pharmaceutically acceptable salt thereof, wherein $R^7$ is

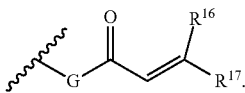

Some embodiments relate to a compound or a pharmaceutically acceptable salt of any of the embodiments of the compounds of formula (I), wherein m is 0, having formula (Id):

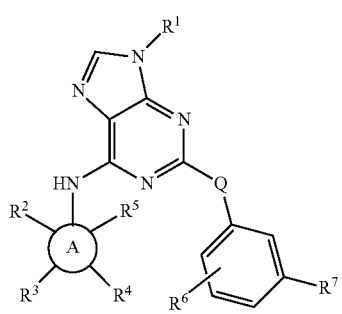

wherein
Q is O or $NR^9$.

Additional embodiments relate to a compound of formula (Id), or a pharmaceutically acceptable salt thereof, wherein $R^6$ is absent.

More embodiments relate to a compound of formula (Id), or a pharmaceutically acceptable salt thereof, wherein $R^7$ is

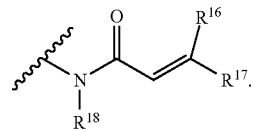

Additional embodiments relate to a compound of formula (Id), or a pharmaceutically acceptable salt thereof, wherein $R^{16}$, $R^{17}$ and $R^{18}$ are hydrogen.

Some embodiments described herein relate to a compound of formula (II):

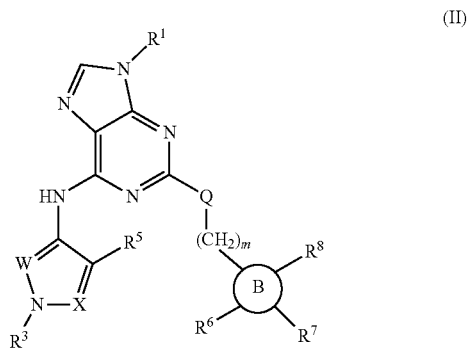

wherein
X is CH or N;
W is $CR^2$ or N,
provided that one of X and W is N and X and W cannot both be N, further provided that when W is $CR^2$, at least one of $R^3$ and $R^5$ is hydrogen;
$R^1$ is hydrogen, $C_1$-$C_6$ alkyl, $C_2$-$C_6$ alkenyl, $C_2$-$C_6$ alkynyl, $C_3$-$C_6$ cycloalkyl, 4-6 membered heterocycloalkyl, or 4-6 membered heteroaryl, wherein the $C_1$-$C_6$ alkyl is optionally substituted by one, two or three substituents selected from the group consisting of halogen, hydroxy, and $C_1$-$C_3$ alkoxy, further wherein the $C_3$-$C_6$ cycloalkyl, the 4-6 membered heterocycloalkyl, and the 4-6 membered heteroaryl are each independently optionally substituted by one, two or three substituents selected from the group consisting of $C_1$-$C_3$ alkyl, hydroxy, and $C_1$-$C_3$ alkoxy;
$R^2$ and $R^5$ are each independently hydrogen, halogen, cyano, difluoromethyl, trifluoromethyl, $C_1$-$C_6$ alkyl, $C_2$-$C_6$ alkenyl, $C_2$-$C_6$ alkynyl, $C_1$-$C_6$ alkoxy, —$N(R^{10})(R^{11})$, $C_3$-$C_5$ cycloalkyl, or 4-6 membered heterocycloalkyl, wherein the $C_1$-$C_6$ alkyl is optionally substituted by one, two or three substituents selected from the group consisting of halogen, hydroxy, $C_1$-$C_6$ alkoxy, and —$N(R^{12})(R^{13})$;
$R^3$ is absent, hydrogen, halogen, $C_1$-$C_6$ alkyl, $C_2$-$C_6$ alkynyl, $C_1$-$C_6$ alkoxy, $C_3$-$C_7$ cycloalkyl, or 3-7 membered heterocycloalkyl, wherein the $C_1$-$C_6$ alkyl and the $C_1$-$C_6$ alkoxy are each optionally substituted by one, two or three $R^{14}$ groups, and further wherein the $C_3$-$C_7$ cycloalkyl and the 3-7 membered heterocycloalkyl are each optionally substituted by one, two or three $R^{15}$ groups;
Q is absent, O, S, or $NR^9$;
ring B is absent, $C_3$-$C_{10}$ cycloalkyl, 3-10 membered heterocycloalkyl, $C_6$-$C_{10}$ aryl, or 5-12 membered heteroaryl;
$R^6$ and $R^8$ are each independently absent, hydrogen, halogen, cyano, hydroxy, difluoromethyl, trifluoromethyl, $C_1$-$C_3$ alkyl, $C_1$-$C_3$ alkoxy, or $C_3$-$C_5$ cycloalkyl, wherein the $C_1$-$C_3$ alkyl is optionally substituted by hydroxy, difluoromethyl, trifluoromethyl, $C_1$-$C_3$ alkoxy, or $C_3$-$C_5$ cycloalkyl;

$R^7$ is

[structures]

G is absent when the attachment point of $R^7$ on ring B is a nitrogen atom, and G is —$NR^{18}$— when ring B is absent or when the attachment point of $R^7$ on ring B is a carbon atom;

$R^9$, $R^{12}$ and $R^{13}$ are each independently hydrogen or $C_1$-$C_3$ alkyl;

$R^{10}$ and $R^{11}$ are each independently hydrogen or $C_1$-$C_6$ alkyl; or $R^{10}$ and $R^{11}$ together with the nitrogen to which they are attached, may combine to form a 4-7 membered heterocycloalkyl ring, when $R^{10}$ and $R^{11}$ are each $C_1$-$C_3$ alkyl, wherein the 4-7 membered heterocycloalkyl ring formed is optionally substituted by one, two, three or four $R^{15}$ groups;

each $R^{14}$ is independently halogen, cyano, $C_1$-$C_3$ alkyl, hydroxy, $C_1$-$C_6$ alkoxy, —$N(R^{19})(R^{20})$, —$CON(R^{21})(R^{22})$, or 3-7 membered heterocycloalkyl, wherein the 3-7 membered heterocycloalkyl is optionally substituted by one, two, three or four $R^{15}$ groups;

each $R^{15}$ is independently halogen, $C_1$-$C_3$ alkyl, hydroxy, $C_1$-$C_6$ alkoxy, —$NH_2$, —$NHCH_3$, or —$N(CH_3)_2$;

$R^{16}$ and $R^{17}$ are each independently hydrogen or $C_1$-$C_6$ alkyl, wherein the $C_1$-$C_6$ alkyl is optionally substituted by —$N(R^{23})(R^{24})$, provided that $R^{16}$ and $R^{17}$ may form a $C_3$-$C_5$ cycloalkyl ring;

$R^{18}$ is hydrogen or $C_1$-$C_3$ alkyl;

each $R^{19}$, $R^{20}$, $R^{21}$, $R^{22}$, $R^{23}$, and $R^{24}$ is independently hydrogen or $C_1$-$C_3$ alkyl; and m is 0, 1 or 2, provided that when ring B is absent, m is 2; or a pharmaceutically acceptable salt thereof.

More embodiments relate to a compound of formula (II), or a pharmaceutically acceptable salt thereof, wherein $R^1$ is $C_1$-$C_6$ alkyl or $C_3$-$C_6$ cycloalkyl, wherein the $C_1$-$C_6$ alkyl is optionally substituted by hydroxy, further wherein the $C_3$-$C_6$ cycloalkyl is optionally substituted by $C_1$-$C_3$ alkyl.

Some embodiments relate to a compound of formula (II), or a pharmaceutically acceptable salt thereof, wherein $R^1$ is methyl, ethyl, isopropyl, or tert-butyl.

Some embodiments relate to a compound of formula (II), or a pharmaceutically acceptable salt thereof, wherein $R^1$ is cyclobutyl optionally substituted by $C_1$-$C_3$ alkyl.

Further embodiments relate to a compound of formula (II), or a pharmaceutically acceptable salt thereof, wherein $R^2$ is hydrogen, methyl, difluoromethyl, or methoxy.

Additional embodiments relate to a compound of formula (II), or a pharmaceutically acceptable salt thereof, wherein $R^2$ is hydrogen or methyl.

Additional embodiments relate to a compound of formula (II), or a pharmaceutically acceptable salt thereof, wherein $R^5$ is hydrogen, $C_1$-$C_6$ alkyl, or $C_1$-$C_6$ alkoxy.

More embodiments relate to a compound of formula (II), or a pharmaceutically acceptable salt thereof, wherein $R^5$ is hydrogen, methyl, or methoxy.

Some embodiments relate to a compound of formula (II), or a pharmaceutically acceptable salt thereof, wherein $R^2$ are $R^5$ are hydrogen.

Some embodiments relate to a compound of formula (II), or a pharmaceutically acceptable salt thereof, wherein $R^3$ is $C_1$-$C_6$ alkyl or 3-7 membered heterocycloalkyl, wherein the $C_1$-$C_6$ alkyl is optionally substituted by one or two $R^{14}$ groups, further wherein the 3-7 membered heterocycloalkyl is optionally substituted by $C_1$-$C_3$ alkyl.

Additional embodiments relate to a compound of formula (II), or a pharmaceutically acceptable salt thereof, wherein $R^3$ is azetidine, pyrrolidine, or piperidine, wherein the azetidine, the pyrrolidine, and the piperidine are each optionally substituted by $C_1$-$C_3$ alkyl.

Additional embodiments relate to a compound of formula (II), or a pharmaceutically acceptable salt thereof, wherein $R^3$ is methyl.

Some embodiments relate to a compound of formula (II), or a pharmaceutically acceptable salt thereof, wherein $R^3$ is 3-7 membered heterocycloalkyl, wherein the 3-7 membered heterocycloalkyl is optionally substituted by one, two or three $R^{15}$ groups.

Further embodiments relate to a compound of formula (II), or a pharmaceutically acceptable salt thereof, wherein $R^3$ is piperidine optionally substituted by $C_1$-$C_3$ alkyl.

More embodiments relate to a compound of formula (II), or a pharmaceutically acceptable salt thereof, wherein Q is absent.

Further embodiments relate to a compound of formula (II), or a pharmaceutically acceptable salt thereof, wherein Q is O.

More embodiments relate to a compound of formula (II), or a pharmaceutically acceptable salt thereof, wherein Q is $NR^9$.

Additional embodiments relate to a compound of formula (II), or a pharmaceutically acceptable salt thereof, wherein m is 0.

Additional embodiments relate to a compound of formula (II), or a pharmaceutically acceptable salt thereof, wherein m is 1.

More embodiments relate to a compound of formula (II), or a pharmaceutically acceptable salt thereof, wherein ring B is 3-10 membered heterocycloalkyl.

Some embodiments relate to a compound of formula (II), or a pharmaceutically acceptable salt thereof, wherein ring B is

[structure]

Some embodiments relate to a compound or a pharmaceutically acceptable salt of any of the embodiments of the compounds of formula (II), having formula (IIa):

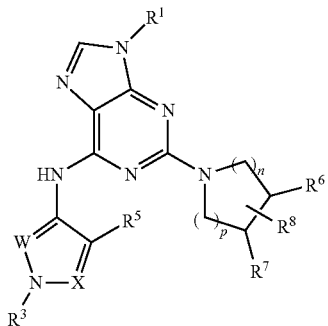

(IIa)

wherein n is 0, 1, or 2; and p is 0, 1, or 2.

Some embodiments relate to a compound of formula (IIa), or a pharmaceutically acceptable salt thereof, wherein n is 0.

Additional embodiments relate to a compound of formula (IIa), or a pharmaceutically acceptable salt thereof, wherein n is 1.

Additional embodiments relate to a compound of formula (IIa), or a pharmaceutically acceptable salt thereof, wherein p is 1.

Some embodiments relate to a compound of formula (IIa), or a pharmaceutically acceptable salt thereof, wherein n is 1 and p is 1.

More embodiments relate to a compound of formula (IIa), or a pharmaceutically acceptable salt thereof, wherein $R^6$ and $R^8$ are each independently hydrogen, halogen, $C_1$-$C_3$ alkyl, or $C_1$-$C_3$ alkoxy.

More embodiments relate to a compound of formula (IIa), or a pharmaceutically acceptable salt thereof, wherein $R^6$ is hydrogen, fluorine, methyl, or methoxy.

Some embodiments relate to a compound of formula (IIa), or a pharmaceutically acceptable salt thereof, wherein $R^6$ is fluorine.

Additional embodiments relate to a compound of formula (IIa), or a pharmaceutically acceptable salt thereof, wherein $R^8$ is hydrogen, fluorine, or methyl.

Additional embodiments relate to a compound of formula (IIa), or a pharmaceutically acceptable salt thereof, wherein $R^8$ is methyl.

Some embodiments relate to a compound of formula (IIa), or a pharmaceutically acceptable salt thereof, wherein $R^7$ is

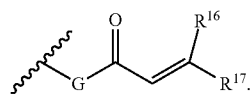

Some embodiments relate to a compound or a pharmaceutically acceptable salt of any of the embodiments of the compounds of formula (II), having formula (IIb):

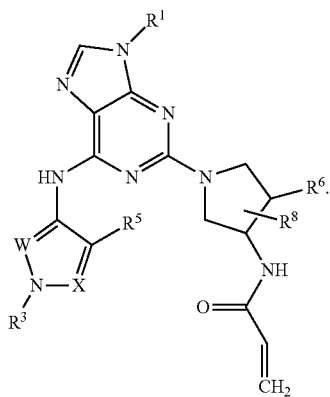

(IIb)

Further embodiments relate to a compound of formula (IIb), or a pharmaceutically acceptable salt thereof, wherein $R^6$ and $R^8$ are each independently hydrogen, halogen, $C_1$-$C_3$ alkyl, or $C_1$-$C_3$ alkoxy.

Some embodiments relate to a compound of formula (IIb), or a pharmaceutically acceptable salt thereof, wherein $R^6$ is hydrogen, fluorine, methyl, or methoxy.

Some embodiments relate to a compound of formula (IIb), or a pharmaceutically acceptable salt thereof, wherein $R^6$ is fluorine.

Additional embodiments relate to a compound of formula (IIb), or a pharmaceutically acceptable salt thereof, wherein $R^8$ is hydrogen, fluorine, or methyl.

Further embodiments relate to a compound of formula (IIb), or a pharmaceutically acceptable salt thereof, wherein $R^8$ is methyl.

Some embodiments relate to a compound or a pharmaceutically acceptable salt of any of the embodiments of the compounds of formula (II), wherein m is 0, having formula (IIc):

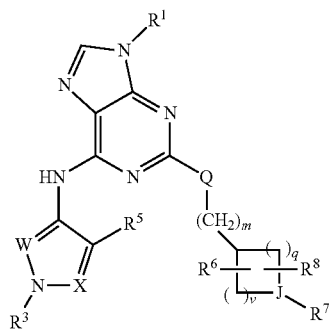

(IIc)

wherein

J is C or N;

q is 0, 1, 2, or 3; and v is 0, 1, 2, or 3, provided that q and v cannot both be 0.

Some embodiments relate to a compound of formula (IIc), or a pharmaceutically acceptable salt thereof, wherein J is C.

More embodiments relate to a compound of formula (IIc), or a pharmaceutically acceptable salt thereof, wherein J is N.

More embodiments relate to a compound of formula (IIc), or a pharmaceutically acceptable salt thereof, wherein q is 1.

Additional embodiments relate to a compound of formula (IIc), or a pharmaceutically acceptable salt thereof, wherein q is 2.

Further embodiments relate to a compound of formula (IIc), or a pharmaceutically acceptable salt thereof, wherein q is 3.

Some embodiments relate to a compound of formula (IIc), or a pharmaceutically acceptable salt thereof, wherein v is 1.

Some embodiments relate to a compound of formula (IIc), or a pharmaceutically acceptable salt thereof, wherein q is 1 and v is 1.

Many embodiments relate to a compound of formula (IIc), or a pharmaceutically acceptable salt thereof, wherein q is 2 and v is 1.

Further embodiments relate to a compound of formula (IIc), or a pharmaceutically acceptable salt thereof, wherein q is 3 and v is 1.

Additional embodiments relate to a compound of formula (IIc), or a pharmaceutically acceptable salt thereof, wherein $R^6$ is hydrogen, halogen, or $C_1$-$C_3$ alkoxy.

Some embodiments relate to a compound of formula (IIc), or a pharmaceutically acceptable salt thereof, wherein $R^6$ is hydrogen, fluorine, or methoxy.

Some embodiments relate to a compound of formula (IIc), or a pharmaceutically acceptable salt thereof, wherein $R^8$ is hydrogen or $C_1$-$C_3$ alkyl.

More embodiments relate to a compound of formula (IIc), or a pharmaceutically acceptable salt thereof, wherein $R^8$ is hydrogen or methyl.

More embodiments relate to a compound of formula (IIc), or a pharmaceutically acceptable salt thereof, wherein $R^7$ is

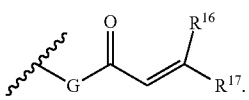

Some embodiments relate to a compound or a pharmaceutically acceptable salt of any of the embodiments of the compounds of formula (II), wherein m is 0, having formula (IId):

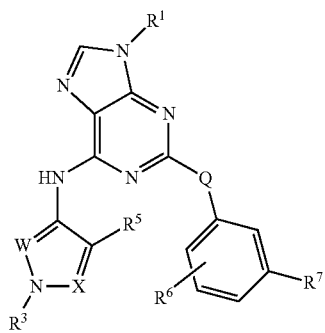

wherein

Q is O or $NR^9$.

Additional embodiments relate to a compound of formula (IId), or a pharmaceutically acceptable salt thereof, wherein $R^6$ is absent.

Some embodiments relate to a compound of formula (IId), or a pharmaceutically acceptable salt thereof, wherein $R^7$ is

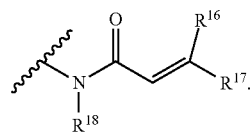

More embodiments relate to a compound of formula (IId), or a pharmaceutically acceptable salt thereof, wherein $R^{16}$, $R^{17}$ and $R^{18}$ are hydrogen.

Some embodiments described herein relate to a compound of formula (III):

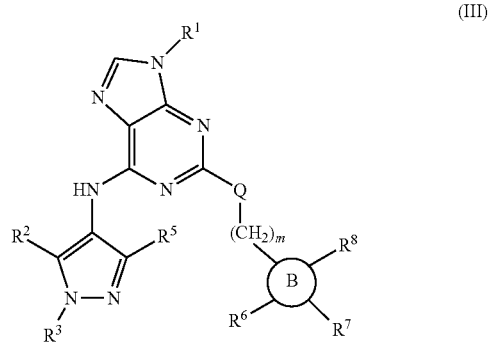

wherein $R^1$ is hydrogen, $C_1$-$C_6$ alkyl, $C_2$-$C_6$ alkenyl, $C_2$-$C_6$ alkynyl, $C_3$-$C_6$ cycloalkyl, 4-6 membered heterocycloalkyl, or 4-6 membered heteroaryl, wherein the $C_1$-$C_6$ alkyl is optionally substituted by one, two or three substituents selected from the group consisting of halogen, hydroxy, and $C_1$-$C_3$ alkoxy, further wherein the $C_3$-$C_6$ cycloalkyl, the 4-6 membered heterocycloalkyl, and the 4-6 membered heteroaryl are each independently optionally substituted by one, two or three substituents selected from the group consisting of $C_1$-$C_3$ alkyl, hydroxy, and $C_1$-$C_3$ alkoxy;

$R^2$ and $R^5$ are each independently hydrogen, halogen, cyano, difluoromethyl, trifluoromethyl, $C_1$-$C_6$ alkyl, $C_2$-$C_6$ alkenyl, $C_2$-$C_6$ alkynyl, $C_1$-$C_6$ alkoxy, —N($R^{10}$)($R^{11}$), $C_3$-$C_5$ cycloalkyl, or 4-6 membered heterocycloalkyl, wherein the $C_1$-$C_6$ alkyl is optionally substituted by one, two or three substituents selected from the group consisting of halogen, hydroxy, $C_1$-$C_6$ alkoxy, and —N($R^{12}$)($R^{13}$), provided that at least one of $R^2$ or $R^5$ is hydrogen;

$R^3$ is absent, hydrogen, halogen, $C_1$-$C_6$ alkyl, $C_2$-$C_6$ alkynyl, $C_1$-$C_6$ alkoxy, $C_3$-$C_7$ cycloalkyl, or 3-7 membered heterocycloalkyl, wherein the $C_1$-$C_6$ alkyl and the $C_1$-$C_6$ alkoxy are each optionally substituted by one, two or three $R^{14}$ groups, and further wherein the $C_3$-$C_7$ cycloalkyl and the 3-7 membered heterocycloalkyl are each optionally substituted by one, two or three $R^{15}$ groups;

Q is absent, O, S, or $NR^9$;

ring B is absent, $C_3$-$C_{10}$ cycloalkyl, 3-10 membered heterocycloalkyl, $C_6$-$C_{10}$ aryl, or 5-12 membered heteroaryl;

$R^6$ and $R^8$ are each independently absent, hydrogen, halogen, cyano, hydroxy, difluoromethyl, trifluoromethyl, $C_1$-$C_3$ alkyl, $C_1$-$C_3$ alkoxy, or $C_3$-$C_5$ cycloalkyl, wherein the $C_1$-$C_3$ alkyl is optionally substituted by hydroxy, difluoromethyl, trifluoromethyl, $C_1$-$C_3$ alkoxy, or $C_3$-$C_5$ cycloalkyl;

R⁷ is

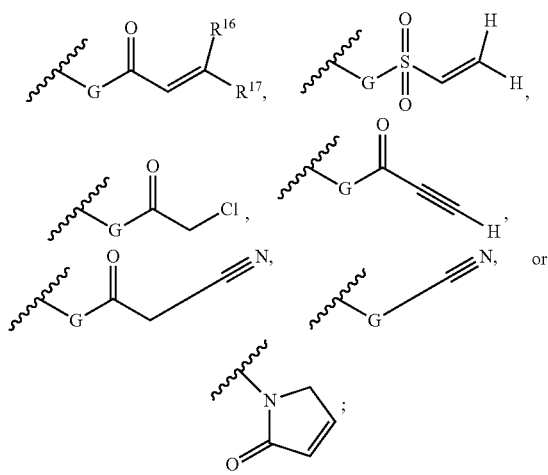

G is absent when the attachment point of R⁷ on ring B is a nitrogen atom, and G is —NR¹⁸— when ring B is absent or when the attachment point of R⁷ on ring B is a carbon atom;

$R^9$, $R^{12}$ and $R^{13}$ are each independently hydrogen or $C_1$-$C_3$ alkyl;

$R^{10}$ and $R^{11}$ are each independently hydrogen or $C_1$-$C_6$ alkyl; or $R^{10}$ and $R^{11}$ together with the nitrogen to which they are attached, may combine to form a 4-7 membered heterocycloalkyl ring, when $R^{10}$ and $R^{11}$ are each $C_1$-$C_3$ alkyl, wherein the 4-7 membered heterocycloalkyl ring formed is optionally substituted by one, two, three or four $R^{15}$ groups;

each $R^{14}$ is independently halogen, cyano, $C_1$-$C_3$ alkyl, hydroxy, $C_1$-$C_6$ alkoxy, —N($R^{19}$)($R^{20}$), —CON($R^{21}$)($R^{22}$), or 3-7 membered heterocycloalkyl, wherein the 3-7 membered heterocycloalkyl is optionally substituted by one, two, three or four $R^{15}$ groups;

each $R^{15}$ is independently halogen, $C_1$-$C_3$ alkyl, hydroxy, $C_1$-$C_6$ alkoxy, —NH₂, —NHCH₃, or —N(CH₃)₂;

$R^{16}$ and $R^{17}$ are each independently hydrogen or $C_1$-$C_6$ alkyl, wherein the $C_1$-$C_6$ alkyl is optionally substituted by —N($R^{23}$)($R^{24}$), provided that $R^{16}$ and $R^{17}$ may form a $C_3$-$C_5$ cycloalkyl ring;

$R^{18}$ is hydrogen or $C_1$-$C_3$ alkyl;

each $R^{19}$, $R^{20}$, $R^{21}$, $R^{22}$, $R^{23}$, and $R^{24}$ is independently hydrogen or $C_1$-$C_3$ alkyl; and m is 0, 1 or 2, provided that when ring B is absent, m is 2;

or a pharmaceutically acceptable salt thereof.

Some embodiments relate to a compound of formula (III), or a pharmaceutically acceptable salt thereof, wherein $R^1$ is $C_1$-$C_6$ alkyl or $C_3$-$C_6$ cycloalkyl, wherein the $C_1$-$C_6$ alkyl is optionally substituted by hydroxy, further wherein the $C_3$-$C_6$ cycloalkyl is optionally substituted by $C_1$-$C_3$ alkyl.

Additional embodiments relate to a compound of formula (III), or a pharmaceutically acceptable salt thereof, wherein $R^1$ is methyl, ethyl, isopropyl, or tert-butyl.

Further embodiments relate to a compound of formula (III), or a pharmaceutically acceptable salt thereof, wherein $R^1$ is cyclobutyl optionally substituted by $C_1$-$C_3$ alkyl.

More embodiments relate to a compound of formula (III), or a pharmaceutically acceptable salt thereof, wherein $R^2$ is hydrogen, methyl, difluoromethyl, or methoxy.

More embodiments relate to a compound of formula (III), or a pharmaceutically acceptable salt thereof, wherein $R^2$ is hydrogen or methyl.

Some embodiments relate to a compound of formula (III), or a pharmaceutically acceptable salt thereof, wherein $R^5$ is hydrogen, $C_1$-$C_6$ alkyl, or $C_1$-$C_6$ alkoxy.

Some embodiments relate to a compound of formula (III), or a pharmaceutically acceptable salt thereof, wherein $R^5$ is hydrogen, methyl, or methoxy.

Additional embodiments relate to a compound of formula (III), or a pharmaceutically acceptable salt thereof, wherein $R^2$ are $R^5$ are hydrogen.

Some embodiments relate to a compound of formula (III), or a pharmaceutically acceptable salt thereof, wherein $R^3$ is $C_1$-$C_6$ alkyl or 3-7 membered heterocycloalkyl, wherein the $C_1$-$C_6$ alkyl is optionally substituted by one or two $R^{14}$ groups, further wherein the 3-7 membered heterocycloalkyl is optionally substituted by $C_1$-$C_3$ alkyl.

Further embodiments relate to a compound of formula (III), or a pharmaceutically acceptable salt thereof, wherein $R^3$ is azetidine, pyrrolidine, or piperidine, wherein the azetidine, the pyrrolidine, and the piperidine are each optionally substituted by $C_1$-$C_3$ alkyl.

Further embodiments relate to a compound of formula (III), or a pharmaceutically acceptable salt thereof, wherein $R^3$ is methyl.

Additional embodiments relate to a compound of formula (III), or a pharmaceutically acceptable salt thereof, wherein $R^3$ is 3-7 membered heterocycloalkyl, wherein the 3-7 membered heterocycloalkyl is optionally substituted by one, two or three $R^{15}$ groups.

Additional embodiments relate to a compound of formula (III), or a pharmaceutically acceptable salt thereof, wherein $R^3$ is piperidine optionally substituted by $C_1$-$C_3$ alkyl.

Some embodiments relate to a compound of formula (III), or a pharmaceutically acceptable salt thereof, wherein Q is absent.

More embodiments relate to a compound of formula (III), or a pharmaceutically acceptable salt thereof, wherein Q is O.

Some embodiments relate to a compound of formula (III), or a pharmaceutically acceptable salt thereof, wherein Q is $NR^9$.

More embodiments relate to a compound of formula (III), or a pharmaceutically acceptable salt thereof, wherein m is 0.

Further embodiments relate to a compound of formula (III), or a pharmaceutically acceptable salt thereof, wherein m is 1.

Some embodiments relate to a compound of formula (III), or a pharmaceutically acceptable salt thereof, wherein ring B is 3-10 membered heterocycloalkyl.

Additional embodiments relate to a compound of formula (III), or a pharmaceutically acceptable salt thereof, wherein ring B is

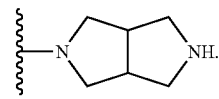

Some embodiments relate to a compound or a pharmaceutically acceptable salt of any of the embodiments of the compounds of formula (III), having formula (IIIa):

(IIIa)

wherein n is 0, 1, or 2; and p is 0, 1, or 2.

More embodiments relate to a compound of formula (IIIa), or a pharmaceutically acceptable salt thereof, wherein n is 0.

Further embodiments relate to a compound of formula (IIIa), or a pharmaceutically acceptable salt thereof, wherein n is 1.

Additional embodiments relate to a compound of formula (IIIa), or a pharmaceutically acceptable salt thereof, wherein p is 1.

Additional embodiments relate to a compound of formula (IIIa), or a pharmaceutically acceptable salt thereof, wherein n is 1 and p is 1.

More embodiments relate to a compound of formula (IIIa), or a pharmaceutically acceptable salt thereof, wherein $R^6$ and $R^8$ are each independently hydrogen, halogen, $C_1$-$C_3$ alkyl, or $C_1$-$C_3$ alkoxy.

More embodiments relate to a compound of formula (IIIa), or a pharmaceutically acceptable salt thereof, wherein $R^6$ is hydrogen, fluorine, methyl, or methoxy.

Some embodiments relate to a compound of formula (IIIa), or a pharmaceutically acceptable salt thereof, wherein $R^6$ is fluorine.

Some embodiments relate to a compound of formula (IIIa), or a pharmaceutically acceptable salt thereof, wherein $R^8$ is hydrogen, fluorine, or methyl.

More embodiments relate to a compound of formula (IIIa), or a pharmaceutically acceptable salt thereof, wherein $R^8$ is methyl.

More embodiments relate to a compound of formula (IIIa), or a pharmaceutically acceptable salt thereof, wherein $R^7$ is Some embodiments relate to a compound or a pharmaceutically acceptable salt of any of the embodiments of the compounds of formula (III), having formula (IIIb):

(IIIb)

More embodiments relate to a compound of formula (IIIb), or a pharmaceutically acceptable salt thereof, wherein $R^6$ and $R^8$ are each independently hydrogen, halogen, $C_1$-$C_3$ alkyl, or $C_1$-$C_3$ alkoxy.

Some embodiments relate to a compound of formula (IIIb), or a pharmaceutically acceptable salt thereof, wherein $R^6$ is hydrogen, fluorine, methyl, or methoxy.

Further embodiments relate to a compound of formula (IIIb), or a pharmaceutically acceptable salt thereof, wherein $R^6$ is fluorine.

Additional embodiments relate to a compound of formula (IIIb), or a pharmaceutically acceptable salt thereof, wherein $R^8$ is hydrogen, fluorine, or methyl.

More embodiments relate to a compound of formula (IIIb), or a pharmaceutically acceptable salt thereof, wherein $R^8$ is methyl.

Some embodiments relate to a compound or a pharmaceutically acceptable salt of any of the embodiments of the compounds of formula (III), having formula (IIIc):

(IIIc)

wherein

J is C or N;

q is 0, 1, 2, or 3; and v is 0, 1, 2, or 3, provided that q and v cannot both be 0.

Some embodiments relate to a compound of formula (IIIc), or a pharmaceutically acceptable salt thereof, wherein J is C.

Some embodiments relate to a compound of formula (IIIc), or a pharmaceutically acceptable salt thereof, wherein J is N.

Further embodiments relate to a compound of formula (IIIc), or a pharmaceutically acceptable salt thereof, wherein q is 1.

Additional embodiments relate to a compound of formula (IIIc), or a pharmaceutically acceptable salt thereof, wherein q is 2.

Additional embodiments relate to a compound of formula (IIIc), or a pharmaceutically acceptable salt thereof, wherein q is 3.

Further embodiments relate to a compound of formula (IIIc), or a pharmaceutically acceptable salt thereof, wherein v is 1.

More embodiments relate to a compound of formula (IIIc), or a pharmaceutically acceptable salt thereof, wherein q is 1 and v is 1.

Some embodiments relate to a compound of formula (IIIc), or a pharmaceutically acceptable salt thereof, wherein q is 2 and v is 1.

More embodiments relate to a compound of formula (IIIc), or a pharmaceutically acceptable salt thereof, wherein q is 3 and v is 1.

Some embodiments relate to a compound of formula (IIIc), or a pharmaceutically acceptable salt thereof, wherein $R^6$ is hydrogen, halogen, or $C_1$-$C_3$ alkoxy.

Further embodiments relate to a compound of formula (IIIc), or a pharmaceutically acceptable salt thereof, wherein $R^6$ is hydrogen, fluorine, or methoxy.

Some embodiments relate to a compound of formula (IIIc), or a pharmaceutically acceptable salt thereof, wherein $R^8$ is hydrogen or $C_1$-$C_3$ alkyl.

Additional embodiments relate to a compound of formula (IIIc), or a pharmaceutically acceptable salt thereof, wherein $R^8$ is hydrogen or methyl.

Additional embodiments relate to a compound of formula (IIIc), or a pharmaceutically acceptable salt thereof, wherein $R^7$ is

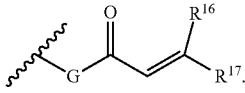

Some embodiments relate to a compound or a pharmaceutically acceptable salt of any of the embodiments of the compounds of formula (III), wherein m is 0, having formula (IIId):

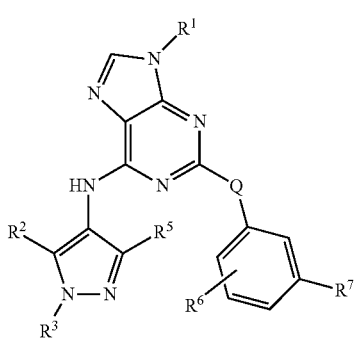

wherein
Q is O or $NR^9$.

Additional embodiments relate to a compound of formula (IIId), or a pharmaceutically acceptable salt thereof, wherein $R^6$ is absent.

More embodiments relate to a compound of formula (IIId), or a pharmaceutically acceptable salt thereof, wherein $R^7$ is

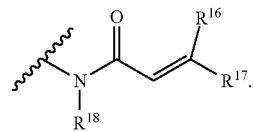

Additional embodiments relate to a compound of formula (IIId), or a pharmaceutically acceptable salt thereof, wherein $R^{16}$, $R^{17}$ and $R^{18}$ are hydrogen.

Some embodiments described herein relate to a compound of formula (IV):

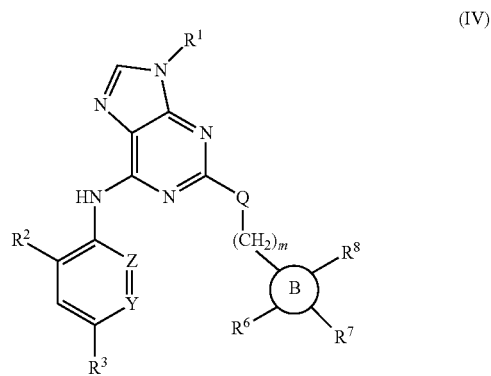

wherein
Y is $CR^4$ or N:
Z is CH or N,
provided that Y and Z cannot both be N;
$R^1$ is hydrogen, $C_1$-$C_6$ alkyl, $C_2$-$C_6$ alkenyl, $C_2$-$C_6$ alkynyl, $C_3$-$C_6$ cycloalkyl, 4-6 membered heterocycloalkyl, or 4-6 membered heteroaryl, wherein the $C_1$-$C_6$ alkyl is optionally substituted by one, two or three substituents selected from the group consisting of halogen, hydroxy, and $C_1$-$C_3$ alkoxy, further wherein the $C_3$-$C_6$ cycloalkyl, the 4-6 membered heterocycloalkyl, and the 4-6 membered heteroaryl are each independently optionally substituted by one, two or three substituents selected from the group consisting of $C_1$-$C_3$ alkyl, hydroxy, and $C_1$-$C_3$ alkoxy;
$R^2$ is hydrogen, halogen, cyano, difluoromethyl, trifluoromethyl, $C_1$-$C_6$ alkyl, $C_2$-$C_6$ alkenyl, $C_2$-$C_6$ alkynyl, $C_1$-$C_6$ alkoxy, —$N(R^{10})(R^{11})$, $C_3$-$C_5$ cycloalkyl, or 4-6 membered heterocycloalkyl, wherein the $C_1$-$C_6$ alkyl is optionally substituted by one, two or three substituents selected from the group consisting of halogen, hydroxy, $C_1$-$C_6$ alkoxy, and —$N(R^{12})(R^{13})$;
$R^3$ is hydrogen, halogen, $C_1$-$C_6$ alkyl, $C_2$-$C_6$ alkynyl, $C_1$-$C_6$ alkoxy, $C_3$-$C_7$ cycloalkyl, or 3-7 membered heterocycloalkyl, wherein the $C_1$-$C_6$ alkyl and the $C_1$-$C_6$ alkoxy are each optionally substituted by one, two or three $R^{14}$ groups, and further wherein the $C_3$-$C_7$ cycloalkyl and the 3-7 membered heterocycloalkyl are each optionally substituted by one, two or three $R^{15}$ groups;
$R^4$ is hydrogen, halogen, $C_1$-$C_6$ alkyl, or $C_3$-$C_6$ cycloalkyl, wherein $R^3$ and $R^4$ may combine to form a $C_5$-$C_7$ cycloalkyl ring or a 5-7 membered heterocycloalkyl ring, further wherein the $C_5$-$C_7$ cycloalkyl ring and the 5-7 membered heterocycloalkyl ring are each independently optionally substituted by one, two or three $R^{14}$ groups;

Q is absent, O, S, or NR$^9$;

ring B is absent, $C_3$-$C_{10}$ cycloalkyl, 3-10 membered heterocycloalkyl, $C_6$-$C_{10}$ aryl, or 5-12 membered heteroaryl;

R$^6$ and R$^8$ are each independently absent, hydrogen, halogen, cyano, hydroxy, difluoromethyl, trifluoromethyl, $C_1$-$C_3$ alkyl, $C_1$-$C_3$ alkoxy, or $C_3$-$C_5$ cycloalkyl, wherein the $C_1$-$C_3$ alkyl is optionally substituted by hydroxy, difluoromethyl, trifluoromethyl, $C_1$-$C_3$ alkoxy, or $C_3$-$C_5$ cycloalkyl;

R$^7$ is

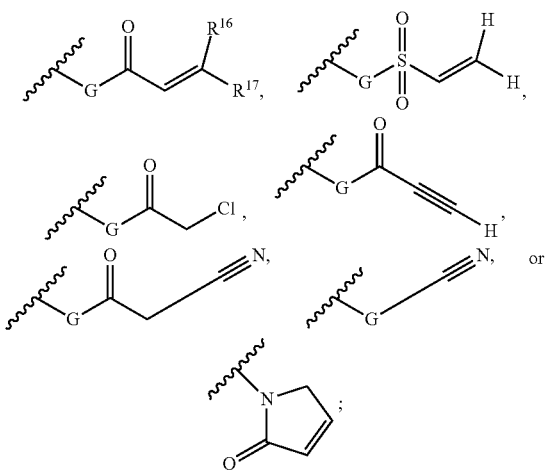

G is absent when the attachment point of R$^7$ on ring B is a nitrogen atom, and G is —NR$^{18}$— when ring B is absent or when the attachment point of R$^7$ on ring B is a carbon atom;

R$^9$, R$^{12}$ and R$^{13}$ are each independently hydrogen or $C_1$-$C_3$ alkyl;

R$^{10}$ and R$^{11}$ are each independently hydrogen or $C_1$-$C_6$ alkyl; or R$^{10}$ and R$^{11}$ together with the nitrogen to which they are attached, may combine to form a 4-7 membered heterocycloalkyl ring, wherein the 4-7 membered heterocycloalkyl ring is optionally substituted by one, two, three or four R$^{15}$ groups;

each R$^{14}$ is independently halogen, cyano, $C_1$-$C_3$ alkyl, hydroxy, $C_1$-$C_6$ alkoxy, —N(R$^{19}$)(R$^{20}$), —CON(R$^{21}$)(R$^{22}$), or 3-7 membered heterocycloalkyl, wherein the 3-7 membered heterocycloalkyl is optionally substituted by one, two, three or four R$^{15}$ groups;

each R$^{15}$ is independently halogen, $C_1$-$C_3$ alkyl, hydroxy, $C_1$-$C_6$ alkoxy, —NH$_2$, —NHCH$_3$, or —N(CH$_3$)$_2$;

R$^{16}$ and R$^{17}$ are each independently hydrogen or $C_1$-$C_6$ alkyl, wherein the $C_1$-$C_6$ alkyl is optionally substituted by —N(R$^{23}$)(R$^{24}$), provided that R$^{16}$ and R$^{17}$ may form a $C_3$-$C_5$ cycloalkyl ring;

R$^{18}$ is hydrogen or $C_1$-$C_3$ alkyl;

each R$^{19}$, R$^{20}$, R$^{21}$, R$^{22}$, R$^{23}$, and R$^{24}$ is independently hydrogen or $C_1$-$C_3$ alkyl; and m is 0, 1 or 2, provided that when ring B is absent, m is 2; or a pharmaceutically acceptable salt thereof.

Some embodiments relate to a compound of formula (IV), or a pharmaceutically acceptable salt thereof, wherein Y is CR$^4$.

More embodiments relate to a compound of formula (IV), or a pharmaceutically acceptable salt thereof, wherein Z is CH.

Some embodiments relate to a compound of formula (IV), or a pharmaceutically acceptable salt thereof, wherein Y is CR$^4$ and Z is CH.

More embodiments relate to a compound of formula (IV), or a pharmaceutically acceptable salt thereof, wherein Y is CR$^4$ and Z is N.

Further embodiments relate to a compound of formula (IV), or a pharmaceutically acceptable salt thereof, wherein Y is N and Z is CH.

Additional embodiments relate to a compound of formula (IV), or a pharmaceutically acceptable salt thereof, wherein R$^1$ is $C_1$-$C_6$ alkyl or $C_3$-$C_6$ cycloalkyl, wherein the $C_1$-$C_6$ alkyl is optionally substituted by hydroxy, further wherein the $C_3$-$C_6$ cycloalkyl is optionally substituted by $C_1$-$C_3$ alkyl.

Additional embodiments relate to a compound of formula (IV), or a pharmaceutically acceptable salt thereof, wherein R$^1$ is methyl, ethyl, isopropyl, or tert-butyl.

Some embodiments relate to a compound of formula (IV), or a pharmaceutically acceptable salt thereof, wherein R$^1$ is cyclobutyl optionally substituted by $C_1$-$C_3$ alkyl.

Some embodiments relate to a compound of formula (IV), or a pharmaceutically acceptable salt thereof, wherein R$^3$ is 3-7 membered heterocycloalkyl, wherein the 3-7 membered heterocycloalkyl is optionally substituted by one, two or three R$^{15}$ groups.

More embodiments relate to a compound of formula (IV), or a pharmaceutically acceptable salt thereof, wherein R$^3$ is piperidine optionally substituted by $C_1$-$C_3$ alkyl.

Further embodiments relate to a compound of formula (IV), or a pharmaceutically acceptable salt thereof, wherein R$^3$ is piperazine optionally substituted by $C_1$-$C_3$ alkyl.

Further embodiments relate to a compound of formula (IV), or a pharmaceutically acceptable salt thereof, wherein R$^3$ is piperazine optionally substituted by methyl.

Some embodiments relate to a compound of formula (IV), or a pharmaceutically acceptable salt thereof, wherein R$^3$ is 4-methylpiperazine.

More embodiments relate to a compound of formula (IV), or a pharmaceutically acceptable salt thereof, wherein R$^2$ is hydrogen, halogen, trifluoromethyl, $C_1$-$C_6$ alkyl, or $C_1$-$C_6$ alkoxy.

Additional embodiments relate to a compound of formula (IV), or a pharmaceutically acceptable salt thereof, wherein R$^2$ is hydrogen, fluorine, trifluoromethyl, methyl, or methoxy.

Additional embodiments relate to a compound of formula (IV), or a pharmaceutically acceptable salt thereof, wherein R$^2$ is hydrogen.

Some embodiments relate to a compound of formula (IV), or a pharmaceutically acceptable salt thereof, wherein R$^4$ is hydrogen.

Some embodiments relate to a compound of formula (IV), or a pharmaceutically acceptable salt thereof, wherein R$^4$ is hydrogen, halogen, or $C_1$-$C_3$ alkyl.

More embodiments relate to a compound of formula (IV), or a pharmaceutically acceptable salt thereof, wherein Q is absent.

More embodiments relate to a compound of formula (IV), or a pharmaceutically acceptable salt thereof, wherein Q is O.

Additional embodiments relate to a compound of formula (IV), or a pharmaceutically acceptable salt thereof, wherein Q is NR$^9$.

Further embodiments relate to a compound of formula (IV), or a pharmaceutically acceptable salt thereof, wherein m is 0.

Some embodiments relate to a compound of formula (IV), or a pharmaceutically acceptable salt thereof, wherein m is 1.

Some embodiments relate to a compound of formula (IV), or a pharmaceutically acceptable salt thereof, wherein ring B is 3-10 membered heterocycloalkyl.

Further embodiments relate to a compound of formula (IV), or a pharmaceutically acceptable salt thereof, wherein ring B is Some embodiments relate to a compound or a pharmaceutically acceptable salt of any of the embodiments of the compounds of formula (IV), having formula (IVa):

(IVa)

wherein
n is 0, 1, or 2; and
p is 0, 1, or 2.

Some embodiments relate to a compound of formula (IVa), or a pharmaceutically acceptable salt thereof, wherein n is 0.

More embodiments relate to a compound of formula (IVa), or a pharmaceutically acceptable salt thereof, wherein n is 1.

More embodiments relate to a compound of formula (IVa), or a pharmaceutically acceptable salt thereof, wherein p is 1.

Some embodiments relate to a compound of formula (IVa), or a pharmaceutically acceptable salt thereof, wherein n is 1 and p is 1.

Some embodiments relate to a compound of formula (IVa), or a pharmaceutically acceptable salt thereof, wherein $R^6$ and $R^8$ are each independently hydrogen, halogen, $C_1$-$C_3$ alkyl, or $C_1$-$C_3$ alkoxy.

Further embodiments relate to a compound of formula (IVa), or a pharmaceutically acceptable salt thereof, wherein $R^6$ is hydrogen, fluorine, methyl, or methoxy.

Further embodiments relate to a compound of formula (IVa), or a pharmaceutically acceptable salt thereof, wherein $R^6$ is fluorine.

Additional embodiments relate to a compound of formula (IVa), or a pharmaceutically acceptable salt thereof, wherein $R^8$ is hydrogen, fluorine, or methyl.

Some embodiments relate to a compound of formula (IVa), or a pharmaceutically acceptable salt thereof, wherein $R^8$ is methyl.

Additional embodiments relate to a compound of formula (IVa), or a pharmaceutically acceptable salt thereof, wherein $R^7$ is Some embodiments relate to a compound or a pharmaceutically acceptable salt of any of the embodiments of the compounds of formula (IV), having formula (IVb):

(IVb)

More embodiments relate to a compound of formula (IVb), or a pharmaceutically acceptable salt thereof, wherein $R^6$ and $R^8$ are each independently hydrogen, halogen, $C_1$-$C_3$ alkyl, or $C_1$-$C_3$ alkoxy.

Some embodiments relate to a compound of formula (IVb), or a pharmaceutically acceptable salt thereof, wherein $R^6$ is hydrogen, fluorine, methyl, or methoxy.

More embodiments relate to a compound of formula (IVb), or a pharmaceutically acceptable salt thereof, wherein $R^6$ is fluorine.

Further embodiments relate to a compound of formula (IVb), or a pharmaceutically acceptable salt thereof, wherein $R^8$ is hydrogen, fluorine, or methyl.

Additional embodiments relate to a compound of formula (IVb), or a pharmaceutically acceptable salt thereof, wherein $R^8$ is methyl.

Some embodiments relate to a compound or a pharmaceutically acceptable salt of any of the embodiments of the compounds of formula (IV), having formula (IVc):

(IVc)

wherein
J is C or N;
q is 0, 1, 2, or 3; and
v is 0, 1, 2, or 3,
provided that q and v cannot both be 0.

Some embodiments relate to a compound of formula (IVc), or a pharmaceutically acceptable salt thereof, wherein J is C.

More embodiments relate to a compound of formula (IVc), or a pharmaceutically acceptable salt thereof, wherein J is N.

More embodiments relate to a compound of formula (IVc), or a pharmaceutically acceptable salt thereof, wherein q is 1.

Some embodiments relate to a compound of formula (IVc), or a pharmaceutically acceptable salt thereof, wherein q is 2.

Some embodiments relate to a compound of formula (IVc), or a pharmaceutically acceptable salt thereof, wherein q is 3.

Further embodiments relate to a compound of formula (IVc), or a pharmaceutically acceptable salt thereof, wherein v is 1.

Additional embodiments relate to a compound of formula (IVc), or a pharmaceutically acceptable salt thereof, wherein q is 1 and v is 1.

Additional embodiments relate to a compound of formula (IVc), or a pharmaceutically acceptable salt thereof, wherein q is 2 and v is 1.

Some embodiments relate to a compound of formula (IVc), or a pharmaceutically acceptable salt thereof, wherein q is 3 and v is 1.

Some embodiments relate to a compound of formula (IVc), or a pharmaceutically acceptable salt thereof, wherein $R^6$ is hydrogen, halogen, or $C_1$-$C_3$ alkoxy.

More embodiments relate to a compound of formula (IVc), or a pharmaceutically acceptable salt thereof, wherein $R^6$ is hydrogen, fluorine, or methoxy.

More embodiments relate to a compound of formula (IVc), or a pharmaceutically acceptable salt thereof, wherein $R^8$ is hydrogen or $C_1$-$C_3$ alkyl.

Additional embodiments relate to a compound of formula (IVc), or a pharmaceutically acceptable salt thereof, wherein $R^8$ is hydrogen or methyl.

Further embodiments relate to a compound of formula (IVc), or a pharmaceutically acceptable salt thereof, wherein $R^7$ is

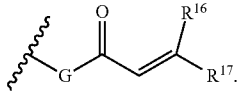

Some embodiments relate to a compound or a pharmaceutically acceptable salt of any of the embodiments of the compounds of formula (IV), wherein m is 0, having formula (IVd):

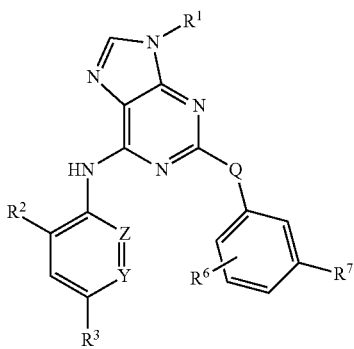

wherein
Q is O or $NR^9$.

Additional embodiments relate to a compound of formula (IVd), or a pharmaceutically acceptable salt thereof, wherein $R^6$ is absent.

Some embodiments relate to a compound of formula (IVd), or a pharmaceutically acceptable salt thereof, wherein $R^7$ is

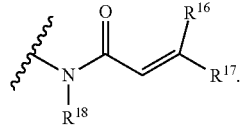

Further embodiments relate to a compound of formula (IVd), or a pharmaceutically acceptable salt thereof, wherein $R^{16}$, $R^{17}$ and $R^{18}$ are hydrogen.

In some embodiments, the compound is selected from:

(S)-NS)-N-(1-(9-isopropyl-6-((4-(4-methylpiperazin-1-yl)phenyl)amino)-9H-purin-2-yl)pyrrolidin-3-yl)acrylamide;

N-((3R,4R)-4-fluoro-1-(9-isopropyl-6-((1-methyl-1H-pyrazol-4-yl)amino)-9H-purin -2-yl)pyrrolidin-3-yl)acrylamide;

N-(3-((9-isopropyl-6-((1-methyl-1H-pyrazol-4-yl)amino)-9H-purin-2-yl)oxy)phenyl)acrylamide trifluoroacetate;

(S)-N-(1-(9-isopropyl-6-((1-methyl-1H-pyrazol-4-yl)amino)-9H-purin-2-yl)pyrrolidin-3-yl)acrylamide;

N-((3R,4R)-4-fluoro-1-(6-((3-methoxy-1-(1-methylazetidin-3-yl)-1H-pyrazol-4-yl)amino)-9-methyl-9H-purin-2-yl)pyrrolidin-3-yl)acrylamide;

1-(3-(9-isopropyl-6-((1-methyl-1H-pyrazol-4-yl)amino)-9H-purin-2-yl)piperidin-1-yl)prop-2-en-1-one;

N-((3R,4R)-4-fluoro-1-(6-((3-methoxy-1-methyl-1H-pyrazol-4-yl)amino)-9-methyl -9H-purin-2-yl)pyrrolidin-3-yl)acrylamide;

N-(1-(9-(tert-butyl)-6-((1-methyl-1H-pyrazol-4-yl)amino)-9H-purin-2-yl)-3-methylazetidin-3-yl)acrylamide;

(S)-N-(1-(9-(tert-butyl)-6-((4-(4-methylpiperazin-1-yl)phenyl)amino)-9H-purin-2-yl)pyrrolidin-3-yl)acrylamide;

N-(1-(9-isopropyl-6-((4-(4-methylpiperazin-1-yl)phenyl)amino)-9H-purin-2-yl)-3-methylpyrrolidin-3-yl)acrylamide;

(S)-N-(1-(9-isopropyl-6-((3-methoxy-1-methyl-1H-pyrazol-4-yl)amino)-9H-purin-2-yl)pyrrolidin-3-yl)acrylamide;

N-(1-(9-isopropyl-6-((4-(4-methylpiperazin-1-yl)phenyl)amino)-9H-purin-2-yl)-3-methylazetidin-3-yl)acrylamide;

N-(1-(9-isopropyl-6((1-methyl-1H-pyrazol-4-yl)amino)-9H-purin-2-yl)-3-methylazetidin-3-yl)acrylamide;

N-((trans)-3-((9-isopropyl-6-((4-(4-methylpiperazin-1-yl)phenyl)amino)-9H-purin-2-yl)oxy)cyclobutyl)acrylamide;

(S)-N-(1-(9-cyclobutyl-6-((4-(4-(methylpiperazin-1-yl)phenyl)amino)-9H-purin-2-yl)pyrrolidin-3-yl)acrylamide;

1-((cis)-5-(9-ethyl-6-((1-methyl-1H-pyrazol-4-yl)amino)-9H-purin-2-yl)hexahydropyrrolo[3,4-c]pyrrol-2 (1H)-yl)prop-2-en-1-one;

1-((cis)-5-(6-((1,5-dimethyl-1H-pyrazol-4-yl)amino)-9-isopropyl-9H-purin-2-yl)hexahydropyrrolo[3,4-c]pyrrol-2 (1H)-yl)prop-2-en-1-one;

1-((cis)-5-(9-(tert-butyl)-6-((4-(4-methylpiperazin-1-yl)phenyl)amino)-9H-purin-2-yl)hexahydropyrrolo[3,4-c]pyrrol-2(1H)-yl)prop-2-en-1-one;

1-((trans)-3-fluoro-4-((9-isopropyl-6-((4-(4-methylpiperazin-1-yl)phenyl)amino) -9H-purin-2-yl)amino)pyrrolidin-1-yl)prop-2-en-1-one;

1-((trans)-3-fluoro-4-((9-methyl-6-((4-(4-methylpiperazin-1-yl)phenyl)amino)-9H -purin-2-yl)amino)pyrrolidin-1-yl)prop-2-en-1-one;

1-((cis)-5-(9-isopropyl-6-((4-(4-methylpiperazin-1-yl)phenyl)amino)-9H-purin-2-yl)hexahydropyrrolo[3,4-c]pyrrol-2(1H)-yl)prop-2-en-1-one;

N-(3-((9-isopropyl-6-((4-(4-methylpiperazin-1-yl)phenyl)amino)-9H-purin-2-yl)oxy)phenyl)acrylamide;

N-(1-(9-isopropyl-6-((4-(4-methylpiperazin-1-yl)phenyl)amino)-9H-purin-2-yl)azetidin-3-yl)acrylamide;

N-(1-(9-isopropyl-6-((4-(4-methylpiperazin-1-yl)phenyl)amino)-9H-purin-2-yl)azetidin-3-yl)-N-methylacrylamide;

1-((cis)-5-(9-isopropyl-6-((1-methyl-1H-pyrazol-4-yl)amino)-9H-purin-2-yl)hexahydropyrrolo[3,4-c]pyrrol-2(1H)-yl)prop-2-en-1-one;

(R)-1-(3-((9-isopropyl-6-((4-(4-methylpiperazin-1-yl)phenyl)amino)-9H-purin-2-yl)oxy)pyrrolidin-1-yl)prop-2-en-1-one;

(R)-1-(3-((9-isopropyl-6-((4-(4-methylpiperazin-1-yl)phenyl)amino)-9H-purin-2-yl)amino)pyrrolidin-1-yl)prop-2-en-1-one;

N-((trans)-3-((9-isopropyl-6-((4-(4-methylpiperazin-1-yl)phenyl)amino)-9H-purin-2-yl)amino)cyclobutyl)-N-methylacrylamide;

N-((trans)-3-((9-isopropyl-6-((4-(4-methylpiperazin-1-yl)phenyl)amino)-9H-purin-2-yl)oxy)cyclobutyl)-N-methylacrylamide;

1-((trans*)-3-fluoro-4-((9-isopropyl-6-((1-methyl-1H-pyrazol-4-yl)amino)-9H-purin-2-yl)amino)pyrrolidin-1-yl)prop-2-en-1-one;

N-(1-(9-isopropyl-6((1-methyl-1H-pyrazol-4-yl)amino)-9H-purin-2-yl)azetidin-3-yl)-N-methylacrylamide;

1-(3-((9-isopropyl-6-((1-methyl-1H-pyrazol-4-yl)amino)-9H-purin-2-yl)amino)-3-methylazetidin-1-yl)prop-2-en-1-one;

1-((cis)-5-(9-methyl-6-((4-(4-methylpiperazin-1-yl)phenyl)amino)-9H-purin-2-yl)hexahydropyrrolo[3,4-c]pyrrol-2(1H)-yl)prop-2-en-1-one;

1-((cis)-5-(9-methyl-6-((1-methyl-1H-pyrazol-4-yl)amino)-9H-purin-2-yl)hexahydropyrrolo[3,4-c]pyrrol-2(1H)-yl)prop-2-en-1-one;

(S)-N-(1-(9-ethyl-6-((4-(4-methylpiperazin-1-yl)phenyl)amino)-9H-purin-2-yl)pyrrolidin-3-yl)acrylamide;

(S)-N-(1-(9-isopropyl-6-((4-(4-isopropylpiperazin-1-yl)phenyl)amino)-9H-purin-2-yl)pyrrolidin-3-yl)acrylamide;

(S)-N-(1-(6-((1,3-dimethyl-1H-pyrazol-4-yl)amino)-9-isopropyl-9H-purin-2-yl)pyrrolidin-3-yl)acrylamide;

(S)-N-(1-(9-methyl-6-((4-(4-methylpiperazin-1-yl)phenyl)amino)-9H-purin-2-yl)pyrrolidin-3-yl)acrylamide;

N-(1-(9-isopropyl-6-((1-(1-methylpiperidin-4-yl)-1H-pyrazol-4-yl)amino)-9H-purin-2-yl)-3-methylazetidin-3-yl)acrylamide;

(S)-N-(1-(6-((4-(4-ethylpiperazin-1-yl)phenyl)amino)-9-isopropyl-9H-purin-2-yl)pyrrolidin-3-yl)acrylamide;

(S)-N-(1-(9-isopropyl-6-((1-(1-methylpiperidin-4-yl)-1H-pyrazol-4-yl)amino)-9H-purin-2-yl)pyrrolidin-3-yl)acrylamide;

N-(1-(6-((1-(2-(dimethylamino)ethyl)-1H-pyrazol-4-yl)amino)-9-isopropyl-9H-purin-2-yl)-3-methylazetidin-3-yl)acrylamide;

(S)-N-(1-(6-((1-(2-(dimethylamino)ethyl)-1H-pyrazol-4-yl)amino)-9-isopropyl-9H-purin-2-yl)pyrrolidin-3-yl)acrylamide;

N-(1-(9-isopropyl-6-((1-(1-methylpyrrolidin-3-yl)-1H-pyrazol-4-yl)amino)-9H-purin-2-yl)-3-methylazetidin-3-yl)acrylamide;

N-((3S)-1-(9-isopropyl-6-((1-(1-methylpyrrolidin-3-yl)-1H-pyrazol-4-yl)amino)-9H-purin-2-yl)pyrrolidin-3-yl)acrylamide;

(S)-N-(1-(9-(2-hydroxyethyl)-6-((4-(4-methylpiperazin-1-yl)phenyl)amino)-9H-purin-2-yl)pyrrolidin-3-yl)acrylamide;

N-((trans)-1-(9-isopropyl-6-((4-(4-methylpiperazin-1-yl)phenyl)amino)-9H-purin-2-yl)-4-methoxypyrrolidin-3-yl)acrylamide;

N-((3S)-1-(9-(1-hydroxypropan-2-yl)-6-((4-(4-methylpiperazin-1-yl)phenyl)amino)-9H-purin-2-yl)pyrrolidin-3-yl)acrylamide;

N-((3R,4S)-1-(9-(tert-butyl)-6-((1-methyl-1H-pyrazol-4-yl)amino)-9H-purin-2-yl)-4-fluoropyrrolidin-3-yl)acrylamide;

N-((cis*)-1-(9-isopropyl-6((1-methyl-1H-pyrazol-4-yl)amino)-9H-purin-2-yl)-4-methoxypyrrolidin-3-yl)acrylamide;

N-((3S,4R)-1-(9-isopropyl-6-((1-methyl-1H-pyrazol-4-yl)amino)-9H-purin-2-yl)-4-methylpyrrolidin-3-yl)acrylamide;

N-((3R,4R)-1-(9-(tert-butyl)-6-((4-(4-methylpiperazin-1-yl)phenyl)amino)-9H-purin-2-yl)-4-fluoropyrrolidin-3-yl)acrylamide;

N-((3R,4R)-4-fluoro-1-(9-isopropyl-6-((3-methoxy-1-methyl-1H-pyrazol-4-yl)amino)-9H-purin-2-yl)pyrrolidin-3-yl)acrylamide;

N-((3R,4R)-1-(9-(tert-butyl)-6-((3-methoxy-1-methyl-1H-pyrazol-4-yl)amino)-9H-purin-2-yl)-4-fluoropyrrolidin-3-yl)acrylamide;

N-((3R,4R)-4-fluoro-1-(9-isopropyl-6-((3-methyl-1-(1-methylpyrrolidin-3-yl)-1H-pyrazol-4-yl)amino)-9H-purin-2-yl)pyrrolidin-3-yl)acrylamide;

N-(1-(9-ethyl-6-((1-methyl-1H-pyrazol-4-yl)amino)-9H-purin-2-yl)-3-methylazetidin-3-yl)acrylamide;

(R)-1-(3((9-isopropyl-6-((1-methyl-1H-pyrazol-4-yl)amino)-9H-purin-2-yl)oxy)piperidin-1-yl)prop-2-en-1-one;

1-((trans)-3-fluoro-4-((9-isopropyl-6-((1-methyl-1H-pyrazol-4-yl)amino)-9H-purin-2-yl)amino)pyrrolidin-1-yl)prop-2-en-1-one;

(R)-1-(3((9-isopropyl-6-((1-methyl-1H-pyrazol-4-yl)amino)-9H-purin-2-yl)oxy)pyrrolidin-1-yl)prop-2-en-1-one;

(S)-N-(1-(6-((1-methyl-1H-pyrazol-4-yl)amino)-9-(1-methylcyclopropyl)-9H-purin-2-yl)pyrrolidin-3-yl)acrylamide;

N-((3R,4R)-1-(6-((1,3-dimethyl-1H-pyrazol-4-yl)amino)-9-isopropyl-9H-purin-2-yl)-4-fluoropyrrolidin-3-yl)acrylamide;

N-((3R,4R)-1-(9-isopropyl-6-((4-(4-methylpiperazin-1-yl)phenyl)amino)-9H-purin-2-yl)-4-methoxypyrrolidin-3-yl)acrylamide;

N-((3R,4R)-1-(9-isopropyl-6-((1-methyl-1H-pyrazol-4-yl)amino)-9H-purin-2-yl)-4-methoxypyrrolidin-3-yl)acrylamide;

1-((cis)-5-(9-isopropyl-6-((4-(4-methylpiperazin-1-yl)phenyl)amino)-9H-purin-2-yl)-3a-methoxyhexahydropyrrolo[3,4-c]pyrrol-2(1H)-yl)prop-2-en-1-one;

N-((3R,4R)-4-fluoro-1-(9-isopropyl-6-((3-methyl-1-(1-methylpyrrolidin-3-yl)-1H-pyrazol-4-yl)amino)-9H-purin-2-yl)pyrrolidin-3-yl)acrylamide;

1-((3R,4R)-3-(((9-isopropyl-6-((1-methyl-1H-pyrazol-4-yl)amino)-9H-purin-2-yl)oxy)methyl)-4-methoxypyrrolidin-1-yl)prop-2-en-1-one;

N-((3S,4S)-1-(6-((1-(2-(dimethylamino)ethyl)-1H-pyrazol-4-yl)amino)-9-isopropyl-9H-purin-2-yl)-4-fluoropyrrolidin-3-yl)acrylamide;

N-((3R,4R)-1-(9-(tert-butyl)-6-((1-(2-(dimethylamino)ethyl)-1H-pyrazol-4-yl)amino)-9H-purin-2-yl)-4-fluoropyrrolidin-3-yl)acrylamide;

N—((S)-1-(9-isopropyl-6-((1-((S)-1-methylpyrrolidin-3-yl)-1H-pyrazol-4-yl)amino) -9H-purin-2-yl)pyrrolidin-3-yl)acrylamide;

N-((3R,4R)-1-(9-(tert-butyl)-6-((1-(1-methylpiperidin-4-yl)-1H-pyrazol-4-yl)amino) -9H-purin-2-yl)-4-fluoropyrrolidin-3-yl)acrylamide;

N-((3R,4R)-4-fluoro-1-(9-isopropyl-6-((1-(1-methylpiperidin-4-yl)-1H-pyrazol-4-yl)amino)-9H-purin-2-yl)pyrrolidin-3-yl)acrylamide;

N-((3R,4R)-4-fluoro-1-(9-isopropyl-6-((3-methoxy-1-((R)-1-methylpyrrolidin-3-yl) -1H-pyrazol-4-yl)amino)-9H-purin-2-yl)pyrrolidin-3-yl)acrylamide;

1-(cis-3a-fluoro-5-(9-isopropyl-6-((1-methyl-1H-pyrazol-4-yl)amino)-9H-purin-2-yl)hexahydropyrrolo[3,4-c]pyrrol-2(1H)-yl)prop-2-en-1-one;

(R)—N-(4,4-difluoro-1-(9-isopropyl-6-((1-methyl-1H-pyrazol-4-yl)amino)-9H-purin -2-yl)pyrrolidin-3-yl)acrylamide;

N-((3R,4R)-1-(9-ethyl-6-((3-methoxy-1-(1-methylpyrrolidin-3-yl)-1H-pyrazol-4-yl)amino)-9H-purin-2-yl)-4-fluoropyrrolidin-3-yl)acrylamide;

N-((3R,4R)-1-(6-((1,3-dimethyl-1H-pyrazol-4-yl)amino)-9-ethyl-9H-purin-2-yl)-4-fluoropyrrolidin-3-yl)acrylamide;

N-((3R,4R)-1-(9-ethyl-6-((3-methoxy-1-methyl-1H-pyrazol-4-yl)amino)-9H-purin-2-yl)-4-fluoropyrrolidin-3-yl)acrylamide;

N-((3R,4R)-1-(6-((3-ethyl-1-methyl-1H-pyrazol-4-yl)amino)-9-isopropyl-9H-purin -2-yl)-4-fluoropyrrolidin-3-yl)acrylamide;

N-((3R,4R)-4-fluoro-1-(6-((3-methoxy-1-(1-methylpyrrolidin-3-yl)-1H-pyrazol-4-yl)amino)-9-methyl-9H-purin-2-yl)pyrrolidin-3-yl)acrylamide;

N-((3R,4R)-1-(9-ethyl-6-((3-methyl-1-(1-methylpyrrolidin-3-yl)-1H-pyrazol-4-yl)amino)-9H-purin-2-yl)-4-fluoropyrrolidin-3-yl)acrylamide;

N-((3R,4R)-4-fluoro-1-(9-methyl-6-((3-methyl-1-(1-methylpyrrolidin-3-yl)-1H -pyrazol-4-yl)amino)-9H-purin-2-yl)pyrrolidin-3-yl)acrylamide;

N-((3R,4R)-1-(6-((1,3-dimethyl-1H-pyrazol-4-yl)amino)-9-methyl-9H-purin-2-yl)-4-fluoropyrrolidin-3-yl)acrylamide;

N-((3R,4R)-4-fluoro-1-(6-((1-(2-hydroxypropyl)-3-methoxy-1H-pyrazol-4-yl)amino)-9-methyl-9H-purin-2-yl)pyrrolidin-3-yl)acrylamide;

N-((3R,4R)-4-fluoro-1-(6-((1-(2-hydroxypropyl)-3-methoxy-1H-pyrazol-4-yl)amino)-9-isopropyl-9H-purin-2-yl)pyrrolidin-3-yl)acrylamide;

N-((3R,4R)-4-fluoro-1-(9-isopropyl-6-((5-methyl-1-((R)-1-methylpyrrolidin-3-yl) -1H-pyrazol-4-yl)amino)-9H-purin-2-yl)pyrrolidin-3-yl)acrylamide;

N-((3R,4R)-1-(9-ethyl-6-((1-(2-hydroxypropyl)-3-methoxy-1H-pyrazol-4-yl)amino) -9H-purin-2-yl)-4-fluoropyrrolidin-3-yl)acrylamide;

N-((3R,4R)-4-fluoro-1-(9-isopropyl-6-((3-methoxy-1-((S)-1-methylpyrrolidin-3-yl) -1H-pyrazol-4-yl)amino)-9H-purin-2-yl)pyrrolidin-3-yl)acrylamide;

N-((3R,4R)-1-(6-((1-ethyl-3-methoxy-1H-pyrazol-4-yl)amino)-9-methyl-9H-purin-2-yl)-4-fluoropyrrolidin-3-yl)acrylamide;

N-((3R,4R)-1-(6-((4-(4-(dimethylamino)piperidin-1-yl)phenyl)amino)-9-isopropyl -9H-purin-2-yl)-4-fluoropyrrolidin-3-yl)acrylamide; and N-((3R,4R)-1-(6-((4-(4-(dimethylamino)piperidin-1-yl)-2-methoxyphenyl)amino)-9-isopropyl-9H-purin-2-yl)-4-fluoropyrrolidin-3-yl)acrylamide, or a pharmaceutically acceptable salt thereof.

In certain embodiments, the compound is selected from:
N-((3R,4R)-4-fluoro-1-(6-((3-methoxy-1-(1-methylazetidin-3-yl)-1H-pyrazol-4-yl)amino)-9-methyl-9H-purin-2-yl)pyrrolidin-3-yl)acrylamide;

N-((3R,4R)-4-fluoro-1-(6-((3-methoxy-1-methyl-1H-pyrazol-4-yl)amino)-9-methyl -9H-purin-2-yl)pyrrolidin-3-yl)acrylamide;

N-((3R,4R)-4-fluoro-1-(9-isopropyl-6-((3-methoxy-1-methyl-1H-pyrazol-4-yl)amino)-9H-purin-2-yl)pyrrolidin-3-yl)acrylamide;

N-((3R,4R)-1-(9-ethyl-6-((3-methoxy-1-methyl-1H-pyrazol-4-yl)amino)-9H-purin-2-yl)-4-fluoropyrrolidin-3-yl)acrylamide;

N-((3R,4R)-4-fluoro-1-(9-methyl-6-((3-methyl-1-(1-methylpyrrolidin-3-yl)-1H -pyrazol-4-yl)amino)-9H-purin-2-yl)pyrrolidin-3-yl)acrylamide;

N-((3R,4R)-1-(6-((1,3-dimethyl-1H-pyrazol-4-yl)amino)-9-methyl-9H-purin-2-yl)-4-fluoropyrrolidin-3-yl)acrylamide;

N-((3R,4R)-4-fluoro-1-(9-isopropyl-6-((3-methoxy-1-((S)-1-methylpyrrolidin-3-yl) -1H-pyrazol-4-yl)amino)-9H-purin-2-yl)pyrrolidin-3-yl)acrylamide;

N-((3R,4R)-1-(6-((1-ethyl-3-methoxy-1H-pyrazol-4-yl)amino)-9-methyl-9H-purin-2-yl)-4-fluoropyrrolidin-3-yl)acrylamide;

N-((3R,4R)-1-(6-((4-(4-(dimethylamino)piperidin-1-yl)phenyl)amino)-9-isopropyl -9H-purin-2-yl)-4-fluoropyrrolidin-3-yl)acrylamide; and N-((3R,4R)-1-(6-((4-(4-(dimethylamino)piperidin-1-yl)-2-methoxyphenyl)amino)-9-isopropyl-9H-purin-2-yl)-4-fluoropyrrolidin-3-yl)acrylamide, or
a pharmaceutically acceptable salt thereof.

Some embodiments relate to a pharmaceutical composition comprising a compound of any of the embodiments of the compounds of formula (I), formula (II), formula (III) or formula (IV), or a pharmaceutically acceptable salt thereof, and a pharmaceutically acceptable carrier or diluent.

Other embodiments relate to a combination of a compound of any of the embodiments of the compounds of formula (I), formula (II), formula (III) or formula (IV), or a pharmaceutically acceptable salt thereof, with an anti-tumor agent, for the treatment of cancer.

More embodiments relate to a method of treating abnormal cell growth in a mammal comprising administering to the mammal an amount of a composition of any of the embodiments of the compounds of formula (I), formula (II), formula (III) or formula (IV), or a pharmaceutically acceptable salt thereof, that is effective in treating abnormal cell growth.

Further embodiments relate to a method of treating abnormal cell growth in a mammal comprising administering to the mammal an amount of a compound of any of the embodiments of the compounds of formula (I), formula (II), formula (III) or formula (IV), or a pharmaceutically acceptable salt thereof, that is effective in treating abnormal cell growth.

Additional embodiments relate to the method of treating abnormal cell growth, wherein the abnormal cell growth is cancer.

Further embodiments relate to the method of treating cancer, wherein the cancer is selected from the group consisting of basal cell cancer, medulloblastoma cancer, liver cancer, rhabdomyosarcoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system, primary central nervous system lymphoma, spinal axis tumors, brain stem glioma and pituitary adenoma, or a combination of one or more of the foregoing cancers.

Further embodiments relate to the method of treating lung cancer, wherein the lung cancer is non-small cell lung cancer.

DETAILED DESCRIPTION OF THE INVENTION

The following abbreviations may be used herein: aq. (aqueous); Boc (tert-butoxycarbonyl); $Boc_2O$ (di-tert-butyl dicarbonate); ca. (approximately); CBZ-Cl (carbobenzyloxychloride); DAST ((diethylamino)sulfur trifluoride); DBAD (dibenzyl azodicarboxylate); DCM (dichloromethane); DEA (diethylamine); DIEA (diisopropylethylamine); DIPEA (N,N-diisopropylethylamine); DMAP (4-dimethylaminopyridine); DMF (dimethylformamide); DMSO (dimethylsulphoxide); dppf (1,1'-bis(diphenylphosphanyl)ferrocene); EDC (1-ethyl-3-(3-dimethylaminopropyl)carbodiimide); ee (enantiomeric excess); eq (equivalent); Et (ethyl); EtOH (ethanol); EtOAc (ethyl acetate); FBS (fetal bovine serum); HOAc (acetic acid); HOBt (hydroxybenzotriazole); HPLC (high-performance liquid chromatography); hr (hour or hours); iPrOH (isopropyl alcohol); iPrOAc (isopropyl acetate); LAH (lithium aluminum hydride); LCMS (liquid chromatography-mass spectrometry); LRMS (low resolution mass spectrometry); mCPBA (meta-chloroperoxybenzoic acid); Me (methyl); MeOH (methanol); min (minute or minutes); MTBE (methyl tertiary-butyl ether); N (normal); N/A (not available); nBuLi (n-butyllithium); nBuOH (n-butyl alcohol); N/D (not determined); NMM (N-methylmorpholine); NMR (nuclear magnetic resonance); Pd/C (palladium on carbon); Ph (phenyl); RPMI (Roswell Park Memorial Institute); rt (room temperature); sat. (saturated); SFC (super-critical fluid chromatography); TEA (triethylamine); tert-PentOH (tert-pentyl alcohol); TFA (trifluoroacetate); THF (tetrahydrofuran); TLC (thin layer chromatography); TsOH (tosylic acid)); and UPLC (ultra performance liquid chromatography).

The term "halogen", as used herein, refers to a fluorine, chlorine, bromine, or iodine atom or fluoro, chloro, bromo, or iodo. Additionally, the term "halogen" refers to F, Cl, Br, or I. The terms fluorine, fluoro and F, for example, are understood to be equivalent herein.

The term "alkyl", as used herein, refers to a saturated monovalent hydrocarbon radical containing, in certain embodiments, from one to six, or from one to three carbon atoms, having straight or branched moieties. The term "$C_1$-$C_6$ alkyl" refers to an alkyl radical containing from one to six carbon atoms, having straight or branched moieties. The term "$C_1$-$C_6$ alkyl" includes within its definition the terms "$C_1$-$C_3$ alkyl" and "$C_1$-$C_4$ alkyl". Examples of alkyl groups include, but are not limited to, methyl, ethyl, propyl, isopropyl, butyl, isobutyl, sec-butyl, tert-butyl, pentyl, 2-pentyl, 3-pentyl, isopentyl, neopentyl, (R)-2-methylbutyl, (S)-2-methylbutyl, 3-methylbutyl, 2,3-dimethylpropyl, 2,3-dimethylbutyl, hexyl, and the like.

The term "alkenyl", as used herein, refers to a saturated monovalent hydrocarbon radical containing, in certain embodiments, from two to six carbon atoms having at least one carbon-carbon double bond. Alkenyl radicals include both straight and branched moieties. The term "$C_2$-$C_6$ alkenyl", refers to an alkenyl radical containing from two to six carbon atoms, having straight or branched moieties. The double bond may or may not be the point of attachment to another group. Alkenyl groups include, but are not limited to, ethenyl, 1-propenyl, 2-propenyl, 2-methyl-2-propenyl, butenyl, pentenyl, 3-hexenyl, and the like.

The term "alkynyl", as used herein, refers to a saturated monovalent hydrocarbon radical containing, in certain embodiments, from two to six carbon atoms having at least one carbon-carbon triple bond. Alkynyl radicals include both straight and branched moieties. The term "$C_2$-$C_6$ alkynyl", refers to an alkynyl radical containing from two to six carbon atoms, having straight or branched moieties. The triple bond may or may not be the point of attachment to another group. Alkynyl groups include, but are not limited to, ethynyl, 1-propynyl, 2-propynyl, 2-methyl-2-propynyl, butynyl, pentynyl, 3-hexynyl, and the like.

The term "alkoxy", as used herein, refers to an alkyl radical that is single bonded to an oxygen atom. The attachment point of an alkoxy radical to a molecule is through the oxygen atom. An alkoxy radical may be depicted as alkyl-O—. The term "$C_1$-$C_6$ alkoxy", refers to an alkoxy radical containing from one to six carbon atoms, having straight or branched moieties. The term "$C_1$-$C_6$ alkoxy" includes within its definition the term "$C_1$-$C_3$ alkoxy". Alkoxy groups, include, but are not limited to, methoxy, ethoxy, propoxy, isopropoxy, butoxy, hexyloxy, and the like.

The term "cycloalkyl", as used herein, refers to a non-aromatic, monocyclic, fused or bridged bicyclic or tricyclic carbocyclic ring group containing, in certain embodiments, from three to ten carbon atoms. As used herein, a cycloalkyl group may optionally contain one or two double bonds. The term "cycloalkyl" also includes spiro cycloalkyl groups, including multi-ring systems joined by a single atom. The terms "$C_3$-$C_{10}$ cycloalkyl", "$C_3$-$C_7$ cycloalkyl", "$C_3$-$C_6$ cycloalkyl", "$C_3$-$C_5$ cycloalkyl", "$C_3$-$C_4$ cycloalkyl", and "$C_5$-$C_7$ cycloalkyl" contain from three to ten, from three to seven, from three to six, from three to five, from three to four, and from five to seven carbon atoms, respectively. Cycloalkyl groups include, but are not limited to, cyclopropyl, cyclobutyl, cyclopentyl, cyclohexyl, cycloheptyl, cyclopentenyl, cyclohexenyl, octahydropentalenyl, octahydro-1H-indenyl, bicyclo[2.2.1]heptanyl, bicyclo[3.2.1]octanyl, bicyclo[5.2.0] nonanyl, adamantanyl, and the like.

The term "heterocycloalkyl", as used herein, refers to a non-aromatic, monocyclic, fused or bridged bicyclic or tricyclic, or spirocyclic ring group containing, in certain embodiments, a total of three to ten ring atoms, in which one to four ring atoms are heteroatoms independently selected from nitrogen, oxygen, and sulfur, and wherein the sulfur atom may be optionally oxidized with one or two oxygen atoms, the remaining ring atoms being carbon, with the proviso that such ring systems may not contain two adjacent oxygen atoms or two adjacent sulfur atoms. The heterocycloalkyl ring may also be substituted by an oxo (=O) group at any available carbon atom. The rings may also have one or more double bonds. Furthermore, such groups may be bonded to the remainder of the compounds of embodiments disclosed herein through either a carbon atom or a heteroatom, if possible. The terms "3-10 membered heterocycloalkyl", "3-7 membered heterocycloalkyl", and "4-6 membered heterocycloalkyl" contain from three to ten, from three to seven, and from three to six carbon atoms, respectively. Examples of heterocycloalkyl groups include, but are not limited to:

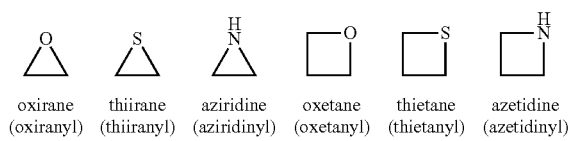
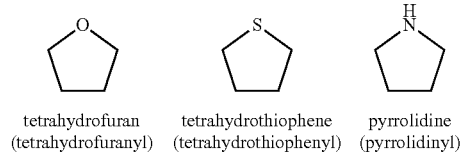
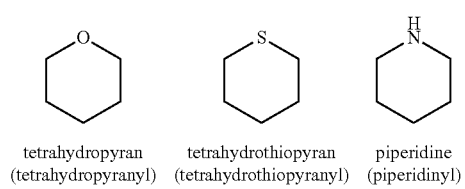
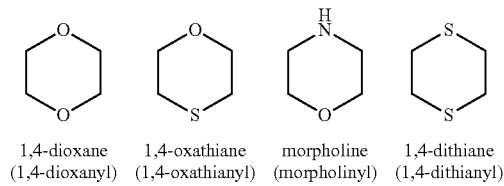
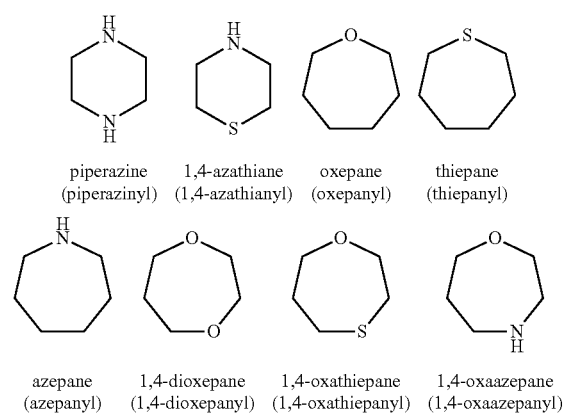
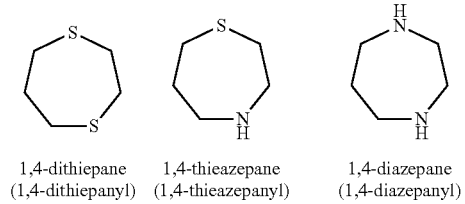
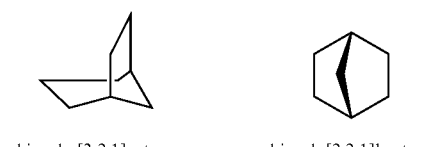
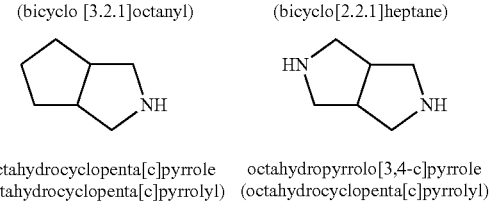

-continued

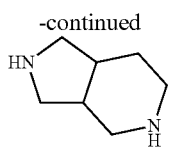

octahydro-1H-pyrrolo[3,4-c]pyridine
(octahydro-1H-pyrrolo[3,4-c]pyridinyl)

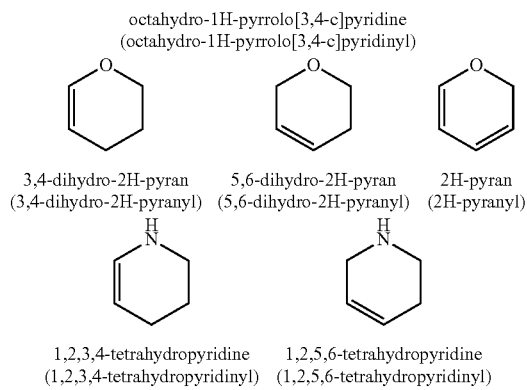

The term "aryl", as used herein, refers to a group derived from an aromatic hydrocarbon containing in certain embodiments, from six to ten carbon atoms. The term "$C_6$-$C_{10}$ aryl" contains from six to ten carbon atoms. Examples of such groups include, but are not limited to, phenyl and naphthyl. The term "aryl" also includes fused polycyclic aromatic ring systems in which an aromatic ring is fused to one or more rings. Examples include, but are not limited to, 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "heteroaryl, as used herein, refers to an aromatic monocyclic or bicyclic heterocyclic group having a total of from 5 to 12 atoms in its ring, and containing from 2 to 9 carbon atoms and from one to four heteroatoms each independently selected from nitrogen, oxygen, and sulfur, with the proviso that the ring of said group does not contain two adjacent oxygen atoms or two adjacent sulfur atoms. The terms "5-12 membered heteroaryl", "4-6 membered heteroaryl", and "3-5 membered heteroaryl" contain from five to twelve, from four to six ring atoms, and from three to five ring atoms, respectively. The heteroaryl groups include benzo-fused ring systems. Examples of heteroaryl groups include, but are not limited to, pyrrolyl, furyl, thienyl, imidazolyl, pyrazolyl, oxazolyl, isoxazolyl, isothiazolyl, triazolyl, oxadiazolyl, furazanyl, thiadiazolyl, thiazolyl, tetrazolyl, pyridinyl, pyrazinyl, pyrimidinyl, pyridazinyl, triazinyl, indolyl, isoindolyl, indolizinyl, benzofuranyl, benzothiophenyl, indazolyl, benzimidazolyl, benzoxazolyl, furo[3,2-b]pyridinyl, benzothiazolyl, benzofurazanyl, purinyl, quinolinyl, isoquinolinyl, quinazolinyl, quinoxalinyl, naphthyridinyl, cinnolinyl, phthalazinyl, pyrido[3,4-d]pyrimidinyl, pteridinyl, and the like.

Also included within the scope of the term "5-12 membered heteroaryl", as used herein, are benzo-fused unsaturated nitrogen heterocycles, which refer to a heterocyclic group in which a heteroatomic ring is fused to one or more aromatic rings. Examples include, but are not limited to, indolinyl, isoindolinyl, tetrahydroquinolinyl, tetrahydroisoquinolinyl, and the like.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

As used herein, an "effective" amount refers to an amount of a substance, agent, compound, or composition that is of sufficient quantity to result in a decrease in severity of disease symptoms, an increase in frequency and duration of disease symptom-free periods, or a prevention of impairment or disability due to the disease affliction—either as a single dose or according to a multiple dose regimen, alone or in combination with other agents or substances. One of ordinary skill in the art would be able to determine such amounts based on such factors as the subject's size, the severity of the subject's symptoms, and the particular composition or route of administration selected. The subject may be a human or non-human mammal (e.g., rabbit, rat, mouse, monkey or other lower-order primate).

Embodiments disclosed herein include isotopically-labeled compounds, which are identical to those recited in formula (I), formula (II), formula (III) or formula (IV), but for the fact that one or more atoms are replaced by an atom having an atomic mass or mass number different from the atomic mass or mass number usually found in nature. Examples of isotopes that can be incorporated into compounds of the embodiments disclosed herein include isotopes of hydrogen, carbon, nitrogen, oxygen, phosphorous, sulfur, fluorine and chlorine, such as, but not limited to, $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein and pharmaceutically acceptable salts of said compounds which contain the aforementioned isotopes and/or other isotopes of other atoms are within the scope of the present embodiments. Certain isotopically-labeled compounds of the embodiments disclosed herein, for example, those into which radioactive isotopes such as $^{3}$H and $^{14}$O are incorporated, are useful in drug and/or substrate tissue distribution assays. Tritiated, i.e., $^{3}$H, and carbon-14, i.e., $^{14}$O, isotopes are particularly preferred for their ease of preparation and detectability. Further, substitution with heavier isotopes such as deuterium, i.e., $^{2}$H, can afford certain therapeutic advantages resulting from greater metabolic stability, for example, increased in vivo half-life or reduced dosage requirements and, hence, may be preferred in some circumstances. Isotopically-labeled compounds of embodiments disclosed herein can generally be prepared by carrying out the procedures disclosed in the Schemes and/or in the Examples and Preparations below, by substituting a readily available isotopically-labeled reagent for a non-isotopically-labeled reagent.

Some embodiments relate to the pharmaceutically acceptable salts of the compounds described herein. Pharmaceutically acceptable salts of the compounds described herein include the acid addition and base addition salts thereof.

Some embodiments also relate to the pharmaceutically acceptable acid addition salts of the compounds described herein. Suitable acid addition salts are formed from acids which form non-toxic salts. Non-limiting examples of suitable acid addition salts, i.e., salts containing pharmacologically acceptable anions, include, but are not limited to, the acetate, acid citrate, adipate, aspartate, benzoate, besylate, bicarbonate/carbonate, bisulphate/sulphate, bitartrate, borate, camsylate, citrate, cyclamate, edisylate, esylate, ethanesulfonate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methanesulfonate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, p-toluenesulfonate, tosylate, trifluoroacetate and xinofoate salts.

Additional embodiments relate to base addition salts of the compounds described herein. Suitable base addition salts are formed from bases which form non-toxic salts. Non-limiting examples of suitable base salts include the aluminium, arginine, benzathine, calcium, choline, diethylamine, diolamine, glycine, lysine, magnesium, meglumine, olamine, potassium, sodium, tromethamine and zinc salts.

The compounds described herein that are basic in nature are capable of forming a wide variety of salts with various inorganic and organic acids. The acids that may be used to prepare pharmaceutically acceptable acid addition salts of such basic compounds described herein are those that form non-toxic acid addition salts, e.g., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds described herein that include a basic moiety, such as an amino group, may form pharmaceutically acceptable salts with various amino acids, in addition to the acids mentioned above.

The chemical bases that may be used as reagents to prepare pharmaceutically acceptable base salts of those compounds of the compounds described herein that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of the embodiments described herein include all stereoisomers (e.g., cis and trans isomers) and all optical isomers of compounds described herein (e.g., R and S enantiomers), as well as racemic, diastereomeric and other mixtures of such isomers. While all stereoisomers are encompassed within the scope of our claims, one skilled in the art will recognize that particular stereoisomers may be preferred.

In some embodiments, the compounds described herein can exist in several tautomeric forms, including the enol and imine form, and the keto and enamine form and geometric isomers and mixtures thereof. All such tautomeric forms are included within the scope of the present embodiments. Tautomers exist as mixtures of a tautomeric set in solution. In solid form, usually one tautomer predominates. Even though one tautomer may be described, the present embodiments includes all tautomers of the present compounds.

The present embodiments also include atropisomers of the compounds described herein. Atropisomers refer to compounds that can be separated into rotationally restricted isomers.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts of compounds described herein are known to one of skill in the art.

The term "solvate" is used herein to describe a molecular complex comprising a compound described herein and one or more pharmaceutically acceptable solvent molecules, for example, ethanol.

The compounds described herein may also exist in unsolvated and solvated forms. Accordingly, some embodiments relate to the hydrates and solvates of the compounds described herein.

Compounds described herein containing one or more asymmetric carbon atoms can exist as two or more stereoisomers. Where a compound described herein contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds described herein containing, for example, an imino, keto, or oxime group, or so-called valence tautomerism in compounds which contain an aromatic moiety. A single compound may exhibit more than one type of isomerism.

Included within the scope of the present embodiments are all stereoisomers, geometric isomers and tautomeric forms of the compounds described herein, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where a compound described herein contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or over-expression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

Further embodiments relate to methods of treating abnormal cell growth in a mammal. Additional embodiments relate to a method of treating abnormal cell growth in a mammal comprising administering to the mammal an amount of a compound described herein that is effective in treating abnormal cell growth.

In other embodiments, the abnormal cell growth is cancer.

In some embodiments, the cancer is selected from the group consisting of lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of two or more of the foregoing cancers.

Additional embodiments relate to methods of treating cancer solid tumors in a mammal. Some embodiments relate to the treatment of cancer solid tumor in a mammal comprising administering to the mammal an amount of a compound described herein that is effective in treating said cancer solid tumor.

In other embodiments, the cancer solid tumor is breast, lung, colon, brain, prostate, stomach, pancreatic, ovarian, skin (melanoma), endocrine, uterine, testicular, or bladder.

Other embodiments relate to the method of treating lung cancer. Further embodiments relate to the method of treating non-small cell lung cancer. Even further embodiments relate to the method of treating non-small cell lung cancer, which is resistant to treatment with gefitinib or erlotinib.

Further embodiments relate to methods of treating abnormal cell growth in a mammal which comprises administering to said mammal an amount of a compound described herein that is effective in treating abnormal cell growth in combination with an anti-tumor agent. The anti-tumor agent may be selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

Other embodiments relate to a combination of a compound of formula (I), formula (II), formula (III) or formula (IV) or a pharmaceutically acceptable salt thereof, with an anti-tumor agent, for the treatment of cancer. The anti-tumor agent may be selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

More embodiments relate to pharmaceutical compositions for treating abnormal cell growth in a mammal comprising an amount of a compound described herein that is effective in treating abnormal cell growth, and a pharmaceutically acceptable carrier.

Additional embodiments relate to a method of treating abnormal cell growth in a mammal, including a human, comprising administering to the mammal an amount of a compound described herein, or a pharmaceutically acceptable salt, solvate, hydrate or prodrug thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In one embodiment the method comprises comprising administering to a mammal an amount of a compound described herein that is effective in treating said cancer solid tumor. In one preferred embodiment the solid tumor is breast, lung, colon, brain, prostate, stomach, pancreatic, ovarian, skin (melanoma), endocrine, uterine, testicular, and bladder cancer.

In another embodiment of said method, said abnormal cell growth is a benign proliferative disease, including, but not limited to, psoriasis, benign prostatic hypertrophy or restinosis.

Some embodiments relate to a method of treating abnormal cell growth in a mammal which comprises administering to said mammal an amount of a compound described herein, or a pharmaceutically acceptable salt, solvate, hydrate or prodrug thereof, that is effective in treating abnormal cell growth in combination with an anti-tumor agent. The anti-tumor agent may be selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

Additional embodiments relate to a pharmaceutical composition for treating abnormal cell growth in a mammal, including a human, comprising an amount of a compound described herein, or a pharmaceutically acceptable salt, solvate, hydrate or prodrug thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

Further embodiments relate to a method of treating abnormal cell growth in a mammal which comprises administering to said mammal an amount of a compound described herein, or a pharmaceutically acceptable salt, solvate, or hydrate thereof, that is effective in treating abnormal cell growth in combination with another anti-tumor agent. The anti-tumor agent may be selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens. Some embodiments contemplate a pharmaceutical composition for treating abnormal cell growth wherein the composition includes a compound described herein, or a pharmaceutically acceptable salt, solvate, or hydrate thereof, that is effective in treating abnormal cell growth, and another anti-tumor agent. The anti-tumor agent may be selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

Yet more embodiments relate to a method of treating a disorder associated with angiogenesis in a mammal, including a human, comprising administering to said mammal an amount of a compound described herein, as defined above, or a pharmaceutically acceptable salt, solvate, hydrate or prodrug thereof, that is effective in treating said disorder in combination with one or more anti-tumor agents listed above. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi, Yersinia* spp., *Bordetella pertussis*, and group A *Streptococcus*.

Some embodiments relate to a method of (and to a pharmaceutical composition for) treating abnormal cell growth in a mammal which comprise an amount of a compound described herein, or a pharmaceutically acceptable salt, solvate, or hydrate thereof, in combination with an amount of one or more substances selected from anti-angiogenesis agents, signal transduction inhibitors inhibitor (e.g., inhibiting the means by which regulatory molecules that govern the fundamental processes of cell growth, differentiation, and survival communicated within the cell), and antiproliferative agents, which amounts are together effective in treating said abnormal cell growth.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound described herein in the methods and pharmaceutical compositions described herein. Examples of useful COX-II inhibitors include CELEBREX™ (celecoxib), Bextra (valdecoxib), paracoxib, Vioxx (rofecoxib), and Arcoxia (etoricoxib). Examples of useful matrix metalloproteinase inhibitors are described in WO 96/33172 (published Oct. 24, 1996), WO 96/27583 (published Mar. 7, 1996), European Patent Application No.

97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds described herein are AG-3340, RO 32-3555, RS 13-0830, and the following compounds:

3-[[4-(4-fluoro-phenoxy)-benzenesulfonyl]-(1-hydroxycarbamoyl-cyclopentyl) -amino]-propionic acid;

3-exo-3-[4-(4-fluoro-phenoxy)-benzenesulfonylamino]-8-oxa-bicyclo[3.2.1]octane -3-carboxylic acid hydroxyamide;

(2R,3R)1-[4-(2-chloro-4-fluoro-benzyloxy)-benzenesulfonyl]-3-hydroxy-3-methyl -piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl) -amino]-propionic acid;

4-[4-(4-chloro-phenoxy)-benzenesulfonylamino]-tetrahydro-pyran-4-carboxylic acid hydroxyamide;

3-[4-(4-chloro-phenoxy)-benzenesulfonylamino]-tetrahydro-pyran-3-carboxylic acid hydroxyamide;

(2R,3R)1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl) -amino]-propionic acid;

3-[[4-(4-fluoro-phenoxy)-benzenesulfonyl]-(4-hydroxycarbamoyl-tetrahydro-pyran -4-yl)-amino]-propionic acid;

3-exo-3-[4-(4-chloro-phenoxy)-benzenesulfonylamino]-8-oxa -bicyclo[3.2.1]octane-3-carboxylic acid hydroxyamide;

3-endo-3-[4-(4-fluoro-phenoxy)-benzenesulfonylamino]-8-oxa -bicyclo[3.2.1]octane-3-carboxylic acid hydroxyamide; and 3-[4-(4-fluoro-phenoxy)-benzenesulfonylamino]-tetrahydro-furan-3-carboxylic acid hydroxyamide;

and pharmaceutically acceptable salts and solvates of said compounds.

VEGF inhibitors, for example, sutent and axitinib, can also be combined with a compound described herein. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), U.S. Pat. No. 6,653,308 (issued Nov. 25, 2003), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); Avastin, an anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with a compound described herein. Such erbB2 inhibitors include Herceptin, 2C4, and pertuzumab. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the embodiments described herein are also described in U.S. Provisional Application No. 60/117,341, filed Jan. 27, 1999, and in U.S. Provisional Application No. 60/117,346, filed Jan. 27, 1999, both of which are herein incorporated by reference in their entirety. Other erbb2 receptor inhibitors include TAK-165 (Takeda) and GW-572016 (Glaxo-Wellcome).

Various other compounds, such as styrene derivatives, have also been shown to possess tyrosine kinase inhibitory properties, and some of tyrosine kinase inhibitors have been identified as erbB2 receptor inhibitors. More recently, five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. Other patent applications that refer to anti-cancer compounds are World Patent Application WO00/44728 (published Aug. 3, 2000), EP 1029853A1 (published Aug. 23, 2000), and WO01/98277 (published Dec. 12, 2001) all of which are incorporated herein by reference in their entirety.

Epidermal growth factor receptor (EGFR) inhibitors may be administered in combination with a compound of the present invention. Such EGFR inhibitors include gefinitib, erlotinib, icotinib, afatinib and dacomitinib. Monoclonal antibody inhibitors of EGFR, such as cetuximab, may also be combined with a compound of the present invention.

c-Met inhibitors may be administered in combination with a compound of the present invention. Such c-Met inhibitors include crizotinib and ARQ-197. Monoclonal antibody inhibitors of c-Met, such as METMab, may also be combined with a compound of the present invention.

Programmed cell death 1 (PD-1) inhibitors may be administered in combination with a compound of the present invention. Such anti PD-1 immuno-oncology agents include anti-PD-1 monoclonal antibodies, nivolumab and pembrolizumab.

Other antiproliferative agents that may be used with the compounds described herein include inhibitors of the enzyme farnesyl protein transferase and inhibitors of the receptor tyrosine kinase PDGFr, including the compounds disclosed and claimed in the following U.S. patent application Ser. No. 09/221,946 (filed Dec. 28, 1998); Ser. No. 09/454,058 (filed Dec. 2, 1999); Ser. No. 09/501,163 (filed Feb. 9, 2000); Ser. No. 09/539,930 (filed Mar. 31, 2000); Ser. No. 09/202,796 (filed May 22, 1997); Ser. No. 09/384,339 (filed Aug. 26, 1999); and Ser. No. 09/383,755 (filed Aug. 26, 1999); and the compounds disclosed and claimed in the following U.S. provisional patent application 60/168,207 (filed Nov. 30, 1999); 60/170,119 (filed Dec. 10, 1999); 60/177,718 (filed Jan. 21, 2000); 60/168,217 (filed Nov. 30, 1999), and 60/200834 (filed May 1, 2000). Each of the foregoing patent applications and provisional patent applications is herein incorporated by reference in their entirety.

A compound described herein may also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present embodiments include those described in U.S. Provisional Application 60/113,647 (filed Dec. 23, 1998) which is herein incorporated by reference in its entirety.

A compound described herein may be applied as a sole therapy or may involve one or more other anti-tumor substances, for example those selected from, for example, mitotic inhibitors, for example vinblastine; alkylating agents, for example cis-platin, oxaliplatin, carboplatin and cyclophosphamide; anti-metabolites, for example 5-fluorouracil, capecitabine, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex (tamoxifen) or, for example anti-androgens such as Casodex (4'-cyano-3-(4-fluorophenylsulphonyl)-2-hydroxy-2-methyl-3'-(trifluoromethyl)propionanilide).

The compounds described herein may be used alone or in combination with one or more of a variety of anti-cancer agents or supportive care agents. For example, the compounds described herein may be used with cytotoxic agents, e.g., one or more selected from the group consisting of a camptothecin, irinotecan HCl (Camptosar), edotecarin, SU-11248, epirubicin (Ellence), docetaxel (Taxotere), paclitaxel, rituximab (Rituxan) bevacizumab (Avastin), imatinib mesylate (Gleevac), Erbitux, gefitinib (Iressa), and combinations thereof. Some embodiments also contemplate the use of the compounds described herein together with hormonal therapy, e.g., exemestane (Aromasin), Lupron, anastrozole (Arimidex), tamoxifen citrate (Nolvadex), Trelstar, and combinations thereof. Further, some embodiments provide a compound described herein alone or in combination with one or more supportive care products, e.g., a product selected from the group consisting of Filgrastim (Neupogen), ondansetron (Zofran), Fragmin, Procrit, Aloxi, Emend, or combinations thereof. Such conjoint treatment may be achieved by way of the simultaneous, sequential or separate dosing of the individual components of the treatment.

The compounds described herein may be used with anti-tumor agents, alkylating agents, antimetabolites, antibiotics, plant-derived antitumor agents, camptothecin derivatives, tyrosine kinase inhibitors, antibodies, interferons, and/or biological response modifiers. In this regard, the following is a non-limiting list of examples of secondary agents that may be used with the compounds described herein.

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, ifosfamide, KW-2170, mafosfamide, and mitolactol; platinum-coordinated alkylating compounds include but are not limited to, cisplatin, carboplatin, eptaplatin, lobaplatin, nedaplatin, oxaliplatin or satrplatin.

Antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, gemcitabine, fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexol, raltitrexed, triapine, trimetrexate, vidarabine, vincristine, vinorelbine; or for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid.

Antibiotics include but are not limited to: aclarubicin, actinomycin D, amrubicin, annamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin or zinostatin.

Hormonal therapy agents, e.g., exemestane (Aromasin), Lupron, anastrozole (Arimidex), doxercalciferol, fadrozole, formestane, anti-estrogens such as tamoxifen citrate (Nolvadex) and fulvestrant, Trelstar, toremifene, raloxifene, lasofoxifene, letrozole (Femara), or anti-androgens such as bicalutamide, flutamide, mifepristone, nilutamide, Casodex® (4'-cyano-3-(4-fluorophenylsulphonyl)-2-hydroxy-2-methyl-3'-(trifluoromethyl)propionanilide) and combinations thereof.

Plant derived anti-tumor substances include for example those selected from mitotic inhibitors, for example vinblastine, docetaxel (Taxotere) and paclitaxel.

Cytotoxic topoisomerase inhibiting agents include one or more agents selected from the group consisting of aclarubicn, amonafide, belotecan, camptothecin, 10-hydroxycamptothecin, 9-aminocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, tafluposide, and topotecan, and combinations thereof.

Immunologicals include interferons and numerous other immune enhancing agents. Interferons include interferon alpha, interferon alpha-2a, interferon, alpha-2b, interferon beta, interferon gamma-1a or interferon gamma-n1. Other agents include PF3512676, filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, OncoVAX-CL, sargramostim, tasonermin, tecleukin, thymalasin, tositumomab, Virulizin, Z-100, epratuzumab, mitumomab, oregovomab, pemtumomab, Provenge.

Biological response modifiers are agents that modify defense mechanisms of living organisms or biological responses, such as survival, growth, or differentiation of tissue cells to direct them to have anti-tumor activity. Such agents include krestin, lentinan, sizofiran, picibanil, or ubenimex.

Other anticancer agents include alitretinoin, ampligen, atrasentan bexarotene, bortezomib. Bosentan, calcitriol, exisulind, finasteride, fotemustine, ibandronic acid, miltefosine, mitoxantrone, I-asparaginase, procarbazine, dacarbazine, hydroxycarbamide, pegaspargase, pentostatin, tazarotne, TLK-286, Velcade, Tarceva, or tretinoin.

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain and Vitaxin.

Platinum-coordinated compounds include but are not limited to, cisplatin, carboplatin, nedaplatin, or oxaliplatin.

Camptothecin derivatives include but are not limited to camptothecin, 10-hydroxycamptothecin, 9-aminocamptothecin, irinotecan, SN-38, edotecarin, and topotecan.

Tyrosine kinase inhibitors include, for example, Iressa and SU5416.

Antibodies include, for example, Herceptin, Erbitux, Avastin, and Rituximab.

Interferons include, for example, interferon alpha, interferon alpha-2a, interferon, alpha-2b, interferon beta, interferon gamma-1a and interferon gamma-n1.

Biological response modifiers include agents that modify defense mechanisms of living organisms or biological responses, such as survival, growth, or differentiation of tissue cells to direct them to have anti-tumor activity. Such agents include, for example, krestin, lentinan, sizofiran, picibanil, and ubenimex.

Other antitumor agents include, for example, mitoxantrone, I-asparaginase, procarbazine, dacarbazine, hydroxycarbamide, pentostatin, and tretinoin. Additionally, PI3K inhibitors and RAS-targeted cancer treatments may be combined with the compounds described herein.

Some embodiments also relate to a pharmaceutical composition comprising a compound of formula (I), formula (II), formula (III), or formula (IV), or a pharmaceutically acceptable salt or solvate thereof, as hereinbefore defined in association with a pharmaceutically acceptable adjuvant, diluent or carrier.

Further embodiments relate to a pharmaceutical composition which comprises mixing a compound of formula (I), formula (II), formula (III), or formula (IV), or a pharmaceutically acceptable salt or solvate thereof, as hereinbefore defined with a pharmaceutically acceptable adjuvant, diluent or carrier.

For the above-mentioned therapeutic uses the dosage administered will, of course, vary with the compound employed, the mode of administration, the treatment desired and the disorder indicated. The daily dosage of the compound of formula (I), formula (II), formula (III), or formula (IV), or pharmaceutically acceptable salt thereof, may be in the range from 1 mg to 1 gram, preferably 1 mg to 250 mg, more preferably 10 mg to 100 mg.

The present embodiments also encompass sustained release compositions.

Administration of the compounds described herein (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The active compound may be applied as a sole therapy or may involve one or more other anti-tumor substances, for example those selected from, for example, mitotic inhibitors, for example vinblastine; alkylating agents, for example cisplatin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex® (tamoxifen) or, for example anti-androgens such as Casodex® (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound described herein as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The examples and preparations provided below further illustrate and exemplify the compounds described herein and methods of preparing such compounds. The scope of the embodiments described herein is not limited in any way by the following examples and preparations. In the following examples, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

In the examples shown, salt forms were occasionally isolated as a consequence of the mobile phase additives during HPLC based chromatographic purification. In these cases, salts such as formate, trifluorooacetate and acetate were isolated and tested without further processing. It will be recognized that one of ordinary skill in the art will be able to realize the free base form by standard methodology (such as using ion exchange columns, or performing simple basic extractions using a mild aqueous base).

In general, the compounds described herein may be prepared by processes known in the chemical arts, particularly in light of the description contained herein. Certain processes for the manufacture of the compounds described herein are provided as further features of the embodiments and are illustrated in the reaction schemes provided below and in the experimental section.

Unless stated otherwise, the variables in Schemes A-F have the same meanings as defined herein.

Scheme A:

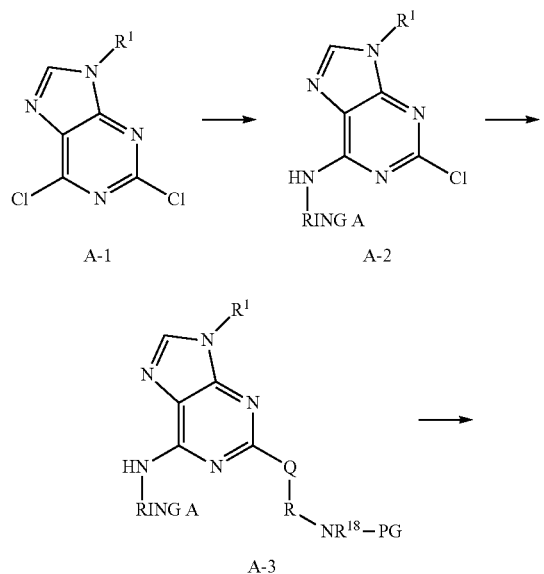

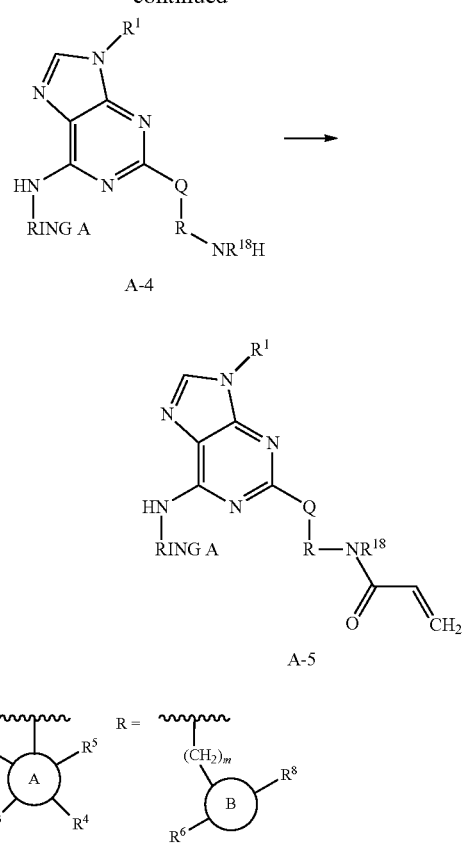

As exemplified in Scheme A, the 2,6-dichloro-9H-purine derivative A-1 is subjected to nucleophillic aromatic substitution, which is defined as displacement of a reactive aromatic halide by a nucleophile, and is generally referred to herein as $S_NAr$ conditions. The $S_NAr$ conditions are either acid mediated, such as treatment with an appropriate aminoheterocycle in the presence of a suitable acid, such as TFA or an HCl salt of the aminoheterocycle, in a suitable solvent, such as iPrOH, or base mediated, such as treatment with an appropriate aminoheterocycle in the presence of a suitable base, such as DIPEA, in a suitable solvent such as nBuOH, to afford the 2-chloro purine A-2. Subsequent chlorine displacement via palladium mediated methodology or treatment under $S_NAr$ conditions affords the substituted purine A-3. Deprotection (removal of the protecting group) under standard conditions known in the art provides A-4. Acylation with either an acyl chloride or amide coupling methodology with an appropriate acid affords A-5.

Scheme B:

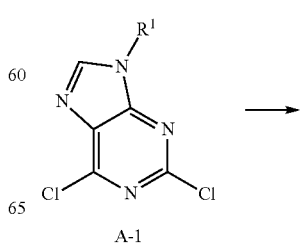

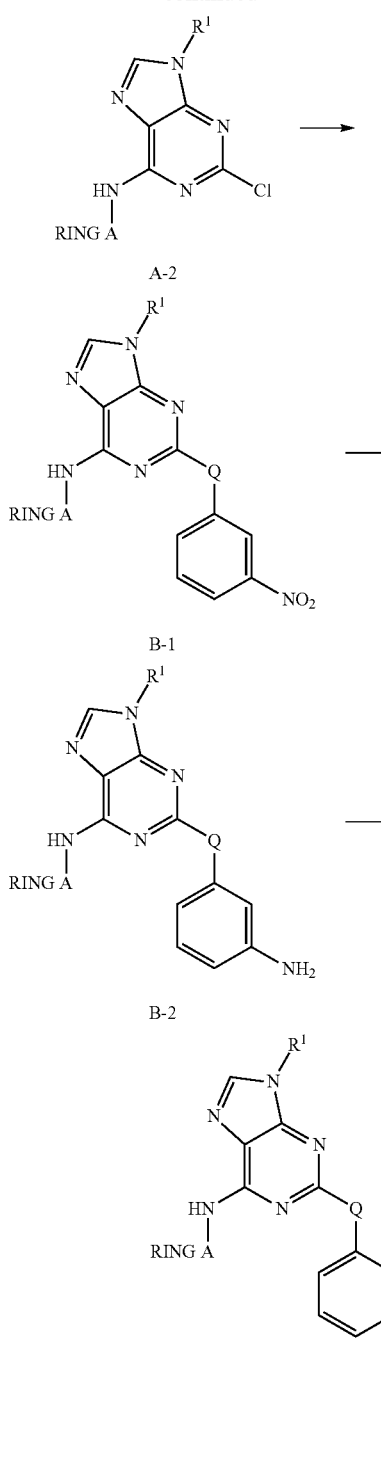
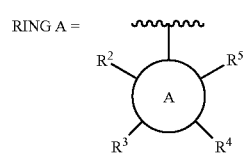

As exemplified in Scheme B, the 2,6-dichloro-9H-purine derivative A-1 is subjected to S$_n$Ar conditions. The S$_n$Ar conditions are either acid mediated, such as treatment with an appropriate aminoheterocycle in the presence of a suitable acid, such as TFA or an HCl salt of the aminoheterocycle, in a suitable solvent, such as iPrOH, or base mediated, such as treatment with an appropriate aminoheterocycle in the presence of a suitable base, such as DIPEA, in a suitable solvent such as nBuOH, to afford the 2-chloro purine A-2. Subsequent chlorine displacement with an aniline via palladium mediated methodology or a phenoxide (generated by using a suitable base such as sodium hydride in THF) affords the substituted purine B-1. Nitro reduction under standard conditions known in the art provides B-2. Acylation with either an acyl chloride or amide coupling methodology with an appropriate acid affords B-3.

Scheme C:

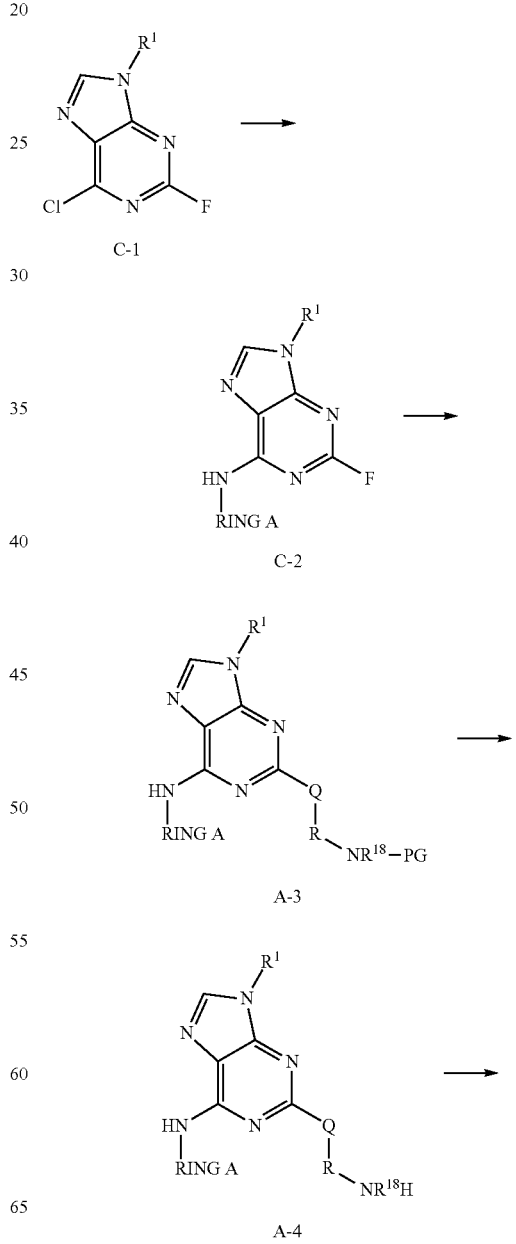

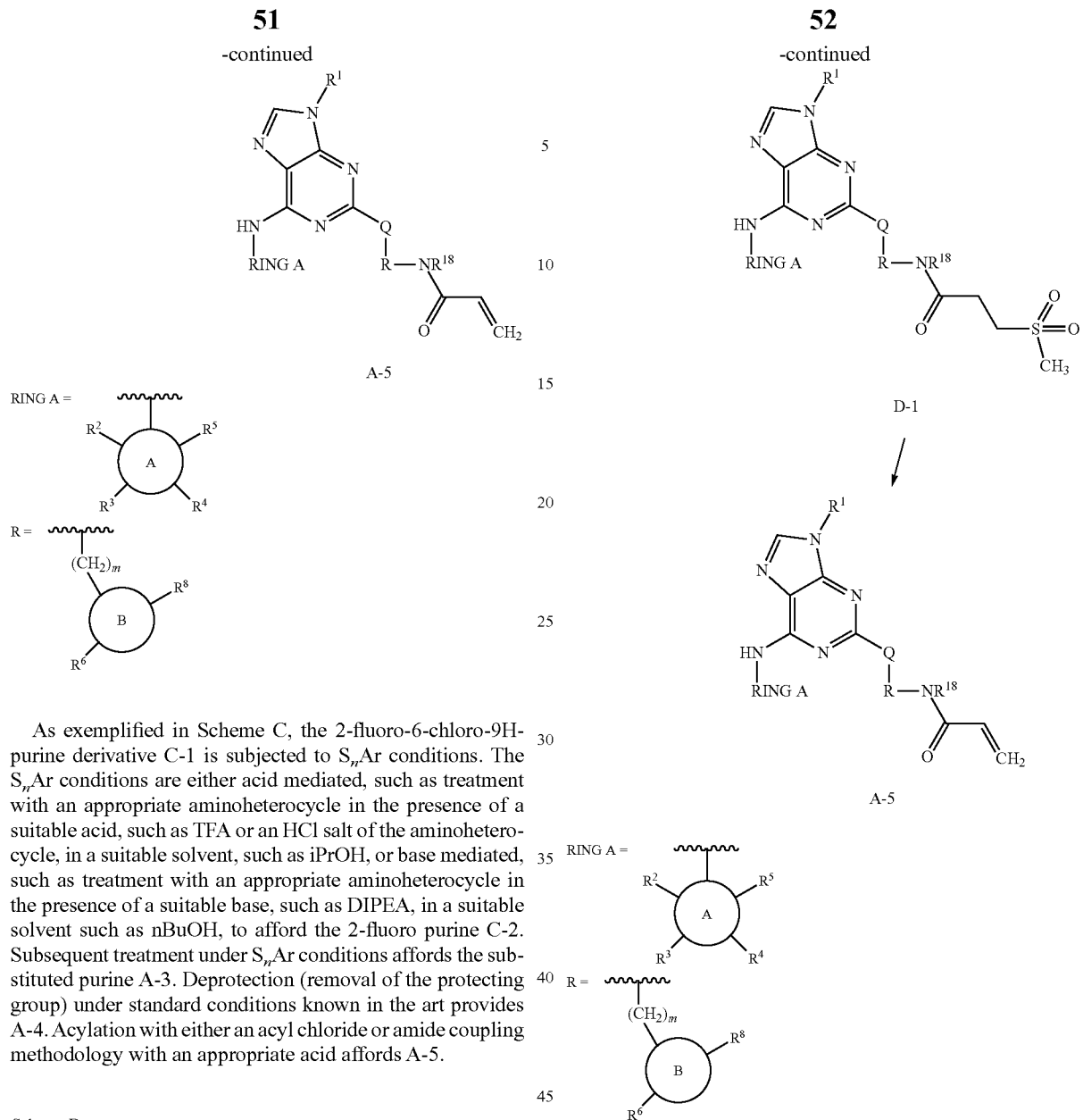

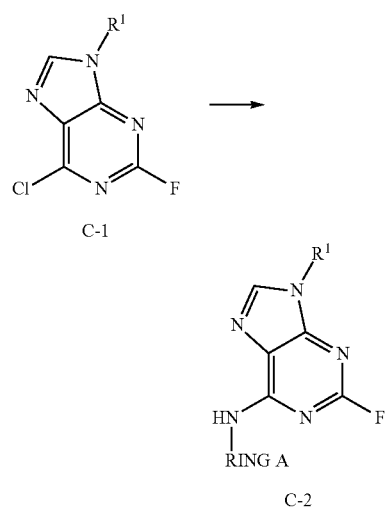

As exemplified in Scheme C, the 2-fluoro-6-chloro-9H-purine derivative C-1 is subjected to $S_nAr$ conditions. The $S_nAr$ conditions are either acid mediated, such as treatment with an appropriate aminoheterocycle in the presence of a suitable acid, such as TFA or an HCl salt of the aminoheterocycle, in a suitable solvent, such as iPrOH, or base mediated, such as treatment with an appropriate aminoheterocycle in the presence of a suitable base, such as DIPEA, in a suitable solvent such as nBuOH, to afford the 2-fluoro purine C-2. Subsequent treatment under $S_nAr$ conditions affords the substituted purine A-3. Deprotection (removal of the protecting group) under standard conditions known in the art provides A-4. Acylation with either an acyl chloride or amide coupling methodology with an appropriate acid affords A-5.

Scheme D:

As exemplified in Scheme D, the 2-fluoro-6-chloro-9H-purine derivative C-1 is subjected to $S_nAr$ conditions. The $S_nAr$ conditions are either acid mediated, such as treatment with an appropriate aminoheterocycle in the presence of a suitable acid, such as TFA or an HCl salt of the aminoheterocycle, in a suitable solvent, such as iPrOH, or base mediated, such as treatment with an appropriate aminoheterocycle in the presence of a suitable base, such as DIPEA, in a suitable solvent such as nBuOH, to afford the 2-fluoro purine C-2. Subsequent $S_nAr$ with a masked acrylamide in the form of a sulphone affords the substituted purine D-1. Alternately, RING A of C-2 contains a protected amine or alcohol that is deprotected under standard conditions known in the art and may, in certain cases, be modified via alkylation or reductive amination prior to the second $S_nAr$ step. Treatment with a suitable base such as potassium tert-butoxide effects sulphone elimination, which affords A-5.

Scheme E:

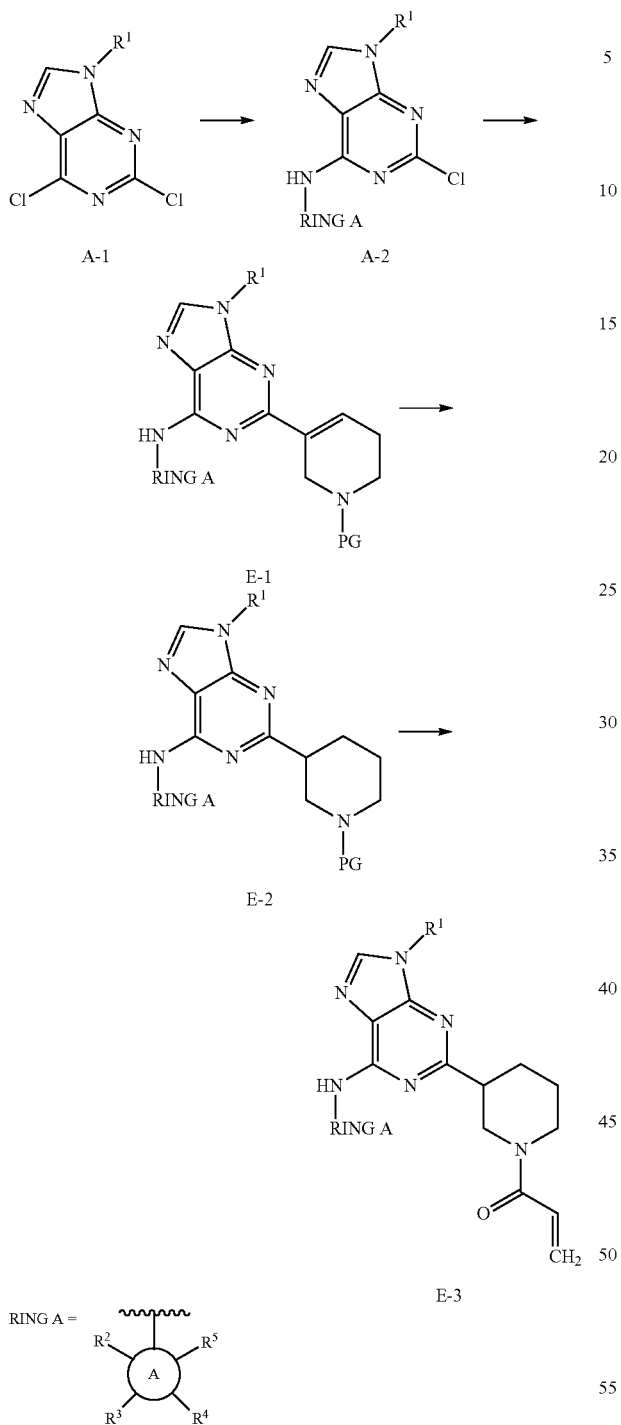

chlorine displacement via palladium mediated methodology, such as reaction with an appropriate boronic ester or acid, affords the substituted purine E-1. Reduction of the intermediate via standard conditions known in the art provides the carbocycle E-2 followed by a deprotection (removal of the protecting group) under standard conditions known in the art and acylation with either an acyl chloride or amide coupling methodology with an appropriate acid affords E-3.

Scheme F:

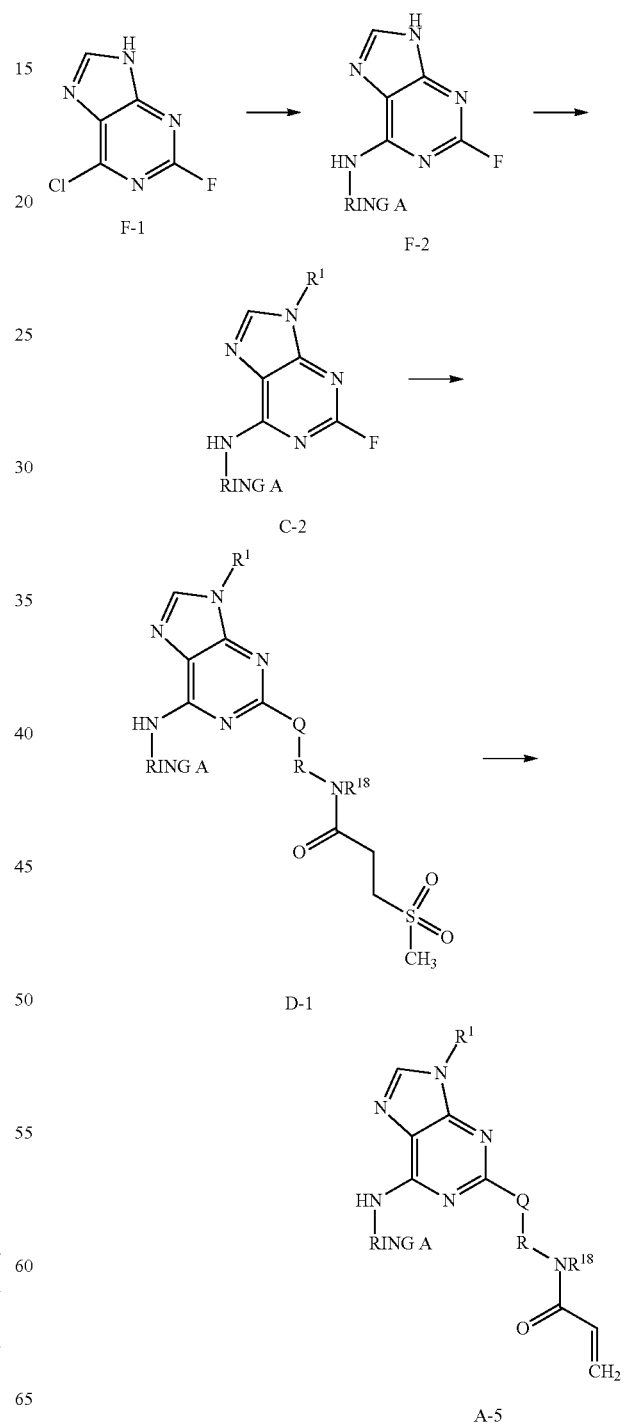

As exemplified in Scheme E, the 2,6-dichloro-9H-purine derivative A-1 is subjected to $S_nAr$ conditions. The $S_nAr$ conditions are either acid mediated, such as treatment with an appropriate aminoheterocycle in the presence of a suitable acid, such as TFA or an HCl salt of the aminoheterocycle, in a suitable solvent, such as iPrOH, or base mediated, such as treatment with an appropriate aminoheterocycle in the presence of a suitable base, such as DIPEA, in a suitable solvent such as nBuOH, to afford the 2-fluoro purine A-2. Subsequent RING A = 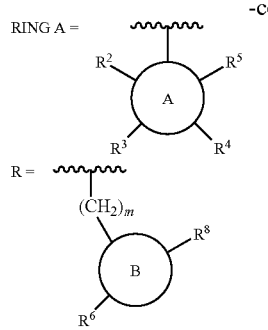

As exemplified in Scheme F, the 6-chloro-2-fluoro-9H-purine F-1 is subjected to $S_nAr$ conditions. The $S_nAr$ conditions are either acid mediated, such as treatment with an appropriate aminoheterocycle in the presence of a suitable acid, such as TFA or an HCl salt of the aminoheterocycle, in a suitable solvent, such as iPrOH, or base mediated, such as treatment with an appropriate aminoheterocycle in the presence of a suitable base, such as DIPEA, in a suitable solvent such as nBuOH, to afford the 2-fluoro purine derivative F-2. Alkylation of the purine core with either an alkyl halide or a dialkyl sulphate affords C-2. Subsequent $S_nAr$ with a masked acrylamide in the form of a sulphone affords the substituted purine D-1. Alternately, RING A of C-2 contains a protected amine or alcohol that is deprotected under standard conditions known in the art and may, in certain cases, be modified via alkylation or reductive amination prior to the second $S_nAr$ step. Treatment with a suitable base such as potassium tert-butoxide effects sulphone elimination, which affords A-5.

EXAMPLES

Example 1 (Scheme A)

Preparation of (S)-N-(1-(9-isopropyl-6-((4-(4-methylpiperazin-1-yl)phenyl)amino)-9H-purin-2-yl)pyrrolidin-3-yl)acrylamide

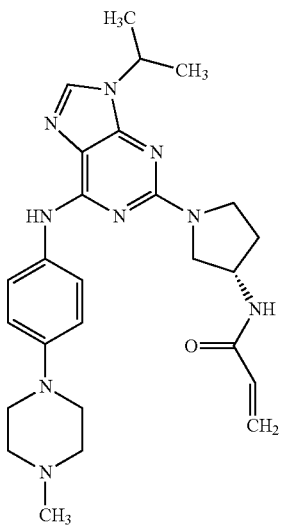 [SMILES: C=CC(=O)N[C@H]1CCN(c2nc(Nc3ccc(N4CCN(C)CC4)cc3)c3ncn(C(C)C)c3n2)C1]

Step 1: Preparation of 2,6-dichloro-9-isopropyl-9H-purine

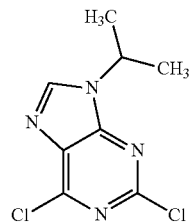

A 500 mL round bottom flask was charged with 2,6-dichloro-9H-purine (1.89 g, 10 mmol), isopropanol (3.1 mL, 40 mmol, 4 mol eq), THF (150 mL), and triphenylphosphine (polystyrene-bound, ~3 mmol/g, 6.7 g, or about 20 mmol load) and the resulting mixture was stirred and cooled in a water bath under nitrogen. A solution of DBAD (4.85 g, 20 mmol) in THF (50 mL) was added dropwise via an addition funnel over 30 min and the resulting reaction mixture stirred at ambient temperature for 20 hr. The resin was removed by filtration and washed well with ethyl acetate. The combined filtrates were evaporated to give a light yellow solid that was purified via flash column chromatography (dry loaded using silica/DCM) with a gradient of 0-50% ethyl acetate in heptanes to give:

1. The title product: 2,6-dichloro-9-isopropyl-9H-purine (2.81 g, contained DBAD by-product, 0.9 mol eq as determined by $^1$H NMR). $^1$H NMR (400 MHz, DMSO-d6) δ ppm 8.86 (s, 1 H) 4.71-4.94 (m, 1 H) 1.55 (d, J=6.85 Hz, 6 H) with 1.39 (s, 16 H for DBAD by-product). m/z (APCI+) for $C_8H_8Cl_2N_4$ 231.1 $(M+H)^+$ with Cl isotope pattern.
2. Other minor regioisomer: 2,6-dichloro-7-isopropyl-7H-purine (229 mg, 10 yield). $^1$H NMR (400 MHz, DMSO-d6) δ ppm 9.06 (s, 1 H) 5.13 (dt, J=13.36, 6.71 Hz, 1 H) 1.59 (d, J=6.72 Hz, 6 H). m/z (APCI+) for $C_8H_8Cl_2N_4$ 231.1 $(M+H)^+$ with Cl isotope pattern.

Step 2: Preparation of 2-chloro-9-isopropyl-N-(4-(4-methylpiperazin-1-yl)phenyl) -9H-purin-6-amine

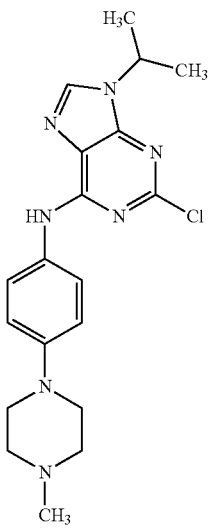 [SMILES: CC(C)n1cnc2c(Nc3ccc(N4CCN(C)CC4)cc3)nc(Cl)nc21]

To a reaction vial was added 2,6-dichloro-9-isopropyl-9H-purine (containing 6.3 mmol), 4-(4-methylpiperazin-1-yl)aniline (1.2 g, 6.3 mmol), isopropanol (32 mL, 0.2 M), and TFA (1 mL, 13 mmol). The reaction vial was capped, stirred and heated at 78° C. (block temperature) for 20 hr. The volatiles were removed to give a dark residue. Sat. aq. NaHCO$_3$ (40 mL) was added. There was dark gummy solid precipitated out. Ethyl acetate (2×120 mL) and DCM (2×80 mL) were used to extract product. The combined organic layers were dried over Na$_2$SO$_4$ and evaporated to give a dark residue that was purified on silica with a gradient of 100% ethyl acetate to 10% ammonia (7 N in methanol)-90% ethyl acetate to give the title product as a light yellow solid (2.1 g, 86% yield). $^1$H NMR (400 MHz, DMSO-d6) δ ppm 10.04 (s, 1 H) 8.38 (s, 1 H) 7.61 (d, J=8.56 Hz, 2 H) 6.93 (d, J=8.93 Hz, 2 H) 4.71 (dt, J=13.39, 6.63 Hz, 1 H) 3.10 (br. s., 4 H) 2.45 (m, J=4.16 Hz, 4 H) 2.22 (s, 3 H) 1.52 (d, J=6.72 Hz, 6 H). m/z (APCI+) for C$_{19}$H$_{24}$ClN$_7$ 386.2 (M+H)$^+$ with Cl isotope pattern. The regiochemistry of the product was also confirmed by small molecule X-ray crystallography.

Step 3: Preparation of (S)-tert-butyl (1-(9-isopropyl-6-((4-(4-methylpiperazin-1-yl)phenyl)amino)-9H-purin-2-yl)pyrrolidin-3-yl)carbamate

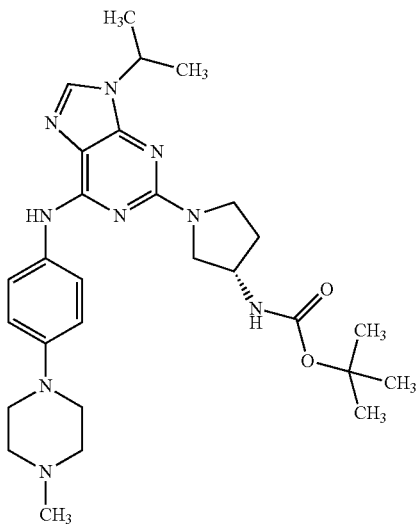 [SMILES: CC(C)n1cnc2c(Nc3ccc(N4CCN(C)CC4)cc3)nc(N3CC[C@H](NC(=O)OC(C)(C)C)C3)nc21]

A mixture of 2-chloro-9-isopropyl-N-(4-(4-methylpiperazin-1-yl)phenyl)-9H-purin-6-amine (2.32 g, 6 mmol), (S)-pyrrolidin-3-yl-carbamic acid tert-butyl ester (1.45 g, 7.8 mmol, 1.3 mol eq), and Cs$_2$CO$_3$ (7.82 g, 24 mmol, 4 mol eq) in tert-pentyl alcohol (60 mL, 0.1 M) was degassed with nitrogen. Chloro(di-2-norbornylphosphino)(2-dimethylaminomethylferrocen-1-yl)palladium(II) (CAS #614753-51-4, 375 mg, 0.6 mmol, 0.1 mol eq) was added, and the mixture degassed for 1 additional min. The vial was capped, stirred and heated at 100° C. (block temperature) for 20 hr. The reaction was cooled, diluted with water (25 mL) and ethyl acetate (150 mL) and the organic layer was separated. The aqueous layer was extracted with more ethyl acetate (50 mL) and the combined organics were dried over Na$_2$SO$_4$ and evaporated to give a residue that was purified via silica flash chromatography with a gradient of 50% heptane-50% ethyl acetate to 100% ethyl acetate and then to 10% ammonia (7 N in methanol)-90% ethyl acetate to give the title product as a light yellow solid (3.20 g, 99% yield). $^1$H NMR (400 MHz, DMSO d6) δ ppm 9.14 (s, 1 H) 7.90 (s, 1 H) 7.85 (d, J=9.05 Hz, 2 H) 7.14 (d, J=5.01 Hz, 1 H) 6.87 (d, J=9.17 Hz, 2 H) 4.61 (quin, J=6.72 Hz, 1 H) 4.05-4.27 (m, 2 H) 3.60-3.80 (m, 2 H) 3.50 (dt, J=10.55, 7.08 Hz, 1 H) 3.35 (dd, J=10.82, 4.83 Hz, 1 H) 3.02-3.11 (m, 4 H) 2.40-2.48 (m, 4 H) 2.22 (s, 3 H) 1.79-1.92 (m, 1 H) 1.50 (d, J=6.85 Hz, 6 H) 1.40 (s, 9 H). m/z (APCI+) for C$_{28}$H$_{41}$N$_9$O$_2$ 536.4 (M+H)$^+$.

Step 4: Preparation of (S)-2-(3-aminopyrrolidin-1-yl)-9-isopropyl-N-(4-(4-methylpiperazin-1-yl)phenyl)-9H-purin-6-amine

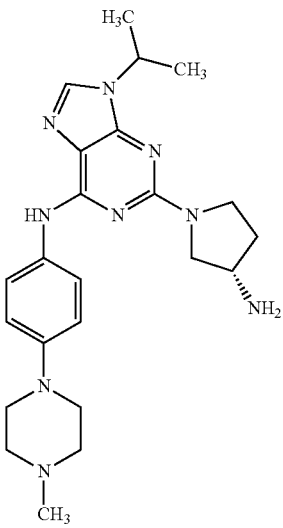 [SMILES: CC(C)n1cnc2c(Nc3ccc(N4CCN(C)CC4)cc3)nc(N3CC[C@H](N)C3)nc21]

To a solution of (S)-tert-butyl (1-(9-isopropyl-6-((4-(4-methylpiperazin-1-yl)phenyl)amino)-9H-purin-2-yl)pyrrolidin-3-yl)carbamate (1.40 g, 2.61 mmol) in DCM (30 mL) was added TFA (2.11 mL, 21 mmol). The reaction vial was capped and stirred for 3 hr. The volatiles were then removed and methanol (50 mL) and aqueous LiOH (2 M, 20 mL) were added and the mixture stirred for 16 hr. The volatiles were removed to give a white solid residue. Water (30 mL) was added and the mixture was sonicated to give a white suspension. The solid was collected by filtration and dried to give the title product as a white solid (1.26 g, 111% yield, ~90% purity). $^1$H NMR (400 MHz, DMSO-d6) δ ppm 9.10 (br. s., 1 H) 7.76-7.94 (m, 3 H) 6.87 (d, J=8.80 Hz, 2 H) 4.60 (dt, J=13.33, 6.66 Hz, 1 H) 3.58-3.72 (m, 2 H) 3.51 (dd, J=10.64, 5.99 Hz, 2 H) 3.06 (br. s., 4 H) 2.45 (br. s., 4 H) 2.22 (s, 3 H) 1.95-2.10 (m, 2 H) 1.58-1.73 (m, 3 H) 1.50 (d, J=6.72 Hz, 6 H). m/z (APCI+) for C$_{23}$H$_{33}$N$_9$ 436.4 (M+H)$^+$.

Step 5: Preparation of (S)-N-(1-(9-isopropyl-6-((4-(4-methylpiperazin-1-yl)phenyl)amino)-9H-purin-2-yl)pyrrolidin-3-yl)acrylamide

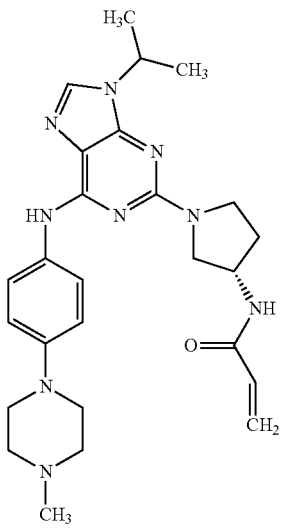 [SMILES: C=CC(=O)N[C@H]1CCN(c2nc(Nc3ccc(N4CCN(C)CC4)cc3)c3ncn(C(C)C)c3n2)C1]

(S)-2-(3-Aminopyrrolidin-1-yl)-9-isopropyl-N-(4-(4-methylpiperazin-1-yl)phenyl)-9H-purin-6-amine (315 mg, 0.7 mmol) was dissolved in DCM:tert-pentyl alcohol (15 mL:1.5 mL) and sat. aq. NaHCO$_3$ (6 mL) was added in one portion. The bi-phasic mixture was stirred vigorously and acryloyl chloride (90 μL, 1.1 mmol, 1.5 mol eq) was added in one portion and the resulting mixture was stirred at ambient temperature for 2 hr. The reaction was diluted with DCM (30 mL) and the organic layer was separated, and the product was extracted with more DCM:tert-pentyl alcohol (9:1, 30 mL). The combined organics were dried over Na$_2$SO$_4$ and evaporated to give a residue that was purified via silica flash chromatography with gradient of 100% ethyl acetate to 100 ethanol to give a crude purity at ~90%. This crude was triturated with ethyl acetate:heptane (4:1, 15 mL). The resulting white solid was collected by filtration, washed with ethyl acetate:heptane (4:1, 10 mL) and dried to give the title product as a white solid (118 mg, 33% yield, ~95% purity). $^1$H NMR (400 MHz, DMSO-d6) δ ppm 9.16 (s, 1 H) 8.36 (d, J=6.72 Hz, 1 H) 7.91 (s, 1 H) 7.85 (d, J=8.80 Hz, 2 H) 6.87 (d, J=8.93 Hz, 2 H) 6.18-6.34 (m, 1 H) 6.03-6.15 (m, 1 H) 5.59 (dd, J=9.96, 2.02 Hz, 1 H) 4.62 (dt, J=13.33, 6.54 Hz, 1 H) 4.43 (d, J=5.14 Hz, 1 H) 3.71-3.87 (m, 1 H) 3.63 (dt, J=12.62, 6.46 Hz, 2 H) 3.43 (dd, J=11.25, 3.30 Hz, 1 H) 3.07 (m, J=4.65 Hz, 4 H) 2.45 (m, J=4.40 Hz, 4 H) 2.22 (s, 4 H) 1.89 (dd, J=11.37, 5.87 Hz, 1 H) 1.51 (d, J=6.72 Hz, 6 H). m/z (APCI+) for C$_{26}$H$_{35}$N$_9$O 490.2 (M+H)$^+$.

Alternative preparation of (S)-N-(1-(9-isopropyl-6-((4-(4-methylpiperazin-1-yl)phenyl)amino)-9H-purin-2-yl)pyrrolidin-3-yl)acrylamide (S)-2-(3-Aminopyrrolidin-1-yl)-9-isopropyl-N-(4-(4-methylpiperazin-1-yl)phenyl) -9H-purin-6-amine (436 mg, 1 mmol) was suspended in DMF (3.3 mL). DIPEA (0.53 mL, 3 mmol, 3 mol eq) and acrylic acid (73 μL, 1.05 mmol, 1.05 mol eq) were added to give a suspension. Propylphosphonic anhydride (CAS 68957-94-8, 50% in DMF, 0.7 mL, 1.2 mmol, 1.2 mol eq) was added in one portion. The reaction mixture warmed up slightly to afford a solution. After 15 min, aqueous Na$_2$CO$_3$ (1 M, 2 mL, 2 mmol) was added and stirred for 30 min. Water (10 mL) and ethyl acetate (50 mL) were added. The organic layer was separated, washed with water (3×10 mL), dried over Na$_2$SO$_4$ and evaporated to give a light yellow foamy solid, which was purified by SFC (Column Zymor-Spher HADP 150×21.2 mm I.D., 5 μm particles. Modifier: ethanol. Gradient 21% (hold 2 min) to 24% (hold 1 min) at 1.5% per min. Flow rate (58 mL/min) to give the title product (167 mg, 34% yield, >95% purity). $^1$H NMR (400 MHz, DMSO-d6) δ ppm 9.17 (s, 1 H) 8.36 (d, J=6.85 Hz, 1 H) 7.91 (s, 1 H) 7.85 (d, J=9.05 Hz, 2 H) 6.87 (d, J=9.05 Hz, 2 H) 6.19-6.32 (m, 1 H) 6.05-6.16 (m, 1 H) 5.59 (dd, J=10.09, 2.38 Hz, 1 H) 4.62 (quin, J=6.72 Hz, 1 H) 4.34-4.48 (m, 1 H) 3.76 (dd, J=11.31, 6.30 Hz, 1 H) 3.54-3.70 (m, 2 H) 3.43 (dd, J=11.19, 3.85 Hz, 1 H) 2.93-3.14 (m, 4 H) 2.39-2.47 (m, 4 H) 2.22 (s, 3 H) 2.12-2.20 (m, 1 H) 1.83-1.95 (m, 1 H) 1.51 (d, J=6.72 Hz, 6 H). m/z (APCI+) for C$_{26}$H$_{35}$N$_9$O 490.4 (M+H)$^+$.

Example 2(Scheme A)

Preparation of N-((3R,4R)-4-fluoro-1-(9-isopropyl-6-((1-methyl-1H-pyrazol-4-yl)amino)-9H-purin-2-yl)pyrrolidin-3-yl)acrylamide

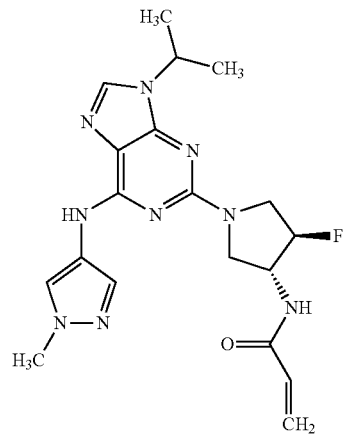

Step 1: Preparation of 2-chloro-9-isopropyl-N-(1-methyl-1H-pyrazol-4-yl)-9H -purin -6-amine

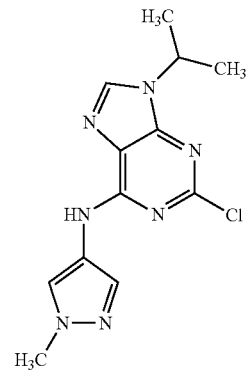 [SMILES: CC(C)n1cnc2c(Nc3cnn(C)c3)nc(Cl)nc21]

2,6-Dichloro-9-isopropyl-9H-purine (1.16 g, 5 mmol), as prepared in step 1 of Example 1, was mixed with 4-amino-1-methylpyrazole (1.02 g, 10 mmol) and DIPEA (1.74 mL, 10 mmol) in nBuOH (33 mL) and was stirred and heated at 100° C. (block temperature) for 1 hr. The reaction was cooled, and the volatiles were removed under vacuum to give a dark residue. Ethyl acetate (120 mL) was added and the mixture was washed with sat. aq. NaHCO$_3$ (3×30 mL), dried over Na$_2$SO$_4$ and evaporated to give a dark residue. This residue was dissolved in ethyl acetate, passed through a thin pad of silica gel, and eluted with 90% ethyl acetate-10% ammonia (7 N in methanol). The eluent was evaporated to afford the title compound as a dark solid (1.43 g, 98% yield). $^1$H NMR (400 MHz, DMSO-d6) δ ppm 10.41 (br. s., 1 H) 8.38 (s, 1 H) 8.00 (s, 1 H) 7.68 (s, 1 H) 4.71 (quin, J=6.72 Hz, 1 H) 3.84 (s, 3 H) 1.52 (d, J=6.72 Hz, 6 H). m/z (APCI+) for C$_{12}$H$_{14}$ClN$_7$ 292.1 with Cl isotope pattern (M+H)$^+$.

Step 2: Preparation of 2-((trans)-3-amino-4-fluoro-pyrrolidin-1-yl)-9-isopropyl-N-(1-methyl-1H-pyrazol-4-yl)-9H-purin-6-amine

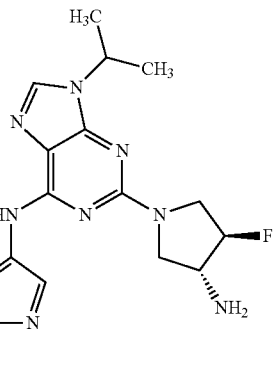

To a solution of 2-chloro-9-isopropyl-N-(1-methyl-1H-pyrazol-4-yl)-9H-purin-6-amine (292 mg, 1.00 mmol) and benzyl [(3,4-trans)-4-fluoropyrrolidin-3-yl]carbamate (357 mg, 1.5 mmol) in tert-pentanol (10 mL) was added Cs$_2$CO$_3$ (1.32 g, 4 mmol). The reaction mixture was degassed with nitrogen for 2 min and then catalyst chloro(di-2-norbornylphosphino)(2-dimethylaminomethylferrocen-1-yl) palladium(II) (CAS #614753-51-4, 60 mg, 0.1 mmol) was added. The reaction vial was capped, stirred and heated at 100° C. (block temperature) for 20 hr. Ethanol (40 mL) was added to the reaction mixture and any insoluble material was removed by filtration. The filtrate was then subjected to hydrogenation using 10% Pd/C (120 mg) and hydrogen balloon for 20 hr. The catalyst was filtered off and the filtrate was evaporated to give a dark residue that was purified via flash chromatography (with gradient of 50% ethyl acetate-50° A) heptane to 100% ethyl acetate, and then to 10% ammonia (7 N) in methanol-90% ethyl acetate). The fractions containing the title product were evaporated to give a crude residue, which was used in the following step.

Step 3: Preparation of N-((3R,4R)-4-fluoro-1-(9-isopropyl-6-((1-methyl-1H -pyrazol-4-yl)amino)-9H-purin-2-yl)pyrrolidin-3-yl)acrylamide

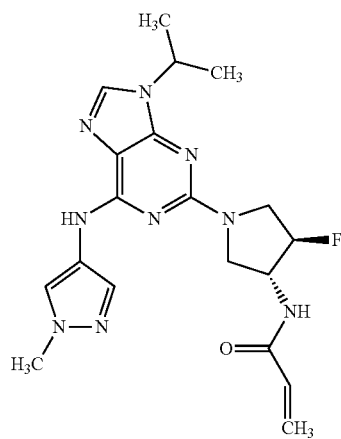 [SMILES: C=CC(=O)N[C@@H]1CN(c2nc(Nc3cnn(C)c3)c3ncn(C(C)C)c3n2)C[C@H]1F]

Crude 2-((trans)-3-amino-4-fluoropyrrolidin-1-yl)-9-isopropyl-N-(1-methyl-1H-pyrazol-4-yl)-9H-purin-6-amine (assumed 1 mmol ca.) was partitioned between DCM (30 mL) and sat. aq. NaHCO$_3$ (10 mL) and stirred vigorously. Acryloyl chloride (121 μL, 1.5 mmol) was added in one portion and the mixture stirred for 30 min. The mixture was then diluted with DCM (50 mL) and the organic layer was separated, dried over Na$_2$SO$_4$ and evaporated to give a dark residue that was subjected to chiral SFC purification to separate the two trans enantiomers (Chiralpak AD-H 21.2×250 mm 5μ column. Eluted with 30% EtOH (200 proof) in CO$_2$ held 38° C. at 100 bar, ~60.0 mL/min, UV detection at λ=260 nm. Peak 1(−) elutes 3.99-4.68 min. Peak 2(+) elutes 5.80-6.38 min). Yielded:

N-((3R,4R)-4-fluoro-1-(9-isopropyl-6-((1-methyl-1H-pyrazol-4-yl)amino)-9H-purin-2-yl)pyrrolidin-3-yl)acrylamide; (absolute stereochemistry later determined by small molecule crystallography of key intermediates), 30.26 mg, 7% yield (in 3 steps), ~99 ee, 90% pure. Optical rotation: $[\alpha]D_{22}$=+28.9° (c 0.09, EtOH). $^1$H NMR (600 MHz, DMSO-17 mm) δ ppm 9.65 (br. s., 1 H) 8.50 (d, J=6.97 Hz, 1 H) 8.00 (s, 1 H) 7.92 (s, 1 H) 7.69 (s, 1 H) 6.20-6.29 (m, 1 H) 6.08-6.18 (m, 1 H) 5.63 (d, J=10.82 Hz, 1 H) 5.03-5.25 (m, 1 H) 4.43-4.70 (m, 2 H) 3.88 (br. s., 2 H) 3.82 (s, 3 H) 3.70 (d, J=10.45 Hz, 2 H) 1.50 (d, J=6.42 Hz, 6 H). m/z (APCI+) for C$_{19}$H$_{24}$FN$_9$O 414.1 (M+H)$^+$.

N-((3S,4S)-4-fluoro-1-(9-isopropyl-6-((1-methyl-1H-pyrazol-4-yl)amino)-9H-purin -2-yl)pyrrolidin-3-yl)acrylamide, 36.7 mg, 9% yield (in 3 steps), >99% ee, 95% pure. Optical rotation: $[\alpha]D_{22}$=−19.06° (c 0.08, EtOH). $^1$H NMR (600 MHz, DMSO-17 mm) δ ppm 9.65 (br. s., 1 H) 8.50 (d, J=6.42 Hz, 1 H) 8.00 (s, 1 H) 7.92 (s, 1 H) 7.69 (s, 1 H) 6.19-6.29 (m, 1 H) 6.11-6.18 (m, 1 H) 5.63 (d, J=11.92 Hz, 1 H) 5.08-5.22 (m, 1 H) 4.46-4.69 (m, 2 H) 3.88 (br. s., 2 H) 3.82 (s, 3 H) 3.64-3.79 (m, 2 H) 1.50 (d, J=6.79 Hz, 6 H). m/z (APCI+) for C$_{19}$H$_{24}$FN$_9$O 414.1 (M+H)$^+$.

Alternative Method for Example 2(Scheme C)

Preparation of N-((3R,4R)-4-fluoro -1-(9-isopropyl-6-((1-methyl-1H-pyrazol-4-yl)amino)-9H-purin-2-yl)pyrrolidin-3-yl)acrylamide Step 1: Preparation of 6-chloro-2-fluoro-9-isopropyl-9H-purine

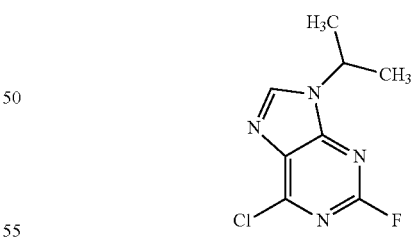

A solution of 6-chloro-2-fluoro-9H-purine (616 mg, 3.57 mmol) in THF (18 mL) was cooled in an ice water bath under nitrogen and iPrOH (858 mg, 14.3 mmol), triphenylphosphine, polymer-bound (2.38 g, 7.14 mmol, ~3 mmol/g), and di-tert-butyl azodicarboxylate (1.730 g, 7.14 mmol) were added. The reaction mixture was allowed to warm to ambient temperature and stirred for 16 hr. The solid resin was removed and washed well with ethyl acetate (50 mL). The filtrate was concentrated down in vacuo to give a light yellow solid residue. This was then loaded onto silica and purified via flash chromatography (eluting with 30-50% ethyl acetate in heptanes) to give the title product as a white solid (445 mg, 58% yield). $^1$H NMR (400 MHz, DMSO-d6) δ ppm 8.83 (s, 1 H) 4.72-4.92 (m, 1 H) 1.57 (d, J=6.85 Hz, 6 H). m/z (APCI+) for $C_8H_8FN_4Cl$ 217.10, 215.10 (M+H)$^+$.

Step 2: Preparation of 2-fluoro-9-isopropyl-N-(1-methyl-1H-pyrazol-4-yl)-9H-purin-6-amine

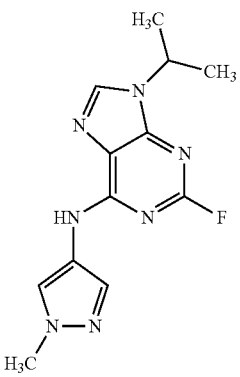 [SMILES: CC(C)n1cnc2c(Nc3cnn(C)c3)nc(F)nc21]

A mixture of 6-chloro-2-fluoro-9-isopropyl-9H-purine (215 mg, 1 mmol), 1-methyl-1H-pyrazol-4-amine (116 mg, 1.2 mmol) in nBuOH (5 mL, 0.2 M) and DIPEA (0.7 mL, 4 mmol) was stirred at ambient temperature for 2 days. LCMS showed major title product with M+1=276.2 amu. This crude product was used in the following step with no isolation.

Step 3: Preparation of benzyl((3R,4R)-4-fluoro-1-(9-isopropyl-6-((1-methyl-1H-pyrazol-4-yl)amino)-9H-purin-2-yl)pyrrolidin-3-yl)carbamate

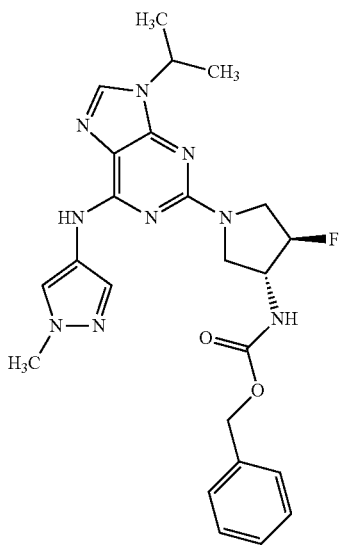

To the above solution of crude 2-fluoro-9-isopropyl-N-(1-methyl-1H-pyrazol-4-yl)-9H-purin-6-amine was added benzyl [(3R,4R)-4-fluoropyrrolidin-3-yl]carbamate (238 mg, 1 mmol). The resulting solution was heated at 100° C. (block temperature) and stirred for 14 hr. After cooling, the volatiles were removed and the residue was purified via flash chromatography (eluting with a gradient of 100% heptane to 100% ethyl acetate and then to 10% ammonia (7 N in methanol-90% ethyl acetate) to give the title compound as a light yellow solid (402 mg, 82% yield (over 2 steps)). $^1$H NMR (400 MHz, DMSO-d6) δ ppm 9.62 (s, 1 H) 7.98 (s, 1 H) 7.91 (s, 1 H) 7.80 (d, J=5.75 Hz, 1 H) 7.71 (s, 1 H) 7.27-7.41 (m, 5 H) 4.98-5.30 (m, 3 H) 4.55-4.68 (m, 1 H) 4.16-4.34 (m, 1 H) 3.76-3.96 (m, 6 H) 3.64-3.71 (m, 1 H) 1.50 (d, J=6.72 Hz, 6 H). $^{19}$F NMR (376 MHz, DMSO-d6) δ ppm −178.93 (br. s., 1F). m/z (APCI+) for $C_{24}H_{28}FN_9O_2$ 494.2 (M+H)$^+$. Chiral purity was determined as below (using racemic sample to compare):

Chiralcel OD-H 4.6×100 mm column with gradient of 5-60% MeOH/DEA in $CO_2$ over 3 minutes at 120 bar, 4 mL/min. Title sample shows ~88 (2.50 min):12 (2.75 min) ratio, ~76% ee. $[α]D_{22}$=+15.6° (c 0.17, EtOH)

Step 4: Preparation of 2-((3R,4R)-3-amino-4-fluoropyrrolidin-1-yl)-9-isopropyl-N-(1-methyl-1H-pyrazol-4-yl)-9H-purin-6-amine

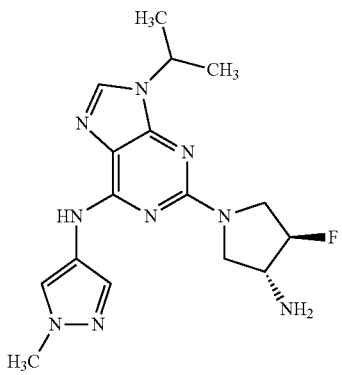 [SMILES: CC(C)n1cnc2c(Nc3cnn(C)c3)nc(N3C[C@@H](N)[C@H](F)C3)nc21]

A mixture of benzyl ((3R,4R)-4-fluoro-1-(9-isopropyl-6-((1-methyl-1H-pyrazol-4-yl)amino)-9H-purin-2-yl)pyrrolidin-3-yl)carbamate (390 mg, 0.8 mmol), ammonium formate (514 mg, 8 mmol) in ethanol (20 mL) was degassed for 3 min and 10%-Pd/C (50 mg) was then added. The reaction was stirred and heated to gentle reflux for 45 min. The catalyst was removed by filtration and washed well with ethanol (40 mL). The combined liquors were concentrated to give a residue, which was taken into water (5 mL) and extracted with DCM-isopropanol (9:1, 2×70 mL). The combined organic extracts were washed with saturated $NaHCO_3$ (5 mL), dried over $Na_2SO_4$ and evaporated to give the title compound as a light yellow solid (272 mg, 96% yield). $^1$H NMR (400 MHz, DMSO-d6) δ ppm 9.58 (s, 1 H) 8.00 (s, 2 H) 7.90 (s, 2 H) 7.73 (s, 1 H) 4.89-5.08 (m, 1 H) 4.56-4.66 (m, 1 H) 3.86-4.00 (m, 1 H) 3.81-3.85 (m, 3 H) 3.58-3.80 (m, 3 H) 3.53 (d, J=11.13 Hz, 1 H) 1.51 (d, J=6.72 Hz, 6 H). $^{19}$F NMR (376 MHz, DMSO-d6) δ ppm −177.42 (s, 1F). m/z (APCI+) for $C_{16}H_{22}FN_9$ 360.2 (M+H)$^+$. Chiral purity was determined as below (using racemic sample to compare):

Chiralcel OD-H 4.6×100 mm column with gradient of 5-60% MeOH/DEA in $CO_2$ over 3 min at 120 bar, 4 mL/min. Title sample showed ~86 (2.04 min):14 (2.21 min) ratio, ~72% ee. $[α]D_{22}$=+4.5° (c 0.14, EtOH).

Step 5: Preparation of N-((3R,4R)-4-fluoro-1-(9-isopropyl-6-((1-methyl-1H -pyrazol-4-yl)amino)-9H-purin-2-yl)pyrrolidin-3-yl)acrylamide

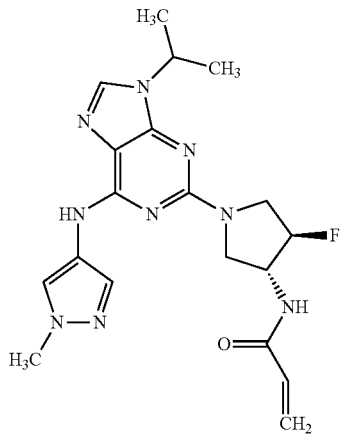 [SMILES: C=CC(=O)N[C@@H]1CN(c2nc(Nc3cnn(C)c3)c3ncn(C(C)C)c3n2)C[C@H]1F]

A mixture of 2-((3R,4R)-3-amino-4-fluoropyrrolidin-1-yl)-9-isopropyl-N-(1-methyl-1H-pyrazol-4-yl)-9H-purin-6-amine (260 mg, 85% purity, corrected 0.62 mmol) in DCM:tert-PentOH (20 mL: 2 mL) and sat. aq. NaHCO₃ (6 mL) was stirred at ambient temperature for 5 min. Acryloyl chloride (60 µL, 0.74 mmol, 1.2 mol eq) was added and stirring continued for 30 min. The organic layer was separated and the aqueous layer was extracted with more DCM:tert-PentOH (2×20 mL: 2 mL). The combined organic layers were dried over Na₂SO₄ and evaporated to give a residue; chiral purity was determined as below:

Chiralpak AD-H 4.6×250 mm column, 30% EtOH at 140 bar, 3 mL/min (~80 ee, [α]D₂₂=+17.1° (c 1.0, EtOH)).

The title product was further purified using chiral SFC (preparative method: Chiralpak AD-H (5µ) 21.2×250 mm column, 36° C., eluted with 30% EtOH (HPLC grade, 200 proof) in CO₂ held at 100 bar, 60.0 mL/min) to give the title compound as a white solid (124 mg, 49% yield) at >99% ee with optical rotation [α]D₂₂=+47.8° (c 0.13 EtOH). ¹H NMR (400 MHz, DMSO-d6) δ ppm 9.65 (s, 1 H) 8.48 (d, J=6.48 Hz, 1 H) 8.00 (s, 1 H) 7.93 (s, 1 H) 7.71 (s, 1 H) 6.09-6.30 (m, 2 H) 5.59-5.66 (m, 1 H) 5.06-5.25 (m, 1 H) 4.63 (quin, J=6.76 Hz, 1 H) 4.50 (dt, J=11.65, 5.85 Hz, 1 H) 3.85-3.96 (m, 2 H) 3.83 (s, 3 H) 3.71 (d, J=11.86 Hz, 2 H) 1.51 (d, J=6.72 Hz, 6 H). ¹⁹F NMR (376 MHz, DMSO-d6) δ ppm −177.73 (s, 1F). m/z (APCI+) for C₁₉H₂₄FN₉O 414.1 (M+H)⁺.

Example 3

(Scheme B): Preparation of N-(3-((9-isopropyl-6-((1-methyl-1H-pyrazol -4-yl)amino)-9H-purin-2-yl)oxy)phenyl)acrylamide trifluoroacetate

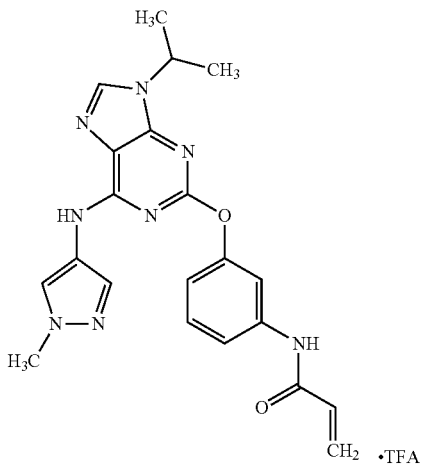 [SMILES: C=CC(=O)Nc1cccc(Oc2nc(Nc3cnn(C)c3)c3ncn(C(C)C)c3n2)c1]

Step 1: Preparation of 9-isopropyl-N-(1-methyl-1H-pyrazol-4-yl)-2-(3-nitrophenoxy)-9H-purin-6-amine

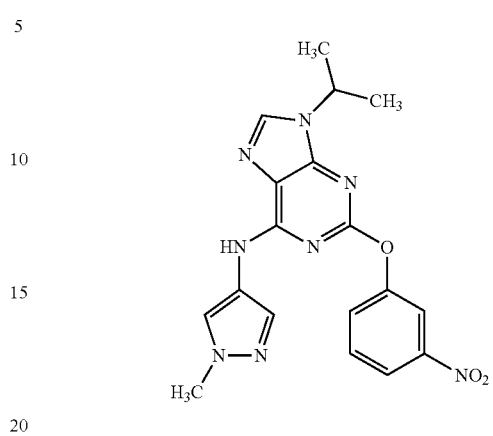

To a solution of 3-nitro-phenol (143 mg, 1.03 mmol) in DMF (15 mL) was added sodium hydride (56 mg, 1.4 mmol) slowly and the mixture was stirred at rt for 30 min. 2-chloro-9-isopropyl-N-(1-methyl-1H-pyrazol-4-yl)-9H-purin-6-amine (200 mg, 0.69 mmol), as prepared in step 1 of Example 2, was added slowly. After the addition, the mixture was stirred at 110° C. overnight. The cooled reaction mixture was poured into water (100 mL) and extracted with EtOAc (2×30 mL). The combined organic extracts were dried over Na₂SO₄, concentrated and the residue was purified by flash column chromatography (MeOH:EtOAc=1:10) to give the title compound (50 mg, 18% yield) as light yellow oil.

Step 2: Preparation of 2-(3-aminophenoxy)-9-isopropyl-N-(1-methyl-1H-pyrazol -4-yl)-9H-purin-6-amine

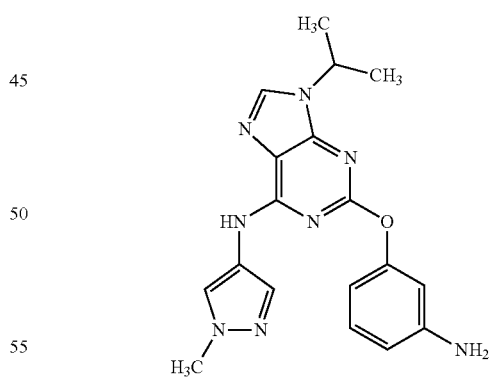

A mixture of 9-isopropyl-N-(1-methyl-1H-pyrazol-4-yl)-2-(3-nitrophenoxy)-9H-purin-6-amine (50 mg, 0.14 mmol), Fe (39 mg, 0.7 mmol), NH₄Cl (75 mg, 1.4 mmol) in EtOAc (10 mL) and water (10 mL) was stirred at rt overnight. The mixture was filtered and the filtrate was extracted with EtOAc (2×10 mL). The combined organic layers were dried over Na₂SO₄ and concentrated to give crude product (46 mg, 100% yield), which was used the next step directly without further purification.

Step 3: Preparation of N-(3-((9-isopropyl-6-((1-methyl-1H-pyrazol-4-yl)amino)-9H-purin-2-yl)oxy)phenyl)acrylamide trifluoroacetate

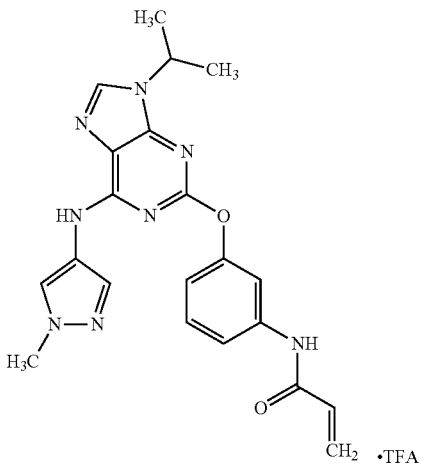 [SMILES: C=CC(=O)Nc1cccc(Oc2nc(Nc3cnn(C)c3)c3ncn(C(C)C)c3n2)c1]

To a solution of 2-(3-aminophenoxy)-9-isopropyl-N-(1-methyl-1H-pyrazol-4-yl)-9H-purin-6-amine (46 mg, 0.14 mmol) in EtOAc (10 mL) was added sat. aq. Na$_2$CO$_3$ (10 mL) and the mixture was stirred at rt for 10 min. Acryloyl chloride (15.2 mg, 0.17 mmol) was then added dropwise and the mixture was stirred at rt for 1 hr. The mixture was then extracted with EtOAc (2×10 mL) and the combined organic layers were washed with water (10 mL), brine (10 mL), dried over Na$_2$SO$_4$ and concentrated. The crude product was purified by preparative HPLC to give the title compound (15 mg, 26° A) yield) as a white solid. $^1$H NMR (400 MHz, DMSO-d$_6$) δ ppm 10.38 (s, 1 H), 10.18 (s, 1 H), 8.23 (s, 1 H), 7.62-7.63 (d, 2 H), 7.44-7.49 (t, 2 H), 7.33 (s, 1 H), 7.16 (s, 1 H), 6.94-6.96 (d, 1 H), 6.41-6.45 (t, 1 H), 6.23-6.27 (d, 1 H), 5.75-5.78 (d, 1 H), 4.67-4.70 (m, 1 H), 3.56 (s, 3 H), 1.53-1.54 (d, 6 H). m/z for C$_{21}$H$_{22}$N$_8$O$_2$ 419.0 (M+H)+.

Example 4

(Scheme D): Preparation of (S)-N-(1-(9-isopropyl-6-((1-methyl-1H-pyrazol-4-yl)amino)-9H-purin-2-yl)pyrrolidin-3-yl)acrylamide

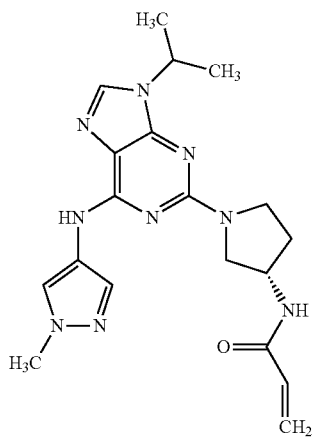 [SMILES: C=CC(=O)N[C@H]1CCN(c2nc(Nc3cnn(C)c3)c3ncn(C(C)C)c3n2)C1]

To a solution of 6-chloro-2-fluoro-9-isopropyl-9H-purine (200 mg, 0.932 mmol), as prepared in step 1 of the alternate method of Example 2, in nBuOH, (4.66 mL) was added 1-methyl-1H-pyrazol-4-amine (109 mg, 1.12 mmol) and DIPEA (482 mg, 3.73 mmol) and the mixture stirred at ambient temperature for 6 hr to yield crude 2-fluoro-9-isopropyl-N-(1-methyl-1H-pyrazol-4-yl)-9H-purin-6-amine. (S)-3-(methylsulfonyl)-N-(pyrrolidin-3-yl)propanamide hydrochloride (289 mg, 1.12 mmol) was then added to the reaction mixture and heated at 100° C. for 16 hr. LCMS showed unreacted intermediate so the reaction was heated at 110° C. for another 24 hr. The reaction was then cooled to ambient temperature and potassium tert-butoxide (3.73 mL, 3.73 mmol) was added and the resulting mixture stirred at ambient temperature for 30 min. Water was added and the reaction was extracted with DCM (3×50 mL), then the aqueous layer was extracted with ethyl acetate (2×50 mL). The combined organic layers were dried with Na$_2$SO$_4$, concentrated, loaded onto silica and purified via flash chromatography using 0-20% EtOH/EtOAc to give the title compound (290 mg, 78% yield) as a pink solid, 1H NMR (400 MHz, DMSO-d6) δ ppm 9.56 (s, 1 H) 8.38 (d, J=6.72 Hz, 1 H) 7.97 (s, 1 H) 7.89 (s, 1 H) 7.75 (s, 1 H) 6.20-6.34 (m, 1 H) 6.05-6.18 (m, 1 H) 5.60 (dd, J=10.03, 2.32 Hz, 1 H) 4.56-4.73 (m, 1 H) 4.43 (br. s., 1 H) 3.76-3.92 (m, 4 H) 3.68 (d, J=5.14 Hz, 2 H) 3.43-3.51 (m, 1 H) 2.15-2.28 (m, 1 H) 1.87-1.99 (m, 1 H) 1.51 (d, J=6.85 Hz, 6 H). m/z for C$_{19}$H$_{25}$N$_9$O 397.25 and 396.30 (M+H)+.

Example 5

(Scheme D): Preparation of N-((3R,4R)-4-fluoro-1-(6-((3-methoxy-1-(1-methylazetidin-3-yl)-1H-pyrazol-4-yl)amino)-9-methyl-9H-purin-2-yl)pyrrolidin-3-yl)acrylamide

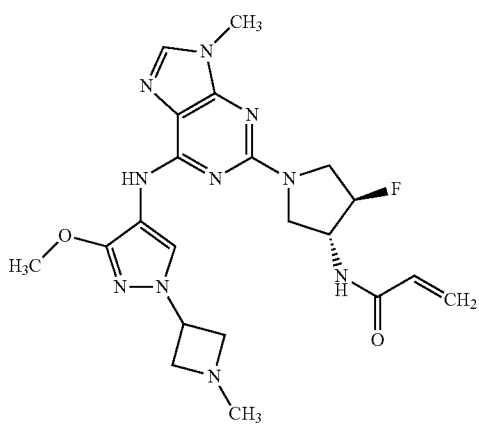 [SMILES: C=CC(=O)N[C@@H]1CN(c2nc(Nc3cn(C4CN(C)C4)nc3OC)c3ncn(C)c3n2)C[C@H]1F]

TFA (4 mL) was added to a solution of crude tert-butyl 3-(4-((2-((3R,4R)-3-fluoro-4-(3-(methylsulfonyl)propanamido)pyrrolidin-1-yl)-9-methyl-9H-purin-6-yl)amino)-3-methoxy-1H-pyrazol-1-yl)azetidine-1-carboxylate (theoretical 0.63 mmol, 1.00 eq)(prepared using the general methodology exemplified in Example 4) in DCM (50 mL). After stirring for 1 hr, the reaction mixture was concentrated to dryness and used in the next step without further purification.

To a solution of the amine generated above in MeOH (15 mL) was added diisopropylethyl amine (300 μL, 1.81 mmol, 2.87 eq), and aqueous formaldehyde solution (150 μL, 2.02 mmol, 3.21 eq, 37% by weight) and the reaction mixture was stirred at ambient temperature. After 15 min, NaBH₄ (65.0 mg, 1.72 mmol, 2.72 eq) was added and the reaction mixture was stirred for 11 hr. LCMS analysis showed the reaction was incomplete and additional portions of aqueous formaldehyde solution (500 μL, 6.73 mmol, 10.7 eq, 37% by weight) and NaBH₄ (250 mg, 6.61 mmol, 10.5 eq) were added. After an additional 1 hr, the reaction mixture was concentrated and used in the next step without further purification.

To a stirred solution of the crude N-methyl azetidine generated above in THF (25 mL) was added a solution of potassium tert-butoxide (2.50 mL, 2.50 mmol, 3.97 eq, 1 M). After 2 hr, the reaction mixture was treated with acetic acid (200 μL) and concentrated. The residue was suspended in DMSO, purified via reverse phase chromatography using a Xbridge Prep C18 column (250 mm×30 mm×5 μm) eluting with a gradient of 5% acetonitrile in water (0.1% HOAc) to 25% acetonitrile in water (0.1% HOAc), and lyophilized to give the title compound (53.7 mg, 16% yield) as a white solid. ¹H NMR (400 MHz, DMSO-d6) δ ppm 8.20 (br. s., 1 H) 8.14 (br. s., 1 H) 7.71 (br. s., 1 H) 6.24 (dd, J=10.0, 16.0 Hz, 1 H) 6.14 (d, J=16.0 Hz, 1 H) 5.60 (d, J=9.3 Hz, 1 H) 5.16 (d, J=51.0 Hz, 1 H) 4.80 (br. s., 1 H) 4.58-4.41 (m, 1 H) 3.99-3.77 (m, 7 H) 3.72-3.55 (m, 6 H). m/z (APCI+) for $C_{21}H_{28}FN_{10}O_2$ 471.2 (M+H)⁺.

Example 6

(Scheme E): Preparation of (−)-1-(3-(9-isopropyl-6-((1-methyl-1H-pyrazol-4-yl)amino)-9H-purin-2-yl)piperidin-1-yl)prop-2-en-1-one

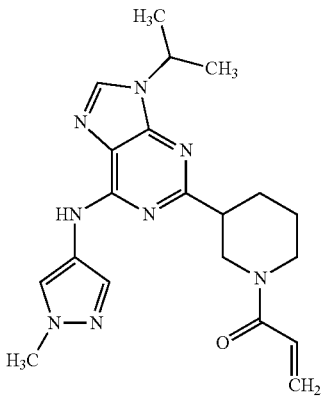 [SMILES: C=CC(=O)N1CCCC(c2nc(Nc3cnn(C)c3)c3ncn(C(C)C)c3n2)C1]

Step 1: Preparation of tert-butyl 3-(9-isopropyl-6((1-methyl-1H-pyrazol-4-yl)amino)-9H-purin-2-yl)-5,6-dihydropyridine-1(2H)-carboxylate

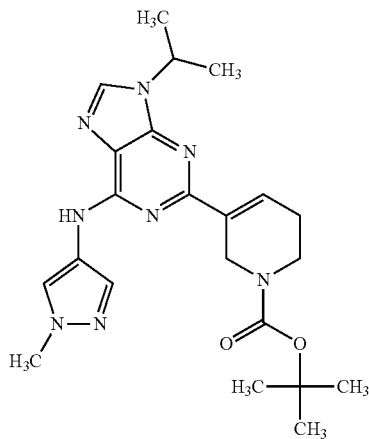 [SMILES: CC(C)n1cnc2c(Nc3cnn(C)c3)nc(C3=CCCN(C(=O)OC(C)(C)C)C3)nc21]

A mixture of 2-chloro-9-isopropyl-N-(1-methyl-1H-pyrazol-4-yl)-9H-purin-6-amine (600 mg, 2 mmol), as prepared in step 1 of Example 2, tert-butyl 5-(4,4,5,5-tetramethyl-1,3,2-dioxaborolan-2-yl)-3,6-dihydropyridine-1(2H)-carboxylate (700 mg, 2.3 mmol, 1.1 mol eq), tripotassium phosphate (1.11 g, 5.1 mmol, 2.5 mol eq), PdCl₂(dppf) (75 mg, 0.1 mmol, 0.05 mol eq) in dioxane (10 mL) and water (5 mL) was degassed, stirred and heated at 80° C. (using microwave at normal absorption level) for 30 min. The reaction was then diluted with ethyl acetate (120 mL), washed with brine (20 mL), dried over Na₂SO₄ and evaporated to give a residue that was purified via flash chromatography with gradients from 50% ethyl acetate-50% heptane to 100% ethyl acetate and then to 10% ammonia (7 N in methanol)-90% ethyl acetate to give the title product as a red solid (901 mg, 100% yield). ¹H NMR (400 MHz, DMSO-d6) δ ppm 9.89 (s, 1 H) 8.29 (s, 1 H) 8.00 (br. s., 1 H) 7.79 (br. s., 1 H) 7.22 (br. s., 1 H) 4.77 (dt, J=13.39, 6.76 Hz, 1 H) 4.45 (br. s., 2 H) 3.84 (s, 3 H) 3.50 (t, J=5.38 Hz, 2 H) 2.36 (d, J=3.18 Hz, 2 H) 1.57 (d, J=6.72 Hz, 6 H) 1.44 (s, 9 H). m/z (APCI+) for $C_{22}H_{30}N_8O_2$ 439.3 (M+H)⁺.

Step 2: Preparation of tert-butyl 3-(9-isopropyl-6-((1-methyl-1H-pyrazol-4-yl)amino)-9H-purin-2-yl)piperidine-1-carboxylate

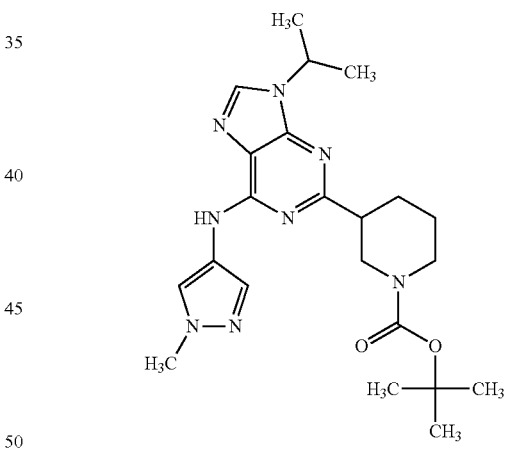

A solution of tert-butyl 3-(9-isopropyl-6-((1-methyl-1H-pyrazol-4-yl)amino)-9H-purin-2-yl)-5,6-dihydropyridine-1(2H)-carboxylate (821 mg, 1.87 mmol) in ethanol (35 mL) was degassed with nitrogen and to this was added 10%-Pd/C (150 mg), and ammonium formate (650 mg, 10 mmol). The resulting mixture was stirred and heated at 60° C. for 3 hr. The reaction was cooled to ambient temperature and the catalyst was removed by filtration. The filtrate was evaporated to give a residue, which was taken into ethyl acetate (100 mL) and the solution washed with water (30 mL), brine (30 mL), dried over Na₂SO₄ and evaporated to give a residue that was purified via flash chromatography with a gradient from 100% heptane to 100% ethyl acetate to afford the title compound (620 mg), which was used in the following step.

71

Step 3: Preparation of 9-isopropyl-N-(1-methyl-1H-pyrazol-4-yl)-2-(piperidin-3-yl) -9H-purin-6-amine

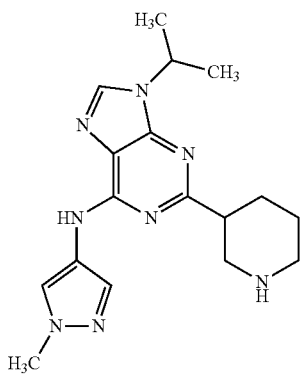 [SMILES: CC(C)n1cnc2c(Nc3cnn(C)c3)nc(C3CCCNC3)nc21]

To a solution of tert-butyl 3-(9-isopropyl-6-((1-methyl-1H-pyrazol-4-yl)amino)-9H-purin-2-yl)piperidine-1-carboxylate (620 mg) in DCM (15 mL) was added TFA (1.2 mL). The resulting solution was stirred at ambient temperature for 1 hr. The volatiles were removed to give the crude title compound that was used in the next step without further purification.

Step 4: Preparation of (−)-1-(3-(9-isopropyl-6-((1-methyl-1H-pyrazol-4-yl)amino) -9H-purin-2-yl)piperidin-1-yl)prop-2-en-1-one

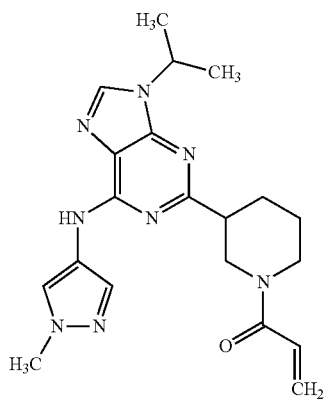 [SMILES: C=CC(=O)N1CCCC(c2nc(Nc3cnn(C)c3)c3ncn(C(C)C)c3n2)C1]

To 9-isopropyl-N-(1-methyl-1H-pyrazol-4-yl)-2-(piperidin-3-yl)-9H-purin-6-amine from the previous reaction was added sat. aq. NaHCO$_3$ (12 mL) and ethyl acetate (30 mL). The mixture was stirred for 10 min, and acryloyl chloride (148 μL, 1.8 mmol) was added and stirred at ambient temperature for 15 min. The organic layer was separated, and the aqueous layer was extracted with ethyl acetate (30 mL). The combined organics were dried over Na$_2$SO$_4$ and evaporated to give a foamy solid (600 mg) that was subjected to chiral SFC purification to separate the two enantiomers (Chiralcel OJ-H 4.6×250 mm column, 20% EtOH, 140 bar, 3.0 mL/min). Peak 1(+) eluted at 3.18 min. Peak 2 (−) as the title product eluted at 5.03 min) (86.4 mg, ~98% ee, 16% yield in 3 steps). [α]$_{D22}$=−76.0° (c 0.14, EtOH). $^1$H NMR (700 MHz, DMSO-

72

17 mm) δ ppm 9.87 (br. s., 1 H) 8.28 (br. s., 1 H) 7.96-8.13 (m, 1 H) 7.74 (d, J=7.26 Hz, 1 H) 6.76-6.91 (m, 1 H) 5.99-6.17 (m, 1 H) 5.53-5.75 (m, 1 H) 4.69-4.84 (m, 2 H) 4.03-4.30 (m, 2 H) 3.84 (s, 3 H) 2.74-3.02 (m, 2 H) 2.11-2.28 (m, 1 H) 1.75-2.01 (m, 2 H) 1.54 (d, J=2.64 Hz, 7 H). m/z (APCI+) for C$_{20}$H$_{26}$N$_8$O 395.1 (M+H)$^+$.

Example 7

(Scheme F): Preparation of N-((3R,4R)-4-fluoro-1-(6-((3-methoxy-1-methyl-1H-pyrazol-4-yl)amino)-9-methyl-9H-purin-2-yl)pyrrolidin-3-yl)acrylamide

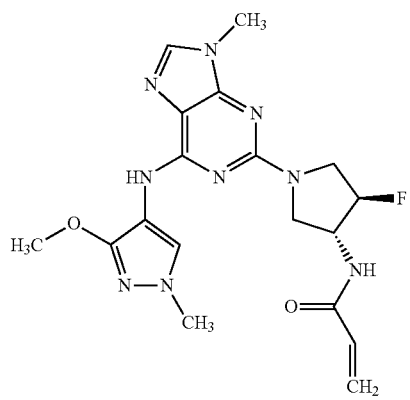 [SMILES: C=CC(=O)N[C@@H]1CN(c2nc(Nc3cn(C)nc3OC)c3ncn(C)c3n2)C[C@H]1F]

Step 1: Preparation of 2-fluoro-N-(3-methoxy-1-methyl-1H-pyrazol-4-yl)-9H-purin -6-amine

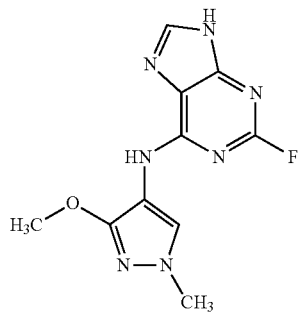 [SMILES: COc1nn(C)cc1Nc1nc(F)nc2[nH]cnc12]

A suspension of 6-chloro-2-fluoro-9H-purine (5.49 g, 31.8 mmol, 1.00 eq), 3-methoxy-1-methyl-1H-pyrazol-4-amine hydrochloride (6.60 g, 40.34 mmol, 1.26 eq), and N,N-diisopropylethylamine (16.6 mL, 95.5 mmol, 3.00 eq) in DMSO (31.8 mL) was stirred at ambient temperature for 19 hr. The reaction mixture was then concentrated in vacuo at 50° C., poured into water (250 mL), and stirred vigorously at 0° C. for 1 hr. The resulting solids were filtered off, washed with ice cold water (20 mL), and dried for 16 hr at 50° C. to give the title compound (7.26 g, 87% yield, 96% purity) as a light yellow solid. $^1$H NMR (400 MHz, DMSO-d6) δ ppm 13.03 (br. s., 1 H) 9.21 (br. s., 1 H) 8.18 (br. s., 1 H) 7.74 (br. s., 1 H) 3.81 (br. s., 3 H) 3.71 (s, 3H). m/z (APCI+) for C$_{10}$H$_{11}$FN$_7$O 264.2 (M+H)$^+$.

Step 2: Preparation of 2-fluoro-N-(3-methoxy-1-methyl-1H-pyrazol-4-yl)-9-methyl-9H-purin-6-amine

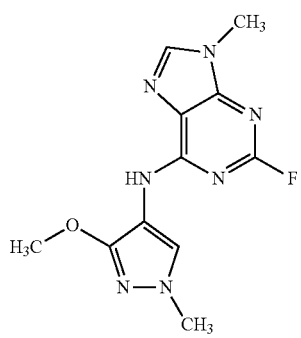 [SMILES: COc1nn(C)cc1Nc1nc(F)nc2c1ncn2C]

To a vigorously stirred suspension of 2-fluoro-N-(3-methoxy-1-methyl-1H-pyrazol-4-yl)-9H-purin-6-amine (7.25 g, 27.5 mmol, 1.00 eq) and potassium carbonate (7.61 g, 55.1 mmol, 2.00 eq) in 1,4-dioxane (92.0 mL), was added dimethyl sulfate (2.90 mL, 30.3 mmol, 1.10 eq) in a dropwise manner over 3 min. After 4 hr, additional portions of 1,4-dioxane (50.0 mL), potassium carbonate (3.80 g, 27.5 mmol, 1.00 eq), and dimethyl sulfate (1.00 mL, 10.4 mmol, 0.30 eq) were added to the reaction mixture. After a further 16 hr, the reaction mixture was concentrated in vacuo, diluted with water (120 mL), and stirred at ambient temperature for 1 hr. The resulting solids were filtered, washed with water (20 mL), and dried for 16 hr at 60° C. to give the title compound (6.42 g, 84% yield, >95% purity) as a light yellow solid. $^1$H NMR (400 MHz, DMSO-d6) δ ppm 9.23 (br. s., 1 H) 8.13 (br. s., 1 H) 7.67 (s, 1 H) 3.78 (s, 3 H) 3.70 (s, 3 H) 3.69 (br. s., 3 H). m/z (APCI+) for $C_{11}H_{13}FN_7O$ 278.2 (M+H)$^+$.

Step 3: Preparation of N-((3R,4R)-4-fluoro-1-(6-((3-methoxy-1-methyl-1H-pyrazol-4-yl)amino)-9-methyl-9H-purin-2-yl)pyrrolidin-3-yl)acrylamide

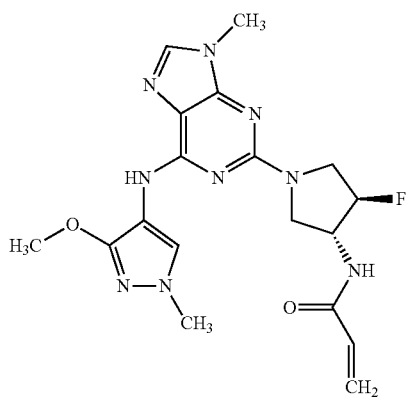 [SMILES: C=CC(=O)N[C@@H]1CN(c2nc(Nc3cn(C)nc3OC)c3ncn(C)c3n2)C[C@H]1F]

To a stirred suspension of 2-fluoro-N-(3-methoxy-1-methyl-1H-pyrazol-4-yl)-9-methyl-9H-purin-6-amine (554 mg, 2.00 mmol, 1.00 eq) and N-((3R,4R)-4-fluoropyrrolidin-3-yl)-3-(methylsulfonyl)propanamide (500 mg, 2.10 mmol, 1.05 eq) in DMSO (4.2 mL) was added N,N-diisopropylethylamine (0.83 mL, 5.00 mmol, 2.50 eq). The reaction mixture was then heated at 100° C. for 16 hr, cooled to ambient temperature, diluted with THF (4 mL), and treated with potassium tert-butoxide (4.00 mL, 1 M in THF, 2.00 eq). After 1 hr, an additional portion of potassium tert-butoxide (0.50 mL, 1 M in THF, 0.25 eq) was added to the reaction mixture. After a further 1 hr, the reaction mixture was poured into phosphate buffer (50 mL, pH=7) and water (50 mL), and extracted with ethyl acetate (5×40 mL). The combined organic layers were combined, dried (Na$_2$SO$_4$), and concentrated under reduced pressure. This crude product was then dissolved in ethyl acetate (40 mL) at 60° C. and then treated with heptanes (20 mL), at which point the solution became cloudy and was allowed to cool to ambient temperature and then to 0° C. After 16 hr at 0° C., the resulting solids were filtered and dried at ambient temperature to give the title compound (620.5 mg, 75% yield) as a white powder. $^1$H NMR (400 MHz, DMSO-d6) δ ppm 8.44 (d, J=6.5 Hz, 1 H) 7.97 (s, 1 H) 7.82 (s, 1 H) 7.78 (s, 1 H) 6.23 (dd, J=10.0, 17.0 Hz, 1 H) 6.14 (dd, J=2.8, 17.0 Hz, 1 H) 5.62 (dd, J=2.8, 10.0 Hz, 1 H) 5.12 (d, J=51.0 Hz, 1 H) 4.46 (td, J=6.0, 11.9 Hz, 1 H) 3.88-3.6 (m, 4 H) 3.82 (s, 3 H) 3.71 (s, 3 H) 3.62 (s, 3 H). m/z (APCI+) for $C_{18}H_{23}FN_9O_2$ 416.3 (M+H)$^+$.

Example 7A (Scheme F): Preparation of N-((3R,4R)-4-fluoro-1-(6-((3-methoxy-1-methyl-1H-pyrazol-4-yl)amino)-9-methyl-9H-purin-2-yl)pyrrolidin-3-yl)acrylamide

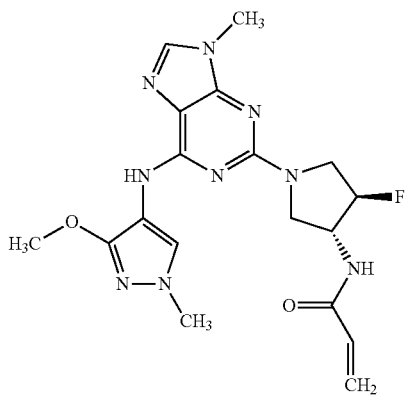 [SMILES: C=CC(=O)N[C@@H]1CN(c2nc(Nc3cn(C)nc3OC)c3ncn(C)c3n2)C[C@H]1F]

Preparation Step 1A: Preparation of (3R,4R)-1-benzyl-3,4-dihydroxypyrrolidine-2,5-dione

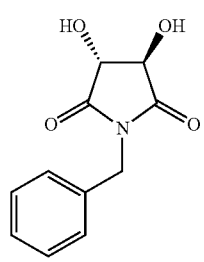 [SMILES: O=C1[C@H](O)[C@@H](O)C(=O)N1Cc1ccccc1]

A mixture of xylene, (1.2 L), benzylamine (120 g, 1.10 mol, 1.0 eq) and L-(+)-tartaric acid (173 g, 1.15 mol, 1.05 eq) were heated at 135° C. for 12 hr (flask jacket temperature). Upon reaction completion, the mixture was cooled to 65° C.

and MeOH (120 mL, 1 vol) was added. The resulting mixture was stirred for 1 hr and the resulting suspension was cooled to 20° C. followed by the addition of EtOAc (480 mL). Stirring was continued at 10° C. for 2 hr. The crude product was isolated by filtration and washed with EtOAc (120 mL) and dried on the filter. The crude product was then taken up in MeOH (480 mL) and heated at a gentle reflux for 1 hr, then cooled to 20° C. and granulated for 1 hr. The suspension was filtered and the precipitate washed with MeOH (240 mL) and dried to give the title compound (191 g, 864 mmol, 79%) as a white granular solid. $^1$H NMR (400 MHz, DMSO-d6) δ ppm 7.38-7.30 (m, 2H) 7.30-7.22 (m, 3 H) 6.32 (br. s., 1 H) 4.59 (d, J=14.8 Hz, 1 H) 4.53 (d, J=14.8 Hz, 1 H) 4.40 (br. D., J=4.3 Hz, 2 H). m/z (EI+) for $C_{11}H_{11}NO_4$ 221.0 (M)$^+$.

Preparation Step 2A: Preparation of (3S,4S)-1-benzylpyrrolidine-3,4-diol

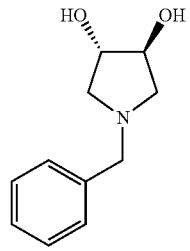 [SMILES: O[C@H]1CN(Cc2ccccc2)C[C@@H]1O]

To a mixture of (3R,4R)-1-benzyl-3,4-dihydroxypyrrolidine-2,5-dione (44 g, 199 mmol, 1.0 eq) and THF (176 mL) at 20° C. (vessel jacket temperature) was added borane-tetrahydrofuran complex (1.0 mol/L) in THF (800 mL, 800 mmol, 1.0 mol/L, 4.0 eq) at a rate to maintain the temperature between 20° C. and 25° C. Over 1 hr, the jacket temperature was ramped to 60° C. and then held for 1 hr. Upon completion, the reaction was cooled to 30° C. and quenched by the slow dropwise addition of MeOH (97 mL, 12 eq) to the mixture at a rate to control off gassing. The reaction mixture was then heated to reflux and concentrated to a low stir volume. The reaction solvent THF was then replaced by a constant volume displacement with MeOH (total of 1.5 L). Once the THF content had been reduced to less than 1 wt %, MeOH was replaced by a constant volume displacement with EtOAc (total of 1.5 L) to reduce the MeOH content to less than 1 wt %. The total volume of EtOAc was then readjusted to about 250 mL (6 vol) and then cooled to 5° C. to crystallize the product. The desired product was isolated by filtration, washed with cold EtOAc (88 mL) and dried to give title compound (27.0 g, 140 mmol, 70%). A second crop of product was isolated by concentration of the combined filtrate and cake wash to half volume, which was then cooled to 5° C., filtered and washed with cold EtOAc (50 mL) to afford additional title compound (4.5 g, 23 mmol, 12%). $^1$H NMR (400 MHz, DMSO-d6) δ ppm 7.33-7.26 (m, 4 H) 7.25-7.20 (m, 1 H) 4.48 (d, J=4.8 Hz, 2 H) 3.38-3.31 (m, 2 H), 3.57 (d, J=13.0 Hz, 1 H) 3.46 (d, J=13.0 Hz, 1 H) 2.74 (dd, J=9.4, 5.9 Hz, 2 H) 2.30 (dd, J=9.4, 4.4 Hz, 2 H). m/z (EI+) for $C_{11}H_{15}NO_2$ 194.2 (M+H)$^+$.

Preparation Step 3A: Preparation of (3aR,6aS)-5-benzyl-2,2-dioxo-tetrahydro-1-oxa-2λ$^6$-thia-3-5-diaza-pentalene-3-carboxylic acid t-butyl ester

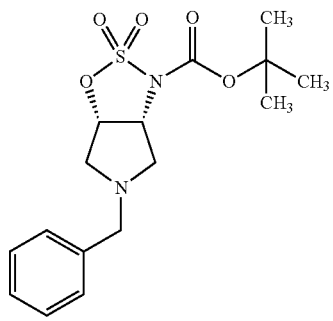 [SMILES: CC(C)(C)OC(=O)N1[C@@H]2CN(Cc3ccccc3)C[C@@H]2OS1(=O)=O]

To a 5 L jacketed reactor (Reactor 1) was added 1,4-dioxane (1.8 L), (3S,4S)-1-benzylpyrrolidine-3,4-diol (180 g, 0.932 mol, 1.0 eq) and TEA (792 mL, 5.68 mol, 6.1 eq) and the resulting mixture stirred at 10° C.

To a 2 L jacketed reactor (Reactor 2) was added 1,4-dioxane (1.6 L) and chlorosulfonyl isocyanate (596 g, 2.80 mol, 3.0 eq) and the resulting solution was cooled to 10° C. A solution of tert-butanol (211 g, 2.85 mol, 3.05 eq) in 1,4-dioxane (180 mL) was added over 45 min while maintaining the temperature between 10° C. and 20° C., and the resulting solution was then stirred for 15 min at 10° C.

The solution in Reactor 2 was transferred to Reactor 1 over 50 min while controlling the internal temperature of Reactor 1 from 10° C. to 20° C. Once the addition was complete, the jacket temperature was warmed at 20° C. and the resulting mixture was stirred for 16 hr. When UPLC analysis confirmed that the bis-alkylated intermediate was fully formed (target <3% mono-alkylated intermediate), the entire batch was filtered and the filtrate was sent into a clean reactor. The residual TEA-HCl cake was washed with dioxane (300 mL) and the wash was combined with the filtrate. The resulting dioxane solution was then heated to 80° C. and held for 3 hr. After sampling for reaction completion (<1% intermediate remaining), the batch was distilled (pot temp=80° C.) under partial vacuum (400 mbar) to less than half volume. The reaction mixture was diluted with EtOAc (2 L) and washed twice with water (2×2 L). The mixture was then washed with 0.5 N sodium bicarbonate (2 L) and then dried over sodium sulfate (360 g, 2 wt eq) and filtered into a clean dry reactor. The EtOAc solution was concentrated under partial vacuum to about 400 mL total volume resulting in the formation of a thick slurry. The mixture was cooled to 0° C. and stirred for 1 hr and then filtered and washed with cold EtOAc (200 mL) and then dried in a vacuum oven at 40° C. to give 173 g of the title compound. A second crop of product was isolated by concentrating the filtrate and then cooling, granulating and filtering to give an additional 28.4 g of the desired product. In total, the title compound was isolated in 61% yield (201 g, 568 mmol). $^1$H NMR (400 MHz, DMSO-d6) δ ppm 7.37-7.29 (m, 4 H) 7.29-7.23 (m, 1 H) 5.36 (dd, J=7.3, 3.8 Hz, 1 H) 4.79-4.73 (m, 1 H) 4.48 (d, J=4.8 Hz, 2 H) 3.38-3.31 (m, 2 H), 3.70 (d, J=13.4 Hz, 1 H) 3.62 (d, J=13.4 Hz, 1 H) 3.13-2.99 (m, 2 H) 2.48-2.40 (m, 2 H) 1.46 (s, 9 H). m/z (EI+) for $C_{16}H_{22}N_2O_5S$ 355.2 (M+H)$^+$.

Preparation Step 4A: Preparation of (3R,4R)-1-benzyl-4-fluoropyrrolidin-3-amine bis-tosylate

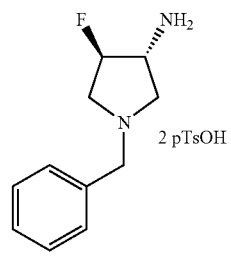 [SMILES: N[C@@H]1CN(Cc2ccccc2)C[C@H]1F]

A solution of 1M tetrabutylammonium fluoride in THF (1.27 L, 1.27 mol, 2.5 eq) and (3aR,6aS)-5-benzyl-2,2-dioxotetrahydro-1-oxa-2$\lambda^6$-thia-3-5-diaza-pentalene-3-carboxylic acid t-butyl ester (180 g, 0.508 mol, 1.0 eq) were heated at 60° C. (jacket temperature) for 2 hr. Upon reaction completion, the mixture was partially distilled under vacuum to remove the THF. After concentration to a low stir volume, THF was displaced with EtOAc (2×500 mL). After again reducing to a low stir volume, EtOAc (3.6 L) and p-toluenesulfonic acid monohydrate (396 g, 2.10 mol, 4.1 eq) were charged and heated at 80° C. for 2 hr. The mixture was cooled to 10° C. over 1.5 hr and then granulated at 10° C. for 2 hr. The solid product was filtered and washed with EtOAc (2×900 mL) and dried at 50° C. in a vacuum oven for 12 hr. The title compound was isolated as an air stable crystalline solid in 83% yield (231 g, 419 mmol). $^1$H NMR (400 MHz, D$_2$O) δ ppm 7.69-7.61 (m, 4 H) 7.56-7.42 (m, 5 H) 7.36-7.29 (m, 4 H) 5.65-5.49 (m, 1 H) 4.47 (br. s., 2H) 4.37-4.23 (m, H) 4.15 (ddd, J=12.8, 8.2, 1.4 Hz, 1 H) 3.88 (dd, J=19.1, 1.2 Hz, 1 H), 3.74 (ddd, J=33.2, 14.0, 5.5 Hz, 1 H) 3.44 (dd, J=12.8, 8.2 Hz, 1 H) 2.34 (s, 6 H). m/z (EI+) for C$_{11}$H$_{15}$FN$_2$ 194.8 (M+H)$^+$.

Preparation Step 5A: N-((3R,4R)-1-benzyl-4-fluoropyrrolidin-3-yl)-3-(methylsulfonyl)propanamide

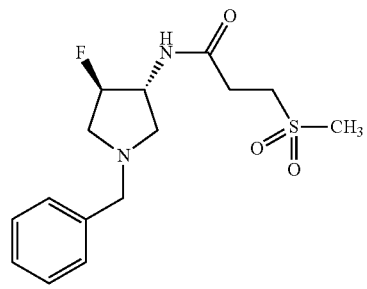 [SMILES: CS(=O)(=O)CCC(=O)N[C@@H]1CN(Cc2ccccc2)C[C@H]1F]

A suspension of 1,1'-carbonyldiimidazole (73.0 g, 441 mmol, 1.1 eq) in acetonitrile (3.3 L) was stirred at 20° C. until a clear solution was obtained. 3-(methylsulfonyl)propanoic acid (67.0 g, 440 mmol, 1.1 eq) was then added and the mixture was stirred at 25° C. for 3 hr. (3R,4R)-1-benzyl-4-fluoropyrrolidin-3-amine bis-tosylate (220 g, 400 mmol, 1.0 eq) was added and the mixture was stirred at 25° C. for 16 hr resulting in a fine white slurry. The solids were filtered off and the byproduct cake washed with acetonitrile (600 mL). The acetonitrile solution was then concentrated to a low stir volume and then taken up in EtOAc (2.0 L) and washed with 1 N aqueous sodium bicarbonate (1.3 L). The aqueous layer was back extracted with EtOAc (500 mL) and the combined EtOAc layers were washed with water (1.0 L). The resulting EtOAc solution was distilled to remove about 2.0 L of distillate and then displaced with 2-propanol under atmospheric conditions until the internal temperature rose to 78° C. while maintaining a total volume of 2 L. The batch was then cooled to 20° C. and granulated at 20° C. for 12 hr resulting in product crystallization. The desired product was isolated by filtration and the cake washed with 2-propanol (600 mL), then dried in an oven at 40° C. under reduced pressure for 12 hr. The title compound (108 g, 308 mmol) was isolated in 77% yield. $^1$H NMR (400 MHz, DMSO-d6) δ ppm 8.36 (br. d., J=7.0 Hz, 1 H) 7.37-7.29 (m, 4 H) 7.29-7.23 (m, 1 H) 4.90 (ddt, J=53.4, 5.3, 2×1.7 Hz, 1 H) 4.25 (dddd, J=26.4, 13.9, 7.0, 1.4 Hz, 1 H) 3.61 (d, J=13.2 Hz, 1 H) 3.57 (d, J=13.2 Hz, 1 H) 3.36-3.28 (m, 2 H) 3.03 (dd, J=9.3, 7.5 Hz, 1 H) 2.97 (s, 3 H) 2.80 (dd, J=24.0, 11.6 Hz, 1 H) 2.66 (ddd, J=30.6, 11.6, 5.3 Hz, 1 H) 2.57 (td, 2×7.7, 1.4 Hz, 2 H) 2.18 (dd, J=9.4, 6.7 Hz, 1 H). m/z (EI+) for C$_{15}$H$_{21}$FN$_2$O$_3$S 329.7 (M+H)$^+$.

Preparation Step 6A: N-((3R,4R)-4-fluoropyrrolidin-3-yl)-3-(methylsulfonyl)propanamide

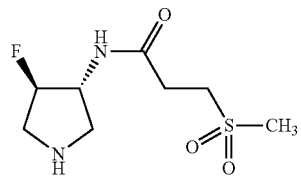

To a Parr reactor was added N-((3R,4R)-1-benzyl-4-fluoropyrrolidin-3-yl)-3-(methylsulfonyl)propanamide (86.5 g, 263 mmol, 1.0 eq), palladium hydroxide (20% on carbon, 2.59 g, 3.69 mmol, 3 wt/wt %) and MeOH (430 mL). The reactor was purged three times with nitrogen (50 psi) and then purged three times with hydrogen (20 psi). The reactor was heated at 50° C. and then pressurized to 50 psi while stirring at 1200 rpm. The material was hydrogenated for 7 hr and then cooled to 20° C. and purged with nitrogen. The mixture was filtered to remove the catalyst and the cake was washed with MeOH (173 mL). The combined filtrate and wash were concentrated to about 200 mL followed by addition of MTBE (200 mL) and then concentrated to a low stir volume. Additional MTBE (200 mL) was added and the resulting slurry granulated at 20° C. for 16 hr. The desired product was isolated by filtration, washed with MTBE (300 mL) and then dried in an oven at 40° C. for 12 hr. The title compound was isolated in 90% yield (53.3 g, 224 mmol) as a white crystalline solid. $^1$H NMR (400 MHz, DMSO-d6) δ ppm 8.15 (br. d., J=6.8 Hz, 1 H) 4.96-4.78 (m, 1 H) 4.14-4.01 (m, 1 H) 3.32 (dd, J=8.0, 7.3 Hz, 2 H) 3.13 (dd, J=11.8, 6.8 Hz, 1 H) 3.01-2.93 (m, 1 H) 2.98 (s, 3 H) 2.88 (d, J=3.0 Hz, 1 H) 2.60 (br. s., 1 H) 2.5 7-2.52 (m, 3 H). m/z (EI+) for C$_8$H$_{15}$FN$_2$O$_3$S 239.1 (M+H)$^+$.

Step 1: Preparation of 2-fluoro-N-(3-methoxy-1-methyl-1H-pyrazol-4-yl)-9H-purin-6-amine

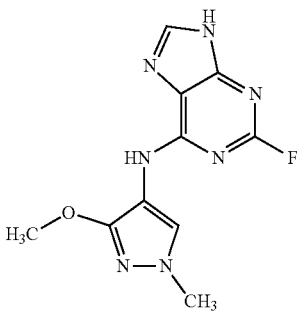 [SMILES: COc1nn(C)cc1Nc1nc(F)nc2[nH]cnc12]

A suspension of 6-chloro-2-fluoro-9H-purine (88% potency, 5.90 kg, 30.20 mol, 1.00 eq), 3-methoxy-1-methyl-1H-pyrazol-4-amine hydrochloride (98% potency, 5.55 kg, 33.22 mol, 1.10 eq), and sodium bicarbonate (10.1 kg, 120.81 mol, 4.00 eq) in EtOAc (106 L) was stirred at 50° C. for 12 hr. The reaction mixture was then cooled to 20° C., granulated for 1 hr, filtered, and the solids were washed with EtOAc (18 L) and dried on the filter. The crude product was charged back into the reactor and suspended in water (106 L) and stirred at 35° C. for 2 hr. The resulting slurry was cooled to 20° C. and the desired product was isolated by filtration and the cake was washed with water (30 L) and then with EtOAc (30 L) and dried for 16 hr at 50° C. to give the title compound (6.26 kg, 23.8 mol, 79% yield) as a light yellow solid. $^1$H NMR (400 MHz, DMSO-d6) δ ppm 13.03 (br. s., 1 H) 9.21 (br. s., 1 H) 8.18 (br. s., 1 H) 7.74 (br. s., 1 H) 3.81 (br. s., 3 H) 3.71 (s, 3 H). m/z (APCI+) for $C_{10}H_{11}FN_7O$ 264.2 (M+H)$^+$.

Step 2: Preparation of 2-fluoro-N-(3-methoxy-1-methyl-1H-pyrazol-4-yl)-9-methyl-9H-purin-6-amine

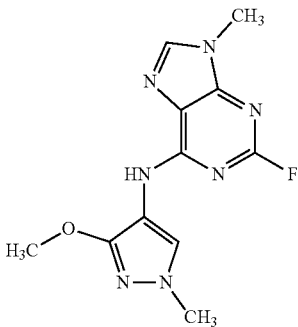 [SMILES: COc1nn(C)cc1Nc1nc(F)nc2c1ncn2C]

To a 100 L reactor fitted with a caustic scrubber was added 2-methyltetrahydrofuran (44.0 L), 2-fluoro-N-(3-methoxy-1-methyl-1H-pyrazol-4-yl)-9H-purin-6-amine (2.20 kg, 8.36 mol, 1.00 eq) and potassium phosphate tribasic (7.10 kg, 33.43 mol mmol, 4.00 eq). The resulting mixture was stirred at 5° C. and dimethyl sulfate (1.42 kg, 11.28 mol, 1.35 eq) was added and the resulting mixture was stirred at 5° C. for 1 hr. The reaction was warmed from 5° C. to 15° C. over 2 hr and then held at 15° C. for 20 hr. The reaction mixture was cooled to 5° C. and quenched with water (44.0 L) while maintaining the internal temperature below 10° C. The mixture was then heated at 50° C. for 2 hr and then cooled to 10° C. and granulated for 2 hr. The product was isolated by filtration and washed with water (11.0 L) and then with 2-methyltetrahydrofuran (11.0 L). The cake was dried under vacuum at 40° C. for 8 hr to give the title compound (1.99 kg, 7.18 mol, 86% yield) as an off white solid. $^1$H NMR (400 MHz, DMSO-d6) δ ppm 9.23 (br. s., 1 H) 8.13 (br. s., 1 H) 7.67 (s, 1 H) 3.78 (s, 3 H) 3.70 (s, 3 H) 3.69 (br. s., 3 H). m/z (APCI+) for $C_{11}H_{13}FN_7O$ 278.2 (M+H)+.

Step 3: Preparation of N-((3R,4R)-4-fluoro-1-(6-((3-methoxy-1-methyl-1H-pyrazol-4-yl)amino)-9-methyl-9H-purin-2-yl)pyrrolidin-3-yl)acrylamide

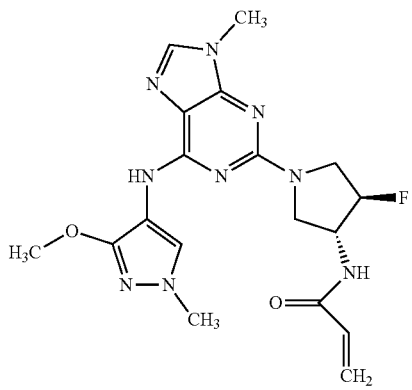 [SMILES: C=CC(=O)N[C@@H]1CN(c2nc(Nc3cn(C)nc3OC)c3ncn(C)c3n2)C[C@H]1F]

To a 200 L Hastelloy reactor heated to 40° C. was added sulfolane (22.4 L) and N-((3R,4R)-4-fluoropyrrolidin-3-yl)-3-(methylsulfonyl)propanamide (4.03 kg, 16.9 mol, 1.05 eq) and stirred the resulting mixture until all solids were dissolved. To this solution was added 2-fluoro-N-(3-methoxy-1-methyl-1H-pyrazol-4-yl)-9-methyl-9H-purin-6-amine (4.47 kg, 16.1 mol, 1.00 eq) and N,N-diisopropylethylamine (8.50 L, 48.7 mol, 3.0 eq) and the mixture heated at 115° C. for 16 hr. The reaction mixture was cooled to 30° C., and a solution of potassium hydroxide (2.26 kg, 40.3 mol, 2.5 eq) in water (44.7 L) was added. After stirring for 4 hr, the reaction mixture was cooled to 20° C., water (44.7 L) was added and the resulting mixture granulated for 12 hr. The crude product was isolated on a Nutsche filter and washed with water (27 L) and then dried under nitrogen on the filter. The reactor was cleaned and then charged with water (35.8 L) and acetone (53.6 L). The crude product cake was charged back into the reactor and heated to 60° C. until all of the solids had dissolved. The batch was then cooled to 40° C. and then transferred into a speck free 100 L reactor via an in-line 10 μm filter. The 200 L reactor, line and filter were rinsed with acetone (5 L) and sent into the 100 L reactor. The batch was concentrated with the jacket temperature set at 70° C. under partial vacuum until the acetone content reduced to 5 wt %, as determined by gas chromatography head space. The batch was then cooled to 20° C. and granulated for 4 hr. The product was filtered, washed with water (18 L) and dried in a vacuum oven at 55° C. for 8 hr. The title compound (3.942 kg, 9.49 mol, 59%) was isolated as a white crystalline solid. $^1$H NMR (400 MHz, DMSO-d6) δ ppm 8.44 (d, J=6.5 Hz, 1 H) 7.97 (s, 1 H) 7.82 (s, 1 H) 7.78 (s, 1 H) 6.23 (dd, J=10.0, 17.0 Hz, 1 H) 6.14 (dd, J=2.8, 17.0 Hz, 1 H) 5.62 (dd, J=2.8, 10.0 Hz, 1 H) 5.12 (d, J=51.0 Hz, 1 H) 4.46 (td, J=6.0, 11.9 Hz, 1 H) 3.88-3.6 (m, 4 H) 3.82 (s, 3 H) 3.71 (s, 3 H) 3.62 (s, 3 H). m/z (APCI+) for $C_{18}H_{23}FN_9O_2$ 416.3 (M+H)$^+$.

Alternative conditions for above general Schemes:

Scheme A: Acid mediated S$_N$Ar with HCl salt.
Preparation of 2-chloro-N-(1,3dimethyl-1H-pyrazol-4-yl)-9-isopropyl-9H-purin-6-amine

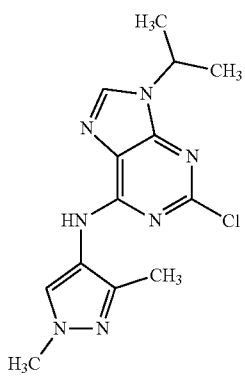 [SMILES: Cc1nn(C)cc1Nc1nc(Cl)nc2c1ncn2C(C)C]

To a solution of 2,6-dichloro-9-isopropyl-9H-purine (421 mg, 1.82 mmol), as prepared in step 1 of Example 1, in iPrOH (9 mL) in a 20 mL microwave vessel was added 1,3-dimethyl-1H-pyrazol-4-amine hydrochloride (300 mg, 2.19 mmol) and the mixture was heated in the microwave at 130° C. for 1.5 hr. The white precipitate formed in the reaction vial was collected to give the title compound (424 mg, 72% yield). $^1$H NMR (400 MHz, DMSO-d6) δ ppm 9.87 (br. s., 1 H) 8.65 (br. s., 1 H) 7.82 (s, 1 H) 4.62-4.85 (m, 1 H) 3.79 (s, 3 H) 2.12 (s, 3 H) 1.53 (d, J=6.72 Hz, 6 H). m/z (APCI+) for $C_{13}H_{16}ClN_7$ 306.2 (M+H)$^+$.

Scheme A: Base mediated S$_N$Ar. Preparation of (S)-tert-butyl(1-(9-isopropyl-6-((4-(4-methylpiperazin-1-yl)phenyl)amino)-9H-purin-2-yl)pyrrolidin-3-yl)carbamate

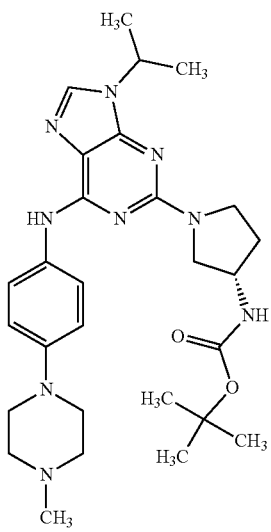 [SMILES: CC(C)n1cnc2c(Nc3ccc(N4CCN(C)CC4)cc3)nc(N3CC[C@H](NC(=O)OC(C)(C)C)C3)nc21]

A mixture of 2-chloro-9-isopropyl-N-(4-(4-methylpiperazin-1-yl)phenyl)-9H-purin-6-amine (200 mg, 0.52 mmol), as prepared in step 2 of Example 1, and (S)-tert-butyl pyrrolidin-3-ylcarbamate (290 g, 1.56 mmol) in nBuOH (10 mL) in a sealed tube was stirred at 120° C. for 48 hr. TLC (CH$_2$Cl$_2$/MeOH=10/1) showed that some of the starting material remained. The reaction mixture was concentrated in vacuum to give the crude product, which was purified by flash chromatography (CH$_2$Cl$_2$/MeOH=50/1 to 10/1) to afford the title compound (250 mg, 90% yield) as a brown gum.

Preparation 1: Preparation of 2,6-dichloro-9-cyclobutyl-9H-purine

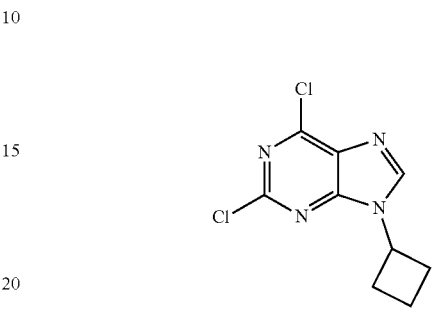

Step 1: Preparation of 2,6-dichloro-N-cyclobutyl-5-nitropyrimidin-4-amine

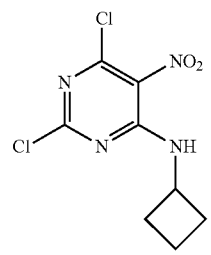 [SMILES: O=[N+]([O-])c1c(Cl)nc(Cl)nc1NC1CCC1]

Cyclobutanamine (0.485 mL, 5.68 mmol) in iPrOH (20 mL) was added to a solution of 2,4,6-trichloro-5-nitropyrimidine (1.29 g, 5.65 mmol) in iPrOH (40 mL) at −78° C. dropwise via addition funnel. After complete addition, the mixture was allowed to warm to rt over 30 min, then DIEA (0.940 mL, 5.66 mmol) was added and the mixture stirred at rt for 10 min. The solvent was removed under reduced pressure and dried to give the title compound as a pale yellow oil which was used without purification.

Step 2: Preparation of 2,6-dichloro-N$^4$-cyclobutylpyrimidine-4,5-diamine

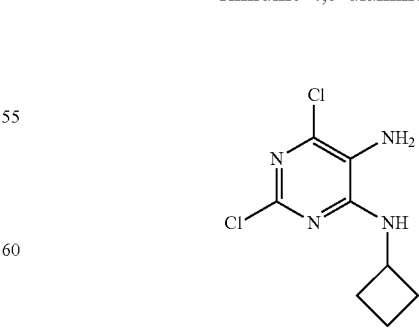

Fe powder (631 mg, 11.3 mmol) was added to a solution of 2,6-dichloro-N-cyclobutyl-5-nitropyrimidin-4-amine (crude, 5.65 mmol) in HOAc (5 mL) and the mixture was stirred at rt for 30 min. The mixture was filtered through Celite® and the volatiles were removed under reduced pressure. The resulting residue was diluted with EtOAc (80 mL) and washed with water (80 mL), sat. NaHCO$_3$ (80 mL) and brine (80 mL). The organic layer was dried over Na$_2$SO$_4$ and concentrated to give the title compound as a brown oil which was used without purification. m/z (APCI+) for C$_8$H$_{10}$Cl$_2$N$_4$ 233.15/235.10 (M+H)$^+$.

Step 3: Preparation of 2,6-dichloro-9-cyclobutyl-9H-purine

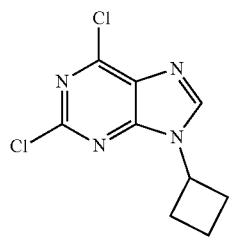 [SMILES: Clc1nc(Cl)c2ncn(C3CCC3)c2n1]

2,6-Dichloro-N$^4$-cyclobutylpyrimidine-4,5-diamine (crude, 5.65 mmol) in diethoxymethyl acetate (8 mL) was stirred and heated at 80° C. for 16 hr. The mixture was cooled to rt, diluted with EtOAc (80 mL) and washed with water (80 mL), sat. NaHCO$_3$ (80 mL) and brine (80 mL). The organic layer was dried over Na$_2$SO$_4$ and concentrated. The crude product was purified via flash chromatography eluting with 20-50% EtOAc/heptanes to give the title compound as an off-white solid (727 mg, 53% yield). $^1$H NMR (400 MHz, DMSO-d$_6$) δ ppm 8.95 (1 H, s) 5.07 (1 H, quin, J=8.56 Hz) 2.59-2.77 (2 H, m) 2.42-2.50 (2 H, m) 1.71-1.96 (2 H, m); m/z (APCI+) for C$_9$H$_8$Cl$_2$N$_4$ 243.10 (M+H)$^+$.

Preparation 2: Preparation of 9-(tert-butyl)-2,6-dichloro-9H-purine

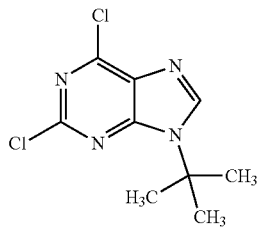

To a suspension of 2,6-dichloro-9H-purine (8.00 g, 40 mmol, 1.00 eq) and Na$_2$SO$_4$ (96.2 g, 677 mmol, 16.0 eq) in tert-butanol (380 mL) was added concentrated H$_2$SO$_4$ (11.3 mL, 211 mmol, 5 eq). The reaction mixture was heated at 120° C. with vigorous stirring under a reflux condenser [Caution: Gas evolution]. During the following 10 hr, additional H$_2$SO$_4$ (26 mL), Na$_2$SO$_4$ (75 g), and tert-butanol (350 mL) were added to the reaction mixture in several portions. After a further 6 hr of heating, the reaction mixture was cooled to ambient temperature, quenched with NaHCO$_3$(s) added portionwise [Caution: Gas evolution], and diluted with water (300 mL) and EtOAc (300 mL). The layers were separated and the aqueous layer was further extracted with EtOAc (2×300 mL). The combined organics were washed with sat. aq. NaHCO$_3$ and brine, dried (Na$_2$SO$_4$), and concentrated under reduced pressure. The crude reaction mixture was purified via flash chromatography eluting with a gradient of 0-50% EtOAc in heptane to give the title compound (4.09 g, 40% yield) as a white solid. $^1$H NMR (400 MHz, DMSO-d6) δ ppm 8.73 (s, 1H) 1.73 (s, 9H). m/z (APCI+) for C$_9$H$_{10}$Cl$_2$N$_4$ 245.1/247.1 (M+H)$^+$.

Preparation 3: Preparation of benzyl [(3,4-trans)-4-fluoropyrrolidin-3-yl]carbamate

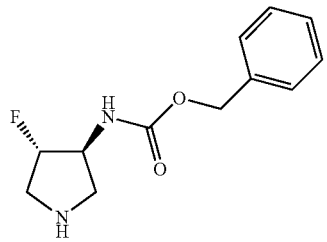 [SMILES: O=C(N[C@H]1CNC[C@@H]1F)OCc1ccccc1]

Step 1: Preparation of tert-butyl 6-oxa-3-azabicyclo[3.1.0]hexane-3-carboxylate

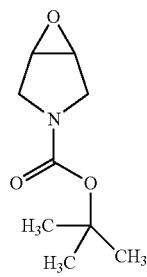

To a stirred solution of tert-butyl 2,5-dihydro-1H-pyrrole-1-carboxylate (130 g, 0.77 mol) in CH$_2$Cl$_2$ (0.8 L) was added mCPBA (233 g, 1.15 mol) portion wise at 5° C. After addition, the resulting mixture was warmed to rt and stirred overnight. The resulting solid was filtered off and the filtrate was washed with sat. aq. Na$_2$SO$_3$ to pH=7-8, then washed with sat. aq. NaHCO$_3$ (3×200 mL) and brine (0.2 L). The organic layer was concentrated and the residue was distilled under reduced pressure to give the title compound (110 g, 77% yield) as a light yellow liquid. Used as is in the next step.

Step 2: Preparation of (trans)-tert-butyl 3-azido-4-hydroxypyrrolidine-1-carboxylate

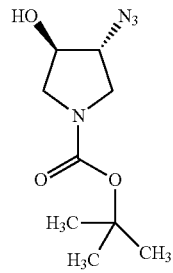

To a stirred solution of tert-butyl 6-oxa-3-azabicyclo[3.1.0]hexane-3-carboxylate (110 g, 0.595 mol) in MeOH/water (1200 mL/200 mL) were added NaN₃ (77.6 g, 1.19 mol) and NH₄Cl (32 g, 0.598 mol). The resulting mixture was stirred at 60° C. overnight. NaOH (0.5 N, 200 mL) was added and the mixture was concentrated to remove MeOH. The residue was extracted with CH₂Cl₂ (3×400 mL) and the combined organic extracts were washed with water, brine, dried over Na₂SO₄, and then concentrated to give the title compound as a yellow liquid (quantitative yield). Used as is in next step.

Step 3: Preparation of (trans)-tert-butyl 3-azido-4-fluoropyrrolidine-1-carboxylate

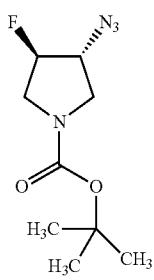

To the solution of (trans)-tert-butyl 3-azido-4-hydroxypyrrolidine-1-carboxylate (120 g, 0.44 mol, 5/6 purity, containing DCM) in DCM (1.2 L) at −78° C. was added dropwise DAST (141 g, 0.88 mol) in DCM (200 mL). After addition, the mixture was stirred at −78° C. for 1 hr, then warmed to rt and stirred overnight. The reaction mixture was poured into sat. Na₂CO₃ (2 L) slowly then the DCM phase was washed with water (1 L), sat. NaCl and dried over Na₂SO₄. Concentrated and purified via flash chromatography (petroleum ether/EtOAc 20/1~10/1) to give the title compound (48 g, 48% yield) as light yellow oil.

Step 4: Preparation of tert-butyl(3,4-trans)-3-amino-4-fluoropyrrolidine-1-carboxylate

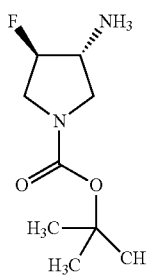

To a stirred solution of (trans)-tert-butyl 3-azido-4-fluoropyrrolidine-1-carboxylate (45 g, 0.196 mol) in THF (0.5 L) was added PPh₃ (67.5 g, 0.25 mol) portionwise at 0-5° C. The resulting mixture was warmed to rt and stirred for 2 hr. 50 mL of water was added and the resulting mixture was heated to reflux overnight. The reaction mixture was then cooled and concentrated to remove volatiles. The residue was diluted with EtOAc (0.2 L), and washed with sat. citric acid (200 mL). The aqueous layer was washed with EtOAc (2×50 mL), then adjusted pH to 7-8 with sat. aq. K₂CO₃, and extracted with EtOAc (5×100 mL). The combined organic extracts were washed with brine (100 mL), dried over Na₂SO₄, concentrated, then dried in vacuo to give the title compound (22.28 g, 56% yield) as a light yellow oil that solidified on standing. ¹H NMR (400 MHz, DMSO-d₆) δ ppm 4.65-4.45 (d, 1H), 3.65-3.49 (m, 1H), 3.48-3.35 (m, 3H), 3.21-3.12 (d, 1H), 1.73 (brs, 2H), 1.39 (s, 9H). m/z (APCI+) for C₉H₁₇FN₂O₂ 149.07 (M+H−56)+.

Step 5: Preparation of tert-butyl(3,4-trans)-3-{[(benzyloxy)carbonyl]amino}-4-fluoropyrrolidine-1-carboxylate

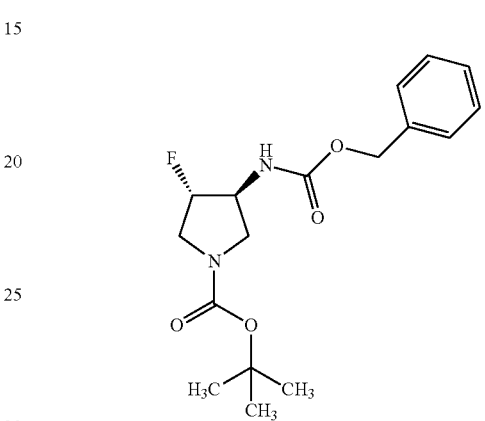

A solution of tert-butyl(3,4-trans)-3-amino-4-fluoropyrrolidine-1-carboxylate (408 mg, 2 mmol) in DCM (20 mL) was cooled in an ice/water bath. DIPEA (0.38 mL, 2.2 mmol) and CBZ-Cl (0.3 mL, 2 mmol) were added and the resulting solution was capped, stirred in the cold bath and allowed to warm to rt gradually over 2 hr. The reaction was diluted with DCM (30 mL) and sat. aq. NaHCO₃ (20 mL) was added. The organic layer was separated, washed with sat. aq. NaHCO₃ (20 mL), dried over Na₂SO₄, and evaporated to give a colorless residue that was purified via flash chromatography (gradient of 100% heptane to 50% ethyl acetate-50% heptane) to give the title product as a colorless oil (635 mg, 94% yield). ¹H NMR (400 MHz, chloroform-d) δ ppm 7.27-7.47 (m, 5 H) 5.12 (br. s., 2 H) 4.28 (br. s., 1 H) 3.31-3.79 (m, 3 H) 1.47 (s, 9 H). m/z (APCI+) for C₁₇H₂₃FN₂O₄ 239.2 (M+H)⁺ (parent MW with loss of Boc group).

Step 6: Preparation of benzyl [(trans)-4-fluoropyrrolidin-3-yl]carbamate

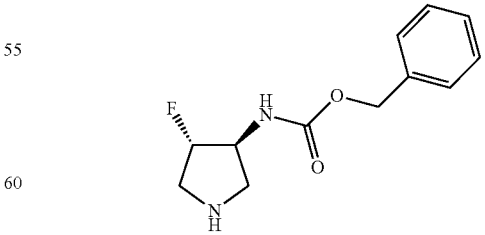

To a solution of tert-butyl(3,4-trans)-3-{[(benzyloxy)carbonyl]amino}-4-fluoropyrrolidine-1-carboxylate (630 mg, 1.9 mmol) in DCM (19 mL) was added TFA (0.56 mL, 5.6 mmol, 3 mol eq) and the resulting reaction was stirred at ambient temperature for 2 hr. The volatiles were removed to give a colorless residue, which was then partitioned in DCM (80 mL) and sat. aq. NaHCO$_3$ (15 mL). The organic layer was separated, and the product was extracted with more DCM (30 mL), dried over Na$_2$SO$_4$ and evaporated to give the title product as a colorless oil (427 mg, 96% yield). $^1$H NMR (400 MHz, chloroform-d) δ ppm 7.30-7.42 (m, 5 H) 4.92-5.19 (m, 3 H) 4.06-4.34 (m, 1 H) 3.46 (dd, J=11.68, 6.54 Hz, 1 H) 3.04-3.30 (m, 2 H) 2.80 (d, J=10.88 Hz, 1 H) 2.33 (br. s., 2 H). $^{19}$F NMR (376 MHz, chloroform-d) δ ppm −75.62 (s, 1 F). m/z (APCI+) for C$_{12}$H$_{15}$FN$_2$O$_2$ 239.1 (M+H)$^+$.

Preparation 4: Preparation of tert-butyl ((3R,4R)-4-fluoropyrrolidin-3-yl)carbamate

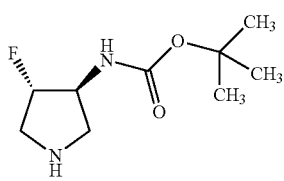

Step 1: Preparation of (trans)-3-azido-4-fluoropyrrolidine

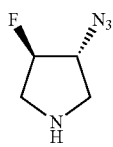

To a solution of (trans)-tert-butyl 3-azido-4-fluoropyrrolidine-1-carboxylate (25 g, 109 mmol), as prepared in step 3 of Preparation 3, in EtOAc (100 mL) was added HCl/EtOAc (50 mL) at 0-5° C. Then the mixture was stirred at rt for 4 hr. The solid was filtered and washed with petroleum ether/EtOAc (2:1, 40 mL) to give the title compound (18 g) as a gray solid, which was used directly in the next step.

Step 2: Preparation of (trans)-benzyl 3-azido-4-fluoropyrrolidine-1-carboxylate

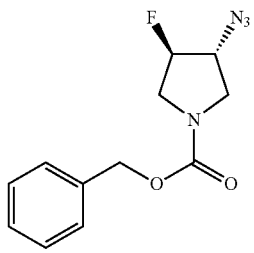

To a stirred mixture of (trans)-3-azido-4-fluoropyrrolidine (18 g) in CH$_2$Cl$_2$ (120 mL) was added DIPEA (35 g, 0.27 mol, 2.5 eq), then CBZ-Cl (22 g, 0.13 mol) was added dropwise at 0-5° C. After addition, the resulting mixture was stirred at rt overnight. The mixture was washed with sat. aq. NH$_4$Cl (150 mL), sat. aq. NaHCO$_3$ (3×40 mL) and brine (40 mL). The organic layer was concentrated and purified by column (petroleum ether/EtOAc=10:1~5:1) to give the title compound (30 g, ~100% yield in two steps, containing residual EtOAc and DCM) as a light yellow oil.

Step 3: Preparation of (trans)-benzyl 3-amino-4-fluoropyrrolidine-1-carboxylate

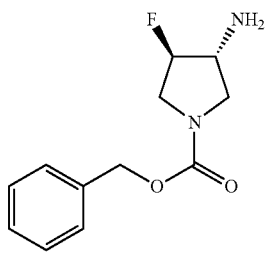 [SMILES: N[C@@H]1CN(C(=O)OCc2ccccc2)C[C@H]1F]

To a stirred solution of (trans)-benzyl 3-azido-4-fluoropyrrolidine-1-carboxylate (30 g, 0.114 mol) in THF (0.3 L) was added PPh$_3$ (33 g, 0.126 mol) portion wise at 0-5° C. The resulting mixture was then warmed to rt and stirred for 2 hr. 30 mL of water was then added and the resulting mixture was heated to reflux overnight. The reaction mixture was concentrated and the residue diluted with EtOAc (0.2 L) and extracted with sat. citric acid (4×100 mL). The combined aqueous extracts were washed with EtOAc (3×50 mL), then adjusted pH to 8 with sat. aq. K$_2$CO$_3$, and extracted with DCM (4×100 mL). The combined organic extracts were washed with brine (100 mL), dried over Na$_2$SO$_4$, concentrated, then dried in vacuo to give the title compound as light yellow oil that solidified on standing to afford an off-white solid (16 g, 59% yield).

Step 4: Preparation of (3R,4R)-benzyl 3-((tert-butoxycarbonyl)amino)-4-fluoropyrrolidine-1-carboxylate

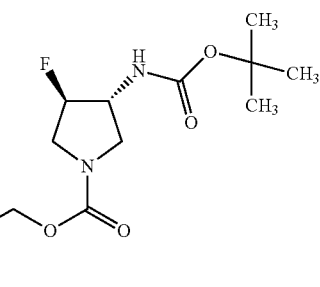

To a solution of (trans)-benzyl 3-amino-4-fluoropyrrolidine-1-carboxylate (16 g, 0.067 mol) in DCM (0.15 L) was added DIPEA (16 g, 0.124 mol) and Boc$_2$O (18 g, 0.083 mol) at 0-5° C. and the resulting mixture was stirred at rt overnight. The mixture was then washed with sat. NH$_4$Cl (3×50 mL), sat. NaCl, dried over Na$_2$SO$_4$, concentrated and purified via silica gel flash chromatography (petroleum ether/EtOAc=3:1) to give the racemic product (19.40 g, 86% yield) as a light yellow oil (solidified on standing to give a white solid). m/z (APCI+) for C$_{17}$H$_{23}$FN$_2$O$_4$ 361.01 (M+23)$^+$ The enantiomers were resolved using Chiralcel OJ-H 21.2×250 mm 5µ column (36° C.) Eluent 14% MeOH in CO$_2$ held at 100 bar Flow 60 mL/min Sample ~35 mg/mL in MeOH, 1.0 mL/inj.;

(3R,4R)-benzyl 3-((tert-butoxycarbonyl)amino)-4-fluoropyrrolidine-1-carboxylate; >99% ee (+); $^1$H NMR (400 MHz, chloroform-d) δ ppm 7.30-7.43 (m, 5 H) 5.15 (s, 2 H) 4.91-5.12 (m, 1 H) 4.10-4.72 (m, 2 H) 3.57-3.84 (m, 3 H) 3.38-3.55 (m, 1 H) 1.45 (s, 9 H); [α]D=+22.3° (c 0.26, MeOH).

(3S,4S)-benzyl 3-((tert-butoxycarbonyl)amino)-4-fluoropyrrolidine-1-carboxylate; ~99% ee (−); $^1$H NMR (400 MHz, chloroform-d) δ ppm 7.30-7.43 (m, 5 H) 5.15 (s, 2 H) 4.92-5.13 (m, 1 H) 4.12-4.62 (m, 2 H) 3.57-3.86 (m, 3 H) 3.38-3.54 (m, 1 H) 1.45 (s, 9 H). [α]D=−29.4° (c 0.16, MeOH).

Step 5: Preparation of tert-butyl ((3R,4R)-4-fluoropyrrolidin-3-yl)carbamate

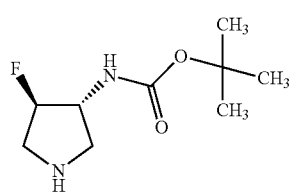

To a solution of (3R,4R)-benzyl 3-((tert-butoxycarbonyl)amino)-4-fluoropyrrolidine-1-carboxylate (3.0 g, 8.8 mmol) in MeOH (50 mL) was added wet Pd/C (0.3 g, 10%) under nitrogen. The suspension was degassed under vacuum and purged with hydrogen three times. The resulting mixture was stirred at rt under hydrogen balloon for 3 hr. The reaction mixture was filtered and the filtrate was concentrated to afford the title compound (1.6 g, 88% yield) as light yellow oil that solidified on standing.

Preparation 5: Preparation of benzyl [(3R,4R)-4-fluoropyrrolidin-3-yl]carbamate

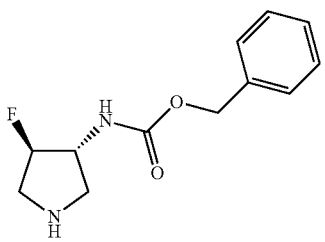

Step 1: Preparation of (2S)-2-phenylbutanedioic acid-tert-butyl (3R,4R)-3-amino-4-fluoropyrrolidine-1-carboxylate (1:1)

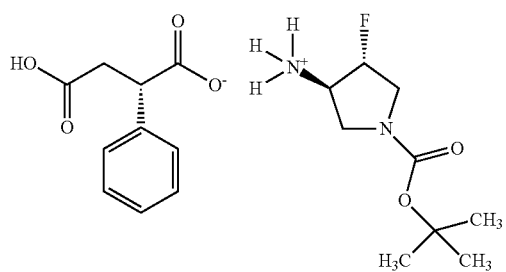

A mixture of tert-butyl(3,4-trans)-3-amino-4-fluoropyrrolidine-1-carboxylate (trans-racemic, 500 mg, 2.45 mmol) and (S)-(+)-phenylsuccinic acid (>99% (CAS 4036-30-0, 480 mg, 2.45 mmol) in ethanol (24.5 mL, 0.1 M) was stirred and heated at 80° C. (block temperature) for 30 min. The resulting solution was removed from the hot plate and allowed to stand at ambient temperature. After 16 hr the resulting crystals were collected by filtration, washed with ethanol (2 mL) and dried to give the title product (500 mg, 51% yield) as a white solid with an ee of 95% (Chiralpak AY-H 4.6×250 mm column, 6% isopropanol at 140 bar, 4 mL/min). This product was determined to be the (R,R) enantiomer based on the X-ray structure of the opposite enantiomer (S,S), which was resolved with (R)-(−)-phenylsuccinic acid. [α]$D_{22}$=+96.5° (c 0.08, EtOH). $^1$H NMR (400 MHz, DMSO-d6) δ ppm 7.50 (br. s., 2 H) 7.19-7.36 (m, 5 H) 4.76-4.95 (m, 1 H) 3.86 (dd, J=9.90, 4.89 Hz, 1 H) 3.32-3.71 (m, 4 H) 3.15 (d, J=10.88 Hz, 1 H) 2.91 (dd, J=16.75, 9.90 Hz, 1 H) 2.54 (dd, J=16.75, 4.89 Hz, 1 H) 1.40 (s, 9 H). $^{19}$F NMR (376 MHz, DMSO-d6) δ ppm −178.71-178.28 (m, 1 F). m/z (APCI+) for $C_{19}H_{27}FN_2O_6$ 105.3 for parent amine (M+H)$^+$.

Step 2: Preparation of tert-butyl (3R,4R)-3-{[(benzyloxy)carbonyl]amino}-4-fluoropyrrolidine-1-carboxylate

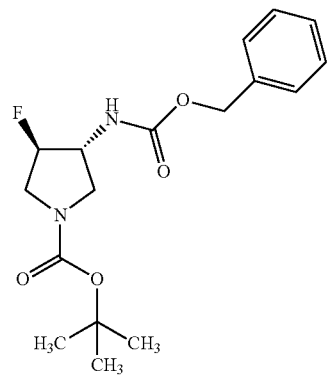 [SMILES: CC(C)(C)OC(=O)N1C[C@@H](F)[C@H](NC(=O)OCc2ccccc2)C1]

A solution of (2S)-2-phenylbutanedioic acid-tert-butyl (3R,4R)-3-amino-4-fluoropyrrolidine-1-carboxylate (1:1) (500 mg, 1.2 mmol) in DCM (20 mL) was cooled in an ice/water bath. DIPEA (0.69 mL, 4 mmol, 3.3 mol eq) was added, followed by CBZ-Cl (185 μL, 1.26 mmol, 1.05 mol eq). The resulting reaction solution was capped, stirred in the cold bath and allowed to warm to rt and stirred for 2 hr. The reaction was diluted with DCM (30 mL) and washed with sat. aq. NaHCO$_3$ (10 mL). The organic layer was separated, dried over Na$_2$SO$_4$, and evaporated to give a colorless residue that was purified via flash chromatography (eluting with a gradient of 100% heptane to 50 ethyl acetate-50% heptane) to give the title compound as a colorless oil (388 mg, 96 yield). $^1$H NMR (400 MHz, chloroform-d) δ ppm 7.30-7.42 (m, 5 H) 5.12 (br. s., 2 H) 4.74-5.04 (m, 1 H) 4.28 (br. s., 1 H) 3.28-3.80 (m, 4 H) 1.47 (s, 9 H). $^{19}$F NMR (376 MHz, chloroform-d) δ ppm −180.76-−178.52 (m, 1 F). m/z (APCI+) for $C_{17}H_{23}FN_2O_4$ 239.2 (M+H)$^+$. Chiral purity was determined as below (using the racemic material to compare):

Chiralcel OJ-H 4.6×250 mm column; 10% MeOH at 140 bar, 3 mL/min ~76 ee; [α]$D_{20}$=+14.3° (c 0.4, EtOH).

Step 3: Preparation of benzyl [(3R,4R)-4-fluoropyrrolidin-3-yl]carbamate

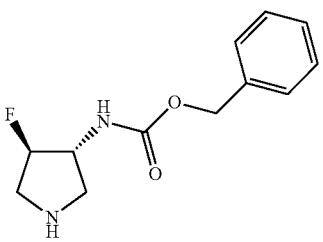 [SMILES: O=C(N[C@@H]1CNC[C@H]1F)OCc1ccccc1]

To a solution of tert-butyl (3R,4R)-3-{[(benzyloxy)carbonyl]amino}-4-fluoropyrrolidine-1-carboxylate (380 mg, 1.2 mmol) in DCM (20 mL) was added TFA (0.34 mL, 3.4 mmol, 3 mol eq). The resulting reaction was stirred at ambient temperature for 2 hr. More TFA (0.34 mL, 3.4 mmol, 3 mol eq) was added and stirring at ambient temperature continued for another 2 hr. The volatiles were removed to give a colorless residue. DCM (30 mL) and aqueous $K_2CO_3$ (1 M, 5 mL) were added. The organic layer was separated, extracted with more DCM (30 mL), dried over $Na_2SO_4$ and evaporated to give the title compound as a colorless gum (246 mg, 92% yield). $^1$H NMR (400 MHz, chloroform-d) δ ppm 7.29-7.43 (m, 5 H) 4.80-5.21 (m, 4 H) 4.07-4.28 (m, 1 H) 3.46 (br. s., 1 H) 2.96-3.30 (m, 2 H) 2.74 (br. s., 1 H). $^{19}$F NMR (376 MHz, chloroform-d) δ ppm −72.38 (s, 1F). m/z (APCI+) for $C_{12}H_{15}FN_2O_2$ 239.2 (M+H)$^+$. Chiral purity was determined as below (using the racemic sample to compare):

Chiralpak AD-H 4.6×100 mm column; 40% MeOH/DEA at 120 bar, 4 mL/min ~75% ee $[α]D_{22}$=−3.3° (C. 0.24, MeOH).

Preparation 6: Preparation of N-((3R,4R)-4-fluoropyrrolidin-3-yl)-3-(methylsulfonyl)propanamide

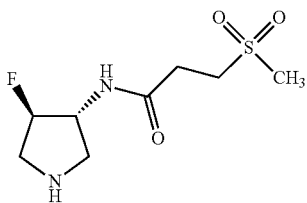

Step 1: Preparation of (3R,4R))-benzyl 3-fluoro-4-(3-(methylsulfonyl)propanamido)pyrrolidine-1-carboxylate

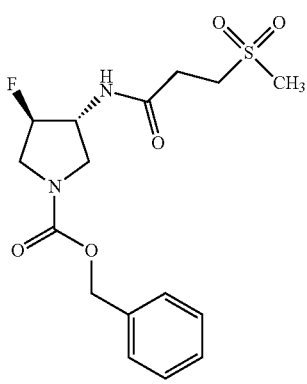 [SMILES: CS(=O)(=O)CCC(=O)N[C@@H]1CN(C(=O)OCc2ccccc2)C[C@H]1F]

To a solution of (3R,4R)-benzyl 3-((tert-butoxycarbonyl)amino)-4-fluoropyrrolidine-1-carboxylate, as prepared in step 4 of Preparation 4, (2.00 g, 5.91 mmol, 1.00 eq) in dichloromethane (30 mL) was added trifluoroacetic acid (1.4 mL, 18.3 mmol, 3.10 eq). After 2.5 hr, an additional portion of trifluoroacetic acid (3.0 mL, 39.2 mmol, 6.63 eq) was added. After a further 3 hr, the reaction mixture was concentrated in vacuo (1 mm Hg) to a syrup and this crude trifluoroacetate salt was carried on without further purification.

The above-obtained material was dissolved in dichloromethane (20 mL) and treated with 4-methyl morpholine (3.0 mL, 27.2 mmol, 4.61 eq), 3-(methylsulfonyl)propanoic acid (1.20 g, 7.89 mmol, 1.34 eq), and N-(3-dimethylaminopropyl)-N'-ethylcarbodiimide hydrochloride (1.30 g, 6.78 mmol, 1.15 eq). After stirring at ambient temperature for 20 hr, the reaction mixture was diluted with dichloromethane (50 mL) and sat. aq. $NaHCO_3$ (50 mL). The layers were separated and the aqueous layer was extracted with dichloromethane (3×30 mL). The combined organic layers were combined, dried ($Na_2SO_4$), and concentrated under reduced pressure. The crude reaction mixture was purified via flash chromatography eluting with a gradient of 3-10% EtOH in EtOAc to give the title compound (1.56 g, 70.9% yield) as a white solid. $^1$H NMR (400 MHz, DMSO-d6) δ ppm 8.43 (d, J=6.2 Hz, 1 H) 7.38 (d, J=4.4 Hz, 4 H) 7.37-7.28 (m, 1 H) 5.10 (s, 2 H) 5.08-4.91 (m, 1 H) 4.29 (br. s., 1 H) 3.72-3.50 (m, 3 H) 3.40 (dd, J=5.2, 11.6 Hz, 1 H) 3.36-3.30 (m, 2 H) 2.97 (s, 3 H) 2.60-2.53 (m, 2 H). m/z (APCI+) for $C_{16}H_{22}FN_2O_5S$ 373.2 (M+H)$^+$.

Step 2: Preparation of N-((3R,4R))-4-fluoropyrrolidin-3-yl)-3-(methylsulfonyl)propanamide

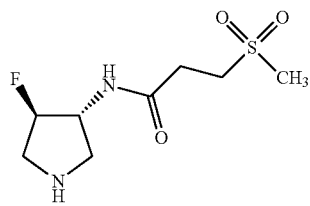

A nitrogen sparged suspension of (3R,4R)-benzyl 3-fluoro-4-(3-(methylsulfonyl)propanamido)pyrrolidine-1-carboxylate (2.80 g, 7.52 mmol, 1.00 eq) and 10% Pd/C (300 mg) in ethanol (250 mL) was stirred under a hydrogen atmosphere (1 atm) for 16 hr. The reaction mixture was then sparged with nitrogen and filtered through a pad of Celite®. The Celite® was washed with additional ethanol (50 mL). The combined filtrates were concentrated under reduced pressure to give the title compound (1.75 g, 98% yield, 95% purity) as a white solid. $^1$H NMR (400 MHz, DMSO-d6) δ ppm 8.13 (d, J=6.7 Hz, 1 H) 4.73-5.02 (m, 1 H) 3.99-4.20 (m, 1 H) 3.32 (t, J=7.6 Hz, 2 H) 3.14 (dd, J=11.7, 6.8 Hz, 2 H) 2.94-3.01 (m, 4 H) 2.87-2.91 (m, 1 H) 2.52-2.59 (m, 3 H). m/z (APCI+) for $C_8H_{16}FN_2O_3S$ 239.2 (M+H)$^+$.

Preparation 7: Preparation of 3-methyl-1-(1-methylpyrrolidin-3-yl)-1H-pyrazol-4-amine

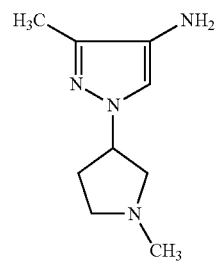

Step 1: Preparation of tert-butyl-3-(3-methyl-4-nitro-1H-pyrazol-1-yl)pyrrolidine-1-carboxylate

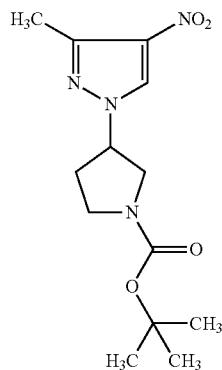

To a solution of 3-methyl-4-nitro-1H-pyrazole (3.0 g, 23.6 mmol, 1.00 eq), tert-butyl-3-hydroxypyrrolidine-1-carboxylate (4.42 g, 23.6 mmol, 1.00 eq), and triphenylphosphine (6.19 g, 23.6 mmol, 1.00 eq) in THF (60 mL) was added a solution of diethyl azodicarboxylate (4.34 mL, 23.6 mmol, 1.00 eq) in THF (10 mL) in a drop-wise manner over 30 min. The reaction mixture was allowed to stir at ambient temperature for 20 hr and then concentrated. The crude reaction mixture was purified via repeated flash chromatography on silica gel eluting with a gradient of 0-35% EtOAc in heptane to give the title compound (2.48 g, 35% yield) as a colorless oil that was the early eluting of two structural isomers. $^1$H NMR (400 MHz, CDCl$_3$) δ ppm 8.15 (s, 1 H) 4.80 (quin, J=5.7 Hz, 1 H) 3.83 (dd, J=6.0, 12.0 Hz, 1 H) 3.79-3.45 (m, 3 H) 2.52 (s, 3 H) 2.38 (q, J=7.0 Hz, 2 H) 1.46 (s, 9 H). m/z (APCI+) for C$_{13}$H$_{21}$N$_4$O$_4$ 197.2 (M+H)$^+$.

Step 2: Preparation of 3-methyl-1-(1-methylpyrrolidin-3-yl)-1H-pyrazol-4-amine

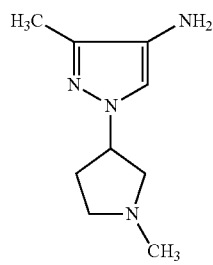

A nitrogen-flushed round bottom flask was charged with tert-butyl-3-(3-methyl-4-nitro-1H-pyrazol-1-yl)pyrrolidine-1-carboxylate (980 mg, 3.31 mmol, 1.00 eq), 10% Pd/C (400 mg) and methanol (35 mL). The reaction mixture was purged with hydrogen for 5 min then stirred vigorously under a hydrogen atmosphere for 12 hr. The reaction mixture was then purged with nitrogen, filtered through Celite®, concentrated, and azeotroped from toluene (2×20 mL) to give a pale red oil that was used in the next step without further purification.

To a solution of the above obtained amine in THF (13 mL) was added a solution of LAH (13.0 mL, 13.0 mmol, 4.00 eq, 1 M in THF) in a drop-wise manner over 5 min. After 15 min, additional THF (20 mL) was added to facilitate stirring. After 24 hr, the reaction mixture was placed in an ambient temperature bath and treated sequentially with water (1 mL), aq. 1 M NaOH (1 mL), and water (3 mL). After stirring for 30 min the reaction mixture was diluted with EtOAc (50 mL) and filtered. The resulting solids were washed with an additional portion of EtOAc (20 mL) and the combined solids were concentrated. The crude reaction mixture was purified via flash chromatography on silica gel eluting with a gradient of 0-5% 7 N methanolic ammonia/DCM to give the title compound (113 mg, 19% yield) as a colorless oil. $^1$H NMR (400 MHz, DMSO-d6) δ ppm 7.00 (s, 1 H) 4.59 (tdd, J=4.8, 7.3, 9.5 Hz, 1 H) 3.55 (br. s., 2 H) 2.74-2.61 (m, 2 H) 2.57 (dd, J=5.0, 9.5 Hz, 1 H) 2.41 (dt, J=6.2, 8.4 Hz, 1 H) 2.25 (s, 3 H) 2.24-2.17 (m, 1 H) 1.97 (s, 3 H) 1.96-1.85 (m, 1 H). m/z (APCI+) for C$_9$H$_{17}$N$_4$ 181.2 (M+H)$^+$.

Preparation 8: Preparation of N-(4,4-difluoropyrrolidin-3-yl)-3-(methylsulfonyl)propanamide hydrochloride

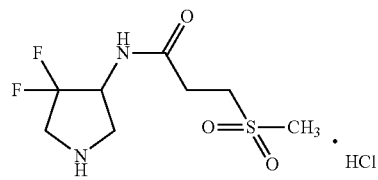 [SMILES: CS(=O)(=O)CCC(=O)NC1CNCC1(F)F ; Cl]

Step 1: Preparation of 2,2-difluoroethenyl-4-methylbenzenesulfonate

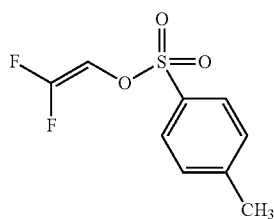

To a 3-necked flask with a stir bar (oven dried), water-cooled condenser, and internal thermometer was added 2,2,2-trifluoroethyl-4-methylbenzenesulfonate (25.4 g, 100 mmol) followed by THF (333 mL, 0.3 M). The mixture was stirred and cooled in an acetone/dry-ice bath (internal temperature at −78° C.). nBuLi (10 M in hexanes, 20 mL, 200 mmol) was added via a syringe over 10 min with internal temperature at about −65° C. The reaction mixture turned to a dark color and was stirred at −78° C. for 20 min. A mixture of water (50 mL) and THF (50 mL) was added dropwise via an addition funnel to quench the reaction (maintained internal temperature at about −70° C.). The mixture was warmed to ambient temperature and ethyl acetate (400 mL) was added. The organic layer was separated and the aqueous layer extracted with ethyl acetate (2×80 mL). The combined organics were washed with brine (50 mL), dried over Na$_2$SO$_4$ and evaporated to give a dark oil (29.3 g) that was purified on silica (220 g column, 60 mL/min) with gradients from 100% heptane to 40% ethyl acetate-60% heptane to give the title product as a colorless oil (22.73 g, 97% yield). $^1$H NMR (400

MHz, chloroform-d) δ ppm 7.83 (d, J=8.31 Hz, 2 H) 7.39 (d, J=8.19 Hz, 2 H) 6.09 (dd, J=14.31, 3.91 Hz, 1 H) 2.48 (s, 3 H). $^{19}$F NMR (376 MHz, chloroform-d) δ ppm −92.88−−88.40 (m, 1 F) −110.58−−107.12 (m, 1 F). The title product did not ionize in LCMS.

Step 2: Preparation of 1-benzyl-4,4-difluoropyrrolidin-3-yl-4-methylbenzenesulfonate

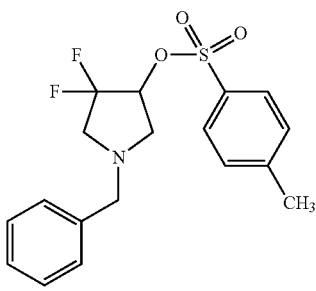 [SMILES: Cc1ccc(S(=O)(=O)OC2CN(Cc3ccccc3)CC2(F)F)cc1]

To a 250 mL flask was added 2,2-difluoroethenyl-4-methylbenzenesulfonate (14.0 g, 60 mmol) and neat N-benzyl-1-methoxy-N-[(trimethylsilyl)methyl]methanamine (61 mL, 240 mmol, 4 mol eq). The flask was flushed with nitrogen, place under nitrogen atmosphere, equipped with a water-cooled condenser then placed into a pre-heated bath (at 130° C.) and stirred for 5 min. TFA (0.6 mL, 6 mmol, 0.1 mol eq) was carefully added over ~5 min. CAUTION: there was smoke and volatile materials generated during TFA addition. Stirring and heating were continued for 30 min. The volatiles were removed to afford a residue. TEA (0.6 mL, ~6 mmol) was added to ensure the free base. The crude material was purified on silica (220 g, 60 mL/min) with gradients from 100% heptane to 20% ethyl acetate-80% heptane to give the title product as a light yellow oil (21.85 g, 100% yield, >85% purity). $^1$H NMR (400 MHz, chloroform-d) δ ppm 7.81 (d, J=8.31 Hz, 2 H) 7.29-7.36 (m, 5 H) 7.23-7.26 (m, 2 H) 4.76-4.92 (m, 1 H) 3.61 (d, J=9.66 Hz, 2 H) 3.20 (dd, J=10.39, 6.72 Hz, 1 H) 2.97-3.12 (m, 1 H) 2.71-2.84 (m, 1 H) 2.66 (ddd, J=10.45, 6.30, 1.47 Hz, 1 H) 2.45 (s, 3 H). $^{19}$F NMR (376 MHz, chloroform-d) δ ppm −100.41−−97.15 (m, 1 F) −111.60−−107.32 (m, 1F). m/z (APCI+) for $C_{18}H_{19}F_2NO_3S$ 368.1 (M+H)+.

Step 3: Preparation of 1-benzyl-4,4-difluoropyrrolidin-3-ol

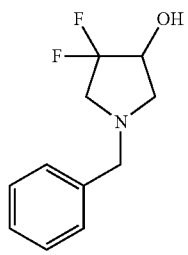 [SMILES: OC1CN(Cc2ccccc2)CC1(F)F]

To a 250 mL 3-necked flask equipped with a stir bar, water-cooled condenser, and an internal thermometer was added 1-benzyl-4,4-difluoropyrrolidin-3-yl-4-methylbenzenesulfonate (10.6 g, 25 mmol after purity correction) and methanol (80 mL). The mixture was stirred under nitrogen atmosphere, and cooled in an ice/water bath (internal temperature at about 10° C.). Magnesium turnings (3 g, 123 mmol, 5 mol eq) were added in small portions. After the Mg was added, the flask was removed from the bath to let the internal temperature warm to 20° C. LCMS of the reaction mixture showed major starting material still remained. The reaction was left stirring and after 1 hr, the internal temperature was at 30° C. (the internal temperature reached 40° C. for a short period of time and then the reaction began to cool down). After 4 hr, the internal temperature dropped to about 23° C. and LCMS showed the reaction was complete with a small amount of solid Mg remaining. The reaction was cooled in a water bath and water (5 mL) was slowly added. Internal temperature rose to about 30° C. for few minutes. The mixture solidified. Aqueous HCl (6 N, 30 mL total) was slowly added. The solid became soluble (pH was about 6). The volatiles were removed to minimum volume and aqueous KOH was added to adjust to pH 8 and the mixture extracted with DCM (3×200 mL). The organic layer was cloudy and was evaporated to a residue. Ethyl acetate (300 mL) was added and gave a fine suspension, which was stirred at rt over night. The insoluble material was removed by filtration and the filtrate was evaporated to give a brown oil (7.9 g). TLC showed Rf 0.6 (major) in 50% heptane-50% ethyl acetate. The crude material was purified on silica (120 g) with gradients from 100% heptane to 30% ethyl acetate-70% heptane to give the title product as a light-yellow oil (4.64 g, 89% yield, ~90% purity). $^1$H NMR (400 MHz, chloroform-d) δ ppm 7.27-7.39 (m, 5 H) 4.17-4.29 (m, 1 H) 3.56-3.75 (m, 2 H) 3.08 (ddd, J=10.15, 5.93, 0.79 Hz, 1 H) 2.86-3.02 (m, 2 H) 2.62 (ddd, J=10.15, 4.89, 2.45 Hz, 1 H) 2.31 (br. s., 1 H). $^{19}$F NMR (376 MHz, chloroform-d) δ ppm −102.24−−98.98 (m, 1 F) −115.46−−111.80 (m, 1 F). m/z (APCI+) for $C_{11}H_{13}F_2NO$ 214.3 (M+H)+.

Step 4: Preparation of tert-butyl 3,3-difluoro-4-hydroxypyrrolidine-1-carboxylate

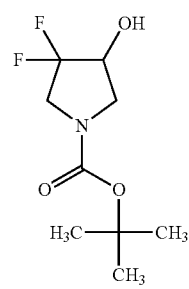

To a 500 mL flask was added 1-benzyl-4,4-difluoropyrrolidin-3-ol (4.6 g, 21.6 mmol), ethanol (200 mL) and Boc anhydride (5.65 g, 26 mmol, 1.2 mol eq). The resulting solution was degassed with nitrogen for 5 min. 20% Pd(OH)$_2$ on carbon (500 mg) was added and the resulting mixture was stirred under hydrogen atmosphere (used 2 balloons) at ambient temperature for 20 hr. The reaction was degassed with nitrogen. The catalyst was removed by filtration. The filtrate was evaporated to give a colorless oil that was purified on silica (40 g) with gradients from 100% heptane to 30% ethyl acetate-70% heptane to give the title product as a colorless oil (3.97 g, 82% yield, >95% purity). $^1$H NMR (400 MHz, chloroform-d) δ ppm 4.20-4.32 (m, 1 H) 3.63-3.82 (m, 3 H) 3.39-3.58 (m, 1 H) 2.52 (d, J=3.67 Hz, 1 H) 1.47 (s, 9 H). $^{19}$F NMR (376 MHz, CHLOROFORM-d) δ ppm −110.98−107.93 (m, 1 F) −125.43−−121.77 (m, 1 F). m/z (APCI+) for $C_9H_{15}F_2NO_3$ 124.3 (M+H)+.

Step 5: Preparation of tert-butyl 3,3-difluoro-4-{[(trifluoromethyl)sulfonyl]oxy}pyrrolidine-1-carboxylate

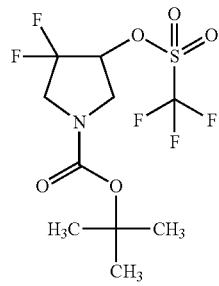

A solution of tert-butyl 3,3-difluoro-4-hydroxypyrrolidine-1-carboxylate (3.4 g, 15.2 mmol) in DCM (152 mL) was cooled to −10° C. (bath temperature, methanol/ice) under nitrogen atmosphere and pyridine (6.2 mL, 76 mmol, 5 mol eq) was added. Triflic anhydride (1 M in DCM, 38 mL, 38 mmol, 2.5 mol eq) was added via an addition funnel over 30 min. The solution turned from colorless to light brown/yellow, and was stirred in the cold bath for another 30 min. The reaction was quenched with aqueous citric acid buffer (0.5 M, about 30 mL used) to give pH 4.5. The organic layer was separated, extracted with more DCM (50 mL) and the combined organic layers were dried over $Na_2SO_4$ and evaporated to give the title product as a red oil (5.56 g, 96% yield, ~95 % purity). $^1$H NMR indicated pyridine (0.3 mol eq) present). $^1$H NMR (400 MHz, chloroform-d) δ ppm 5.18 (d, J=1.96 Hz, 1 H) 3.65-4.01 (m, 4 H) 1.49 (s, 9 H). $^{19}$F NMR (376 MHz, chloroform-d) δ ppm −75.59−−72.94 (m, 2 F) −78.39 (s, 1 F) −109.56−−105.09 (m, 1 F) −122.17−−117.49 (m, 1 F). The title product was not stable enough under LCMS condition.

Step 6: Preparation of tert-butyl 4-azido-3,3-difluoropyrrolidine-1-carboxylate

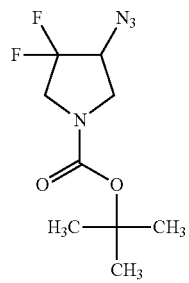

tert-Butyl 3,3-difluoro-4-{[(trifluoromethyl)sulfonyl]oxy}pyrrolidine-1-carboxylate (5.56 g, 15.2 mmol) was dissolved in DMF (20 mL) and cooled in an ice bath under nitrogen atmosphere. Tetrabutylammonium azide (TBA-$N_3$, 4.8 g, 17 mmol, 1.1 mol eq) in DMF (15 mL) was added slowly over 15 min via an addition funnel. The reaction mixture was stirred in the cold bath and was allowed to warm to ambient temperature gradually. After 16 hr, the reaction was diluted with MTBE (300 mL), washed with sat. aq. $NaHCO_3$ (2×30 mL), and brine (2×30 mL), dried over $Na_2SO_4$ and evaporated to give a residue. This crude material was purified on silica (40 g) with gradients from 100% heptane to 20% ethyl acetate-80% heptane to give the title product as a colorless oil (3.02 g, 80% yield, >95% purity). $^1$H NMR (400 MHz, chloroform-d) δ ppm 4.06 (dtd, J=8.86, 5.41, 5.41, 3.91 Hz, 1 H) 3.65-3.83 (m, 3 H) 3.36-3.57 (m, 1 H) 1.47 (s, 9 H). $^{19}$F NMR (376 MHz, chloroform-d) δ ppm −106.10−−102.44 (m, 1 F) −120.14−−116.68 (m, 1 F). m/z (ESI+) for $C_9H_{14}F_2N_4O_2$ 149 (small)/123 (M+H)+.

Step 7: Preparation of tert-butyl 4-amino-3,3-difluoropyrrolidine-1-carboxylate

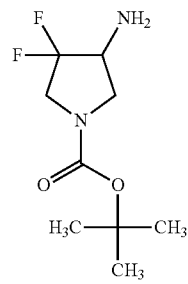

A solution of tert-butyl 4-azido-3,3-difluoropyrrolidine-1-carboxylate (3.01 g, 12.1 mmol) in ethanol (300 mL) was degassed with nitrogen and 20% Pd/C (300 mg) was added. The resulting mixture was stirred under hydrogen atmosphere (balloon) for 16 hr. The catalyst was removed by filtration. The filtrate was evaporated to give the title product as an oil (2.63 g, 98% yield, >85% purity). $^1$H NMR (400 MHz, chloroform-d) δ ppm 3.73-3.87 (m, 2 H) 3.69 (d, J=10.64 Hz, 1 H) 3.50-3.62 (m, 1 H) 3.13 (d, J=6.85 Hz, 1 H) 1.45-1.48 (m, 9 H). $^{19}$F NMR (376 MHz, chloroform-d) δ ppm −115.05−−110.78 (m, 1F) −120.95−−117.90 (m, 1 F). m/z (APCI+) for $C_9H_{16}F_2N_2O_2$ 123 (M+H)+.

Step 8: Preparation of tert-butyl 3,3-difluoro-4-{[3-(methylsulfonyl)propanoyl]amino}pyrrolidine-1-carboxylate

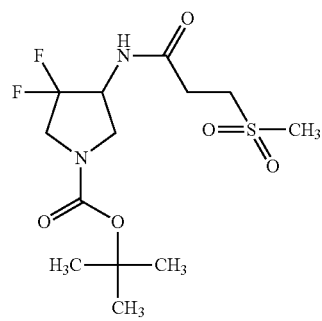 [SMILES: CC(C)(C)OC(=O)N1CC(NC(=O)CCS(C)(=O)=O)C(F)(F)C1]

To a reaction flask was added tert-butyl 4-amino-3,3-difluoropyrrolidine-1-carboxylate (1.36 g, 6.12 mmol), 3-(methylsulfonyl)propanoic acid (1.02 g, 6.73 mmol, 1.1 mol eq), DCM (31 mL, 0.4 M), NMM (1.35 mL, 12.2 mmol, 2 mol eq), HOBt (1.31 g, 9.2 mmol, 1.5 mol eq) and EDC-HCl (1.85 g, 9.2 mmol, 1.5 mol eq). The resulting suspension was stirred at ambient temperature under a nitrogen atmosphere for 2 hr. The reaction was diluted with DCM (80 mL), washed with aqueous $NaHCO_3$ (2×30 mL) and the organic layer was dried over Na₂SO₄ and evaporated to give a residue that was purified via silica flash chromatography eluting with gradients from 100% heptane to 100% ethyl acetate to give the title product as a white foamy solid (1.65 g, 76% yield, >95% purity). ¹H NMR (400 MHz, chloroform-d) δ ppm 6.45 (br. s., 1 H) 4.68-4.89 (m, 1 H) 3.94 (dd, J=10.70, 8.62 Hz, 1 H) 3.62-3.86 (m, 2 H) 3.43 (t, J=7.15 Hz, 2 H) 3.18 (br. s., 1 H) 2.97 (s, 3 H) 2.84 (td, J=7.15, 1.96 Hz, 2 H) 1.47 (s, 9 H). ¹⁹F NMR (376 MHz, chloroform-d) δ ppm −112.79-−110.52 (m, 1 F) −114.51-−113.30 (m, 1 F). m/z (APCI+) for $C_{13}H_{22}F_2N_2O_5S$ 257.1 (M+H)+.

Step 9: Preparation of N-(4,4-difluoropyrrolidin-3-yl)-3-(methylsulfonyl)propanamide hydrochloride

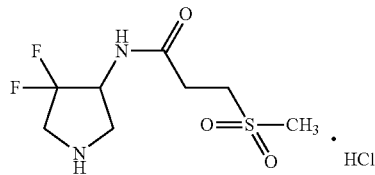

To a solution of tert-butyl 3,3-difluoro-4-{[3-(methylsulfonyl)propanoyl]amino}pyrrolidine-1-carboxylate (1.60 g, 4.5 mmol) in acetonitrile (45 mL) was added HCl (4 M in dioxane, 4.5 mL, 18 mmol, 4 mol eq). The resulting solution turned to a white suspension after 1 hr, and was stirred at ambient temperature for 3 hr. The volatiles were removed to dryness to give a white solid, which was suspended in ethyl ether (100 mL). The white solid was collected by filtration, washed with ether (20 mL) and dried to give the title product as a white solid (1.26 g, 96% yield, >95% purity, assumed 1 HCl salt). ¹H NMR (400 MHz, DMSO-d6) δ ppm 9.99 (br. s., 2 H) 8.75 (br. s., 1 H) 4.71-4.95 (m, 1 H) 3.58-3.89 (m, 3 H) 3.28-3.43 (m, 2 H) 3.16 (t, J=10.88 Hz, 2 H) 2.99 (s, 3 H) 2.67 (t, J=7.58 Hz, 2 H). ¹⁹F NMR (376 MHz, DMSO-d6) δ ppm −108.27-−107.26 (m, 1 F) −109.70-−108.82 (m, 1 F). m/z (APCI+) for $C_8H_{14}F_2N_2O_3S$ 257.2 (M+H)+.

Preparation 9: Preparation of tert-butyl (+/−)-cis-3a-methoxyhexahydropyrrolo[3,4-c]pyrrole-2(1H)-carboxylate

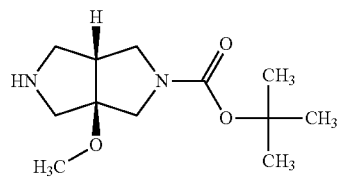

Step 1: Preparation of 3,3-dimethoxypyrrolidine-2,5-dione

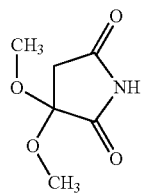

Bromine (24.8 g, 154 mmol) was added dropwise to a solution of maleimide (10 g, 103 mmol) in MeOH (400 mL) at 0° C. The reaction mixture was stirred at rt for 16 hr, and then concentrated in vacuo. Sodium (9.6 g, 412 mmol) was added to MeOH (400 mL) at 0° C. Once the sodium was dissolved, the crude material in MeOH (200 mL) was added dropwise. The reaction mixture was stirred at rt overnight. The mixture was neutralized by slow addition of 6 M HCl, and then separated between water and EtOAc (100 mL). The aqueous layer was washed with EtOAc (2×100 mL), and then the combined organic extracts were washed with brine (100 mL), dried over MgSO₄ and concentrated to afford the title compound (12.3 g, 75% yield) as a yellow solid.

Step 2: Preparation of 3-methoxy-1H-pyrrole-2,5-dione

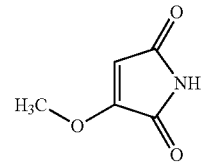

To a solution of 3,3-dimethoxypyrrolidine-2,5-dione (12.3 g, 77 mmol) in toluene (500 mL) was added TsOH·water (1.46 g, 7.7 mmol). A Dean Stark Trap was attached and the reaction mixture was refluxed overnight. TLC (petroleum ether/EtOAc=1/1) showed the reaction was complete. The mixture was concentrated and purified by column chromatography (from petroleum ether/EtOAc=2/1 to petroleum ether/EtOAc=1/1) to afford 3-methoxy-1H-pyrrole-2,5-dione (6.9 g, 70% yield) as an orange solid.

Step 3: Preparation of (+/−)-cis-5-benzyl-3a-methoxytetrahydropyrrolo[3,4-c]pyrrole-1,3(2H,3aH)-dione

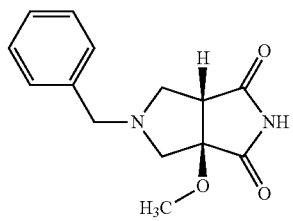 [SMILES: CO[C@@]12CN(Cc3ccccc3)C[C@@H]1C(=O)NC2=O]

Note: preparation was done in 5 batches in parallel.
To a solution of 3-methoxy-1H-pyrrole-2,5-dione (3 g, 24 mmol) and TFA (0.34 g, 3 mmol) in CH₂Cl₂ (300 mL) was added slowly a solution of N-(methoxymethyl)-N-(trimethylsilylmethyl)benzylamine (14.2 g, 48 mmol) in CH₂Cl₂ (100 mL) at a rate such to maintain the internal reaction temperature <2° C. The resulting solution was slowly warmed to ambient temperature and stirred overnight. TLC (petroleum ether/EtOAc=1/1) showed the reaction was complete. The combined five batches of reaction mixture was diluted with saturated sodium bicarbonate (100 mL), and the organics was dried over MgSO₄, concentrated and purified by column chromatography (from petroleum ether/EtOAc=10/1 to petroleum ether/EtOAc=1/1) to afford title product (18 g, for 5 batches, 58% yield) as a light yellow oil, which was further purified by preparative HPLC to afford pure title product (4.5 g, 14.6% yield) as an oil.

Step 4: Preparation of (+/−)-cis-2-benzyl-3a-methoxyoctahydropyrrolo[3,4-c]pyrrole

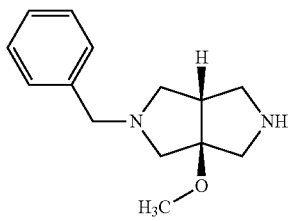 [SMILES: CO[C@]12CNC[C@H]1CN(Cc1ccccc1)C2]

To a solution of (+/−)-cis-5-benzyl-3a-methoxytetrahydropyrrolo[3,4-c]pyrrole-1,3(2H,3aH)-dione (4.5 g, 17 mmol) in THF (200 mL) was added LAH solution (35 mL, 35 mmol, 1 M in THF) at 0° C. The resulting mixture was stirred at 45° C. overnight. TLC (petroleum ether/EtOAc=1/1) showed the reaction was complete. The mixture was quenched by water (3 mL) and filtered. The filtrate was concentrated to afford crude title compound (3.7 g, crude), which was used for the next step directly.

Step 5: Preparation of (+/−)-cis-tert-butyl 5-benzyl-3a-methoxyhexahydropyrrolo[3,4-c]pyrrole-2(1H)-carboxylate

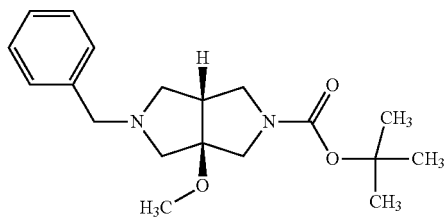 [SMILES: CO[C@@]12CN(Cc3ccccc3)C[C@@H]1CN(C(=O)OC(C)(C)C)C2]

To a solution of (+/−)-cis-2-benzyl-3a-methoxyoctahydropyrrolo[3,4-c]pyrrole (3.7 g, crude) in CH$_3$CN (150 mL) was added Boc$_2$O (7.63 g, 35 mmol), Et$_3$N (7.07 g, 70 mmol) and DMAP (0.43 g, 3.5 mmol). The resulting mixture was stirred at 45° C. for three days. The mixture was concentrated and purified by column chromatography (from petroleum ether/EtOAc=20/1 to petroleum ether/EtOAc=2/1) to afford the title compound (1.5 g, 26% yield via two steps) as a red oil.

Step 6: Preparation of (+/−)-cis-tert-butyl 3a-methoxyhexahydropyrrolo[3,4-c]pyrrole-2(1H)-carboxylate

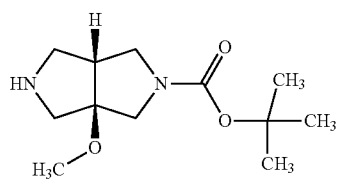 [SMILES: CO[C@@]12CNC[C@@H]1CN(C(=O)OC(C)(C)C)C2]

To a solution of (+/−)-cis-tert-butyl 5-benzyl-3a-methoxyhexahydropyrrolo[3,4-c]pyrrole-2(1H)-carboxylate (1.5 g, 4.5 mmol) in MeOH (100 mL) was added Pd(OH)$_2$/C (300 mg) under nitrogen. The suspension was degassed under vacuum and purged with hydrogen three times. The mixture was stirred at 40-50° C. under hydrogen (45 psi) overnight. TLC (petroleum ether/EtOAc=2/1) showed the reaction was complete. The mixture was filtered, concentrated and purified by column chromatography (CH$_2$Cl$_2$/MeOH=15/1) to afford the title compound (454 mg, 41% yield) as a yellow gum. $^1$H NMR (400 MHz, CDCl$_3$) δ 3.95 (brs., 2 H), 3.51-3.78 (m, 3 H), 3.36-3.50 (m, 2 H), 3.14-3.35 (m, 4 H), 2.83-3.08 (m, 2 H), 2.75 (brs., 1 H), 1.45 (s, 9 H). m/z (APCI+) for C$_{12}$H$_{22}$N$_2$O$_3$ [M−56+H]$^+$.

Preparation 10: Preparation of (+/−)-cis-2-benzyl-3a-fluorooctahydropyrrolo[3,4-c]pyrrole

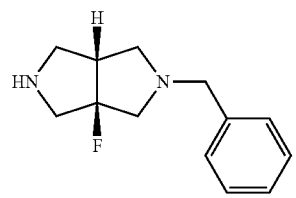 [SMILES: F[C@@]12CNC[C@@H]1CN(Cc1ccccc1)C2]

Step 1: Preparation of 4-(benzylamino)-3,3-difluoro-4-oxobutanoic acid

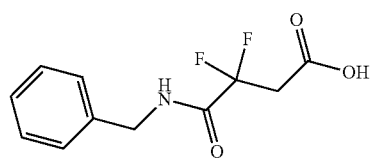 [SMILES: O=C(O)CC(F)(F)C(=O)NCc1ccccc1]

To a solution of 2,2-difluorosuccinic acid (2.15 g, 14.0 mmol) in iPrOAc (23 mL) was added trifluoroacetic anhydride (2.34 mL, 16.7 mmol) in one portion at ambient temperature. The reaction solution was stirred at 50° C. for 2 hr. The reaction solution was allowed to cool to 5° C. in an ice bath. Benzyl amine (2.29 mL, 20.9 mmol) was added dropwise while the reaction temperature was maintained below 20° C. The solution was stirred at ambient temperature for 2 hr. The reaction was quenched with water (10 mL) followed by saturated Na$_2$CO$_3$ to pH 8-9. The separated organic phase was discarded. The aqueous phase was acidified with 6 N HCl to pH 1 and extracted with EtOAc (2×100 mL). The combined organic phase was washed with 2 N HCl, brine (100 mL), dried over MgSO$_4$ filtered and concentrated. The intermediate was carried forward without further purification (2.89 g, 56.8% yield). $^1$H NMR (400 MHz, CDCl$_3$) δ ppm 7.28-7.42 (m, 5 H) 7.14-7.21 (m, 1 H) 6.77 (br. s., 1 H) 4.54 (d, J=5.87 Hz, 2 H) 3.39 (t, J=14.18 Hz, 2 H).

Step 2: Preparation of 1-benzyl-3,3-difluoropyrrolidine-2,5-dione

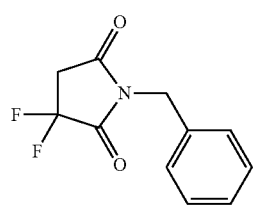 [SMILES: O=C1CC(F)(F)C(=O)N1Cc1ccccc1]

To a solution of the crude 4-(benzylamino)-3,3-difluoro-4-oxobutanoic acid in iPrOAc (40 mL), SOCl₂ (2.04 mL, 27.9 mmol, 2 eq) was added at ambient temperature. The reaction solution was stirred at 55° C. for 4 hr. The reaction was cooled to 0-5° C. Half saturated brine (50 mL) was added slowly to quench the excess SOCl₂. The organic phase was washed with brine (70 mL) and 2 M Na₂CO₃ (about 50 mL) to pH=8-9, extracted two times with EtOAc. The combined organic layer was washed with brine (50 mL), the organic phase was dried over MgSO₄, filtered and concentrated. The crude residue was diluted with CH₂Cl₂ and filtered to remove precipitate. The concentrated filtrate was purified by column chromatography and eluted with 2-20% EtOAc/Heptane to obtain the title compound as a clear oil (1.74 g, 65%) $^1$H NMR (400 MHz, CDCl₃) δ ppm 7.30-7.43 (m, 5 H) 4.76 (s, 2 H) 3.18 (t, J=12.53 Hz, 2 H).

Step 3: Preparation of (+/−)-cis-2,5-dibenzyl-3a-fluorotetrahydropyrrolo[3,4-c]pyrrole-1,3(2H,3aH)-dione

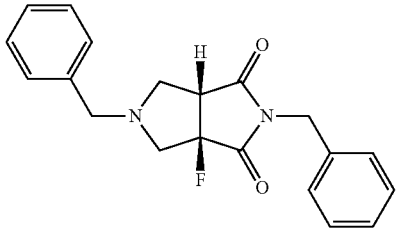 [SMILES: O=C1[C@H]2CN(Cc3ccccc3)C[C@@]2(F)C(=O)N1Cc1ccccc1]

To a solution of 1-benzyl-3,3-difluoropyrrolidine-2,5-dione (325 mg, 1.44 mmol) in acetonitrile (3.6 mL), LiF (56 mg, 1.50 eq) and a stir bar were added. The reaction mixture was sonicated for 2.5 hr at rt. N-(Methoxymethyl)-N-(trimethylsilylmethyl)benzylamine (0.4 mL, 1.59 mmol, 1.10 eq) and LiF (37 mg, 1.44 mmol, 1 eq) were added and continued to sonicate for 0.5 hr. The reaction mixture was concentrated and the salt was removed by filtration. The crude residue was purified by column chromatography and eluted with 2 to 20% EtOAc/heptane and purified further with 2 to 10% EtOAc/heptane. The desired fractions were faintly ultraviolet active but were visualized with KMnO₄ stain. The title compound was isolated as a yellow oil (196 mg, 40% yield). $^1$H NMR (400 MHz, DMSO-d₆) δ ppm 7.10-7.43 (m, 10 H) 4.57-4.75 (m, 2 H) 3.63 (s, 2 H) 3.56-3.65 (m, 1 H) 3.33-3.41 (m, 1 H) 3.13 (d, J=9.29 Hz, 1 H) 2.74 (dd, J=9.35, 7.03 Hz, 1 H) 2.57-2.70 (m, 1 H). m/z (APCI+) for C₂₀H₂₀FN₂O₂ 339.20 (M+H)⁺.

Step 4: Preparation of (+/−)-cis-tert-butyl 5-benzyl-3a-fluoro-4,6-dioxohexahydropyrrolo[3,4-c]pyrrole-2(1H)-carboxylate

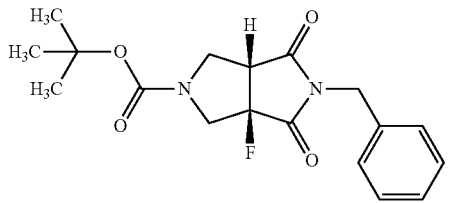 [SMILES: CC(C)(C)OC(=O)N1C[C@@H]2C(=O)N(Cc3ccccc3)C(=O)[C@]2(F)C1]

To a nitrogen purged solution of (+/−)-cis-2,5-dibenzyl-3a-fluorotetrahydropyrrolo[3,4-c]pyrrole-1,3(2H,3aH)-dione (195 mg, 0.576 mmol) in EtOH (3 mL) was added 20% Pd(OH)₂/C (60 mg). The reaction was evacuated and back-filled with hydrogen three times, then Boc₂O (151 mg, 0.691 mmol, 1.2 eq) was added. The reaction was evacuated and back-filled with hydrogen again then run under a hydrogen atmosphere (balloon). After 1.5 hr, an additional 20% Pd(OH)₂/C (40 mg) was added and stirred for 18 hr. The reaction mixture was filtered and washed with MeOH. The filtrate was concentrated and placed on the column eluting with 2 to 25 EtOAc/heptane to obtain the title compound (160 mg, 80% yield). $^1$H NMR (400 MHz, DMSO-d₆) δ ppm 7.25-7.39 (m, 3 H) 7.21 (d, J=7.34 Hz, 2 H) 4.62 (s, 2 H) 3.89-4.08 (m, 2 H) 3.60-3.83 (m, 3 H) 1.37 (s, 9 H). m/z (APCI+) for C₁₈H₂₁FN₂O₄—C₂H₉O₅ 249.20 (M+H-Boc)⁺.

Step 5: Preparation of (+/−)-cis-2-benzyl-3a-fluorooctahydropyrrolo[3,4-c]pyrrole

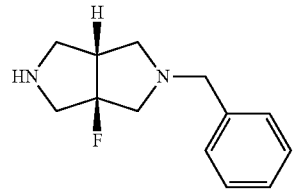 [SMILES: F[C@@]12CNC[C@@H]1CN(Cc1ccccc1)C2]

(+/−)-cis-tert-Butyl-5-benzyl-3a-fluoro-4,6-dioxohexahydropyrrolo[3,4-c]pyrrole-2(1H)-carboxylate (160 mg, 0.459 mmol) was dissolved in THF (4.5 mL), and BH₃.Me₂S (0.174 mL, 1.84 mmol, 4.00 eq) was added at ambient temperature. The reaction mixture was stirred at 55° C. for 1.5 hr. A light slurry was formed during the reaction. The reaction was then cooled to 0° C. and quenched with dry MeOH (2 mL) dropwise followed by concentrated HCl until pH=4. The reaction solution was stirred at 0-10° C. for 1 hr. The temperature was raised to 55° C. for 1.5 hr was then cooled to rt and stirred for 20 hr. The reaction mixture was concentrated under reduced pressure, diluted with MeOH, neutralized by passing through an SCX column with MeOH and then 7 N NH₃/MeOH and obtained the free amine. The title product was carried forward without further purification (100 mg, crude) m/z (APCI+) for C₁₃H₁₇FN₂ 221.25 (M+H)⁺.

Preparation of tert-butyl 3-(4-amino-3-methoxy-1H-pyrazol-1-yl)azetidine-1-carboxylate

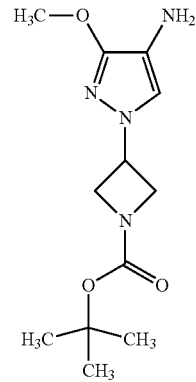 [SMILES: COc1nn(C2CN(C(=O)OC(C)(C)C)C2)cc1N]

Step 1: Preparation of tert-butyl 3-(3-methoxy-4-nitro-1H-pyrazol-1-yl)azetidine-1-carboxylate

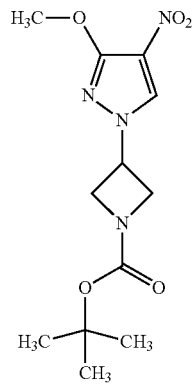

To a cooled (0° C.) suspension of 3-methoxy-4-nitro-1H-pyrazole (1.00 g, 6.99 mmol, 1.00 eq), tert-butyl-3-hydroxy-pyrrolidine-1-carboxylate (2.12 g, 12.2 mmol, 1.75 eq), and polystyrene bound triphenylphosphine (4.06 g, 12.2 mmol, 1.75 eq, 3 mmol/gram) in THF (45 mL) was added diethyl azodicarboxylate (2.42 mL, 13.0 mmol, 1.90 eq) in a drop-wise manner over 3 min. The reaction mixture was allowed to warm to ambient temperature and stirred for 15 hr. The reaction mixture was then diluted with EtOAc (60 mL), filtered and the filtrate concentrated. The crude reaction mixture was purified via flash chromatography on silica gel eluting with a gradient of 0-60% EtOAc in heptane to give the title compound (1.52 g, 72.9% yield) as a white solid. $^1$H NMR (400 MHz, CDCl$_3$) δ ppm 8.12 (s, 1H) 4.87 (tt, J=5.6, 7.5 Hz, 1H) 4.40-4.28 (m, 4H) 4.09 (s, 3H) 1.48 (s, 9H). m/z (APCI+) for C$_7$H$_{11}$N$_4$O$_3$ 198.9 (M−Boc+H)$^+$.

Step 2: Preparation of tert-butyl 3-(4-amino-3-methoxy-1H-pyrazol-1-yl)azetidine-1-carboxylate

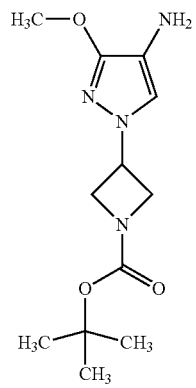

A nitrogen-flushed round bottom flask was charged with tert-butyl 3-(3-methoxy-4-nitro-1H-pyrazol-1-yl)azetidine-1-carboxylate (188 mg, 0.63 mmol, 1.00 eq), 10% Pd/C (100 mg) and methanol (10 mL). The reaction mixture was sparged with hydrogen for 5 min then stirred vigorously under hydrogen atmosphere for 18 hr. The reaction mixture was then sparged with nitrogen, filtered through Celite®, concentrated, and azeotroped from toluene (2×20 mL) to give an oil that was used without further purification. $^1$H NMR (400 MHz, DMSO-d6) δ ppm 7.04 (s, 1H), 4.82 (tt, J=5.4, 7.9 Hz, 1H), 4.15 (t, J=8.3 Hz, 2H), 4.04-3.95 (m, 2H), 3.79 (s, 3H), 3.44 (br. s., 2H), 1.40 (s, 9H). m/z (APCI+) for C$_7$H$_{13}$N$_4$O 169.2 (M−Boc+H)$^+$.

Preparation 11: Preparation of 1-(3-methoxy-4-amino-1H-pyrazol-1-yl)propan-2-ol

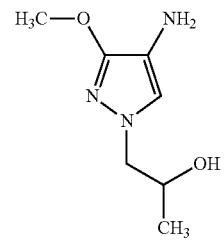

Step 1: Preparation of 1-(3-methoxy-4-nitro-1H-pyrazol-1-yl)propan-2-ol

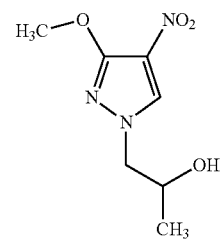

To a suspension of 3-methoxy-4-nitro-1H-pyrazole (2.00 g, 14.0 mmol, 1.00 eq) and cesium carbonate (13.7 g, 41.9 mmol, 3.0 eq) was added 1-bromo-2-propanol (2.70 mL, 22.4 mmol, 1.60 eq, 70% purity) and the reaction mixture was heated at 60° C. After 3.5 hr, an additional portion of 1-bromo-2-propanol (2.70 mL, 22.4 mmol, 1.60 eq, 70% purity) was added. After a further 12 hr, the reaction mixture was cooled to ambient temperature and diluted with water (100 mL) and EtOAc (50 mL). The layers were separated and the aqueous phase was extracted with EtOAc (4×50 mL). The combined organics were washed with water (50 mL) and brine (50 mL), dried (Na$_2$SO$_4$), concentrated, and purified via flash chromatography on silica gel eluting with a gradient of 0-50% EtOAc in heptane to give the title compound (945 mg, 34% yield) as a white solid. $^1$H NMR (400 MHz, CDCl$_3$) δ ppm 8.09 (s, 1H), 4.32-4.22 (m, 1H), 4.06 (s, 3H), 4.05 (dd, J=5.0, 13.0 Hz, 1H), 3.87 (dd, J=8.0, 13.0 Hz, 1H), 2.60 (br. s., 1H), 1.29 (d, J=6.4 Hz, 3H). m/z (APCI+) for C$_7$H$_{12}$N$_3$O$_4$ 201.9 (M+H)$^+$.

Step 2: Preparation of 1-(3-methoxy-4-amino-1H-pyrazol-1-yl)propan-2-ol

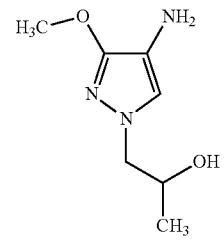

A nitrogen-flushed round bottom flask was charged with 1-(3-methoxy-4-nitro-1H-pyrazol-1-yl)propan-2-ol (345 mg, 1.72 mmol, 1.00 eq), 10% Pd/C (200 mg) and methanol (20 mL). The reaction mixture was sparged with hydrogen for 10 min then stirred vigorously under hydrogen atmosphere for 14 hr. The reaction mixture was then sparged with nitrogen, filtered through Celite®, and concentrated to give the title compound as an oil that was used without further purification. $^1$H NMR (400 MHz, DMSO-d6) δ ppm 6.92 (s, 1H) 4.70 (d, J=4.9 Hz, 1H) 3.89-3.77 (m, 1H) 3.74 (s, 3H) 3.73-3.55 (m, 2H) 0.97 (d, J=6.2 Hz, 3H). m/z (APCI+) for $C_7H_{14}N_3O_2$ 172.3 (M+H)$^+$.

Preparation 12: Preparation of (S)-3-methoxy-1-(1-methylpyrrolidin-3-yl)-1H-pyrazol-4-amine

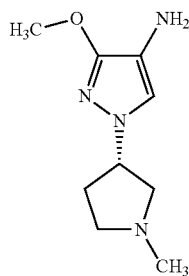

Step 1: Preparation of (S)-3-methoxy-1-(1-methylpyrrolidin-3-yl)-4-nitro-1H-pyrazole

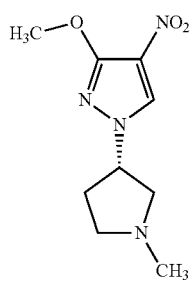 [SMILES: COc1nn([C@H]2CCN(C)C2)cc1[N+](=O)[O-]]

To a suspension of 3-methoxy-4-nitro-1H-pyrazole (2.00 g, 14.0 mmol, 1.00 eq), (R)-1-methyl-pyrrolidin-3-ol (1.56 g, 15.4 mmol, 1.10 eq), and polystyrene bound triphenylphosphine (6.53 g, 19.6 mmol, 1.40 eq, 3 mmol/gram) in THF (140 mL) was added a solution of di-tert-butyl azodicarboxylate (4.51 g, 19.6 mmol, 1.40 eq) in THF (25 mL) in a drop-wise manner over 5 min. The reaction mixture was allowed to stir for 18 hr. The reaction mixture was then diluted with EtOAc (100 mL), filtered and the filtrate concentrated. The crude reaction mixture was purified via flash chromatography on silica gel eluting with a gradient of 50-100% EtOAc in heptane then to 10% 7 N methanolic ammonia/EtOAc to give the title compound (2.39 g, 80% yield) as a white solid. $^1$H NMR (400 MHz, DMSO-d6) δ ppm 8.69 (s, 1H), 4.84-4.72 (m, 1H), 3.94 (s, 3H), 2.86-2.75 (m, 2H), 2.72 (dd, J=7.0, 10.0 Hz, 1H), 2.40 (dt, J=6.2, 8.4 Hz, 1H), 2.36-2.29 (m, 1H), 2.28 (s, 3H), 2.16-2.06 (m, 1H). m/z (APCI+) for $C_9H_{15}N_4O_3$ 227.2 (M+H)$^+$.

Step 2: Preparation of (S)-3-methoxy-1-(1-methylpyrrolidin-3-yl)-1H-pyrazol-4-amine

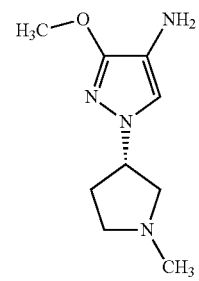

A nitrogen-flushed round bottom flask was charged with (S)-3-methoxy-1-(1-methylpyrrolidin-3-yl)-4-nitro-1H-pyrazole (300 mg, 1.33 mmol, 1.00 eq), 10% Pd/C (200 mg) and methanol (20 mL). The reaction mixture was sparged with hydrogen for 10 min then stirred vigorously under hydrogen atmosphere for 16 hr. The reaction mixture was then sparged with nitrogen, filtered through Celite®, and concentrated to give an oil that was used without further purification. $^1$H NMR (400 MHz, DMSO-d6) δ ppm 6.99 (s, 1H), 4.51 (tdd, J=4.8, 7.3, 9.3 Hz, 1H), 3.74 (s, 3H), 3.36 (br. s., 2H), 2.71-2.61 (m, 2H), 2.57 (dd, J=4.8, 9.5 Hz, 1H), 2.40 (dt, J=6.5, 8.3 Hz, 1H), 2.25 (s, 3H), 2.23-2.14 (m, 1H), 1.94-1.84 (m, 1H). m/z (APCI+) for $C_9H_{17}N_4O$ 197.3 (M+H)$^+$.

The following examples were made with non-critical changes or substitutions to the exemplified procedures that would be understood by one skilled in the art.

TABLE 1

| Example No. (Scheme) | Structure and Compound Name | LRMS m/z | ¹H NMR |
|---|---|---|---|
| 1 (Scheme A) | 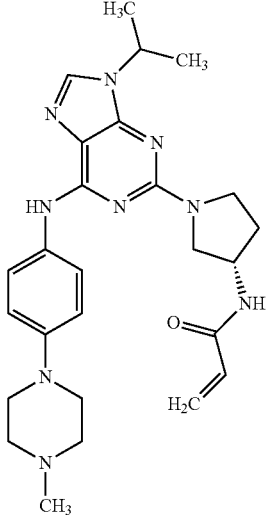<br>(S)-N-(1-(9-isopropyl-6-((4-(4-methylpiperazin-1-yl)phenyl)amino)-9H-purin-2-yl)pyrrolidin-3-yl)acrylamide | 490.2 [M + H]⁺ | ¹H NMR (400 MHz, DMSO-d6) δ ppm 9.16 (s, 1 H) 8.36 (d, J = 6.72 Hz, 1 H) 7.91 (s, 1 H) 7.85 (d, J = 8.80 Hz, 2 H) 6.87 (d, J = 8.93 Hz, 2 H) 6.18-6.34 (m, 1 H) 6.03-6.15 (m, 1 H) 5.59 (dd, J = 9.96, 2.02 Hz, 1 H) 4.62 (dt, J = 13.33, 6.54 Hz, 1 H) 4.43 (d, J = 5.14 Hz, 1 H) 3.71-3.87 (m, 1 H) 3.63 (dt, J = 12.62, 6.46 Hz, 2 H) 3.43 (dd, J = 11.25, 3.30 Hz, 1 H) 3.07 (m, J = 4.65 Hz, 4 H) 2.45 (m, J = 4.40 Hz, 4 H) 2.22 (s, 4 H) 1.89 (dd, J = 11.37, 5.87 Hz, 1 H) 1.51 (d, J = 6.72 Hz, 6 H) |
| 2 (Schemes A and C) | 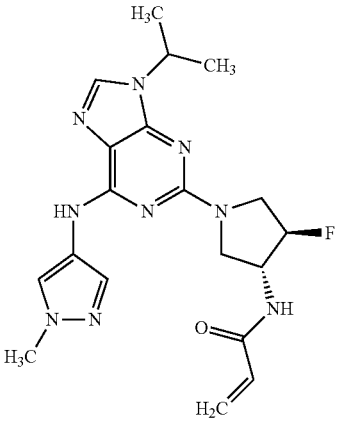<br>N-((3R,4R)-4-fluoro-1-(9-isopropyl-6-((1-methyl-1H-pyrazol-4-yl)amino)-9H-purin-2-yl)pyrrolidin-3-yl)acrylamide | 414.1 [M + H]⁺ | ¹H NMR (600 MHz, DMSO-17 mm) δ ppm 9.65 (br. s., 1 H) 8.50 (d, J = 6.97 Hz, 1 H) 8.00 (s, 1 H) 7.92 (s, 1 H) 7.69 (s, 1 H) 6.20-6.29 (m, 1 H) 6.08-6.18 (m, 1 H) 5.63 (d, J = 10.82 Hz, 1 H) 5.03-5.25 (m, 1 H) 4.43-4.70 (m, 2 H) 3.88 (br. s., 2 H) 3.82 (s, 3 H) 3.70 (d, J = 10.45 Hz, 2 H) 1.50 (d, J = 6.42 Hz, 6 H) |

TABLE 1-continued

| Example No. (Scheme) | Structure and Compound Name | LRMS m/z | ¹H NMR |
|---|---|---|---|
| 3 (Scheme B) | 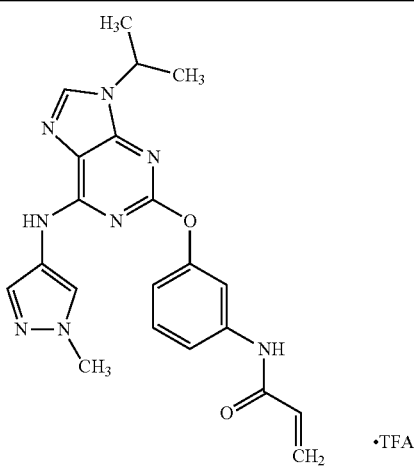<br>N-(3-((9-isopropyl-6-((1-methyl-1H-pyrazol-4-yl)amino)-9H-purin-2-yl)oxy)phenyl)acrylamide trifluoroacetate | 419.0 [M + H]⁺ | ¹H NMR (400 MHz, DMSO-d6) δ ppm 10.38 (s, 1H), 10.18 (s, 1H), 8.23 (s, 1H), 7.62-7.63 (d, 2H), 7.44-7.49 (t, 2H), 7.33 (s, 1H), 7.16 (s, 1H), 6.94-6.96 (d, 1H), 6.41-6.45 (q, 1H), 6.23-6.27 (d, 1H), 5.75-5.78 (d, 1H), 4.67-4.70 (m, 1H), 3.56 (s, 3H), 1.53-1.54 (d, 6H) |
| 4 (Scheme D) | 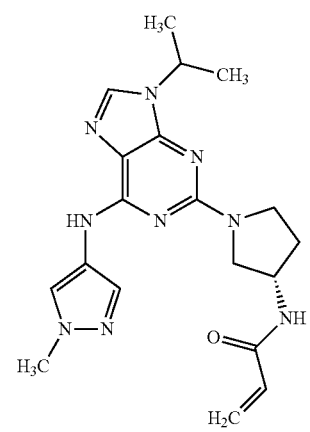<br>(S)-N-(1-(9-isopropyl-6-((1-methyl-1H-pyrazol-4-yl)amino)-9H-purin-2-yl)pyrrolidin-3-yl)acrylamide | 396.3 [M + H]⁺ | ¹H NMR (400 MHz, DMSO-d6) δ ppm 9.56 (s, 1 H) 8.38 (d, J = 6.72 Hz, 1 H) 7.97 (s, 1 H) 7.89 (s, 1 H) 7.75 (s, 1 H) 6.20-6.34 (m, 1 H) 6.05-6.18 (m, 1 H) 5.60 (dd, J = 10.03, 2.32 Hz, 1 H) 4.56-4.73 (m, 1 H) 4.43 (br. s., 1 H) 3.76-3.92 (m, 4 H) 3.68 (d, J = 5.14 Hz, 2 H) 3.43-3.51 (m, 1 H) 2.15-2.28 (m, 1 H) 1.87-1.99 (m, 1 H) 1.51 (d, J = 6.85 Hz, 6 H) |
| 5 (Scheme D) | 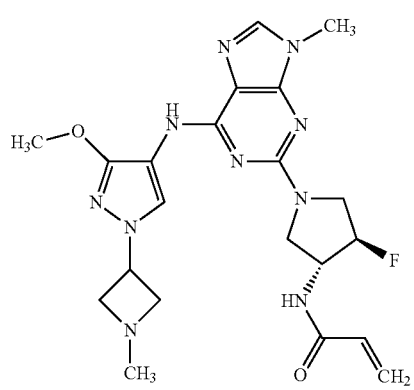<br>N-((3R,4R)-4-fluoro-1-(6-((3-methoxy-1-(1-methylazetidin-3-yl)-1H-pyrazol-4-yl)amino)-9-methyl-9H-purin-2-yl)pyrrolidin-3-yl)acrylamide | 471.2 [M + H]+ | ¹H NMR (400 MHz, DMSO-d6) δ ppm 8.20 (br. s., 1H), 8.14 (br. s., 1H), 7.71 (br. s., 1H), 6.24 (dd, J = 10.0, 16.0 Hz, 1H), 6.14 (d, J = 16.0 Hz, 1H), 5.60 (d, J = 9.3 Hz, 1H), 5.16 (d, J = 51.0 Hz, 1H), 4.80 (br. s., 1H), 4.58-4.41 (m, 1H), 3.99-3.77 (m, 7H), 3.72-3.55 (m, 6H) |

TABLE 1-continued

| Example No. (Scheme) | Structure and Compound Name | LRMS m/z | $^1$H NMR |
|---|---|---|---|
| 6 (Scheme E) | 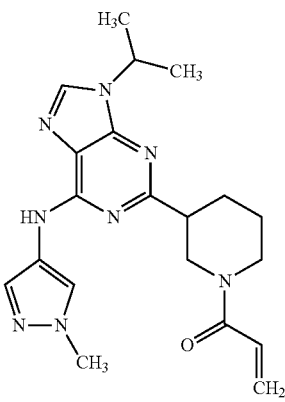<br>1-(3-(9-isopropyl-6-((1-methyl-1H-pyrazol-4-yl)amino)-9H-purin-2-yl)piperidin-1-yl)prop-2-en-1-one (single enantiomer with unknown absolute stereochemistry) | 395.1 [M + H]$^+$ | $^1$H NMR (700 MHz, DMSO-17 mm) δ ppm 9.87 (br. s., 1 H) 8.28 (br. s., 1 H) 7.96-8.13 (m, 1 H) 7.74 (d, J = 7.26 Hz, 1 H) 6.76-6.91 (m, 1 H) 5.99-6.17 (m, 1 H) 5.53-5.75 (m, 1 H) 4.69-4.84 (m, 2 H) 4.03-4.30 (m, 2 H) 3.84 (s, 3 H) 2.74-3.02 (m, 2 H) 2.11-2.28 (m, 1 H) 1.75-2.01 (m, 2 H) 1.54 (d, J = 2.64 Hz, 7 H) |
| 7 (Scheme F) | 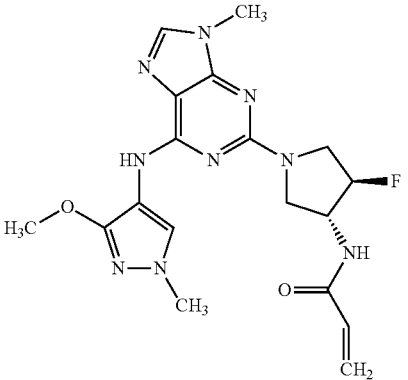<br>N-((3R,4R)-4-fluoro-1-(6-((3-methoxy-1-methyl-1H-pyrazol-4-yl)amino)-9-methyl-9H-purin-2-yl)pyrrolidin-3-yl)acrylamide | 416.1 [M + H]+ | $^1$H NMR (400 MHz, DMSO-d6) δ ppm 8.44 (d, J = 6.5 Hz, 1 H) 7.97 (s, 1 H) 7.82 (s, 1 H) 7.78 (s, 1 H) 6.23 (dd, J = 10.0, 17.0 Hz, 1 H) 6.14 (dd, J = 2.8, 17.0 Hz, 1 H) 5.62 (dd, J = 2.8, 10.0 Hz, 1 H) 5.12 (d, J = 51.0 Hz, 1 H) 4.46 (td, J = 6.0, 11.9 Hz, 1 H) 3.88-3.6 (m, 4 H) 3.82 (s, 3 H) 3.71 (s, 3 H) 3.62 (s, 3 H) |
| 8 (Scheme A) | 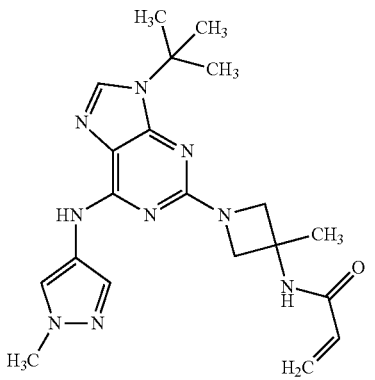<br>N-(1-(9-(tert-butyl)-6-((1-methyl-1H-pyrazol-4-yl)amino)-9H-purin-2-yl)-3-methylazetidin-3-yl)acrylamide | 410.2 [M + H]$^+$ | $^1$H NMR (600 MHz, DMSO-17 mm) δ ppm 9.66 (s, 1 H) 8.56 (s, 1 H) 7.96 (s, 1 H) 7.85 (s, 1 H) 7.70 (s, 1 H) 6.15-6.25 (m, 1 H) 6.04-6.13 (m, 1 H) 5.54-5.64 (m, 1 H) 4.12 (d, J = 8.44 Hz, 2 H) 3.94 (d, J = 7.52 Hz, 2 H) 3.81 (s, 3 H) 1.68 (s, 9 H) 1.60 (s, 3 H) |

TABLE 1-continued

| Example No. (Scheme) | Structure and Compound Name | LRMS m/z | ¹H NMR |
|---|---|---|---|
| 9 (Scheme A) | 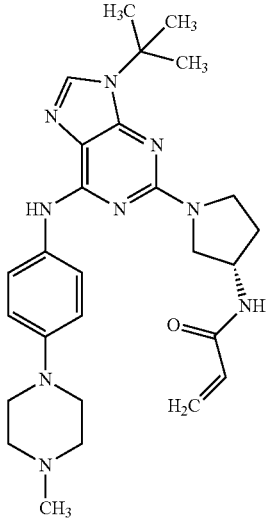<br>(S)-N-(1-(9-(tert-butyl)-6-((4-(4-methylpiperazin-1-yl)phenyl)amino)-9H-purin-2-yl)pyrrolidin-3-yl)acrylamide | 504.2 [M + H]⁺ | ¹H NMR (600 MHz, DMSO-17 mm) δ ppm 9.17 (s, 1 H) 8.40 (d, J = 6.60 Hz, 1 H) 7.85 (d, J = 8.25 Hz, 2 H) 7.83 (s, 1 H) 6.88 (d, J = 8.99 Hz, 2 H) 6.19-6.29 (m, 1 H) 6.06-6.15 (m, 1 H) 5.53-5.64 (m, 1 H) 4.44 (d, J = 4.77 Hz, 1 H) 3.76 (dd, J = 11.28, 6.51 Hz, 1 H) 3.57-3.68 (m, 2 H) 3.07 (br. s., 4 H) 2.45 (br. s., 4 H) 2.22 (s, 4 H) 1.85-1.95 (m, 1 H) 1.70 (s, 9 H) |
| 10 (Scheme A) | 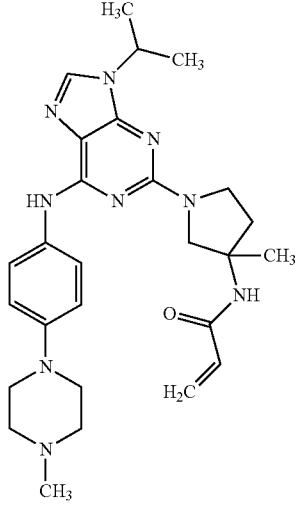<br>N-(1-(9-isopropyl-6-((4-(4-methylpiperazin-1-yl)phenyl)amino)-9H-purin-2-yl)-3-methylpyrrolidin-3-yl)acrylamide (*single enantiomer with unknown absolute stereochemistry) | 504.2 [M + H]⁺ | ¹H NMR (600 MHz, DMSO-17 mm) δ ppm 9.19 (s, 1 H) 8.05-8.21 (m, 1 H) 7.92 (s, 1 H) 7.87 (d, J = 8.62 Hz, 2 H) 6.89 (d, J = 8.99 Hz, 2 H) 6.21-6.36 (m, 1 H) 6.09 (d, J = 1.83 Hz, 1 H) 5.47-5.62 (m, 1 H) 4.55-4.70 (m, 1 H) 3.84-4.00 (m, 1 H) 3.54-3.69 (m, 2 H) 3.47-3.52 (m, 1 H) 3.08 (br. s., 4 H) 2.46 (t, J = 4.58 Hz, 4 H) 2.38-2.43 (m, 1 H) 2.23 (s, 3 H) 1.92-2.00 (m, 1 H) 1.51 (d, J = 6.79 Hz, 6 H) 1.49 (s, 3 H) |

TABLE 1-continued

| Example No. (Scheme) | Structure and Compound Name | LRMS m/z | ¹H NMR |
|---|---|---|---|
| 11 (Scheme A) | 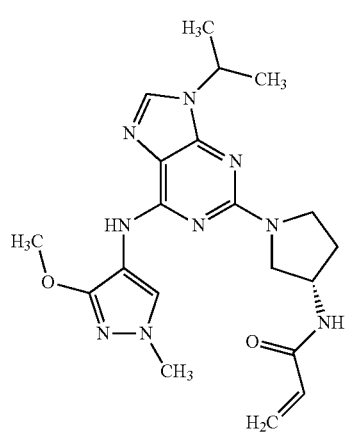<br>(S)-N-(1-(9-isopropyl-6-((3-methoxy-1-methyl-1H-pyrazol-4-yl)amino)-9H-purin-2-yl)pyrrolidin-3-yl)acrylamide | 426.1 [M + H]⁺ | ¹H NMR (600 MHz, DMSO-17 mm) δ ppm 8.35-8.43 (m, 1 H) 7.87-7.94 (m, 2 H) 7.75-7.84 (m, 1 H) 6.21-6.31 (m, 1 H) 6.06-6.16 (m, 1H) 5.55-5.63 (m, 1 H) 4.55-4.67 (m, 1 H) 4.32-4.46 (m, 1 H) 3.83 (s, 3 H) 3.71-3.76 (m, 1 H) 3.70 (s, 3 H) 3.56-3.64 (m, 2 H) 3.44-3.48 (m, 1H) 2.13-2.22 (m, 1 H) 1.83-1.93 (m, 1H) 1.50 (d, J = 6.79 Hz, 6 H) |
| 12 (Scheme A) | 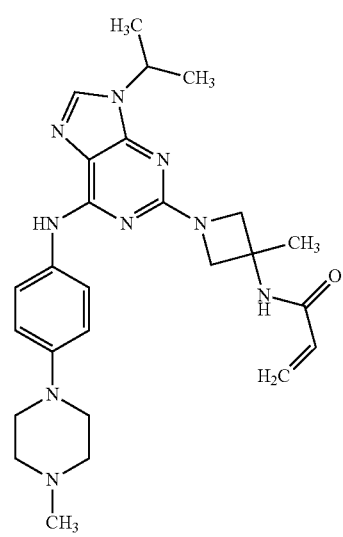<br>N-(1-(9-isopropyl-6-((4-(4-methylpiperazin-1-yl)phenyl)amino)-9H-purin-2-yl)-3-methylazetidin-3-yl)acrylamide | 490.2 [M + H]⁺ | ¹H NMR (600 MHz, DMSO-17 mm) δ ppm 9.31 (s, 1 H) 8.57 (s, 1 H) 7.99 (s, 1 H) 7.82 (d, J = 8.99 Hz, 2 H) 6.88 (d, J = 8.99 Hz, 2 H) 6.18-6.26 (m, 1 H) 6.03-6.13 (m, 1 H) 5.55-5.63 (m, 1 H) 4.57-4.66 (m, 1 H) 4.11 (d, J = 8.44 Hz, 2 H) 3.91 (s, 2 H) 3.05-3.11 (m, 4 H) 2.42-2.48 (m, 4 H) 2.22 (s, 3 H) 1.58 (s, 3 H) 1.50 (d, J = 6.79 Hz, 6 H) |

TABLE 1-continued

| Example No. (Scheme) | Structure and Compound Name | LRMS m/z | $^1$H NMR |
|---|---|---|---|
| 13 (Scheme A) | 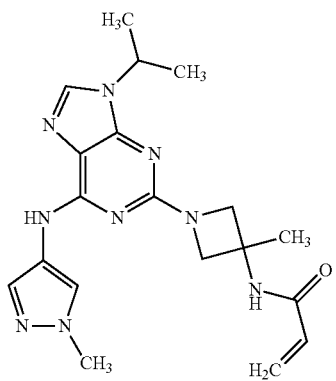 N-(1-(9-isopropyl-6-((1-methyl-1H-pyrazol-4-yl)amino)-9H-purin-2-yl)-3-methylazetidin-3-yl)acrylamide | 396.1 [M + H]$^+$ | $^1$H NMR (600 MHz, DMSO-17 mm) δ ppm 9.61-9.78 (m, 1 H) 8.21-8.38 (m, 1 H) 7.97 (d, J = 4.95 Hz, 2 H) 7.71 (s, 1 H) 6.17-6.30 (m, 1 H) 6.11 (d, J = 2.02 Hz, 1 H) 5.55-5.66 (m, 1 H) 4.50-4.68 (m, 1 H) 4.15 (d, J = 8.07 Hz, 2 H) 3.91-4.02 (m, 2 H) 3.82 (s, 3 H) 1.60 (s, 3 H) 1.43-1.52 (m, 6 H) |
| 14 (Scheme A) | 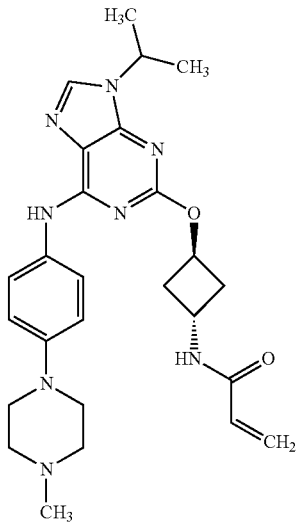 N-((trans)-3-((9-isopropyl-6-((4-(4-methylpiperazin-1-yl)phenyl)amino)-9H-purin-2-yl)oxy)cyclobutyl)acrylamide | 491.6 [M + H]$^+$ | $^1$H NMR (400 MHz, DMSO-d6) δ ppm 9.61 (s, 1 H) 8.51 (d, J = 6.60 Hz, 1 H) 8.13 (s, 1 H) 7.70 (d, J = 8.80 Hz, 2 H) 6.88 (d, J = 8.93 Hz, 2 H) 6.18-6.32 (m, 1 H) 6.05-6.14 (m, 1 H) 5.61 (dd, J = 10.03, 1.83 Hz, 1 H) 5.17-5.31 (m, 1 H) 4.57-4.71 (m, 1 H) 4.27-4.40 (m, 1 H) 3.02-3.12 (m, 4 H) 2.37-2.48 (m, 8 H) 2.22 (s, 3 H) 1.52 (d, J = 6.72 Hz, 6 H) |

TABLE 1-continued

| Example No. (Scheme) | Structure and Compound Name | LRMS m/z | ¹H NMR |
|---|---|---|---|
| 15 (Scheme A) | (S)-N-(1-(9-cyclobutyl-6-((4-(4-(methylpiperazin-1-yl) phenyl)amino)-9H-purin-2-yl)pyrrolidin-3-yl)acrylamide | 502.2 [M + H]⁺ | ¹H NMR (400 MHz, DMSO-d6) δ ppm 9.28 (1 H, s) 8.40 (1 H, d, J = 6.97 Hz) 8.03 (1 H, s) 7.90 (2 H, d, J = 8.93 Hz) 6.93 (2 H, d, J = 9.05 Hz) 6.19-6.34 (1 H, m) 6.05-6.17 (1 H, m) 5.60 (1 H, dd, J = 9.90, 2.32 Hz) 4.88 (1 H, t, J = 8.44 Hz) 4.44 (1 H, d, J = 5.01 Hz) 3.77 (1 H, dd, J = 11.25, 6.24 Hz) 3.54-3.71 (2 H, m) 3.45 (1 H, dd, J = 11.00, 3.30 Hz) 3.27-3.38 (7 H, m) 3.22 (2 H, br. s.) 2.67 (2 H, t, J = 10.33 Hz) 2.56-2.63 (2 H, m) 2.36-2.47 (2 H, m) 2.11-2.27 (1 H, m) 1.67-1.99 (3 H, m) |
| 16 (Scheme A) | 1-((cis)-5-(9-ethyl-6-((1-methyl-1H-pyrazol-4-yl)amino)-9H-purin-2-yl)hexahydropyrrolo[3,4-c]pyrrol-2(1H)-yl)prop-2-en-1-one | 408.2 [M + H]⁺ | ¹H NMR (400 MHz, DMSO-d6) δ ppm 9.62 (s, 1H), 7.99 (s, 1H), 7.85 (s, 1H), 7.72 (s, 1H), 6.56-6.63 (p, 1H), 6.11-6.16 (dd, 1H), 5.65-5.68 (dd, 1H), 4.02-4.08 (m, 2H), 3.82-3.86 (m, 6H), 3.69-3.75 (m, 1H), 3.55-3.59 (m, 1H), 3.33-3.47 (m, 3H), 2.99-3.08 (m, 2H), 1.37-1.41 (t, 3H) |
| 17 (Scheme A) | 1-((cis)-5-(6-((1,5-dimethyl-1H-pyrazol-4-yl)amino)-9-isopropyl-9H-purin-2-yl)hexahydropyrrolo[3,4-c]pyrrol-2(1H)-yl)prop-2-en-1-one | 436.3 [M + H]⁺ | ¹H NMR (400 MHz, CDCl₃) δ ppm 7.96 (s, 1H), 7.58 (s, 1H), 6.44-6.40 (m, 2H), 5.71-5.68 (m, 1 H), 4.70 (m, 1H), 3.95-3.85 (m, 7H), 3.67-6.54 (m, 4H), 3.11-3.04 (m, 2H), 2.32 (s, 3H), 1.59-1.55 (m, 6H) |

TABLE 1-continued

| Example No. (Scheme) | Structure and Compound Name | LRMS m/z | ¹H NMR |
|---|---|---|---|
| 18 (Scheme A) | 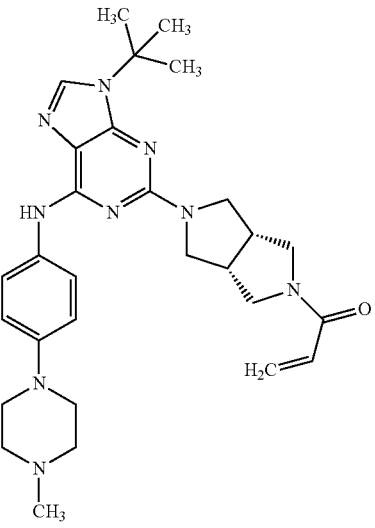<br>1-((cis)-5-(9-(tert-butyl)-6-((4-(4-methylpiperazin-1-yl)phenyl)amino)-9H-purin-2-yl)hexahydropyrrolo[3,4-c]pyrrol-2(1H)-yl)prop-2-en-1-one | 530.4 [M + H]⁺ | ¹H NMR (400 MHz, DMSO-d6) δ ppm 9.15 (s, 1H) 7.86 (d, J = 8.8 Hz, 2H) 7.83 (s, 1H) 6.89 (d, J = 8.7 Hz, 2H) 6.58 (dd, J = 10.4, 16.8 Hz, 1H) 6.12 (d, J = 16.8 Hz, 1H) 5.65 (d, J = 10.3 Hz, 1H) 3.74-3.91 (m, 3H) 3.68 (dd, J = 7.6, 12.5 Hz, 1H) 3.55 (dd, J = 4.6, 10.4 Hz, 1H) 3.33-3.49 (m, 4H) 3.09 (br. s., 5H) 2.91-3.02 (m, 1H) 2.27 (br. s., 3H) 1.70 (s, 9H).<br>(note: some peaks hidden by solvent) |
| 19 (Scheme A) | 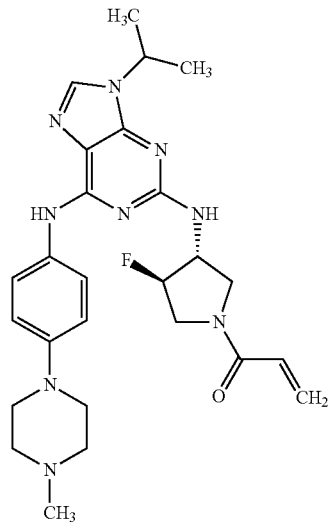<br>1-((trans)-3-fluoro-4-((9-isopropyl-6-((4-(4-methylpiperazin-1-yl)phenyl)amino)-9H-purin-2-yl)amino)pyrrolidin-1-yl)prop-2-en-1-one | 509.2 [M + H]⁺ | ¹H NMR (600 MHz, DMSO-17 mm) δ ppm 9.27 (br. s., 1 H) 7.95 (s, 1 H) 7.79 (t, J = 8.99 Hz, 2 H) 6.93-7.06 (m, 1 H) 6.85 (d, J = 8.80 Hz, 2 H) 6.58 (dt, J = 16.78, 10.68 Hz, 1 H) 6.16 (ddd, J = 16.74, 4.81, 2.48 Hz, 1 H) 5.64-5.74 (m, 1 H) 5.16-5.37 (m, 1 H) 4.55-4.66 (m, 1 H) 4.37-4.52 (m, 1 H) 3.88-4.00 (m, 1 H) 3.79-3.87 (m, 1 H) 3.61-3.76 (m, 2 H) 3.01-3.08 (m, 4 H) 2.39-2.47 (m, 4 H) 2.21 (s, 3 H) 1.51 (d, J = 6.42 Hz, 6 H) |

| Example No. (Scheme) | Structure and Compound Name | LRMS m/z | ¹H NMR |
|---|---|---|---|
| 20 (Scheme A) | 1-((trans)-3-fluoro-4-((9-methyl-6-((4-(4-methylpiperazin-1-yl)phenyl)amino)-9H-purin-2-yl)amino)pyrrolidin-1-yl)prop-2-en-1-one | 480.1 [M + H]⁺ | ¹H NMR (600 MHz, DMSO-17 mm) δ ppm 9.29 (br. s., 1 H) 7.85 (s, 1 H) 7.81 (dd, J = 8.99, 7.34 Hz, 2 H) 6.95-7.20 (m, 1 H) 6.86 (d, J = 8.99 Hz, 2 H) 6.59 (dt, J = 16.69, 10.18 Hz, 1 H) 6.18 (ddd, J = 16.78, 4.86, 2.38 Hz, 1 H) 5.71 (ddd, J = 10.22, 5.27, 2.48 Hz, 1 H) 5.20-5.36 (m, 1 H) 4.41-4.59 (m, 1 H) 3.80-4.01 (m, 2 H) 3.66-3.76 (m, 2 H) 3.62 (s, 3 H) 3.02-3.11 (m, 4 H) 2.42-2.48 (m, 4 H) 2.22 (s, 3 H) |
| 21 (Scheme A) | 1-((cis)-5-(9-isopropyl-6-((4-(4-methylpiperazin-1-yl)phenyl)amino)-9H-purin-2-yl)hexahydropyrrolo[3,4-c]pyrrol-2(1H)-yl)prop-2-en-1-one | 516.4 [M + H]⁺ | ¹H NMR (400 MHz, DMSO-d6) δ ppm 9.16 (s, 1 H) 7.91 (s, 1 H) 7.85 (d, J = 9.05 Hz, 2 H) 6.88 (d, J = 9.17 Hz, 2 H) 6.58 (dd, J = 16.87, 10.39 Hz, 1 H) 6.12 (dd, J = 16.75, 2.45 Hz, 1 H) 5.65 (dd, J = 10.27, 2.32 Hz, 1 H) 4.61 (dt, J = 13.48, 6.77 Hz, 1 H) 3.74-3.89 (m, 4 H) 3.68 (dd, J = 12.72, 7.70 Hz, 1 H) 3.54 (dd, J = 10.33, 5.44 Hz, 1 H) 3.34-3.46 (m, 4 H) 3.03-3.14 (m, 4 H) 2.40-2.47 (m, 4 H) 2.23 (s, 3 H) 1.50 (d, J = 6.72 Hz, 6 H) |

TABLE 1-continued

| Example No. (Scheme) | Structure and Compound Name | LRMS m/z | $^1$H NMR |
|---|---|---|---|
| 22 (Scheme B) | 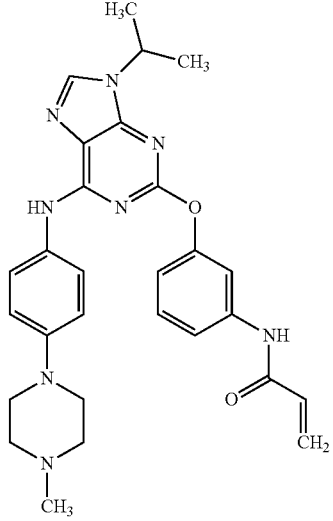<br>N-(3-((9-isopropyl-6-((4-(4-methylpiperazin-1-yl)phenyl)amino)-9H-purin-2-yl)oxy)phenyl)acrylamide (isolated as a formic acid salt) | 513.3 [M + H]$^+$ | $^1$H NMR (400 MHz, DMSO-d6) δ ppm 10.33 (s, 1H), 9.78 (s, 1H), 8.21-8.24 (d, 2H), 7.58-7.62 (t, 2H), 7.44-7.47 (d, 2H), 7.39-7.41 (t, 1H), 6.89-6.91 (m, 1H), 6.63-6.65 (d, 2H), 6.41-6.43 (m, 1H), 6.27-6.28 (d, 1H), 5.75-5.77 (d, 1H), 4.65-4.70 (m, 1H), 3.00 (s, 4H), 2.45 (s, 4H), 2.23 (s, 3H), 1.51-1.53 (d, 6H). (isolated as a formic acid salt) |
| 23 (Scheme A) | 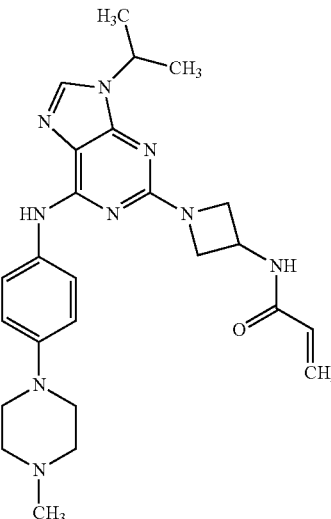<br>N-(1-(9-isopropyl-6-((4-(4-methylpiperazin-1-yl)phenyl)amino)-9H-purin-2-yl)azetidin-3-yl)acrylamide | 476.3 [M + H]$^+$ | $^1$H NMR (400 MHz, methanol-d4) δ ppm 8.41 (formic acid, residue), 7.87 (s, 1H), 7.84-7.82 (d, 2H), 7.04-7.02 (d, 2H), 6.30-6.28 (m, 2H), 5.70-5.67 (m, 1H), 4.76-4.71 (m, 1H), 4.55-4.54 (m, 1H), 3.93-3.92 (m, 1H), 3.77-3.72 (m, 2H), 3.59-3.55 (m, 1H), 3.37-3.34 (m, 8H), 2.90 (s, 3H), 2.33-2.28 (m, 1H), 2.06-2.01 (m, 1H), 1.59-1.58 (d, 6H) |

TABLE 1-continued

| Example No. (Scheme) | Structure and Compound Name | LRMS m/z | $^1$H NMR |
|---|---|---|---|
| 24 (Scheme A) | 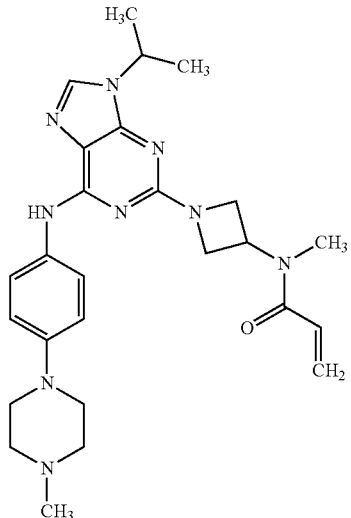<br>N-(1-(9-isopropyl-6-((4-(4-methylpiperazin-1-yl)phenyl)amino)-9H-purin-2-yl)azetidin-3-yl)-N-methylacrylamide | 490.3 [M + H]$^+$ | $^1$H NMR (400 MHz, methanol-d4) δ ppm 7.94 (s, 1H), 7.77-7.75 (d, 2H), 7.00-6.97 (d 2H), 6.80-6.73 (m, 1H), 6.29-6.18 (m, 1H), 5.80-5.75 (m, 1H), 5.28-5.13 (m, 1H), 4.77-4.71 (m, 1H), 4.42-4.34 (m, 2H), 4.24-4.16 (m, 2H), 3.24-3.17 (m, 7H), 2.63-2.61 (m, 4H), 2.35 (s, 3H), 1.59-1.57 (m, 6H) |
| 25 (Scheme A) | 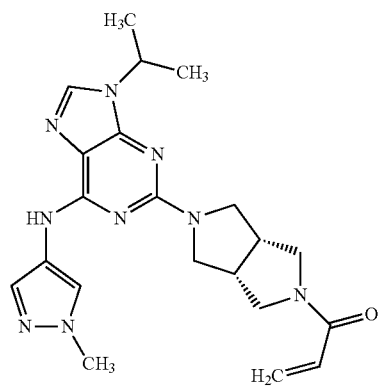<br>1-((cis)-5-(9-isopropyl-6-((1-methyl-1H-pyrazol-4-yl)amino)-9H-purin-2-yl)hexahydropyrrolo[3,4-c]pyrrol-2(1H)-yl)prop-2-en-1-one | 422.2 [M + H]$^+$ | $^1$H NMR (600 MHz, DMSO-d6) δ ppm 9.43 (s, 1 H) 7.96 (s, 1 H) 7.85 (s, 1 H) 7.65 (s, 1 H) 6.48-6.59 (m, 1 H) 6.07-6.15 (m, 1 H) 5.63-5.70 (m, 1 H) 4.52-4.62 (m, 1 H) 3.83 (dd, J = 10.82, 7.70 Hz, 2 H) 3.78 (s, 3 H) 3.62-3.70 (m, 1 H) 3.47-3.54 (m, 1 H) 3.42 (br. s, 1 H) 3.29-3.36 (m, 1 H) 3.03-3.10 (m, 2 H) 2.93-3.02 (m, 2 H) 1.44 (d, J = 6.79 Hz, 6 H) |

TABLE 1-continued

| Example No. (Scheme) | Structure and Compound Name | LRMS m/z | ¹H NMR |
|---|---|---|---|
| 26 (Scheme A) | 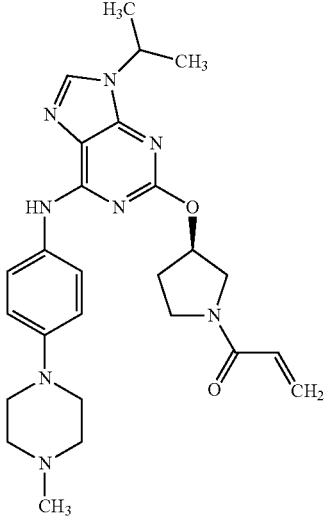<br>(R)-1-(3-((9-isopropyl-6-((4-(4-methylpiperazin-1-yl)phenyl)amino)-9H-purin-2-yl)oxy)pyrrolidin-1-yl)prop-2-en-1-one | 491.0 [M + H]⁺ | ¹H NMR (400 MHz, DMSO-d6) δ ppm 9.69 (s, 1H), 8.16 (s, 1H), 7.70-7.66 (m, 2H), 6.94-6.92 (d, 2H), 6.66-6.51 (m, 1H), 6.16-6.12 (m, 1H), 5.70-5.64 (m, 1H), 5.48-5.42 (d, 1H), 4.67-6.63 (m, 1H), 3.92-3.47 (m, 4H), 3.14 (s, 4H), 2.63 (s, 4H), 2.34-2.16 (m, 5H), 1.53-1.51 (d, 6H) |
| 27 (Scheme A) | 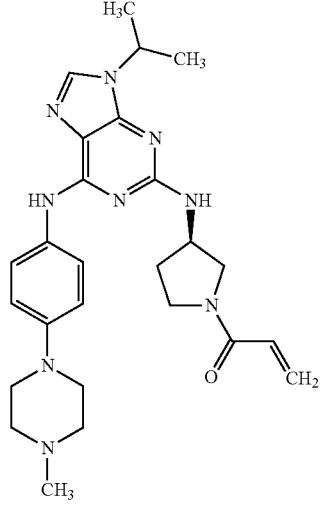<br>(R)-1-(3-((9-isopropyl-6-((4-(4-methylpiperazin-1-yl)phenyl)amino)-9H-purin-2-yl)amino)pyrrolidin-1-yl)prop-2-en-1-one (isolated as a bis-formate salt) | 490.3 [M + H]⁺ | ¹H NMR (400 MHz, DMSO-d6) δ ppm 9.24 (brs, 1H), 8.17 (s, 2H), 7.94 (s, 1H), 7.78-7.82 (m, 2H), 6.83-6.89 (m, 3H), 6.49-6.60 (m, 1H), 6.10-6.16 (m, 1H), 5.62-5.67 (m, 1H), 4.57-4.60 (m, 1H), 4.34-4.42 (m, 1H), 3.90-3.91 (m, 0.5H), 3.42-3.74 (m, 3.5H), 3.12 (brs, 4H), 2.66 (brs, 4H), 2.36 (s, 3H), 1.97-2.23 (m, 2H), 1.49-1.51 (m, 6H). (isolated as a bis-formate salt) |

TABLE 1-continued

| Example No. (Scheme) | Structure and Compound Name | LRMS m/z | $^1$H NMR |
|---|---|---|---|
| 28 (Scheme A) | 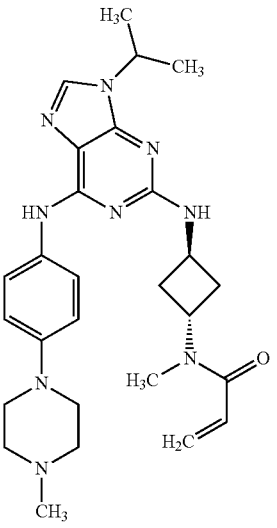<br>N-((trans)-3-((9-isopropyl-6-((4-(4-methylpiperazin-1-yl)phenyl)amino)-9H-purin-2-yl)amino)cyclobutyl)-N-methylacrylamide | 504.3 [M + H]$^+$ | $^1$H NMR (400 MHz, DMSO-d6) δ ppm 9.15 (s, 1H), 7.92 (s, 1H), 7.81-7.83 (d, 2H), 7.02 (s, 1H), 6.88-6.90 (d, 2H), 6.71-6.78 (m, 1H), 6.05-6.09 (m, 1H), 5.65-5.67 (s, 1H), 5.20 (s, 0.5H), 4.85 (s, 0.5H), 4.55-4.61 (m, 1H), 4.22 (s, 1H), 2.95-3.10 (m, 7H), 2.74-2.65 (m, 6H), 2.28 (s, 5H), 1.49-1.51 (d, 6H). (some peaks hidden by solvent) |
| 29 (Scheme A) | 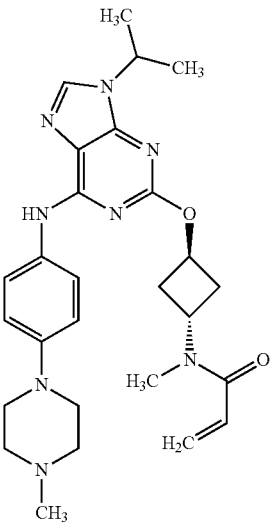<br>N-((trans)-3-((9-isopropyl-6-((4-(4-methylpiperazin-1-yl)phenyl)amino)-9H-purin-2-yl)oxy)cyclobutyl)-N-methylacrylamide | 505.2 [M + H]$^+$ | $^1$H NMR (400 MHz, DMSO-d6) δ ppm 9.65 (s, 1H), 8.14 (s, 1H), 7.68-7.70 (d, 2H), 6.90-6.93 (d, 2H), 6.70-6.76 (m, 1H), 6.05 (m, 1H), 5.65 (m, 1H), 5.15 (m, 1.5H), 4.83 (m, 0.5H), 4.62-4.67 (m, 1H), 2.95-3.09 (m, 7H), 2.67 (m, 2H), 2.47 (m, 4H), 2.25-2.42 (m, 2H), 2.23 (s, 3H), 1.50-1.52 (d, 6H) |

TABLE 1-continued

| Example No. (Scheme) | Structure and Compound Name | LRMS m/z | ¹H NMR |
|---|---|---|---|
| 30 (Scheme A) | 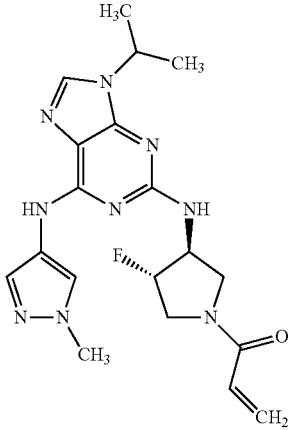 1-((trans*)-3-fluoro-4-((9-isopropyl-6-((1-methyl-1H-pyrazol-4-yl)amino)-9H-purin-2-yl)amino)pyrrolidin-1-yl)prop-2-en-1-one (*single enantiomer with unknown absolute stereochemistry) | 414.1 [M + H]⁺ | ¹H NMR (600 MHz, DMSO-17 mm) δ ppm 9.65 (br. s., 1 H) 8.05-8.17 (m, 1 H) 7.93 (s, 1 H) 7.72 (s, 1 H) 6.95-7.12 (m, 1 H) 6.53-6.65 (m, 1 H) 6.18 (dt, J = 16.69, 2.93 Hz, 1 H) 5.71 (dd, J = 10.27, 2.20 Hz, 1 H) 5.16-5.41 (m, 1 H) 4.41-4.65 (m, 2 H) 3.82-4.04 (m, 2 H) 3.79 (s, 3 H) 3.64-3.76 (m, 2 H) 1.51 (d, J = 6.60 Hz, 6 H) |
| 31 (Scheme A) | 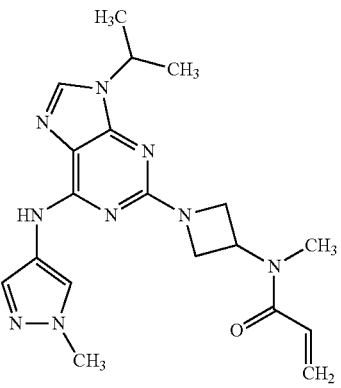 N-(1-(9-isopropyl-6-((1-methyl-1H-pyrazol-4-yl)amino)-9H-purin-2-yl)azetidin-3-yl)-N-methylacrylamide | 396.1 [M + H]+ | ¹H NMR (600 MHz, DMSO-17 mm) δ ppm 9.65 (br. s., 1 H) 7.95 (s, 1 H) 7.91 (s, 1 H) 7.60 (s, 1 H) 6.62-6.82 (m, 1 H) 5.97-6.16 (m, 1 H) 5.57-5.75 (m, 1 H) 4.93-5.29 (m, 1 H) 4.47-4.64 (m, 1 H) 4.17-4.35 (m, 2 H) 3.92-4.12 (m, 2 H) 3.74 (s, 3 H) 3.10 (br. s., 3 H) 1.42 (d, J = 6.73 Hz, 6 H) |
| 32 (Scheme A) | 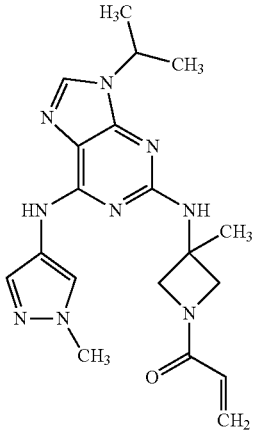 1-(3-((9-isopropyl-6-((1-methyl-1H-pyrazol-4-yl)amino)-9H-purin-2-yl)amino)-3-methylazetidin-1-yl)prop-2-en-1-one | 396.2 [M + H]+ | N/A |

TABLE 1-continued

| Example No. (Scheme) | Structure and Compound Name | LRMS m/z | ¹H NMR |
|---|---|---|---|
| 33 (Scheme A) | 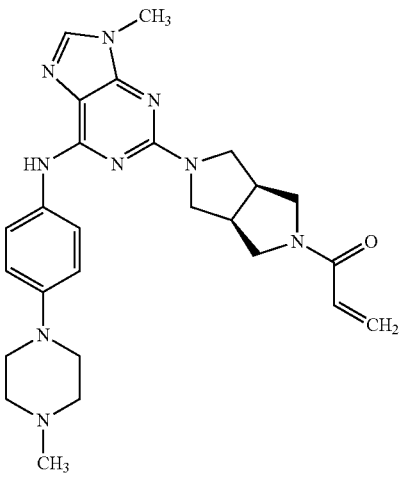<br>1-((cis)-5-(9-methyl-6-((4-(4-methylpiperazin-1-yl)phenyl)amino)-9H-purin-2-yl)hexahydropyrrolo[3,4-c]pyrrol-2(1H)-yl)prop-2-en-1-one | 488.0 [M + H]+ | ¹H NMR (400 MHz, DMSO-d6) δ ppm 9.26 (s, 1H), 7.87-7.89 (d, 2H), 7.81 (s, 1H), 6.90-6.92 (d, 2H), 6.55-6.62 (q, 1H), 6.10-6.15 (dd, 1H), 5.64-5.67 (dd, 1H), 3.78-3.84 (m, 3H), 3.76-3.77 (m, 1H), 3.61 (s, 3H), 3.45-3.50 (m, 1H), 3.41-3.44 (m, 3H), 3.08-3.14 (m, 4H), 2.98-3.08 (m, 2H), 2.68 (m, 4H), 2.38 (m, 3H) |
| 34 (Scheme A) | 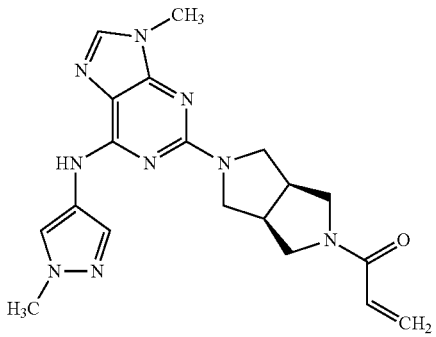<br>1-((cis)-5-(9-methyl-6-((1-methyl-1H-pyrazol-4-yl)amino)-9H-purin-2-yl)hexahydropyrrolo[3,4-c]pyrrol-2(1H)-yl)prop-2-en-1-one | 394.0 [M + H]+ | ¹H NMR (400 MHz, DMSO-d6) δ ppm 9.61 (s, 1H), 7.98 (m, 1H), 7.78 (s, 1H), 7.72 (s, 1H), 6.55-6.62 (q, 1H), 6.10-6.15 (dd, 1H), 5.65-5.68 (dd, 1H), 3.82-3.85 (m, 6H), 3.67-3.69 (m, 1H), 3.57 (s, 3H), 3.53-3.56 (m, 1H), 3.48-3.53 (m, 3H), 3.00-3.10 (m, 2H) |
| 35 (Scheme A) | 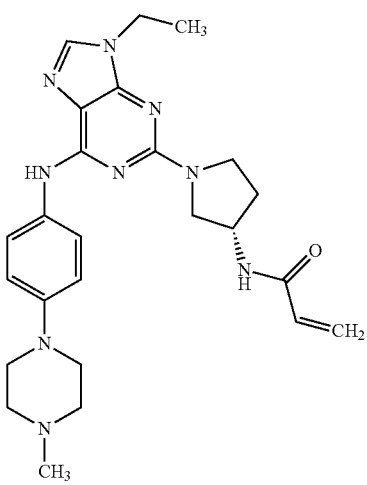<br>(S)-N-(1-(9-ethyl-6-((4-(4-methylpiperazin-1-yl)phenyl)amino)-9H-purin-2-yl)pyrrolidin-3-yl)acrylamide | 476.0 [M + H]+ | ¹H NMR (400 MHz, DMSO-d6) δ ppm 9.24 (s, 1H), 8.40-8.42 (d, 1H), 7.85-7.87 (m, 3H), 6.87-6.90 (m, 2H), 6.09-6.28 (m, 2H), 5.58-5.61 (m, 1H), 4.42-4.43 (m, 1H), 4.05-4.09 (m, 2H), 3.62-3.75 (m, 1H), 3.40-3.43 (m, 1H), 3.06-3.09 (m, 4H), 2.47-2.50 (m, 4H), 2.20-2.23 (m, 4H), 1.89-1.90 (m, 1H), 1.37-1.41 (m, 3H) |

TABLE 1-continued

| Example No. (Scheme) | Structure and Compound Name | LRMS m/z | $^1$H NMR |
|---|---|---|---|
| 36 (Scheme A) | 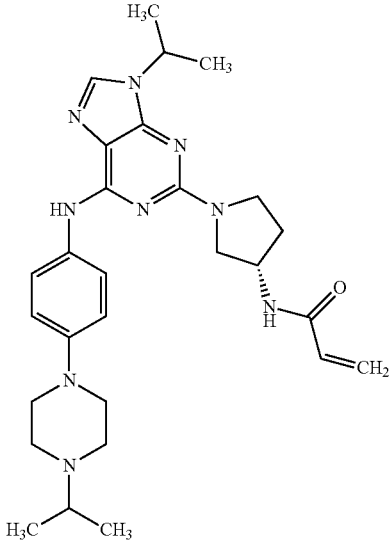<br>(S)-N-(1-(9-isopropyl-6-((4-(4-isopropylpiperazin-1-yl)phenyl)amino)-9H-purin-2-yl)pyrrolidin-3-yl)acrylamide | 518.1 [M + H]+ | $^1$H NMR (400 MHz, DMSO-d6) δ ppm 9.23 (s, 1H), 844-8.42 (d, 1H), 7.93 (s, 1H), 7.87-7.85 (d, 2H), 6.89-6.86 (m, 2H), 6.29-6.22 (m, 1H), 6.14-6.09 (m, 1H), 5.61-5.58 (m, 1H), 4.65-4.60 (m, 1H), 4.43-4.42 (m, 1H), 3.78-3.74 (m, 1H), 3.67-3.60 (m, 2H), 3.51 (m, 1H), 3.06-3.05 (brs, 4H), 2.70-2.68 (m, 1H), 2.58 (brs, 4H), 2.20-2.17 (m, 1H), 1.92-1.89 (m, 1H), 1.51-1.50 (d, 6H), 1.02-1.00 (d, 6H) |
| 37 (Scheme A) | 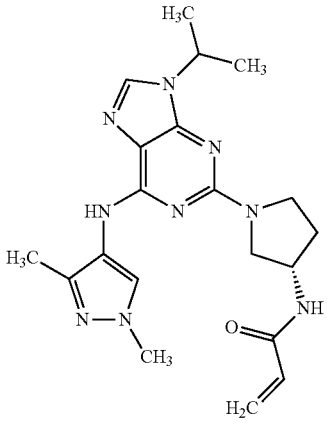<br>(S)-N-(1-(6-((1,3-dimethyl-1H-pyrazol-4-yl)amino)-9-isopropyl-9H-purin-2-yl)pyrrolidin-3-yl)acrylamide | 410.2 [M + H]+ | $^1$H NMR (600 MHz, DMSO-17 mm) δ ppm 8.59-8.74 (m, 1 H) 8.37 (d, J = 6.73 Hz, 1 H) 7.90 (s, 2 H) 6.20-6.31 (m, 1 H) 6.12 (dd, J = 17.12, 2.19 Hz, 1 H) 5.55-5.65 (m, 1 H) 4.61 (s, 1 H) 4.33-4.46 (m, 1 H) 3.75 (s, 4 H) 3.52-3.66 (m, 2 H) 3.42-3.47 (m, 1 H) 2.16 (s, 4 H) 1.83-1.96 (m, 1H) 1.50 (d, J = 6.73 Hz, 6 H) |

TABLE 1-continued

| Example No. (Scheme) | Structure and Compound Name | LRMS m/z | $^1$H NMR |
|---|---|---|---|
| 38 (Scheme A) | 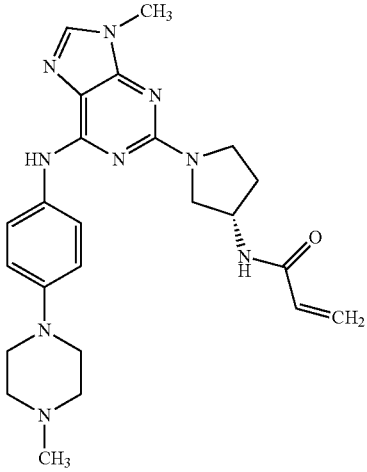<br>(S)-N-(1-(9-methyl-6-((4-(4-methylpiperazin-1-yl)phenyl)amino)-9H-purin-2-yl)pyrrolidin-3-yl)acrylamide | 462.1 [M + H]+ | $^1$H NMR (400 MHz, DMSO-d6) δ ppm 9.24 (s, 1H), 8.39-8.41 (d, 1H), 7.81-7.88 (m, 3H), 6.87-6.89 (m, 2H), 6.09-6.28 (m, 2H), 5.58-5.61 (m, 1H), 4.42-4.43 (m, 1H), 3.74-3.78 (m, 1H), 3.62-3.66 (m, 5H), 3.40-3.50 (m, 1H), 3.06-3.08 (m, 4H), 2.44-2.46 (m, 4H), 2.17-2.43 (m, 4H), 1.89-1.90 (m, 1H) |
| 39 (Scheme A) | 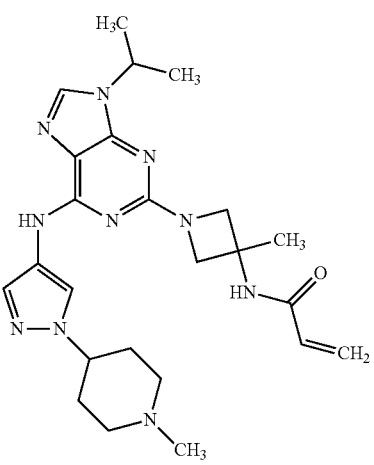<br>N-(1-(9-isopropyl-6-((1-(1-methylpiperidin-4-yl)-1H-pyrazol-4-yl)amino)-9H-purin-2-yl)-3-methylazetidin-3-yl)acrylamide | 479.2 [M + H]+ | $^1$H NMR (400 MHz, DMSO-d6) δ ppm 9.72 (s, 1 H), 8.58 (s, 1 H), 8.05 (s, 1 H), 7.97 (s, 1 H), 7.75 (s, 1 H), 6.22-6.12 (m, 2 H), 5.63-5.59 (m, 1 H), 4.61 (m, 1 H), 4.17-3.94 (m, 5 H), 2.88-2.84 (m, 2 H), 2.22 (s, 3 H), 2.10-1.98 (m, 6 H), 1.61 (s, 3H), 1.51-1.49 (d, 6 H) |

TABLE 1-continued

| Example No. (Scheme) | Structure and Compound Name | LRMS m/z | ¹H NMR |
|---|---|---|---|
| 40 (Scheme A) | 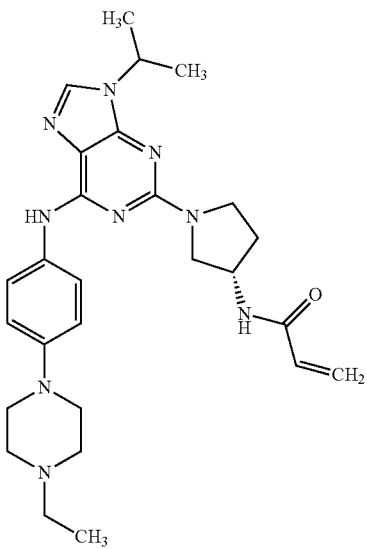<br>(S)-N-(1-(6-((4-(4-ethylpiperazin-1-yl)phenyl)amino)-9-isopropyl-9H-purin-2-yl)pyrrolidin-3-yl)acrylamide | 504.3 [M + H]+ | ¹H NMR (400 MHz, DMSO-d6) δ ppm 9.21 (s, 1H), 8.41-8.40 (m, 1H), 7.90 (s, 1H), 7.86-7.84 (d, 2H), 6.88-6.86 (d, 2H), 6.27-6.20 (m, 1H), 6.11-6.08 (m, 1H), 5.59-5.56 (m, 1H), 4.62-4.58 (m, 1H), 4.42-4.41 (m, 1H), 3.77-3.72 (m, 1H), 3.63-3.60 (m, 2H), 3.43-3.41 (m, 1H), 3.10 (s, 4H), 2.57 (m, 4H), 2.44-2.43 (m, 2H), 1.89-1.87(m, 1H), 1.49-1.48 (m, 6H), 1.05-1.02 (m, 3H) |
| 41 (Scheme A) | 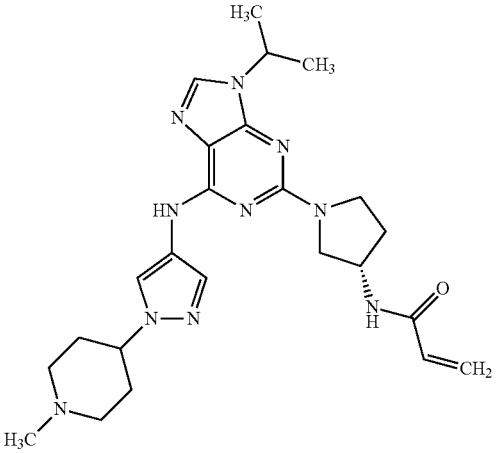<br>(S)-N-(1-(9-isopropyl-6-((1-(1-methylpiperidin-4-yl)-1H-pyrazol-4-yl)amino)-9H-purin-2-yl)pyrrolidin-3-yl)acrylamide | 479.2 [M + H]+ | ¹H NMR (400 MHz, DMSO-d6) δ ppm 9.63 (s, 1 H), 8.44 (d, 1 H), 8.11 (s, 1 H), 7.91 (s, 1 H), 7.76 (s, 1 H), 6.26-6.11 (m, 2 H), 5.64-5.60 (m, 1 H), 4.62-4.44 (m, 2 H), 4.07 (m, 2 H), 3.83-3.69 (m, 3 H), 2.88-2.84 (m, 2 H), 2.22 (s, 4 H), 2.08-1.92 (m, 7 H), 1.52-1.5 (m, 6H) |

TABLE 1-continued

| Example No. (Scheme) | Structure and Compound Name | LRMS m/z | ¹H NMR |
|---|---|---|---|
| 42 (Scheme A) | 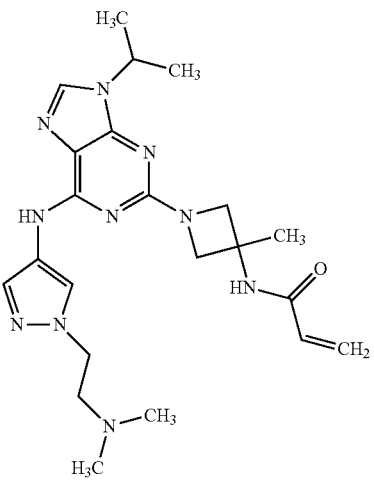<br>N-(1-(6-((1-(2-(dimethylamino)ethyl)-1H-pyrazol-4-yl)amino)-9-isopropyl-9H-purin-2-yl)-3-methylazetidin-3-yl)acrylamide | 453.1 [M + H]+ | ¹H NMR (300 MHz, DMSO) δ ppm 9.71 (s, 1H), 8.57 (s, 1H), 8.10 (s, 1H), 7.97 (s, 1H), 7.70 (s, 1H), 6.28-6.07 (m, 2H), 5.63-5.58 (m, 1H), 4.66-4.57 (m, 1H), 4.18-4.15 (m, 4H), 3.97-3.95 (m, 2H), 2.65-2.61 (t, 2H), 2.19 (s, 6H), 1.61 (s, 3H), 1.51-1.49 (d, 6H) |
| 43 (Scheme A) | 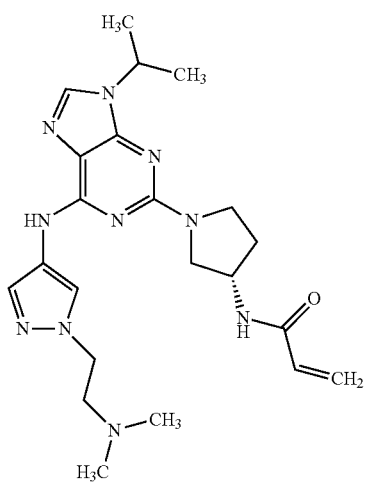<br>(S)-N-(1-(6-((1-(2-(dimethylamino)ethyl)-1H-pyrazol-4-yl)amino)-9-isopropyl-9H-purin-2-yl)pyrrolidin-3-yl)acrylamide | 453.2 [M + H]+ | ¹H NMR (300 MHz, DMSO) δ ppm 9.62 (s, 1H), 8.45-8.43 (d, 1H), 8.14 (s, 1H), 7.91 (s, 1H), 7.70 (s, 1H), 6.31-6.10 (m, 2H), 5.62-5.59 (m, 1H), 4.67-4.58 (m, 1H), 4.47-4.46 (m, 1H), 4.18-4.14 (t, 2H), 3.83-3.68 (m, 3H), 3.49-3.45 (m, 1H), 2.64-2.60 (t, 2H), 2.28-2.17 (m, 7H), 1.96-1.93 (m, 1H), 1.52-1.50 (d, 6H) |

TABLE 1-continued

| Example No. (Scheme) | Structure and Compound Name | LRMS m/z | ¹H NMR |
|---|---|---|---|
| 44 (Scheme A) | 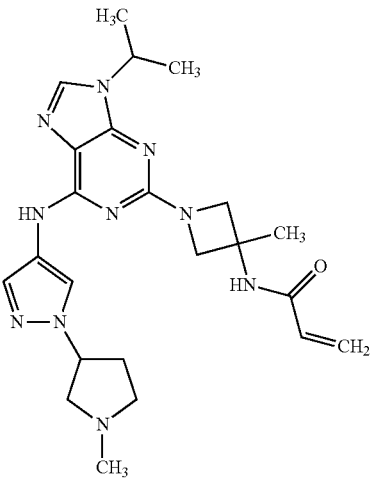 N-(1-(9-isopropyl-6-((1-(1-methylpyrrolidin-3-yl)-1H-pyrazol-4-yl)amino)-9H-purin-2-yl)-3-methylazetidin-3-yl)acrylamide | 487.1 [M + Na]+ | ¹H NMR (300 MHz, DMSO) δ ppm 9.74 (s, 1H), 8.56 (s, 1H), 8.31 (s, 1H), 7.97 (s, 1H), 7.63 (s, 1H), 6.29-6.07 (m, 2H), 5.62-5.59 (m, 1H), 4.85 (m, 1H), 4.66-4.57 (m, 1H), 4.18-4.15 (d, 2H), 3.97-3.94 (d, 2H), 2.89-2.73 (m, 3H), 2.43-2.33 (m, 5H), 1.96 (m, 1H), 1.51-1.49 (d, 9H) |
| 45 (Scheme A) | 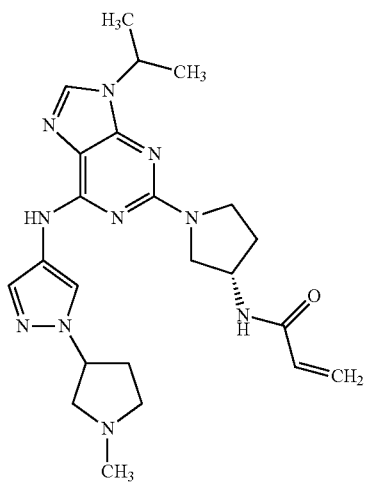 N-((3S)-1-(9-isopropyl-6-((1-(1-methylpyrrolidin-3-yl)-1H-pyrazol-4-yl)amino)-9H-purin-2-yl)pyrrolidin-3-yl)acrylamide | 487.1 [M + Na]+ | ¹H NMR (300 MHz, DMSO) δ ppm 9.66 (s, 1H), 8.45-8.43 (d, 1H), 8.36 (s, 1H), 7.91 (s, 1H), 7.62 (s, 1H), 6.32-6.09 (m, 2H), 5.63-5.59 (m, 1H), 4.84 (m, 1H), 4.67-4.58 (m, 1H), 4.47 (m, 1H), 3.83-3.45 (m, 4H), 2.84-2.71 (m, 3H), 2.38-2.20 (m, 6H), 1.94 (m, 2H), 1.52-1.50 (d, 6H) |

TABLE 1-continued

| Example No. (Scheme) | Structure and Compound Name | LRMS m/z | ¹H NMR |
|---|---|---|---|
| 46 (Scheme A) | 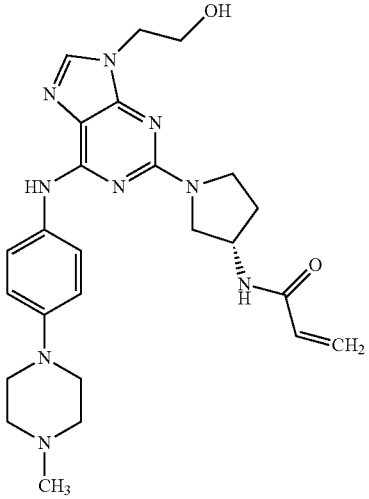<br>(S)-N-(1-(9-(2-hydroxyethyl)-6-((4-(4-methylpiperazin-1-yl)phenyl)amino)-9H-purin-2-yl)pyrrolidin-3-yl)acrylamide | 492.2 [M + H]+ | ¹H NMR (700 MHz, DMSO-d6) δ ppm 9.22 (s, 1 H) 8.38 (d, J = 6.82 Hz, 1 H) 7.86 (d, J = 9.02 Hz, 2 H) 7.79 (s, 1 H) 6.88 (d, J = 9.24 Hz, 2 H) 6.24 (dd, J = 17.06, 10.23 Hz, 1 H) 6.11 (dd, J = 17.06, 2.31 Hz, 1 H) 5.53-5.64 (m, 1 H) 5.07 (t, J = 5.28 Hz, 1 H) 4.36-4.47 (m, 1 H) 4.08 (t, J = 5.50 Hz, 2 H) 3.70-3.80 (m, 3 H) 3.65 (br. s., 1 H) 3.56-3.62 (m, 1 H) 3.39-3.46 (m, 1 H) 3.08 (br. s., 4 H) 2.47 (br. s., 4 H) 2.24 (s, 3 H) 2.15-2.21 (m, 1 H) 1.85-1.93 (m, 1 H) |
| 47 (Scheme C) | 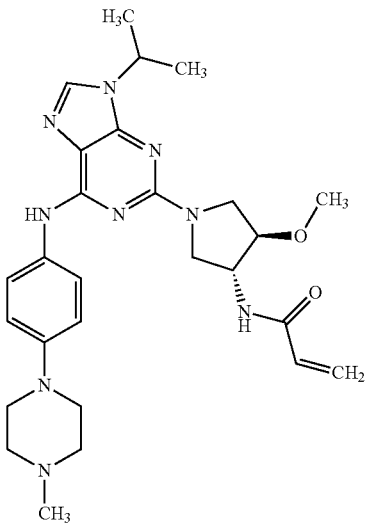<br>N-((trans)-1-(9-isopropyl-6-((4-(4-methylpiperazin-1-yl)phenyl)amino)-9H-purin-2-yl)-4-methoxypyrrolidin-3-yl)acrylamide | 520.1 [M + H]+ | ¹H NMR (700 MHz, DMSO-d6) δ ppm 9.07-9.28 (m, 1 H) 8.14-8.28 (m, 1 H) 7.84-7.94 (m, 1 H) 7.70-7.80 (m, 2 H) 6.76-6.96 (m, 2 H) 6.27-6.38 (m, 1 H) 6.00-6.11 (m, 1 H) 5.44-5.58 (m, 1 H) 4.53-4.60 (m, 1 H) 4.47-4.53 (m, 1 H) 3.90-3.95 (m, 1 H) 3.69-3.75 (m, 1 H) 3.62-3.68 (m, 1 H) 3.55-3.62 (m, 1 H) 3.24 (s, 3 H) 3.15-3.20 (m, 1 H) 2.97-3.03 (m, 4 H) 2.34-2.40 (m, 4 H) 2.15 (s, 3 H) 1.42-1.46 (m, 6 H) |

TABLE 1-continued

| Example No. (Scheme) | Structure and Compound Name | LRMS m/z | ¹H NMR |
|---|---|---|---|
| 48 (Scheme A) | 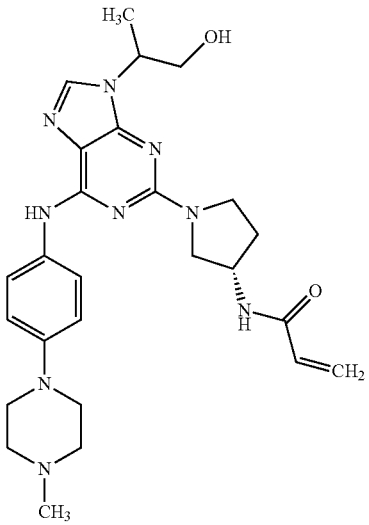<br>N-((3S)-1-(9-(1-hydroxypropan-2-yl)-6-((4-(4-methylpiperazin-1-yl)phenyl)amino)-9H-purin-2-yl)pyrrolidin-3-yl)acrylamide | 506.2 [M + H]+ | ¹H NMR (700 MHz, DMSO-d6) δ ppm 9.21 (s, 1 H) 8.39 (d, J = 6.82 Hz, 1 H) 7.81-7.88 (m, 3 H) 6.88 (d, J = 9.24 Hz, 2 H) 6.24 (dd, J = 17.17, 10.12 Hz, 1 H) 6.11 (dd, J = 17.17, 2.20 Hz, 1 H) 5.54-5.64 (m, 1 H) 5.10 (t, J = 5.50 Hz, 1 H) 4.49 (d, J = 5.28 Hz, 1 H) 4.35-4.44 (m, 1 H) 3.81 (dt, J = 11.44, 5.94 Hz, 1 H) 3.75 (dd, J = 11.11, 6.27 Hz, 1 H) 3.69 (dt, J = 10.73, 5.09 Hz, 1 H) 3.64 (br. s., 1 H) 3.56-3.61 (m, 1 H) 3.07 (br. s., 4 H) 2.47 (br. s., 4 H) 2.23 (s, 3 H) 2.16-2.20 (m, 1 H) 1.84-1.94 (m, 1 H) 1.46 (d, J = 7.04 Hz, 3 H) |
| 49 (Scheme A) | 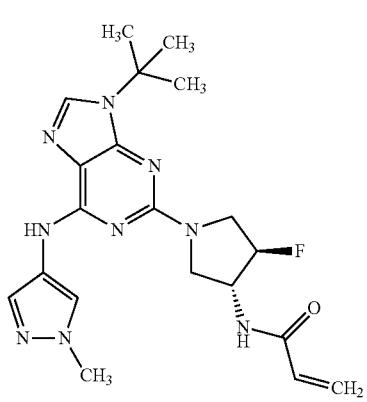<br>N-((3R,4S)-1-(9-(tert-butyl)-6-((1-methyl-1H-pyrazol-4-yl)amino)-9H-purin-2-yl)-4-fluoropyrrolidin-3-yl)acrylamide | 428.1 [M + H]⁺ | ¹H NMR (400 MHz, DMSO-d6) δ ppm 9.67 (s, 1H), 8.57-8.56 (d, 1H), 8.02 (s, 1H), 7.85 (s, 1H) 7.71 (s, 1H), 6.29-6.13 (m, 2H), 5.66-5.62 (m, 1 H), 5.23-5.10 (m, 1H), 4.55-4.49 (m, 1H), 3.91-3.66 (m, 7H), 1.71 (s, 9H) |

TABLE 1-continued

| Example No. (Scheme) | Structure and Compound Name | LRMS m/z | ¹H NMR |
|---|---|---|---|
| 50 (Scheme C) | 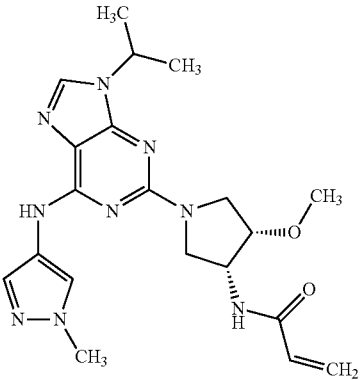<br>N-((cis*)-1-(9-isopropyl-6-((1-methyl-1H-pyrazol-4-yl)amino)-9H-purin-2-yl)-4-methoxypyrrolidin-3-yl)acrylamide (*single enantiomer with unknown absolute stereochemistry) | 426.1 [M + H]+ | ¹H NMR (700 MHz, DMSO-d6) δ ppm 9.52-9.68 (m, 1 H) 8.18-8.36 (m, 1 H) 7.92-8.00 (m, 1 H) 7.90 (s, 1 H) 7.76 (s, 1 H) 6.33-6.46 (m, 1 H) 6.09-6.20 (m, 1 H) 5.56-5.67 (m, 1 H) 4.45-4.70 (m, 2 H) 3.98-4.07 (m, 1 H) 3.81 (s, 4 H) 3.69-3.79 (m, 2 H) 3.40-3.47 (m, 1 H) 3.32 (s, 3 H) 1.50 (d, J = 6.60 Hz, 6 H) |
| 51 (Scheme A) | 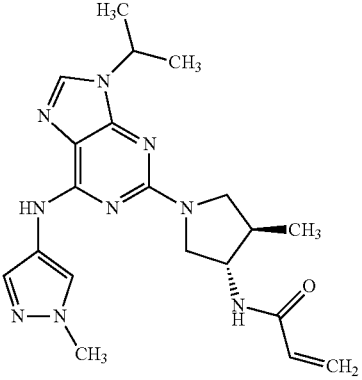<br>N-((3S,4R)-1-(9-isopropyl-6-((1-methyl-1H-pyrazol-4-yl)amino)-9H-purin-2-yl)-4-methylpyrrolidin-3-yl)acrylamide | 410.2 [M + H]+ | N/A |

TABLE 1-continued

| Example No. (Scheme) | Structure and Compound Name | LRMS m/z | ¹H NMR |
|---|---|---|---|
| 52 (Scheme A) | 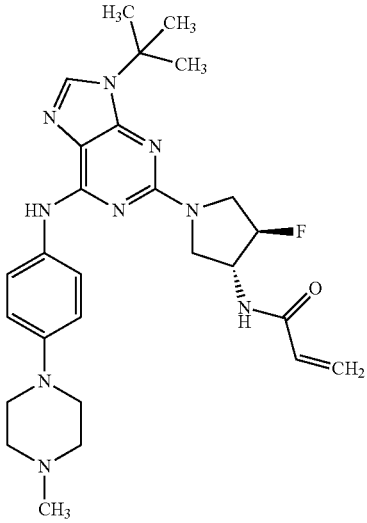<br>N-((3S,4R)-1-(9-(tert-butyl)-6-((4-(4-methylpiperazin-1-yl)phenyl)amino)-9H-purin-2-yl)-4-fluoropyrrolidin-3-yl)acrylamide | 544.2 [M + Na]⁺ | ¹H NMR (400 MHz, methanol-d4) δ ppm 7.89 (s, 1 H) 7.80 (d, J = 9.03 Hz, 2 H) 7.03 (d, J = 9.03 Hz, 2 H) 6.23-6.36 (m, 2 H) 5.69 (dd, J = 7.65, 4.39 Hz, 1 H) 5.06-5.29 (m, 1 H) 4.62 (dd, J = 11.42, 5.40 Hz, 1 H) 3.79-4.04 (m, 4 H) 3.16-3.27 (m, 4 H) 2.63-2.75 (m, 4 H) 2.39 (s, 3 H) 1.81 (s, 9 H) |
| 53 (Scheme A) | 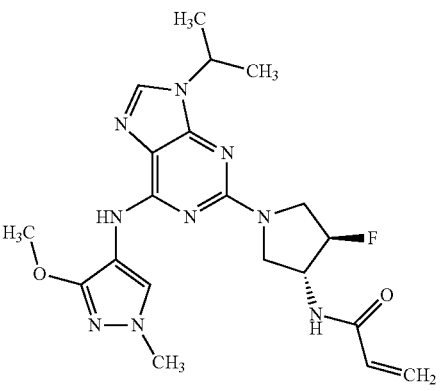<br>N-((3R,4R)-4-fluoro-1-(9-isopropyl-6-((3-methoxy-1-methyl-1H-pyrazol-4-yl)amino)-9H-purin-2-yl)pyrrolidin-3-yl)acrylamide | 444.3 [M + H]⁺ | ¹H NMR (400 MHz, DMSO-d6) δ ppm 8.51-8.50 (d, 1H), 8.03 (s, 1H), 7.92 (s, 1H), 7.83 (s, 1H) 6.28-6.13 (m, 2H), 5.65-5.62 (m, 1 H), 5.19-5.06 (m, 1H), 4.66-4.59 (m, 1H), 4.48-4.47 (m, 1H), 3.83-3.62 (m, 10H), 1.51-1.50 (d, 6H) |

TABLE 1-continued

| Example No. (Scheme) | Structure and Compound Name | LRMS m/z | ¹H NMR |
|---|---|---|---|
| 54 (Scheme D) | 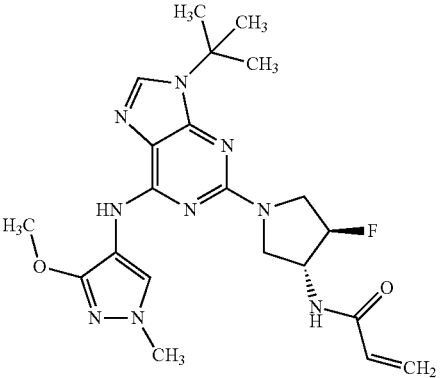<br>N-((3R,4R)-1-(9-(tert-butyl)-6-((3-methoxy-1-methyl-1H-pyrazol-4-yl)amino)-9H-purin-2-yl)-4-fluoropyrroloidin-3-yl)acrylamide | 458.2 [M + H]+ | ¹H NMR (400 MHz, DMSO-d6) δ ppm 8.47 (d, J = 6.60 Hz, 1 H) 7.90 (s, 1 H) 7.76-7.85 (m, 2 H) 6.20-6.34 (m, 1 H) 5.98-6.19 (m, 1 H) 5.57-5.69 (m, 1 H) 4.98-5.26 (m, 1 H) 4.38-4.64 (m, 1 H) 3.84 (s, 4 H) 3.73-3.83 (m, 2 H) 3.72 (s, 3 H) 3.63 (d, J = 12.10 Hz, 1 H) 1.72 (s, 9 H) |
| 55 (Scheme C) | 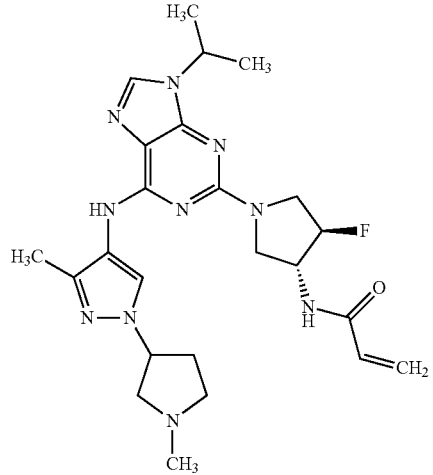<br>N-((3R,4R)-4-fluoro-1-(9-isopropyl-6-((3-methyl-1-(1-methylpyrrolidin-3-yl)-1H-pyrazol-4-yl)amino)-9H-purin-2-yl)pyrrolidin-3-yl)acrylamide (isolated as an acetate salt) | 497.3 [M + H]+ | ¹H NMR (400 MHz, DMSO-d6) δ ppm 8.75 (br. s., 1 H) 8.47 (d, J = 6.5 Hz, 1 H) 8.22 (d, J = 4.8 Hz, 1 H) 7.94 (br. s., 1 H) 6.23 (dd, J = 10.0, 17.0 Hz, 1 H) 6.14 (dd, J = 2.0, 17.0 Hz, 1 H) 5.62 (dd, J = 2.4, 9.8 Hz, 1 H) 5.23-5.04 (m, 1 H) 4.77 (br. s., 1 H) 4.63 (td, J = 6.8, 13.5 Hz, 1 H) 4.48 (td, J = 5.9, 11.9 Hz, 1 H) 3.87-3.62 (m, 4 H) 2.87-2.61 (m, 3 H) 2.34 (d, J = 6.1 Hz, 2 H) 2.26 (br. s., 3 H) 2.19 (s, 3 H) 1.95 (br. s., 3 H) 1.51 (d, J = 6.7 Hz, 6 H). (isolated as an acetate salt) |
| 56 (Scheme A) | 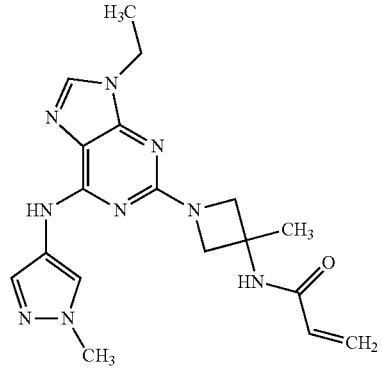<br>N-(1-(9-ethyl-6-((1-methyl-1H-pyrazol-4-yl)amino)-9H-purin-2-yl)-3-methylazetidin-3-yl)acrylamide | 382.3 (M + H)+ | ¹H NMR (400 MHz, DMSO-d6) δ ppm 9.74 (br. s, 1 H,) 8.55 (s, 1 H) 7.97 (s, 1 H) 7.93 (s, 1 H) 7.71 (s, 1 H) 6.20 (d, J = 9.90 Hz, 1H) 6.12 (d, J = 2.08 Hz, 1H) 5.60 (d, J = 11.98 Hz, 1H) 4.17 (d, J = 8.68 Hz, 2H) 4.02-4.11 (m, 2H) 3.97 (d, J = 8.19 Hz, 2H) 3.82 (s, 3H) 1.60 (s, 3 H) 1.39 (t, J = 7.21 Hz, 3H) |

TABLE 1-continued

| Example No. (Scheme) | Structure and Compound Name | LRMS m/z | ¹H NMR |
|---|---|---|---|
| 57 (Scheme A) | 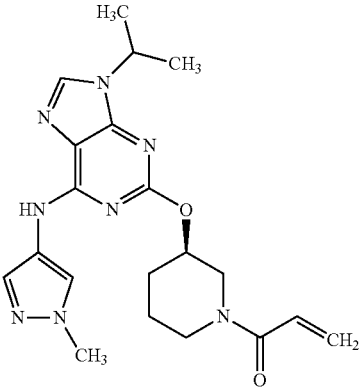<br>(R)-1-(3-((9-isopropyl-6-((1-methyl-1H-pyrazol-4-yl)amino)-9H-purin-2-yl)oxy)piperidin-1-yl)prop-2-en-1-one | 411.3 (M + H)⁺ | ¹H NMR (400 MHz, DMSO-d6) δ 9.34-9.57 (m, 1H), 7.94 (s, 1H), 7.83 (s, 1H), 7.56 (s, 1H), 6.39-6.64 (m, 1H), 5.94 (dd, J = 2.14, 16.81 Hz, 1H), 5.46 (d, J = 9.29 Hz, 1H), 4.90 (td, J = 3.65, 7.24 Hz, 1H), 4.58 (td, J = 6.74, 13.54 Hz, 1H), 3.97 (br. s., 1H), 3.72 (s, 3H), 3.59 (dd, J = 4.95, 11.80 Hz, 1H), 3.46 (br. s., 1H), 3.28-3.42 (m, 1H), 2.03 (td, J = 4.49, 8.62 Hz, 1H), 1.66-1.81 (m, 3H), 1.39-1.51 (m, 6H) |
| 58 (Scheme A) | 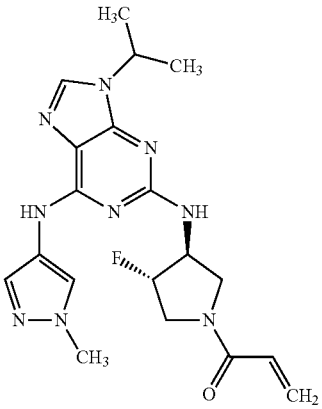<br>1-((trans)-3-fluoro-4-((9-isopropyl-6-((1-methyl-1H-pyrazol-4-yl)amino)-9H-purin-2-yl)amino)pyrrolidin-1-yl)prop-2-en-1-one | 414.2 (M + H)⁺ | ¹H NMR (400 MHz, DMSO-d6) δ 9.53 (d, J = 3.67 Hz, 1H), 8.04-8.23 (m, 1H), 7.86 (d, J = 1.71 Hz, 1H), 7.61 (s, 1H), 6.82 (d, J = 6.97 Hz, 1H), 6.53 (td, J = 10.85, 16.81 Hz, 1H), 6.12 (td, J = 2.63, 16.75 Hz, 1H), 5.65 (td, J = 3.04, 9.93 Hz, 1H), 5.18 (s, 1H), 4.55 (dt, J = 2.20, 6.72 Hz, 2H), 4.07 (s, 1H), 3.82-3.98 (m, 2H), 3.64-3.78 (m, 4H), 1.43 (d, J = 6.48 Hz, 6H) |
| 59 (Scheme A) | 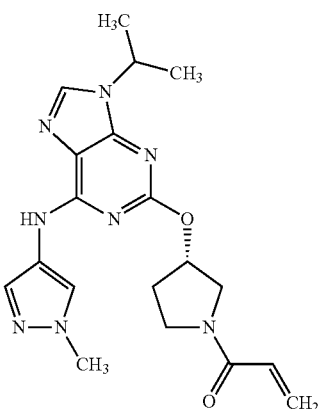<br>(R)-1-(3-((9-isopropyl-6-((1-methyl-1H-pyrazol-4-yl)amino)-9H-purin-2-yl)oxy)pyrrolidin-1-yl)prop-2-en-1-one | 397.2 (M + H)⁺ | ¹H NMR (400 MHz, DMSO-d6) δ ppm 9.46 (s, 1H), 7.94 (s, 1H), 7.84 (s, 1H), 7.59 (s, 1H), 6.38-6.62 (m, 1H), 6.07 (d, J = 2.32 Hz, 1H), 5.58 (s, 1H), 5.38-5.50 (m, 1H), 4.51-4.69 (m, 1H), 3.82-3.94 (m, 1H), 3.74 (s, 3H), 3.64 (br. s., 3H), 2.05-2.31 (m, 2H), 1.46 (d, J = 6.85 Hz, 6H) |

TABLE 1-continued

| Example No. (Scheme) | Structure and Compound Name | LRMS m/z | ¹H NMR |
|---|---|---|---|
| 60 (Scheme A) | 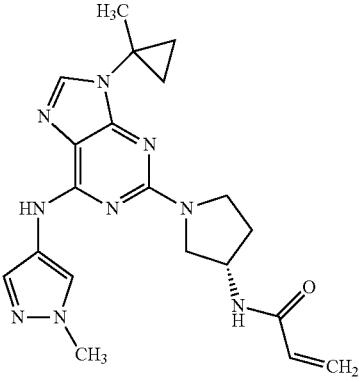<br>(S)-N-(1-(6-((1-methyl-1H-pyrazol-4-yl)amino)-9-(1-methylcyclopropyl)-9H-purin-2-yl)pyrrolidin-3-yl)acrylamide | 408.3 (M + H)⁺ | ¹H NMR (400 MHz, DMSO-d6) δ ppm 9.13 (s, 1 H) 8.06-8.19 (m, 1 H) 7.94 (s, 1 H) 7.75 (s, 1 H) 7.74 (s, 1 H) 6.21-6.35 (m, 1 H) 6.15 (d, J = 2.32 Hz, 1H) 5.58 (dd, J = 10.21, 2.26 Hz, 1H) 4.31-4.53 (m, 1 H) 3.88 (s, 1 H) 3.82 (s, 3 H) 3.72-3.79 (m, 1 H) 3.62-3.71 (m, 1 H) 3.44-3.53 (m, 1H) 2.17-2.32 (m, 1 H) 1.82-2.05 (m, 1 H) 1.59 (s, 3 H) 1.21 (s, 2 H) 0.95 (d, J = 1.47 Hz, 2H) |
| 61 (Scheme A) | 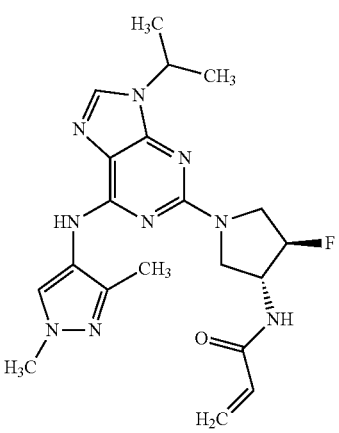<br>N-((3R,4R)-1-(6-((1,3-dimethyl-1H-pyrazol-4-yl)amino)-9-isopropyl-9H-purin-2-yl)-4-fluoropyrrolidin-3-yl)acrylamide | 428.2 [M + H]+ | ¹H NMR (400 MHz, DMSO-d6) δ ppm 8.77 (s, 1H), 8.51-8.49 (d, 1H), 7.95-7.91 (d, 2H), 6.28-6.13 (m, 2H), 5.65-5.62 (m, 1H), 5.20-5.07 (m, 1H), 4.67-4.62 (m, 1 H), 4.51-4.44 (m, 1H), 3.84-3.66 (m, 7H), 2.17 (s, 3H), 1.53-1.51 (d, 6H) |

TABLE 1-continued

| Example No. (Scheme) | Structure and Compound Name | LRMS m/z | ¹H NMR |
|---|---|---|---|
| 62 (Scheme A) | 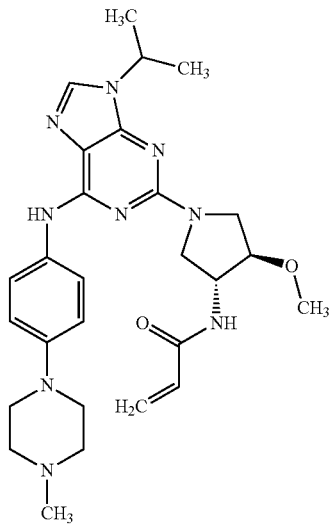<br>N-((3R,4R)-1-(9-isopropyl-6-((4-(4-methylpiperazin-1-yl)phenyl)amino)-9H-purin-2-yl)-4-methoxypyrrolidin-3-yl)acrylamide | 520.3 [M + H]+ | ¹H NMR (600 MHz, DMSO-d6) δ ppm 9.24 (s, 1H), 8.43 (d, J = 7.15 Hz, 1H), 7.94 (s, 1H), 7.86 (d, J = 8.99 Hz, 2H), 6.90 (d, J = 8.99 Hz, 2H), 6.20-6.33 (m, 1H), 6.10-6.19 (m, 1H), 5.47-5.69 (m, 1H), 4.57-4.72 (m, 1H), 4.41 (t, J = 6.51 Hz, 1H), 3.84 (d, J = 2.02 Hz, 1H), 3.70-3.80 (m, 2H), 3.64 (d, J = 12.10 Hz, 1H), 3.54 (d, J = 11.74 Hz, 1H), 3.37 (s, 3H), 3.01-3.12 (m, 4H), 2.40-2.48 (m, 4H), 2.22 (s, 3H), 1.52 (d, J = 6.79 Hz, 6H) |
| 63 (Scheme A) | 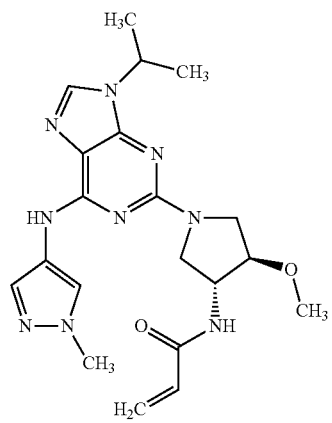<br>N-((3R,4R)-1-(9-isopropyl-6-((1-methyl-1H-pyrazol-4-yl)amino)-9H-purin-2-yl)-4-methoxypyrrolidin-3-yl)acrylamide | 426.1 [M + H]+ | ¹H NMR (400 MHz, DMSO-d6) δ ppm 9.60 (s, 1H), 8.42 (d, J = 7.09 Hz, 1H), 7.99 (s, 1H), 7.91 (s, 1H), 7.73 (s, 1H), 6.24 (d, J = 10.03 Hz, 1H), 6.16 (d, J = 2.32 Hz, 1H), 5.61 (dd, J = 2.38, 9.96 Hz, 1H), 4.62 (s, 1H), 4.32-4.47 (m, 1H), 3.71-3.97 (m, 6H), 3.68 (s, 1H), 3.48-3.61 (m, 1H), 3.34-3.42 (m, 3H), 1.51 (d, J = 6.72 Hz, 6H) |

TABLE 1-continued

| Example No. (Scheme) | Structure and Compound Name | LRMS m/z | $^1$H NMR |
|---|---|---|---|
| 64 (Scheme A) | 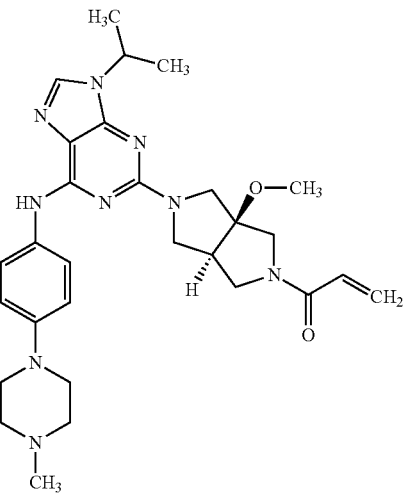<br>1-((cis)-5-(9-isopropyl-6-((4-(4-methylpiperazin-1-yl)phenyl)amino)-9H-purin-2-yl)-3a-methoxyhexahydropyrrolo[3,4-c]pyrrol-2(1H)-yl)prop-2-en-1-one (single enantiomer with unknown ABS) | 568.2 [M + Na]+ | $^1$H NMR (400 MHz, methanol-d4) δ ppm 7.90 (s, 1 H) 7.78 (d, J = 9.03 Hz, 2 H) 7.02 (d, J = 9.03 Hz, 2 H) 6.64 (ddd, J = 16.81, 10.42, 2.38 Hz, 1 H) 6.24-6.36 (m, 1 H) 5.73-5.82 (m, 1 H) 4.76 (dt, J = 13.49, 6.68 Hz, 1 H) 3.85-4.06 (m, 5 H) 3.64-3.72 (m, 1 H) 3.47-3.62 (m, 2 H) 3.43 (d, J = 1.76 Hz, 3 H) 3.16-3.24 (m, 4 H) 3.03-3.15 (m, 1 H) 2.66 (dd, J = 9.66, 4.64 Hz, 4 H) 2.37 (s, 3 H) 1.60 (d, J = 6.53 Hz, 6 H) |
| 65 (Scheme C) | 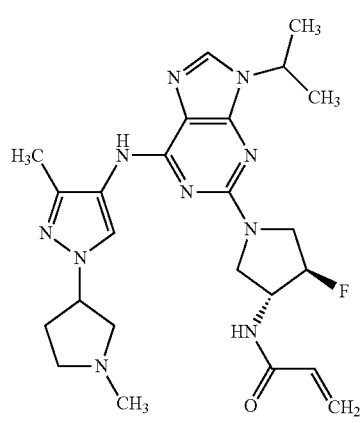<br>N-((3R,4R)-4-fluoro-1-(9-isopropyl-6-((3-methyl-1-(1-methylpyrrolidin-3-yl)-1H-pyrazol-4-yl)amino)-9H-purin-2-yl)pyrrolidin-3-yl)acrylamide | 497.3 [M + H]+ | $^1$H NMR (600 MHz, DMSO-d6) δ ppm 8.97 (br. s., 1H), 8.53 (d, J = 6.7 Hz, 1H), 8.30 (s, 1H), 7.95 (s, 1H), 6.21 (dd, J = 9.7, 17.0 Hz, 1H), 6.14 (dd, J = 2.5, 17.0 Hz, 1H), 5.63 (dd, J = 2.2, 10.0 Hz, 1H), 5.13 (d, J = 51.0 Hz, 1H), 4.79-4.73 (m, 1H), 4.62 (td, J = 6.8, 13.5 Hz, 1H), 4.49 (td, J = 6.1, 12.3 Hz, 1H), 3.87-3.76 (m, 2H), 3.67-3.57 (m, 2H), 2.83-2.77 (m, 1H), 2.73 (dd, J = 3.1, 9.7 Hz, 1H), 2.65 (dd, J = 7.0, 10.0 Hz, 1H), 2.40-2.28 (m, 2H), 2.24 (s, 3H), 2.19 (s, 3H), 1.93 (br. s., 1H), 1.49 (d, J = 6.7 Hz, 6H) |

TABLE 1-continued

| Example No. (Scheme) | Structure and Compound Name | LRMS m/z | 1H NMR |
|---|---|---|---|
| 66 (Scheme A) | 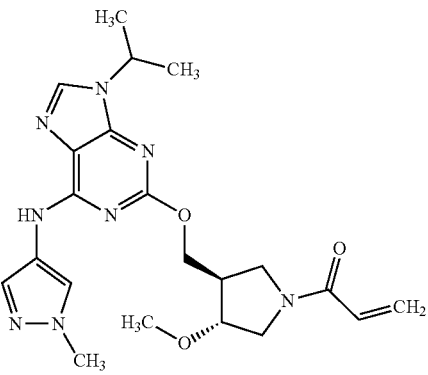<br>1-((3R,4R)-3-(((9-isopropyl-6-((1-methyl-1H-pyrazol-4-yl)amino)-9H-purin-2-yl)oxy)methyl)-4-methoxypyrrolidin-1-yl)prop-2-en-1-one | 441.2 [M + H]+ | 1H NMR (400 MHz, DMSO-d6) δ ppm 9.56 (s, 1H), 8.04 (s, 1H), 7.96 (s, 1H), 7.69 (s, 1H), 6.57 (dd, J = 10.39, 16.87 Hz, 1H), 6.12 (dd, J = 2.38, 16.81 Hz, 1H), 5.64 (dd, J = 2.26, 10.33 Hz, 1H), 4.62-4.85 (m, 1H), 4.37-4.50 (m, 1H), 4.27-4.36 (m, 1H), 3.98-3.98 (m, 1H), 3.93-4.02 (m, 1H), 3.84 (s, 4H), 3.38-3.62 (m, 2H), 3.32 (s, 3H), 2.70-2.89 (m, 1H), 1.55 (d, J = 6.85 Hz, 6H) |
| 67 (Scheme A) | 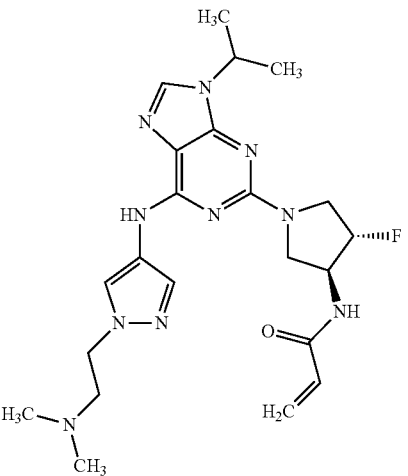<br>N-((3S,4S)-1-(6-((1-(2-(dimethylamino)ethyl)-1H-pyrazol-4-yl)amino)-9-isopropyl-9H-purin-2-yl)-4-fluoropyrrolidin-3-yl)acrylamide | 471.1 [M + H]+ | 1H NMR (400 MHz, CDCl3) δ ppm 8.00 (s, 1 H), 7.63-7.56 (m, 3 H), 6.37-6.33 (m, 1 H), 6.13-6.06 (m, 2 H), 5.70-5.67 (m, 1 H), 5.29-5.17 (m, 1 H), 4.71-4.66 (m, 2 H), 4.22-4.19 (t, 2 H), 3.97-3.86 (m, 4H), 2.78-2.73 (m, 2 H), 2.27 (s, 6H), 1.57-1.56 (d, 6H) |

TABLE 1-continued

| Example No. (Scheme) | Structure and Compound Name | LRMS m/z | $^1$H NMR |
|---|---|---|---|
| 68 (Scheme A) | 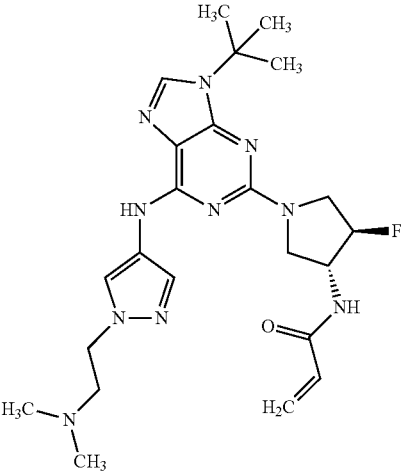<br>N-((3R,4R)-1-(9-(tert-butyl)-6-((1-(2-(dimethylamino)ethyl)-1H-pyrazol-4-yl)amino)-9H-purin-2-yl)-4-fluoropyrrolidin-3-yl)acrylamide | 485.2 [M + H]+ | $^1$H NMR (400 MHz, CDCl$_3$) δ ppm 8.00 (s, 1 H), 7.61-7.58 (d, 3 H), 6.38-6.34 (m, 1 H), 6.22 (brs, 1 H), 6.14-6.08 (m, 1 H), 5.69-5.66 (m, 1 H), 5.29-5.17 (m, 1 H), 4.72 (m, 1 H), 4.22-4.19 (t, 2 H), 3.99-3.86 (m, 4H), 2.78-2.75 (t, 2 H), 2.27 (s, 6H), 1.74 (s, 9H) |
| 69 (Scheme D) | 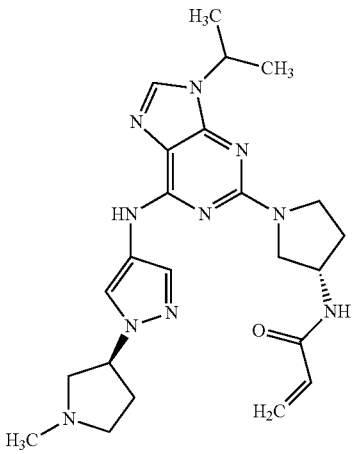<br>N-((S)-1-(9-isopropyl-6-((1-((S)-1-methylpyrrolidin-3-yl)-1H-pyrazol-4-yl)amino)-9H-purin-2-yl)pyrrolidin-3-yl)acrylamide | 465.1 [M + H]+ | $^1$H NMR (400 MHz, DMSO) δ ppm 9.65 (s, 1H), 8.42-8.44 (d, 1H), 8.36 (s, 1H), 7.90 (s, 1H), 7.62 (s, 1H), 6.23-6.30 (m, 1H), 6.10-6.15 (m, 1H), 5.59-5.62 (m, 1H), 4.82-4.84 (m, 1H), 4.60-4.64 (m, 1H), 4.47-4.48 (m, 1H), 3.67-3.83 (m, 3H), 3.46-3.48 (m, 1H), 2.71-2.85 (m, 3H), 2.29-2.37 (m, 6H), 1.93-1.96 (m, 2H), 1.50-1.52 (d, 6H) |

TABLE 1-continued

| Example No. (Scheme) | Structure and Compound Name | LRMS m/z | ¹H NMR |
|---|---|---|---|
| 70 (Scheme A) | 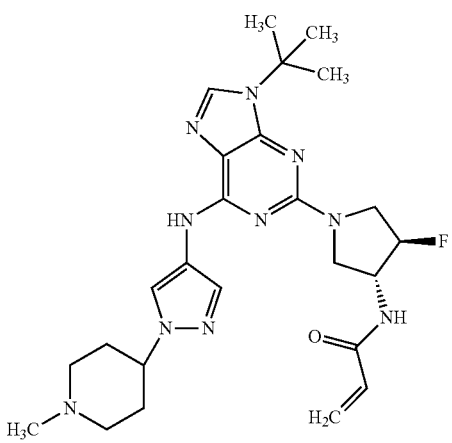<br>N-((3R,4R)-1-(9-(tert-butyl)-6-((1-(1-methylpiperidin-4-yl)-1H-pyrazol-4-yl)amino)-9H-purin-2-yl)-4-fluoropyrrolidin-3-yl)acrylamide | 533.1 [M + Na]+ | ¹H NMR (400 MHz, CDCl₃) δ ppm 8.04 (s, 1H), 7.75 (s, 1H), 7.65 (s, 1H), 7.60 (s, 1H), 6.38-6.34 (d, 1H), 6.17-6.10 (m, 2H), 5.70-5.67 (m, 1H), 5.32-5.20 (m, 1H), 4.73 (m, 1H), 4.20-4.16 (m, 1H), 4.01-3.83 (m, 4H), 3.12-3.09 (m, 2H), 2.46-2.21 (m, 9H), 1.75 (s, 9H) |
| 71 (Scheme A) | 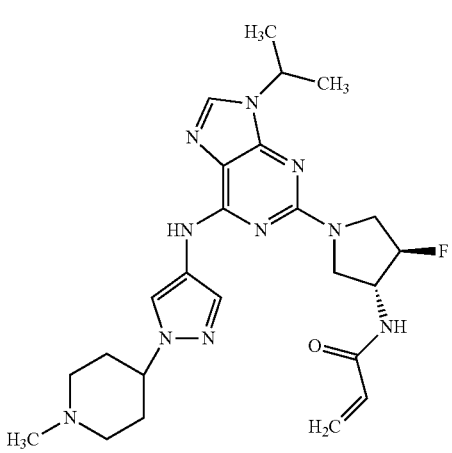<br>N-((3R,4R)-4-fluoro-1-(9-isopropyl-6-((1-(1-methylpiperidin-4-yl)-1H-pyrazol-4-yl)amino)-9H-purin-2-yl)pyrrolidin-3-yl)acrylamide | 497.1 [M + H]+ | ¹H NMR (400 MHz, CDCl₃) δ ppm 7.99 (s, 1H), 7.90 (s, 1H), 7.64 (s, 1H), 7.56 (s, 1H), 6.38-6.33 (m, 1H), 6.25 (m, 1H), 6.16-6.10 (m, 1 H), 5.69-5.67 (m, 1H), 5.31-5.18 (m, 1H), 4.72-4.66 (m, 2H), 4.15-4.13 (m, 1H), 3.98-3.83 (m, 4H), 3.06-3.03 (m, 2H), 2.38 (s, 3H), 2.25-2.10 (m, 6H), 1.57-1.55 (d, 6H) |

TABLE 1-continued

| Example No. (Scheme) | Structure and Compound Name | LRMS m/z | $^1$H NMR |
|---|---|---|---|
| 72 (Scheme D) | 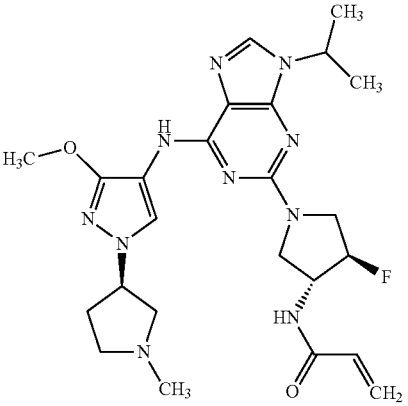<br>N-((3R,4R)-4-fluoro-1-(9-isopropyl-6-((3-methoxy-1-((R)-1-methylpyrrolidin-3-yl)-1H-pyrazol-4-yl)amino)-9H-purin-2-yl)pyrrolidin-3-yl)acrylamide | 513.2 [M + H]+ | $^1$H NMR (400 MHz, DMSO-d6) δ ppm 8.48 (d, J = 6.72 Hz, 1 H) 8.13 (s, 1 H) 7.98 (s, 1 H) 7.92 (s, 1 H) 6.19-6.30 (m, 1 H) 6.09-6.17 (m, 1 H) 5.57-5.68 (m, 1 H) 5.03-5.25 (m, 1 H) 4.66-4.76 (m, 1 H) 4.62 (quin, J = 6.72 Hz, 1 H) 4.43-4.54 (m, 1 H) 3.84 (s, 4 H) 3.59-3.83 (m, 3 H) 2.72-2.88 (m, 2 H) 2.57-2.68 (m, 1 H) 2.30-2.36 (m, 2 H) 2.26 (s, 3 H) 1.87-2.01 (m, 1 H) 1.50 (d, J = 6.85 Hz, 6 H) |
| 73 (Scheme D) | 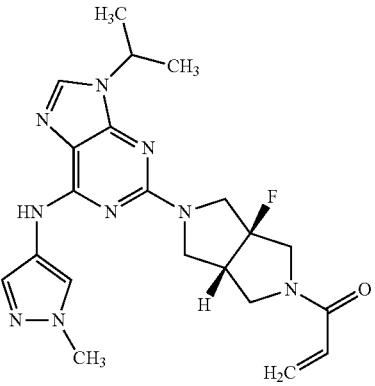<br>1-(cis-3a-fluoro-5-(9-isopropyl-6-((1-methyl-1H-pyrazol-4-yl)amino)-9H-purin-2-yl)hexahydropyrrolo[3,4-c]pyrrol-2(1H)-yl)prop-2-en-1-one | 440.2 [M + H]+ | $^1$H NMR (600 MHz, DMSO-d6) δ ppm 9.27 (br. s., 1 H) 7.92 (s, 1 H) 7.84 (s, 1 H) 7.64 (s, 1 H) 6.41-6.57 (m, 1 H) 6.13 (ddd, J = 16.68, 3.80, 1.32 Hz, 1 H) 5.66-5.79 (m, 1 H) 4.51-4.62 (m, 1 H) 3.80-4.08 (m, 5 H) 3.76 (s, 3 H) 3.56 (dd, J = 11.34, 5.05 Hz, 1 H) 3.40 (dt, J = 11.23, 5.43 Hz, 1 H) 3.34 (dd, J = 13.02, 5.27 Hz, 1 H) 3.07-3.27 (m, 1 H) 1.42 (d, J = 6.73 Hz, 6 H) |
| 74 (Scheme D) | 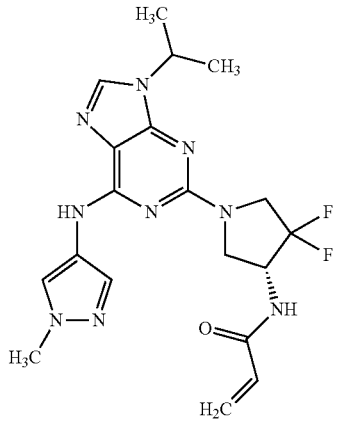<br>(R)-N-(4,4-difluoro-1-(9-isopropyl-6-((1-methyl-1H-pyrazol-4-yl)amino)-9H-purin-2-yl)pyrrolidin-3-yl)acrylamide | 432.1 [M + H]+ | $^1$H NMR (600 MHz, DMSO-d6) δ ppm 9.73 (s, 1 H) 8.67 (d, J = 8.62 Hz, 1 H) 7.92-8.00 (m, 2 H) 7.70 (s, 1 H) 6.34 (dd, J = 17.15, 10.18 Hz, 1 H) 6.20 (dd, J = 17.15, 2.11 Hz, 1 H) 5.65-5.74 (m, 1 H) 4.89-5.05 (m, 1 H) 4.63 (quin, J = 6.79 Hz, 1 H) 3.97-4.18 (m, 3 H) 3.82 (s, 3 H) 3.49-3.60 (m, 1 H) 1.51 (d, J = 6.79 Hz, 6 H) |

TABLE 1-continued

| Example No. (Scheme) | Structure and Compound Name | LRMS m/z | ¹H NMR |
|---|---|---|---|
| 75 (Scheme C) | 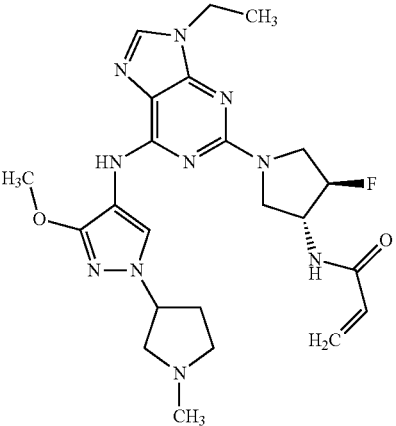<br>N-((3R,4R)-1-(9-ethyl-6-((3-methoxy-1-(1-methylpyrrolidin-3-yl)-1H-pyrazol-4-yl)amino)-9H-purin-2-yl)-4-fluoropyrrolidin-3-yl)acrylamide | 499.3 [M + H]+ | ¹H NMR (600 MHz, DMSO-d6) δ ppm 8.49 (d, J = 6.60 Hz, 1 H) 8.14 (br. s., 1 H) 8.04 (s, 1 H) 7.86 (br. s., 1 H) 6.17-6.31 (m, 1 H) 6.03-6.17 (m, 1 H) 5.53-5.69 (m, 1 H) 5.02-5.24 (m, 1 H) 4.63-4.77 (m, 1 H) 4.38-4.55 (m, 1 H) 4.07 (q, J = 7.15 Hz, 2 H) 3.84 (s, 6 H) 3.67 (d, J = 11.74 Hz, 1 H) 2.81 (dt, J = 8.44, 4.03 Hz, 1 H) 2.76 (dd, J = 9.81, 3.03 Hz, 1 H) 2.59-2.66 (m, 1 H) 2.29-2.37 (m, 2 H) 2.26 (s, 3 H) 1.89-1.99 (m, 1 H) 1.39 (t, J = 7.24 Hz, 3 H) |
| 76 (Scheme D) | 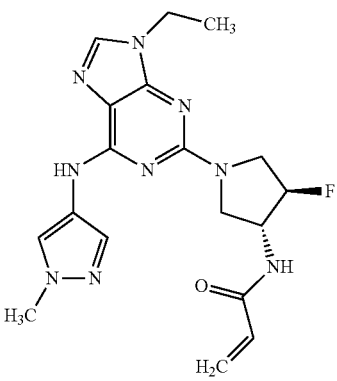<br>N-((3R,4R)-1-(6-((1,3-dimethyl-1H-pyrazol-4-yl)amino)-9-ethyl-9H-purin-2-yl)-4-fluoropyrrolidin-3-yl)acrylamide | 435.9 [M + Na]+ | ¹H NMR (400 MHz, CDCl₃) δ ppm 7.85 (s, 1H), 7.45 (s, 1H), 7.12 (s, 1H), 6.90 (brs, 1H), 6.42-6.37 (m, 1H), 6.25-6.18 (m, 1H), 5.70-5.67 (m, 1H), 5.29-5.16 (m, 1H), 4.75-4.74 (m, 1H), 4.07-4.02 (m, 2H), 3.93-3.79 (m, 7H), 2.28 (s, 3H), 1.48-1.44 (t, 3H) |
| 77 (Scheme D) | 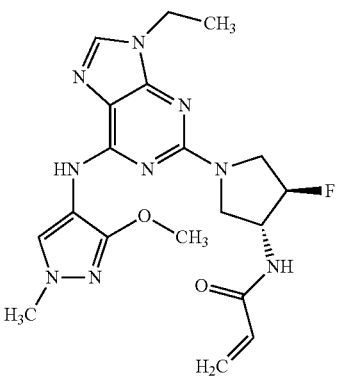<br>N-((3R,4R)-1-(9-ethyl-6-((3-methoxy-1-methyl-1H-pyrazol-4-yl)amino)-9H-purin-2-yl)-4-fluoropyrrolidin-3-yl)acrylamide | 452.1 [M + Na]+ | ¹H NMR (400 MHz, CDCl₃) δ ppm 7.92 (brs, 1H), 7.58 (s, 1H), 7.38 (s, 1H), 6.90 (s, 1H), 6.46-6.32 (m, 2H), 5.68-5.65 (m, 1H), 5.35-5.23 (m, 1H), 4.72 (m, 1H), 3.97-3.75 (m, 9H), 3.66 (s, 3H), 1.43-1.39 (t, 3H) |

TABLE 1-continued

| Example No. (Scheme) | Structure and Compound Name | LRMS m/z | ¹H NMR |
|---|---|---|---|
| 78 (Scheme D) | 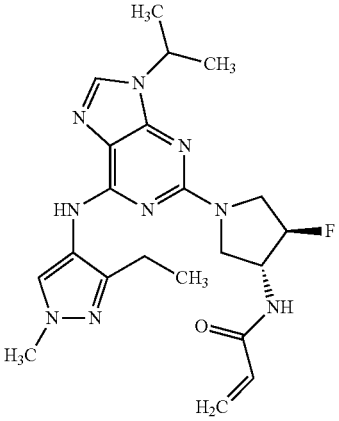<br>N-((3R,4R)-1-(6-((3-ethyl-1-methyl-1H-pyrazol-4-yl)amino)-9-isopropyl-9H-purin-2-yl)-4-fluoropyrrolidin-3-yl)acrylamide | 442.1 [M + H]+ | ¹H NMR (400 MHz, CDCl₃) δ ppm 7.92 (s, 1H), 7.56 (s, 1H), 7.27 (s, 1H), 6.39-6.35 (d, 1H), 6.24 (brs, 1H), 6.17-6.10 (m, 1H), 5.71-5.68 (d, 1H), 5.29-5.16 (m, 1H), 4.72-4.64 (m, 2H), 4.02-3.80 (m, 7H), 2.72-2.67 (m, 2H), 1.57-1.55 (d, 6H), 1.31-1.27 (t, 3H) |
| 79 (Scheme D) | 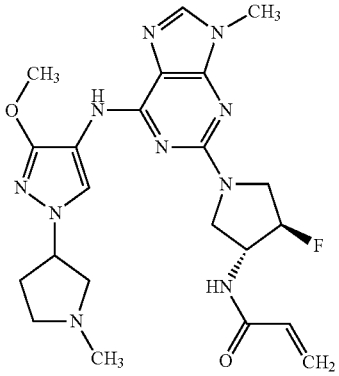<br>N-((3R,4R)-4-fluoro-1-(6-((3-methoxy-1-(1-methylpyrrolidin-3-yl)-1H-pyrazol-4-yl)amino)-9-methyl-9H-purin-2-yl)pyrrolidin-3-yl)acrylamide | 565.3 [M + H]+ | ¹H NMR (700 MHz, DMSO-d6) δ ppm 8.49 (d, J = 5.72 Hz, 1 H) 8.15 (br. s., 1 H) 8.07-8.13 (m, 1 H) 7.80 (s, 1 H) 6.19-6.29 (m, 1 H) 6.09-6.17 (m, 1 H) 5.63 (dd, J = 10.12, 1.98 Hz, 1 H) 5.06-5.24 (m, 1 H) 4.69 (br. s., 1 H) 4.41-4.54 (m, 1 H) 3.82-3.85 (m, 3 H) 3.73-3.90 (m, 3 H) 3.68 (d, J = 11.66 Hz, 1 H) 3.62 (s, 3 H) 2.80 (d, J = 7.70 Hz, 2 H) 2.63 (t, J = 8.25 Hz, 1 H) 2.29-2.37 (m, 2 H) 2.26 (s, 3 H) 1.90 (br. s., 1 H) |
| 80 (Scheme D) | 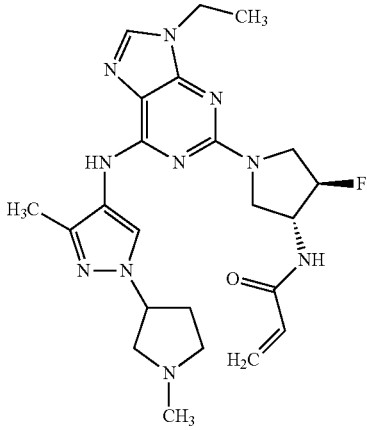<br>N-((3R,4R)-1-(9-ethyl-6-((3-methyl-1-(1-methylpyrrolidin-3-yl)-1H-pyrazol-4-yl)amino)-9H-purin-2-yl)-4-fluoropyrrolidin-3-yl)acrylamide (single diastereoisomer with unknown ABS) | 483.4 [M + H]+ | ¹H NMR (700 MHz, DMSO-d6) δ ppm 8.82 (br. s., 1 H) 8.49 (br. s., 1 H) 8.25 (br. s., 1 H) 7.88 (br. s., 1 H) 6.22 (d, J = 9.90 Hz, 1 H) 6.08-6.17 (m, 1 H) 5.63 (d, J = 9.90 Hz, 1 H) 5.05-5.22 (m, 1 H) 4.77 (br. s., 1 H) 4.48 (br. s., 1 H) 4.07 (d, J = 6.60 Hz, 3 H) 3.82 (d, J = 12.32 Hz, 3 H) 2.65-2.85 (m, 3 H) 2.34 (br. s., 2 H) 2.26 (br. s., 3 H) 2.19 (br. s., 3 H) 1.95 (br. s., 1 H) 1.35-1.42 (m, 3 H). |

TABLE 1-continued

| Example No. (Scheme) | Structure and Compound Name | LRMS m/z | ¹H NMR |
|---|---|---|---|
| 81 (Scheme D) | 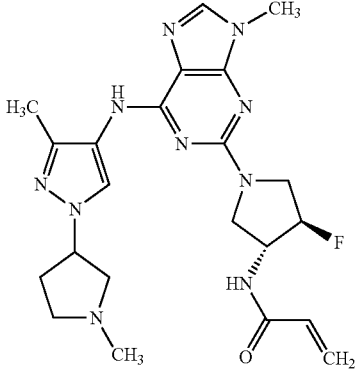<br>N-((3R,4R)-4-fluoro-1-(9-methyl-6-((3-methyl-1-(1-methylpyrrolidin-3-yl)-1H-pyrazol-4-yl)amino)-9H-purin-2-yl)pyrrolidin-3-yl)acrylamide (single diastereoisomer with unknown ABS) | 469.2 [M + H]+ | ¹H NMR (700 MHz, DMSO-d6) δ ppm 8.83 (br. s., 1 H) 8.49 (d, J = 5.94 Hz, 1 H) 8.26 (d, J = 9.02 Hz, 1 H) 7.82 (s, 1 H) 6.20-6.29 (m, 1 H) 6.11-6.18 (m, 1 H) 5.63 (dd, J = 10.12, 2.20 Hz, 1 H) 5.05-5.21 (m, 1 H) 4.71-4.83 (m, 1 H) 4.48 (dt, J = 12.05, 5.97 Hz, 1 H) 3.74-3.91 (m, 3 H) 3.69 (d, J = 11.66 Hz, 1 H) 3.63 (s, 3 H) 2.73-2.90 (m, 2 H) 2.62-2.69 (m, 1 H) 2.29-2.41 (m, 2 H) 2.26 (d, J = 3.96 Hz, 3 H) 2.19 (s, 3 H) 1.90-2.00 (m, 1 H) |
| 82 (Scheme D) | 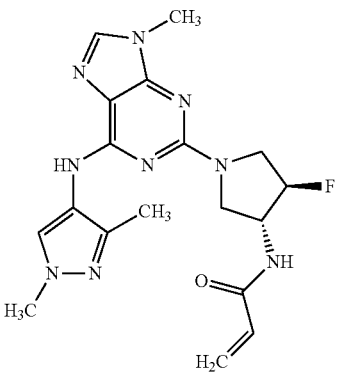<br>N-((3R,4R)-1-(6-((1,3-dimethyl-1H-pyrazol-4-yl)amino)-9-methyl-9H-purin-2-yl)-4-fluoropyrrolidin-3-yl)acrylamide | 422.0 [M + Na]+ | ¹H NMR (400 MHz, CDCl₃) δ ppm 7.92 (s, 1H), 7.48 (s, 1H), 7.12 (m, 1H), 6.34-6.39 (d, 1H), 6.08-6.15 (m, 2H), 5.68-5.71 (m, 1H), 5.17-5.30 (m, 1H), 4.72 (m, 1H), 3.82-3.95 (m, 7H), 3.68 (s, 3H), 2.30 (s, 3H) |
| 83 (Scheme D) | 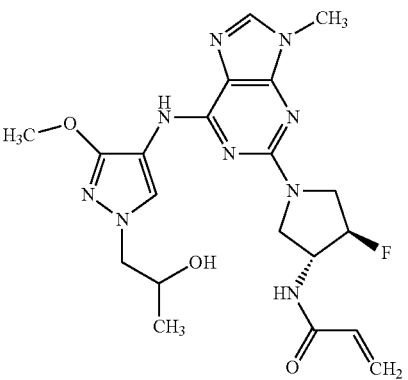<br>N-((3R,4R)-4-fluoro-1-(6-((1-(2-hydroxypropyl)-3-methoxy-1H-pyrazol-4-yl)amino)-9-methyl-9H-purin-2-yl)pyrrolidin-3-yl)acrylamide | 460.2 [M + H]+ | ¹H NMR (400 MHz, DMSO-d6) δ ppm 8.45 (d, J = 6.5 Hz, 1H), 7.97 (s, 1H), 7.90 (br. s., 1H), 7.78 (s, 1H), 6.29-6.19 (m, 1H), 6.18-6.10 (m, 1H), 5.65-5.59 (m, 1H), 5.11 (d, J = 51.0 Hz, 1H), 4.82 (d, J = 4.9 Hz, 1H), 4.45 (td, J = 5.9, 11.9 Hz, 1H), 3.98-3.89 (m, 1H), 3.85 (d, J = 7.5 Hz, 2H), 3.83 (s, 3H), 3.79 (m, 1H), 3.66 (d, J = 12.0, 1H), 3.62 (s, 3H), 2.54 (s, 2H), 1.04 (d, J = 6.1 Hz, 3H) |

| Example No. (Scheme) | Structure and Compound Name | LRMS m/z | ¹H NMR |
|---|---|---|---|
| 84 (Scheme D) | 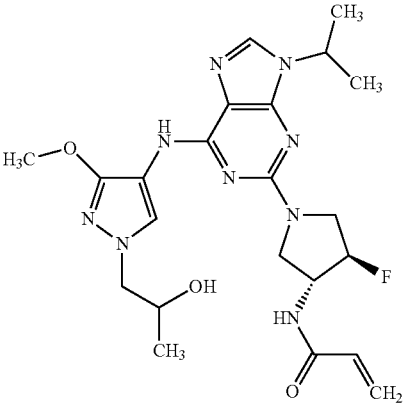 N-((3R,4R)-4-fluoro-1-(6-((1-(2-hydroxypropyl)-3-methoxy-1H-pyrazol-4-yl)amino)-9-isopropyl-9H-purin-2-yl)pyrrolidin-3-yl)acrylamide | 488.2 [M + H]+ | ¹H NMR (400 MHz, DMSO-d6) δ ppm 8.46 (d, J = 6.6 Hz, 1H), 7.96 (s, 1H), 7.90 (s, 2H), 6.24 (dd, J = 10.0, 16.5 Hz, 1H), 6.14 (dd, J = 3.0, 16.5 Hz, 1H), 5.62 (dd, J = 2.9, 10.0 Hz, 1H), 5.11 (d, J = 51.0 Hz, 1H), 4.82 (d, J = 4.9 Hz, 1H), 4.62 (quin, J = 6.7 Hz, 1H), 4.46 (td, J = 5.9, 11.7 Hz, 1H), 3.99-3.90 (m, 1H), 3.89-3.67 (m, 5H), 3.83 (s, 3H), 3.63 (d, J = 11.9 Hz, 1H), 1.50 (d, J = 6.7 Hz, 6H), 1.05 (d, J = 6.1 Hz, 3H) |
| 85 (Scheme D) | 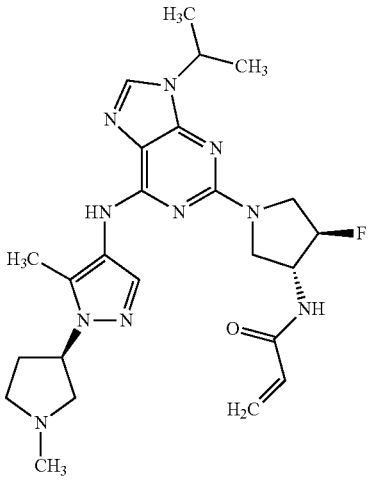 N-((3R,4R)-4-fluoro-1-(9-isopropyl-6-((5-methyl-1-((R)-1-methylpyrrolidin-3-yl)-1H-pyrazol-4-yl)amino)-9H-purin-2-yl)pyrrolidin-3-yl)acrylamide | 497.2 [M + H]+ | ¹H NMR (600 MHz, DMSO-d6) δ ppm 8.79 (br. s., 1 H) 8.43 (d, J = 6.60 Hz, 1 H) 7.91 (s, 1 H) 7.70 (br. s., 1 H) 6.18-6.27 (m, 1 H) 6.09-6.16 (m, 1 H) 5.62 (dd, J = 9.90, 2.38 Hz, 1 H) 5.02-5.20 (m, 1 H) 4.79-4.90 (m, 1 H) 4.62 (dt, J = 13.57, 6.79 Hz, 1 H) 4.38-4.52 (m, 1 H) 3.66-3.80 (m, 3 H) 3.58 (d, J = 11.55 Hz, 1 H) 3.00 (t, J = 8.34 Hz, 1 H) 2.69 (td, J = 8.12, 5.04 Hz, 1 H) 2.53-2.61 (m, 2 H) 2.28 (s, 3 H) 2.24-2.26 (m, 1 H) 2.23 (s, 3 H) 2.17-2.22 (m, 1 H) 1.50 (d, J = 6.60 Hz, 6 H) |
| 86 (Scheme D) | 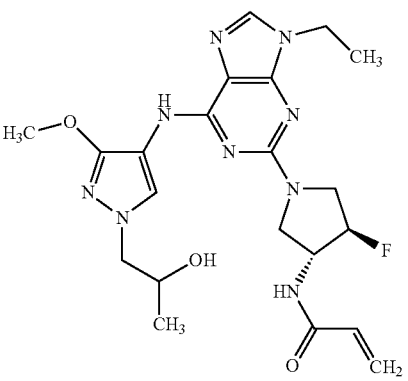 N-((3R,4R)-1-(9-ethyl-6-((1-(2-hydroxypropyl)-3-methoxy-1H-pyrazol-4-yl)amino)-9H-purin-2-yl)-4-fluoropyrrolidin-3-yl)acrylamide | 474.2 [M + H]+ | ¹H NMR (400 MHz, DMSO-d6) δ ppm 8.46 (d, J = 6.5 Hz, 1H), 7.96 (s, 1H), 7.90 (br. s., 1H), 7.84 (s, 1H), 6.24 (dd, J = 9.8, 16.5 Hz, 1H), 6.14 (dd, J = 3.0, 17.0 Hz, 1H), 5.62 (dd, J = 3.0, 10.0 Hz, 1H), 5.11 (d, J = 51.0 Hz, 1H), 4.82 (br. s., 1H), 4.46 (td, J = 5.8, 11.6 Hz, 1H), 4.06 (q, J = 7.3 Hz, 2H), 3.94 (br. s., 1H), 3.87-3.69 (m, 5H), 3.83 (s, 3H), 3.64 (d, J = 12.0 Hz, 1H), 1.39 (t, J = 7.3 Hz, 3H), 1.04 (d, J = 6.1 Hz, 3H) |

| Example No. (Scheme) | Structure and Compound Name | LRMS m/z | $^1$H NMR |
|---|---|---|---|
| 87 (Scheme D) | 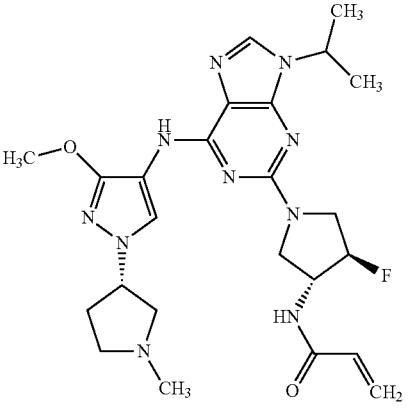<br>N-((3R,4R)-4-fluoro-1-(9-isopropyl-6-((3-methoxy-1-((S)-1-methylpyrrolidin-3-yl)-1H-pyrazol-4-yl)amino)-9H-purin-2-yl)pyrrolidin-3-yl)acrylamide | 513.2 [M + H]+ | $^1$H NMR (400 MHz, DMSO-d6) δ ppm 8.48 (d, J = 6.5 Hz, 1H), 8.15-8.07 (m, 1H), 8.01 (s, 1H), 7.92 (s, 1H), 6.29-6.19 (m, 1H), 6.18-6.10 (m, 1H), 5.63 (dd, J = 2.7, 10.0 Hz, 1H), 5.13 (d, J = 51.0 Hz, 1H), 4.76 (br. s., 1H), 4.62 (td, J = 6.7, 13.4 Hz, 1H), 4.48 (td, J = 5.9, 11.6 Hz, 1H), 3.91-3.79 (m, 3H), 3.85 (s, 3H), 3.79-3.59 (m, 3H), 2.98-2.70 (m, 3H), 2.36-2.28 (m, J = 4.4 Hz, 2H), 1.98 (br. s., 1H), 1.50 (d, J = 6.7 Hz, 6H) |
| 88 (Scheme D) | 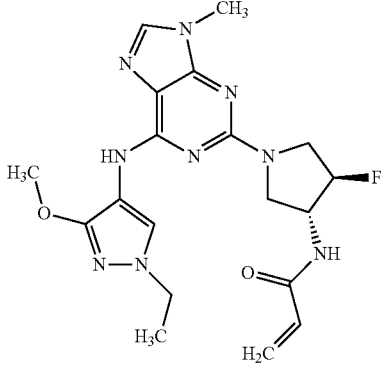<br>N-((3R,4R)-1-(6-((1-ethyl-3-methoxy-1H-pyrazol-4-yl)amino)-9-methyl-9H-purin-2-yl)-4-fluoropyrrolidin-3-yl)acrylamide | 430.2 [M + H]+ | $^1$H NMR (400 MHz, DMSO-d6) δ ppm 8.44 (d, J = 6.5 Hz, 1 H) 7.98 (s, 1 H) 7.87 (s, 1 H) 7.78 (s, 1 H) 6.23 (dd, J = 9.7, 17.0 Hz, 1 H) 6.14 (dd, J = 3.0, 17.0 Hz, 1 H) 5.62 (dd, J = 3.0, 9.7 Hz, 1 H) 5.13 (d, J = 51.0 Hz, 1 H) 4.45 (td, J = 5.7, 11.7 Hz, 1 H) 3.99 (q, J = 7.2 Hz, 2 H) 3.83 (s, 3 H) 3.84-3.69 (m, 3 H) 3.66 (d, J = 11.9 Hz, 1 H) 3.62 (s, 3 H) 1.33 (t, J = 7.2 Hz, 3 H) |

TABLE 1-continued

| Example No. (Scheme) | Structure and Compound Name | LRMS m/z | ¹H NMR |
|---|---|---|---|
| 89 (Scheme D) | 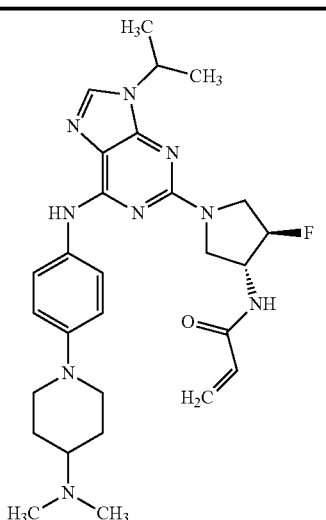<br>N-((3R,4R)-1-(6-((4-(4-(dimethylamino)piperidin-1-yl)phenyl)amino)-9-isopropyl-9H-purin-2-yl)-4-fluoropyrrolidin-3-yl)acrylamide | 536.1 [M + H]+ | ¹H NMR (400 MHz, MeOD) δ ppm 8.50 (br. s., 1 H) 7.91 (s, 1 H) 7.81-7.79 (d, 2 H) 7.06-7.04 (d, 2 H) 6.29-6.27 (m, 2 H) 5.71-5.68 (m, 1 H) 5.24-5.11 (d, 1 H) 4.78-4.75 (m, 1 H) 4.63-4.61 (m, 1 H) 3.98-3.80 (m, 6 H) 3.25-3.20 (m, 1 H) 2.87 (s, 6 H) 2.82-2.76 (t, 2 H) 2.19-2.16 (d, 2 H) 1.89-1.86 (m, 2 H) 1.62-1.60 (m, 6 H) |
| 90 (Scheme D) | 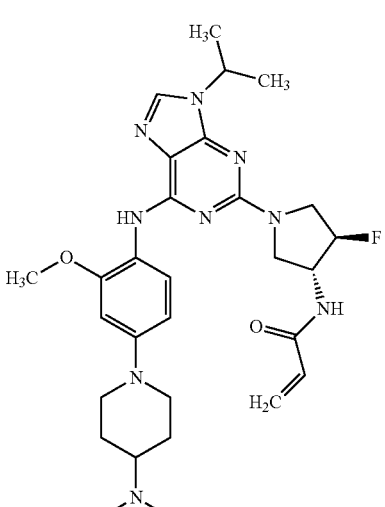<br>N-((3R,4R)-1-(6-((4-(4-(dimethylamino)piperidin-1-yl)-2-methoxyphenyl)amino)-9-isopropyl-9H-purin-2-yl)-4-fluoropyrrolidin-3-yl)acrylamide | 566.3 [M + H]+ | ¹H NMR (400 MHz, MeOD) δ ppm 8.60-8.57 (d, 1 H) 8.52 (br. s., 1 H) 7.93 (s, 1 H) 6.74 (d, 1 H) 6.67-6.64 (m, 1 H) 6.29-6.27 (m, 2 H) 5.71-5.68 (m, 1 H) 5.24-5.11 (d, 1 H) 4.78-4.75 (m, 1 H) 4.63-4.61 (m, 1 H) 4.00-3.83 (m, 9 H) 3.25-3.23 (m, 1 H) 2.87-2.77 (m, 8 H) 2.19-2.16 (m, 2 H) 1.89-1.85 (m, 2 H) 1.62-1.60 (m, 6 H) | pEGFR Y1068 ELISA Assay:

In order to profile the effect of EGFR T790M inhibitors in cells with different EGFR mutation status, inhibition of phosphorylation of EGFR at Tyr1068 (Y1068) was determined in cells with wildtype EGFR or various EGFR mutations—either EGFR single mutant (L858R, E746-A750 deletion) or EGFR double mutant (L858R+T790M, deletion+T790M).

Phosphorylation of EGFR at Y1068 was measured by PathScan® Phospho-EGF Receptor (Try1068) Sandwich ELISA kit (#7240, Cell Signaling Technology®, Danvers, Mass.). The PathScan® Phospho-EGF Receptor (Tyr1068) Sandwich ELISA Kit is a solid phase sandwich enzyme-linked immunosorbent assay (ELISA) that detects endogenous levels of phospho-EGF Receptor (Tyr1068) protein. The following non-small cell lung cancer (NSCLC) cell lines were evaluated in this assay: A549 (EGFR wildtype, endogenous), NCI-H1975 (EGFR L858R+T790M, endogenous), NCI-H3255 (EGFR L858R), PC9 (EGFR del), and PC9-DRH (EGFR del/T790M). A549 and NCI-H1975 cells were purchased from the American Type Culture Collection (Manassas, Va.). PC9 cells were purchased from RIKEN BioResouce Center (Japan). NCI-H3255 cells were licensed from NCI. PC9-DRH cells were generated by long term maintenance in the presence of dacomitinib to achieve resistance to dacomitinib and acquire T790M mutation. All cells were cultured according to ATCC recommendations. A549, NCI-H1975, PC9, and NCI-H3255 cells were grown in RPMI media (Invitrogen, Carlsbad, Calif.) supplemented with 10% FBS (Sigma, St Louis, Mo.), and with 1% Penn/Strep (Invitrogen). PC9-DRH cells were grown in RPMI with 10% FBS and 1 µM dacomitinib.

Cells were plated at 40,000/well in complete culture media (50 µL/well) on the bottom of clear tissue culture treated microtiter plates (#3595, Corning Inc, Corning, N.Y.) and allowed to adhere overnight at 37° C., 5% $CO_2$. The following day, compound dilution plates were prepared in 96 well clear V-bottom 0.5 mL polypropylene block plates (#3956, Corning, Inc). Each compound was prepared as a DMSO stock solution (10 mM). Compounds were tested in duplicate on each plate, with an 11-point serial dilution curve (1:3 dilution). Compound treatment (50 µL) was added from the compound dilution plate to the cell plate. The highest compound concentration was 1 or 10 µM (final), with a 0.3% final DMSO (#D-5879, Sigma) concentration. Plates were then incubated for 2 hr at 37° C., 5% $CO_2$. For A549 (EGFR wildtype) assay, cells were plated in full-serum (10%) media for 24 hr prior to compound treatment; cells were treated in full serum media as described and then stimulated for 10 min with EGF (40 ng/mL/starvation media, Invitrogen). Immediately prior to the end of the incubation, ice-cold lysis buffer was prepared (1× Cell Lysis Buffer (#9803, Cell Signaling Technology), 1 mM sodium orthovanadate ($Na_3VO_4$, #96508, Sigma), 1 mM phenylmethanesulfonyl fluoride (PMSF, 52332, CalBiochem/EMD Chemicals), complete Mini EDTA-free Protease Inhibitor Cocktail Tablet (1 tablet/ 10 mL, #11836170001, Roche, Indianapolis, Ind.), and PhosSTOP Phosphatase Inhibitor Cocktail Tablet (1 tablet/10 mL, #04906837001, Roche) in pure water. At the end of 2 hr, media was flicked off and cells were washed once with ice-cold 1 mM $Na_3VO_4$ in PBS (100 µL/well, Invitrogen). The wash was then flicked off and ice-cold lysis buffer was added to the cells (50 µL/well). The plate was shaken for 20-30 min at 4° C. to completely lyse the cells. Sample diluent (50 µL/well) was added to the ELISA plate, and the lysate (50 µL) was diluted into the sample diluent in each well of the ELISA plate. Plates were sealed and incubated overnight at 4° C. with shaking. The next day, wells were washed four times with 1× Wash Buffer; plates were taped on lint-free paper after the final wash prior to adding Add Detection Antibody (green, 100 µL/well) to each well and incubating for 1 hr at 37° C. After incubation, wells were washed as described. HRP-Linked secondary antibody (red, 100 µL/well) was added to each well and incubated for 30 min at 37° C. After incubation, the wells were washed as described. TMB Substrate (100 µL/well) was added to each well and the plate incubated for 10 min at 37° C. or 30 min at rt maximum. Stop Solution (100 µL/well) was added to each well at the end of the incubation and plates were shaken gently for a few seconds. Absorbance was read at 450 nm within 30 min after addition of Stop Solution on a PerkinElmer EnVision Excite Multilabel Reader Method for Absorbance or on a Molecular Devices SpectraMax[384] Reader for absorbance. Data were analyzed using a four-parameter fit in Microsoft Excel.

The results of the pEGFR Y1068 ELISA assay for the compounds tested are listed in Table 2.

TABLE 2

| Example Number | H1975 $IC_{50}$ (nM) | PC9 $IC_{50}$ (nM) | H3255 $IC_{50}$ (nM) | PC9-DRH $IC_{50}$ (nM) | A549 $IC_{50}$ (nM) |
|---|---|---|---|---|---|
| 1 | 19 | 22 | 19 | 18 | 277 |
| 2 | 7 | 9 | 2 | 2 | 178 |
| 3 | 20 | N/D | N/D | 8 | 162 |
| 4 | 52 | 52 | 59 | N/D | 652 |
| 5 | 17 | N/D | N/D | 8 | 546 |
| 6 | 1041 | N/D | N/D | N/D | 10000 |
| 7 | 12 | 5 | 4 | 2 | 307 |
| 8 | 97 | N/D | N/D | 37 | 4479 |
| 9 | 32 | N/D | N/D | 26 | 2735 |
| 10 | 846 | N/D | N/D | N/D | 10000 |
| 11 | 162 | N/D | N/D | N/D | 2840 |
| 12 | 6 | N/D | N/D | 10 | 140 |
| 13 | 40 | 40 | 80 | 25 | 2442 |
| 14 | 285 | N/D | N/D | N/D | 10000 |
| 15 | 55 | N/D | N/D | N/D | 117 |
| 16 | 88 | N/D | N/D | 91 | 507 |
| 17 | 468 | N/D | N/D | 2500 | 10000 |
| 18 | 32 | N/D | N/D | 27 | 4572 |
| 19 | 10 | N/D | N/D | 25 | 194 |
| 20 | 11 | N/D | N/D | 2 | 119 |
| 21 | 14 | 8 | 8 | 18 | 181 |
| 22 | 6 | N/D | N/D | 9 | 39 |
| 23 | 39 | N/D | N/D | N/D | 1424 |
| 24 | 39 | N/D | N/D | N/D | 1140 |
| 25 | 49 | N/D | N/D | 6 | 805 |
| 26 | 25 | N/D | N/D | N/D | 682 |
| 27 | 29 | N/D | N/D | N/D | 387 |
| 28 | 48 | N/D | N/D | N/D | 723 |
| 29 | 35 | 40 | 35 | 61 | 698 |
| 30 | 82 | N/D | N/D | N/D | 3855 |
| 31 | 76 | N/D | N/D | N/D | 1353 |
| 32 | 65 | N/D | N/D | N/D | 1233 |
| 33 | 18 | N/D | N/D | 4 | 324 |
| 34 | 161 | N/D | N/D | N/D | 2666 |
| 35 | 11 | N/D | N/D | N/D | 95 |
| 36 | 8 | N/D | N/D | 9 | 242 |
| 37 | 391 | N/D | N/D | N/D | 7607 |
| 38 | 15 | N/D | N/D | 6 | 255 |
| 39 | 66 | 20 | N/D | 10 | 2848 |
| 40 | 8 | N/D | N/D | 5 | 74 |
| 41 | 64 | 38 | 9 | 3 | 3040 |
| 42 | 26 | N/D | N/D | 38 | 1347 |
| 43 | 74 | N/D | N/D | 18 | 1476 |
| 44 | 24 | N/D | N/D | 7 | 1152 |
| 45 | 26 | 7 | N/D | 3 | 1907 |
| 46 | 387 | 31 | 7 | N/D | 4192 |
| 47 | 14 | N/D | N/D | 19 | 308 |
| 48 | 204 | N/D | N/D | N/D | 4361 |
| 49 | 21 | 8 | 3 | 2 | 787 |
| 50 | 26 | 8 | 3 | 34 | 587 |
| 51 | N/D | N/D | N/D | N/D | N/D |
| 52 | 742 | N/D | N/D | 6 | 10000 |
| 53 | 5 | 2 | 2 | 1 | 160 |
| 54 | 17 | 16 | N/D | 4 | 673 |
| 55 | 9 | 3 | 2 | 3 | 273 |
| 56 | 108 | N/D | N/D | 2 | 504 |
| 57 | 89 | N/D | N/D | 44 | 3040 |
| 58 | 58 | N/D | N/D | N/D | 983 |
| 59 | 162 | N/D | N/D | N/D | 4047 |
| 60 | 317 | N/D | N/D | N/D | 1386 |
| 61 | 6138 | 6651 | N/D | 2127 | 10000 |
| 62 | 6 | 3 | 1 | 2 | 32 |
| 63 | 32 | 14 | N/D | 5 | 551 |
| 64 | 8 | N/D | N/D | 8 | 127 |
| 65 | 14 | 11 | N/D | 9 | 1255 |
| 66 | N/D | N/D | N/D | N/D | N/D |
| 67 | 8 | N/D | N/D | N/D | 90 |
| 68 | 18 | N/D | N/D | N/D | 707 |
| 69 | 37 | N/D | N/D | N/D | 712 |
| 70 | 29 | N/D | N/D | N/D | 609 |
| 71 | 20 | N/D | N/D | N/D | 167 |
| 72 | 6 | 2 | 5 | 3 | 142 |
| 73 | 9 | N/D | N/D | N/D | 92 |
| 74 | 5 | N/D | N/D | 2 | 49 |
| 75 | 11 | N/D | 1 | 2 | 64 |
| 76 | 30 | N/D | N/D | 2 | 394 |
| 77 | 8 | N/D | 2 | 2 | 83 |
| 78 | 7 | N/D | N/D | 3 | 649 |
| 79 | 6 | 3 | 3 | 1 | 100 |
| 80 | 22 | N/D | N/D | 10 | 425 |

TABLE 2-continued

| Example Number | H1975 IC$_{50}$ (nM) | PC9 IC$_{50}$ (nM) | H3255 IC$_{50}$ (nM) | PC9-DRH IC$_{50}$ (nM) | A549 IC$_{50}$ (nM) |
|---|---|---|---|---|---|
| 81 | 19 | 21 | 15 | 8 | 575 |
| 82 | N/D | N/D | N/D | N/D | N/D |
| 83 | 132 | N/D | N/D | N/D | 3452 |
| 84 | 15 | 45 | 9 | 3 | 1198 |
| 85 | 17 | 104 | 34 | 15 | 647 |
| 86 | 32 | N/D | N/D | N/D | 1218 |
| 87 | 3 | N/D | 2 | 3 | 64 |
| 88 | 6 | 6 | 2 | 1 | 194 |
| 89 | N/D | N/D | N/D | 3 | N/D |
| 90 | N/D | N/D | N/D | 9 | N/D |

What is claimed is:

1. A compound of formula (IIIa):

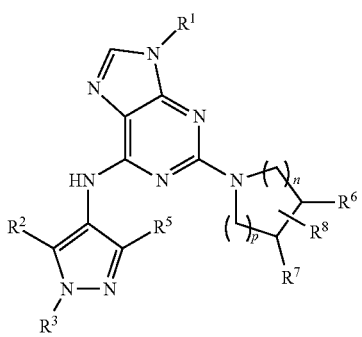

wherein $R^1$ is hydrogen, $C_1$-$C_6$ alkyl, $C_2$-$C_6$ alkenyl, $C_2$-$C_6$ alkynyl, $C_3$-$C_6$ cycloalkyl, 4-6 membered heterocycloalkyl, or 4-6 membered heteroaryl, wherein the $C_1$-$C_6$ alkyl is optionally substituted by one, two or three substituents selected from the group consisting of halogen, hydroxy, and $C_1$-$C_3$ alkoxy, further wherein the $C_3$-$C_6$ cycloalkyl, the 4-6 membered heterocycloalkyl, and the 4-6 membered heteroaryl are each independently optionally substituted by one, two or three substituents selected from the group consisting of $C_1$-$C_3$ alkyl, hydroxy, and $C_1$-$C_3$ alkoxy;

$R^2$ and $R^5$ are each independently hydrogen, halogen, cyano, difluoromethyl, trifluoromethyl, $C_1$-$C_6$ alkyl, $C_2$-$C_6$ alkenyl, $C_2$-$C_6$ alkynyl, $C_1$-$C_6$ alkoxy, —N($R^{10}$)($R^{11}$), $C_3$-$C_5$ cycloalkyl, or 4-6 membered heterocycloalkyl, wherein the $C_1$-$C_6$ alkyl is optionally substituted by one, two or three substituents selected from the group consisting of halogen, hydroxy, $C_1$-$C_6$ alkoxy, and —N($R^{12}$)($R^{13}$), provided that at least one of $R^2$ or $R^5$ is hydrogen;

$R^3$ is hydrogen, halogen, $C_1$-$C_6$ alkyl, $C_2$-$C_6$ alkynyl, $C_1$-$C_6$ alkoxy, $C_3$-$C_7$ cycloalkyl, or 3-7 membered heterocycloalkyl, wherein the $C_1$-$C_6$ alkyl and the $C_1$-$C_6$ alkoxy are each optionally substituted by one, two or three $R^{14}$ groups, and further wherein the $C_3$-$C_7$ cycloalkyl and the 3-7 membered heterocycloalkyl are each optionally substituted by one, two or three $R^{15}$ groups;

$R^6$ and $R^8$ are each independently hydrogen, halogen, cyano, hydroxy, difluoromethyl, trifluoromethyl, $C_1$-$C_3$ alkyl, $C_1$-$C_3$ alkoxy, or $C_3$-$C_5$ cycloalkyl, wherein the $C_1$-$C_3$ alkyl is optionally substituted by hydroxy, difluoromethyl, trifluoromethyl, $C_1$-$C_3$ alkoxy, or $C_3$-$C_5$ cycloalkyl;

$R^7$ is

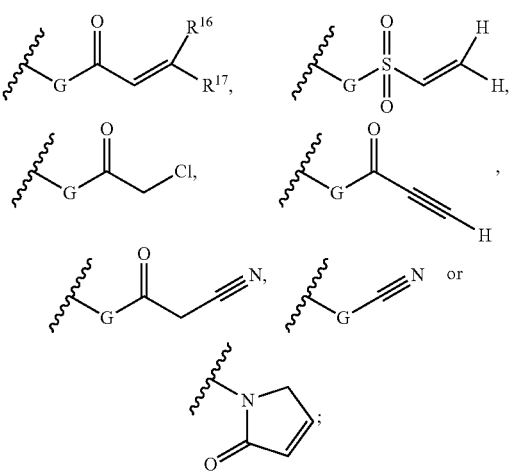

G is —N$R^{18}$—;

$R^{10}$ and $R^{11}$ are each independently hydrogen or $C_1$-$C_6$ alkyl; or $R^{10}$ and $R^{11}$ together with the nitrogen to which they are attached, may combine to form a 4-7 membered heterocycloalkyl ring, when $R^{10}$ and $R^{11}$ are each $C_1$-$C_3$ alkyl, wherein the 4-7 membered heterocycloalkyl ring formed is optionally substituted by one, two, three or four $R^{15}$ groups;

$R^{12}$ and $R^{13}$ are each independently hydrogen or $C_1$-$C_3$ alkyl;

each $R^{14}$ is independently halogen, cyano, $C_1$-$C_3$ alkyl, hydroxy, $C_1$-$C_6$ alkoxy, —N($R^{19}$)($R^{20}$), —CON($R^{21}$)($R^{22}$), or 3-7 membered heterocycloalkyl, wherein the 3-7 membered heterocycloalkyl is optionally substituted by one, two, three or four $R^{15}$ groups;

each $R^{15}$ is independently halogen, $C_1$-$C_3$ alkyl, hydroxy, $C_1$-$C_6$ alkoxy, —NH$_2$, —NHCH$_3$, or —N(CH$_3$)$_2$;

$R^{16}$ and $R^{17}$ are each independently hydrogen or $C_1$-$C_6$ alkyl, wherein the $C_1$-$C_6$ alkyl is optionally substituted by —N($R^{23}$)($R^{24}$), provided that $R^{16}$ and $R^{17}$ may form $C_3$-$C_5$ cycloakyl ring;

$R^{18}$ is hydrogen or $C_1$-$C_3$ alkyl;

each $R^{19}$, $R^{20}$, $R^{21}$, $R^{22}$, $R^{23}$, and $R^{24}$ is independently hydrogen or $C_1$-$C_3$ alkyl;

n is 0, 1, or 2; and p is 0, 1, or 2; or a pharmaceutically acceptable salt thereof.

2. The compound or salt of claim 1, wherein n is 0.

3. The compound or salt of claim 1, wherein $R^6$ and $R^8$ are each independently hydrogen, halogen, $C_1$-$C_3$ alkyl, or $C_1$-$C_3$ alkoxy.

4. The compound or salt of claim 1, wherein $R^6$ is hydrogen, fluorine, methyl, or methoxy.

5. The compound or salt of claim 1, wherein $R^6$ is fluorine.

6. The compound or salt of claim 1, wherein $R^8$ is hydrogen, fluorine, or methyl.

7. The compound or salt of claim 1, having formula (IIIb):

(IIIb)

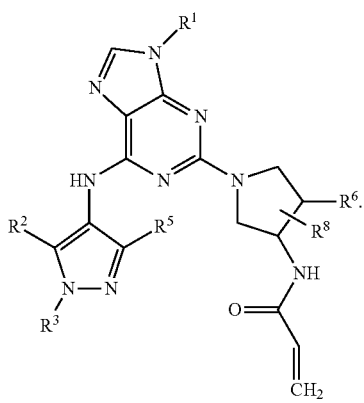

8. A compound, which is

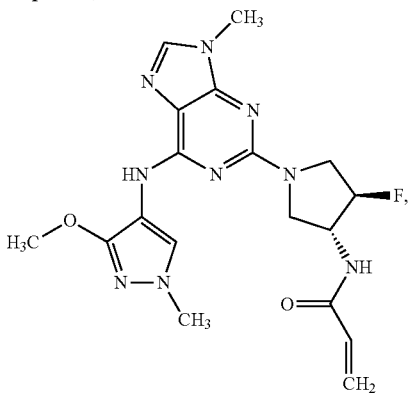

or a pharmaceutically acceptable salt thereof.

9. A pharmaceutical composition comprising a compound of claim 1, or a pharmaceutically acceptable salt thereof, and a pharmaceutically acceptable carrier or diluent.

10. A pharmaceutical composition comprising a compound, which is

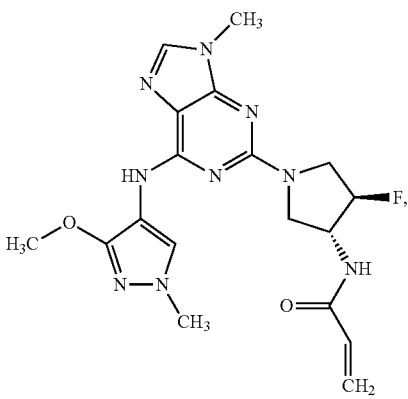 [SMILES: C=CC(=O)N[C@@H]1CN(c2nc(Nc3cn(C)nc3OC)c3ncn(C)c3n2)C[C@H]1F]

or a pharmaceutically acceptable salt thereof, and a pharmaceutically acceptable carrier or diluent.

11. A method of treating lung cancer in a mammal comprising administering to the mammal an amount of a compound of claim 1, or a pharmaceutically acceptable salt thereof, that is effective in treating lung cancer.

* * * * *